United States Patent
An et al.

(10) Patent No.: US 10,428,389 B2
(45) Date of Patent: *Oct. 1, 2019

(54) METHOD FOR DETECTING METHYLATION OF COLORECTAL CANCER SPECIFIC METHYLATION MARKER GENE FOR COLORECTAL CANCER DIAGNOSIS

(71) Applicant: GENOMICTREE, Inc., Daejeon (KR)

(72) Inventors: Sung Whan An, Daejeon (KR); Tae Jeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/661,054

(22) Filed: Jul. 27, 2017

(65) Prior Publication Data

US 2017/0335407 A1  Nov. 23, 2017

Related U.S. Application Data

(63) Continuation-in-part of application No. 15/010,379, filed on Jan. 29, 2016, now Pat. No. 9,752,197, which is a continuation-in-part of application No. 13/994,732, filed as application No. PCT/KR2011/009710 on Dec. 16, 2011, now Pat. No. 9,315,870.

(30) Foreign Application Priority Data

Dec. 16, 2010  (KR) .................... 10-2010-0129208

(51) Int. Cl.
*C07H 21/04* (2006.01)
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 5,474,796 A | 12/1995 | Brennan | |
| 5,786,146 A | 7/1998 | Herman et al. | |
| 9,315,870 B2 * | 4/2016 | An | C07K 14/705 |
| 9,359,646 B2 | 6/2016 | An et al. | |
| 9,365,900 B2 | 6/2016 | An et al. | |
| 9,752,197 B2 * | 9/2017 | An | C12Q 1/6886 |
| 2010/0303795 A1 | 12/2010 | Sorensen et al. | |
| 2012/0101023 A1 * | 4/2012 | Zwarthoff | C12Q 1/6886 |
| | | | 514/1.1 |
| 2012/0264640 A1 * | 10/2012 | An | C12Q 1/686 |
| | | | 506/9 |
| 2014/0045180 A1 | 2/2014 | An et al. | |
| 2016/0145694 A1 | 5/2016 | An et al. | |

FOREIGN PATENT DOCUMENTS

| | | | | |
|---|---|---|---|---|
| DE | 20121960 U1 | 1/2004 | | |
| EP | 1862555 | * 12/2007 | ............... | C12Q 1/68 |
| EP | 1862555 A1 | 12/2007 | | |
| KR | 1020120055917 A | 6/2012 | | |
| WO | 2007149269 A2 | 12/2007 | | |
| WO | 2010123354 A2 | 10/2010 | | |
| WO | WO 2010/123354 | * 10/2010 | ............... | C12Q 1/68 |

OTHER PUBLICATIONS

"*Homo sapiens* BAC clone RP11-598O12 from 4, complete sequence", "GenBank", May 29, 2002, pp. AC110794.3, Publisher: https://www.ncbi.nlm.nih.gov/nuccore/AC110794.3.
Sulewska, A., et al., "Detection of DNA methylation in eucaryotic cells", "Folio Histochemica Et Cytobiologica", 2007, pp. 315-324, vol. 45, No. 4.
Ahlquist, D., et al., "Colorectal Cancer Screening by Detection of Altered Human DNA in Stool: Feasibility of a Multitarget Assay Panel", "Gastroenterology", Nov. 2000, pp. 1219-1227, vol. 119, No. 5.
Alfonso, J., et al., "The stress-regulated protein M6a is a key modulator for neurite outgrowth and filopodium/spine formation", "Proceedings of National Academy of Sciences", Nov. 22, 2005, pp. 17196-17201, vol. 102, No. 47.
Bai, F., et al., "Establishment and characterization of a high metastatic potential in the peritoneum for human gastric cancer by orthotopic tumor cell implantation", "Dig Dis Sci.", Apr. 3, 2007, pp. 1571-1578, vol. 52, No. 6.
Chen, X., et al, "Detecting tumor-related alterations in plasma or serum DNA of patients diagnosed with breast cancer", "Clin Cancer Res.", Sep. 1999, pp. 2297-2303, vol. 5, No. 9.
Esteller, M., et al., "Detection of Aberrant Promoter Hypermethylation of Tumor Suppressor Genes in Serum DNA from Non-Small Cell Lung Cancer Patients", "Cancer Research", Jan. 1, 1999, pp. 67-70, vol. 59.

(Continued)

*Primary Examiner* — Jeanine A Goldberg
(74) *Attorney, Agent, or Firm* — Hultquist, PLLC; Steven J. Hultquist

(57) ABSTRACT

The present disclosure relates to a method for detecting methylation of the bowel-cancer-specific methylation marker GPM6A (NM_201591, glycoprotein M6A) gene in order to diagnose bowel cancer, and more specifically relates to a method for providing information for diagnosing bowel cancer by detecting the methylation of a bowel-cancer-specific marker gene that is specifically methylated in bowel cancer cells. The method for detecting methylation and a diagnostic composition, kit and nucleic-acid chip according to the present disclosure can be used to advantage in diagnosing bowel cancer more accurately and quickly than by normal methods as they permit bowel cancer to be diagnosed at the initial genetic transformation step and so allow early diagnosis.

5 Claims, 4 Drawing Sheets

Specification includes a Sequence Listing.

(56) References Cited

OTHER PUBLICATIONS

Fraga, M., et al., "The affinity of different Mbd proteins for a specific methylated locus depends on their intrinsic binding properties", "Nucleic Acids Research", Mar. 15, 2003, pp. 1765-1774, vol. 31, No. 6.

Gitan, R., et al., "Methylation-Specific Oligonucleotide Microarray: A New Potential for High-Throughput Methylation Analysis", "Genome Research", Dec. 2001, pp. 158-164, vol. 12.

Goessl, C., et al., "Fluorescent Methylation-specific Polymerase Chain Reaction for DNA-based Detection of Prostate Cancer in Bodily Fluids", "Cancer Research", Nov. 1, 2000, pp. 5941-5945, vol. 60.

Hoehn, B., et al., "Abstract 4517: Syndecan-2 methylation is an early detection biomarker for colorectal cancer with high sensitivity and specificity in small serum sample volumes", "Cancer Research", Apr. 15, 2012, p. 4517 vol. 72 (8 Supplement).

"Illumina DNA Methylation Analysis Data Sheet", "Data Sheet: Epigenetics", Apr. 6, 2012, pp. 1-7; (http://www.illumina.com/Documents/products/datasheets/datasheet_dna_methylation_analysis.pdf).

Jan, K., et al, "Abnormal DNA methylation according to the histologic types of early gastric adenocarcinoma", "Histopathology", Sep. 5, 2012, pp. 76-77, vol. 61 (Supplement 1).

Kimura, N., et al., "Methylation profiles of genes utilizing newly developed CpG island methylation microarray on colorectal cancer patients", "Nucleic acids research", Mar. 10, 2005, p. e46, vol. 33, No. 5.

Kopreski, M., et al., "Detection of Tumor Messenger RNA in the Serum of Patients with Malignant Melanoma", "Clinical Cancer Research", Aug. 1999, pp. 1961-1965, vol. 5.

Malik, K., et al., "Epigenetic gene deregulation in cancer", "British Journal of Cancer", Dec. 2000, pp. 1583-1588, vol. 83, No. 12.

Matsusaka, K., et al., "Classification of Epstein-Barr Virus-Positive Gastric Cancers by Definition of DNA Methylation Epigenotypes", "Cancer Research", Dec. 1, 2011, pp. 7187-7197, vol. 71, No. 23.

Miyashiro, I., et al., "Molecular Strategy for Detecting Metastatic Cancers with Use of Multiple Tumor-specific MAGE-A Genes", "Clinical Chemistry", Mar. 2001, pp. 505-512, vol. 47, No. 3.

Moon, Y.H., et al., "Methylated DNA Isolation Assay-Medicated DNA Methylation Detection and Whole-Genome Methylation Profiling", "American Biotechnology Laboratory", Oct. 2009, pp. 23-25, vol. 27, No. 10.

Mukobata, S., et al., "M6a acts as a nerve growth factor-gated Ca2+ channel in neuronal differentiation", "Biochemical and Biophysical Research Communications", Oct. 2002, pp. 722-728, vol. 297.

Palmisano, W., et al., "Predicting Lung Cancer by Detecting Aberrant Promoter Methylation in Sputum", "Cancer Research", Nov. 1, 2000, pp. 5954-5958, vol. 60.

Robertson, K., et al., "DNA Methylation: past, present and future directions", "Carcinogenesis", Mar. 2000, pp. 461-467, vol. 21, No. 3.

Sanchez-Cespedes, M., et al., "Gene Promoter Hypermethylation in Tumors and Serum of Head and Neck Cancer Patients", "Cancer Research", Feb. 15, 2000, pp. 892-895, vol. 60.

Sato, F., et al., "CpG Island Hypermethylation in Progression of Esophageal and Gastric Cancer", "Cancer", Dec. 16, 2005, pp. 483-493, vol. 106, No. 3.

Shimizu, F., et al., "Isolation and mapping of the human glycoprotein M6 gene (GPM6A) to 4q33->q34", "Cytogenetics and Cell Genetics", 1996, pp. 138-139, vol. 74, No. 1-2.

Singal, R., et al., "DNA Methylation", "Blood", Jun. 15, 1999, pp. 4059-4070, vol. 93, No. 12.

Sozzi, G., et al, "Detection of Microsatellite Alterations in Plasma DNA of Non-Small Cell Lung Cancer Patients: A Prospect for Early Diagnosis", "Clinical Cancer Research", Oct. 1999, pp. 2689-2692, vol. 5.

Sueoka, E., et al., "Heterogeneous Nuclear Ribonucleoprotein B1 as a New Marker of Early Detection for Human Lung Cancers", "Cancer Research", Apr. 1, 1999, pp. 1404-1407, vol. 59.

Toyota, M., et al., "Identification of differentially methylated sequences in colorectal cancer by methylated CpG island amplification", "Cancer Research", May 15, 1999, pp. 2307-2312, vol. 59.

Tran, A., et al., "In silico enhanced restriction enzyme based methylation analysis of the human glioblastoma genome using Agilent 244K CpG Island microarrays", "Frontiers in Neroscience", Jan. 4, 2010, pp. 1-13, vol. 3.

Wiksten, J., et al., "Epithelial and stromal syndecan-1 expression as predictor of outcome in patients with gastric cancer", "Int. J. Cancer (Pred. Oncol.)", Jan. 20, 2001, pp. 1-6, vol. 95.

Zourdhis, H., et al., "Methylation Subtypes and Large-Scale Epigenetic Alterations in Gastric Cancer", "Science Translational Medicine", Oct. 17, 2012, pp. 1-12, vol. 4, No. 156.

Note: For the non-patent literature citations that no month of publication is indicated, the year of publication is more than 1 year prior to the effective filing date of the present application.

* cited by examiner

A. Colorectal cancer cell line

B. DNA isolated from feces

Normal person (n=4)

Colorectal cancer patients (n=8)

M: methylated, UM: unmethylated

SEQUENCE LISTING

<160> NUMBER OF SEQ ID NOS: 1428

<210> SEQ ID NO 1
<211> LENGTH: 700
<212> TYPE: DNA
<213> ORGANISM: Homo sapiens

<400> SEQUENCE: 1

```
ggtctaccgt gctgggggcg gtatttggga aataaagaaa gactaagaga cccaggatcc     60
gaatagcgag gcgattacag ggagatctct gtcctcccga gttcccacgt tttcatgttc    120
tctttgggga gcaagttgaa acggggcacg agaaatggaa acttcctaaa acttccactt    180
tgtacaggtt tgagcagagg aaggtgctgg tgcagggcca gactgggggac aatttctagt   240
cccctttcca acgaagtgcc catttgcaca aaaggtttga ggttgaggct gaaggctgat    300
tcttcctaaa ttccacctgg gtaaacagcg tgattaaaag ggcgtccaca ctggctcggg    360
tcactggacg gtggagttcg gcgcagttca gcttcgctca agtttccagg cagggtccgc    420
ttattcggtg cttagcggag gcagcttgga atagctccag gaatgtgact gcgtgtggcg    480
gaggggagga agaactgggt gtgaaatagc cgattcacac ccagcactag gacgcagggt    540
cccacgagtc acctcgaaga gcgagggaga agctggggag gagaaagcac tcgccatccc    600
tggactggcg tatccacagg cgcaggggag atgctgctct ccgcggttg ccgactgcgt     660
tcagcccgca gcccgagtta ctcttccaac cccagcccgc                          700
```

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2

```
gtatttggga aataaagaaa                                                 20
```

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3

```
gactaagaga cccaggatcc gaatagcgag                                      30
```

<210> SEQ ID NO 4
<211> LENGTH: 40
<212> TYPE: DNA
<213> ORGANISM: Artificial Sequence
<220> FEATURE:
<223> OTHER INFORMATION: Synthetic Construct

<400> SEQUENCE: 4

```
gttcccacgt tttcatgttc tctttgggga gcaagttgaa                           40
```

<210> SEQ ID NO 5
<211> LENGTH: 50
<212> TYPE: DNA
<213> ORGANISM: Artificial Sequence
<220> FEATURE:
<223> OTHER INFORMATION: Synthetic Construct

<400> SEQUENCE: 5

```
ggcgtccaca ctggctcggg tcactggacg gtggagttcg gcgcagttca                    50

<210> SEQ ID NO 6
<211> LENGTH: 60
<212> TYPE: DNA
<213> ORGANISM: Artificial Sequence
<220> FEATURE:
<223> OTHER INFORMATION: Synthetic Construct

<400> SEQUENCE: 6
agtttccagg cagggtccgc ttattcggtg cttagcggag gcagcttgga atagctccag         60

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
tgttgatttt tggtgtattg a                                                  21

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
aacacatcaa crtcctaatt acata                                              25

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
tgtttggtgt aggggaagt                                                     20

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
cccraaaaaa ttattttacc tcca                                               24

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct

<400> SEQUENCE: 11
gggaaataaa gaaagattaa gaga                                               24

<210> SEQ ID NO 12
<211> LENGTH: 19
<212> TYPE: DNA
```

```
<213> ORGANISM: Artificial Sequence
<220> FEATURE:
<223> OTHER INFORMATION: Synthetic Construct

<400> SEQUENCE: 12
accccrtttc aacttactc                                               19

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
attttagtgg tttaaagatg                                              20

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
tgggtgtatt gagagattt                                               19

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
aagattaaga gatttaggat                                              20

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16 ttaaagggc gtttatattg gttcg                                         25

<210> SEQ ID NO 17
<211> LENGTH: 24
<212> TYPE: DNA
<213> ORGANISM: Artificial Sequence
<220> FEATURE:
<223> OTHER INFORMATION: Synthetic Construct

<400> SEQUENCE: 17
cctcgctctt cgaaataact cgta                                         24

<210> SEQ ID NO 18
<211> LENGTH: 26
<212> TYPE: DNA
<213> ORGANISM: Artificial Sequence
<220> FEATURE:
<223> OTHER INFORMATION: Synthetic Construct

<400> SEQUENCE: 18
tagggttcgt ttattcggtg tttagc                                       26
```

```
<210> SEQ ID NO 19
<211> LENGTH: 24
<212> TYPE: DNA
<213> ORGANISM: Artificial Sequence
<220> FEATURE:
<223> OTHER INFORMATION: Synthetic Construct

<400> SEQUENCE: 19
cctcgctctt cgaaataact cgta                                              24

<210> SEQ ID NO 20
<211> LENGTH: 25
<212> TYPE: DNA
<213> ORGANISM: Artificial Sequence
<220> FEATURE:
<223> OTHER INFORMATION: Synthetic Construct

<400> SEQUENCE: 20
taaaagggtg tttatattgg tttgg                                             25

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct

<400> SEQUENCE: 21
ccctcactct tcaaaataac tcata                                             25

<210> SEQ ID NO 22
<211> LENGTH: 29
<212> TYPE: DNA
<213> ORGANISM: Artificial Sequence
<220> FEATURE:
<223> OTHER INFORMATION: Synthetic Construct

<400> SEQUENCE: 22
ggtagggttt gtttatttgg tgtttagtg                                         29

<210> SEQ ID NO 23
<211> LENGTH: 26
<212> TYPE: DNA
<213> ORGANISM: Artificial Sequence
<220> FEATURE:
<223> OTHER INFORMATION: Synthetic Construct

<400> SEQUENCE: 23
tccctcactc ttcaaaataa ctcata                                            26

<210> SEQ ID NO 24
<211> LENGTH: 14
<212> TYPE: DNA
<213> ORGANISM: Artificial Sequence
<220> FEATURE:
<223> OTHER INFORMATION: Synthetic Construct

<400> SEQUENCE: 24
attattttgg ttat                                                         14

<210> SEQ ID NO 25
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 25
aaaaacacgt acaa                                                            14

<210> SEQ ID NO 26
<211> LENGTH: 18
<212> TYPE: DNA
<213> ORGANISM: Artificial Sequence
<220> FEATURE:
<223> OTHER INFORMATION: Synthetic Construct

<400> SEQUENCE: 26
gtatttagga gagagatt                                                        18

<210> SEQ ID NO 27
<211> LENGTH: 14
<212> TYPE: DNA
<213> ORGANISM: Artificial Sequence
<220> FEATURE:
<223> OTHER INFORMATION: Synthetic Construct

<400> SEQUENCE: 27
ttattttggt tatc                                                            14

<210> SEQ ID NO 28
<211> LENGTH: 14
<212> TYPE: DNA
<213> ORGANISM: Artificial Sequence
<220> FEATURE:
<223> OTHER INFORMATION: Synthetic Construct

<400> SEQUENCE: 28
aaaaacacgt acaa                                                            14

<210> SEQ ID NO 29
<211> LENGTH: 14
<212> TYPE: DNA
<213> ORGANISM: Artificial Sequence
<220> FEATURE:
<223> OTHER INFORMATION: Synthetic Construct

<400> SEQUENCE: 29
tattttggtt atcg                                                            14

<210> SEQ ID NO 30
<211> LENGTH: 14
<212> TYPE: DNA
<213> ORGANISM: Artificial Sequence
<220> FEATURE:
<223> OTHER INFORMATION: Synthetic Construct

<400> SEQUENCE: 30
aaaaacacgt acaa                                                            14

<210> SEQ ID NO 31
<211> LENGTH: 14
<212> TYPE: DNA
<213> ORGANISM: Artificial Sequence
<220> FEATURE:
<223> OTHER INFORMATION: Synthetic Construct

<400> SEQUENCE: 31
attttggtta tcga                                                            14

```
<210> SEQ ID NO 32
<211> LENGTH: 14
<212> TYPE: DNA
<213> ORGANISM: Artificial Sequence
<220> FEATURE:
<223> OTHER INFORMATION: Synthetic Construct

<400> SEQUENCE: 32
aaaaacacgt acaa                                                              14

<210> SEQ ID NO 33
<211> LENGTH: 14
<212> TYPE: DNA
<213> ORGANISM: Artificial Sequence
<220> FEATURE:
<223> OTHER INFORMATION: Synthetic Construct

<400> SEQUENCE: 33
ttttggttat cgag                                                              14

<210> SEQ ID NO 34
<211> LENGTH: 14
<212> TYPE: DNA
<213> ORGANISM: Artificial Sequence
<220> FEATURE:
<223> OTHER INFORMATION: Synthetic Construct

<400> SEQUENCE: 34
aaaaacacgt acaa                                                              14

<210> SEQ ID NO 35
<211> LENGTH: 14
<212> TYPE: DNA
<213> ORGANISM: Artificial Sequence
<220> FEATURE:
<223> OTHER INFORMATION: Synthetic Construct

<400> SEQUENCE: 35
tttggttatc gagt                                                              14

<210> SEQ ID NO 36
<211> LENGTH: 14
<212> TYPE: DNA
<213> ORGANISM: Artificial Sequence
<220> FEATURE:
<223> OTHER INFORMATION: Synthetic Construct

<400> SEQUENCE: 36
aaaaacacgt acaa                                                              14

<210> SEQ ID NO 37
<211> LENGTH: 14
<212> TYPE: DNA
<213> ORGANISM: Artificial Sequence
<220> FEATURE:
<223> OTHER INFORMATION: Synthetic Construct

<400> SEQUENCE: 37
ttggttatcg agtc                                                              14

<210> SEQ ID NO 38
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 38
aaaaacacgt acaa                                                    14

<210> SEQ ID NO 39
<211> LENGTH: 14
<212> TYPE: DNA
<213> ORGANISM: Artificial Sequence
<220> FEATURE:
<223> OTHER INFORMATION: Synthetic Construct

<400> SEQUENCE: 39
tggttatcga gtcg                                                    14

<210> SEQ ID NO 40
<211> LENGTH: 14
<212> TYPE: DNA
<213> ORGANISM: Artificial Sequence
<220> FEATURE:
<223> OTHER INFORMATION: Synthetic Construct

<400> SEQUENCE: 40
aaaaacacgt acaa                                                    14

<210> SEQ ID NO 41
<211> LENGTH: 14
<212> TYPE: DNA
<213> ORGANISM: Artificial Sequence
<220> FEATURE:
<223> OTHER INFORMATION: Synthetic Construct

<400> SEQUENCE: 41
ggttatcgag tcgg                                                    14

<210> SEQ ID NO 42
<211> LENGTH: 14
<212> TYPE: DNA
<213> ORGANISM: Artificial Sequence
<220> FEATURE:
<223> OTHER INFORMATION: Synthetic Construct

<400> SEQUENCE: 42
aaaaacacgt acaa                                                    14

<210> SEQ ID NO 43
<211> LENGTH: 14
<212> TYPE: DNA
<213> ORGANISM: Artificial Sequence
<220> FEATURE:
<223> OTHER INFORMATION: Synthetic Construct

<400> SEQUENCE: 43
gttatcgagt cggt                                                    14

<210> SEQ ID NO 44
<211> LENGTH: 14
<212> TYPE: DNA
<213> ORGANISM: Artificial Sequence
<220> FEATURE:
<223> OTHER INFORMATION: Synthetic Construct

<400> SEQUENCE: 44
aaaaacacgt acaa                                                    14

<210> SEQ ID NO 45
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 45
ttatcgagtc ggtt                                                     14

<210> SEQ ID NO 46
<211> LENGTH: 14
<212> TYPE: DNA
<213> ORGANISM: Artificial Sequence
<220> FEATURE:
<223> OTHER INFORMATION: Synthetic Construct

<400> SEQUENCE: 46
aaaaacacgt acaa                                                     14

<210> SEQ ID NO 47
<211> LENGTH: 14
<212> TYPE: DNA
<213> ORGANISM: Artificial Sequence
<220> FEATURE:
<223> OTHER INFORMATION: Synthetic Construct

<400> SEQUENCE: 47
tatcgagtcg gttg                                                     14

<210> SEQ ID NO 48
<211> LENGTH: 14
<212> TYPE: DNA
<213> ORGANISM: Artificial Sequence
<220> FEATURE:
<223> OTHER INFORMATION: Synthetic Construct

<400> SEQUENCE: 48
aaaaacacgt acaa                                                     14

<210> SEQ ID NO 49
<211> LENGTH: 14
<212> TYPE: DNA
<213> ORGANISM: Artificial Sequence
<220> FEATURE:
<223> OTHER INFORMATION: Synthetic Construct

<400> SEQUENCE: 49
atcgagtcgg ttgt                                                     14

<210> SEQ ID NO 50
<211> LENGTH: 14
<212> TYPE: DNA
<213> ORGANISM: Artificial Sequence
<220> FEATURE:
<223> OTHER INFORMATION: Synthetic Construct

<400> SEQUENCE: 50
aaaaacacgt acaa                                                     14

<210> SEQ ID NO 51
<211> LENGTH: 14
<212> TYPE: DNA
<213> ORGANISM: Artificial Sequence
<220> FEATURE:
<223> OTHER INFORMATION: Synthetic Construct

<400> SEQUENCE: 51
```
tcgagtcggt tgtg                                                    14

<210> SEQ ID NO 52
<211> LENGTH: 14
<212> TYPE: DNA
<213> ORGANISM: Artificial Sequence
<220> FEATURE:
<223> OTHER INFORMATION: Synthetic Construct

<400> SEQUENCE: 52
aaaaacacgt acaa                                                    14

<210> SEQ ID NO 53
<211> LENGTH: 14
<212> TYPE: DNA
<213> ORGANISM: Artificial Sequence
<220> FEATURE:
<223> OTHER INFORMATION: Synthetic Construct

<400> SEQUENCE: 53
cgagtcggtt gtgg                                                    14

<210> SEQ ID NO 54
<211> LENGTH: 14
<212> TYPE: DNA
<213> ORGANISM: Artificial Sequence
<220> FEATURE:
<223> OTHER INFORMATION: Synthetic Construct

<400> SEQUENCE: 54
aaaaacacgt acaa                                                    14

<210> SEQ ID NO 55
<211> LENGTH: 14
<212> TYPE: DNA
<213> ORGANISM: Artificial Sequence
<220> FEATURE:
<223> OTHER INFORMATION: Synthetic Construct

<400> SEQUENCE: 55
gagtcggttg tggg                                                    14

<210> SEQ ID NO 56
<211> LENGTH: 14
<212> TYPE: DNA
<213> ORGANISM: Artificial Sequence
<220> FEATURE:
<223> OTHER INFORMATION: Synthetic Construct

<400> SEQUENCE: 56
aaaaacacgt acaa                                                    14

<210> SEQ ID NO 57
<211> LENGTH: 14
<212> TYPE: DNA
<213> ORGANISM: Artificial Sequence
<220> FEATURE:
<223> OTHER INFORMATION: Synthetic Construct

<400> SEQUENCE: 57
agtcggttgt gggg                                                    14

<210> SEQ ID NO 58
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 58
aaaaacacgt acaa                                                          14

<210> SEQ ID NO 59
<211> LENGTH: 14
<212> TYPE: DNA
<213> ORGANISM: Artificial Sequence
<220> FEATURE:
<223> OTHER INFORMATION: Synthetic Construct

<400> SEQUENCE: 59
gtcggttgtg gggt                                                          14

<210> SEQ ID NO 60
<211> LENGTH: 14
<212> TYPE: DNA
<213> ORGANISM: Artificial Sequence
<220> FEATURE:
<223> OTHER INFORMATION: Synthetic Construct

<400> SEQUENCE: 60
aaaaacacgt acaa                                                          14

<210> SEQ ID NO 61
<211> LENGTH: 14
<212> TYPE: DNA
<213> ORGANISM: Artificial Sequence
<220> FEATURE:
<223> OTHER INFORMATION: Synthetic Construct

<400> SEQUENCE: 61
tcggttgtgg ggtg                                                          14

<210> SEQ ID NO 62
<211> LENGTH: 14
<212> TYPE: DNA
<213> ORGANISM: Artificial Sequence
<220> FEATURE:
<223> OTHER INFORMATION: Synthetic Construct

<400> SEQUENCE: 62
aaaaacacgt acaa                                                          14

<210> SEQ ID NO 63
<211> LENGTH: 14
<212> TYPE: DNA
<213> ORGANISM: Artificial Sequence
<220> FEATURE:
<223> OTHER INFORMATION: Synthetic Construct

<400> SEQUENCE: 63
cggttgtggg gtgt                                                          14

<210> SEQ ID NO 64
<211> LENGTH: 14
<212> TYPE: DNA
<213> ORGANISM: Artificial Sequence
<220> FEATURE:
<223> OTHER INFORMATION: Synthetic Construct

<400> SEQUENCE: 64
aaaaacacgt acaa                                                          14
```

```
<210> SEQ ID NO 65
<211> LENGTH: 14
<212> TYPE: DNA
<213> ORGANISM: Artificial Sequence
<220> FEATURE:
<223> OTHER INFORMATION: Synthetic Construct

<400> SEQUENCE: 65
ggttgtgggg tgtt                                                          14

<210> SEQ ID NO 66
<211> LENGTH: 14
<212> TYPE: DNA
<213> ORGANISM: Artificial Sequence
<220> FEATURE:
<223> OTHER INFORMATION: Synthetic Construct

<400> SEQUENCE: 66
aaaaacacgt acaa                                                          14

<210> SEQ ID NO 67
<211> LENGTH: 14
<212> TYPE: DNA
<213> ORGANISM: Artificial Sequence
<220> FEATURE:
<223> OTHER INFORMATION: Synthetic Construct

<400> SEQUENCE: 67
gttgtggggt gttg                                                          14

<210> SEQ ID NO 68
<211> LENGTH: 14
<212> TYPE: DNA
<213> ORGANISM: Artificial Sequence
<220> FEATURE:
<223> OTHER INFORMATION: Synthetic Construct

<400> SEQUENCE: 68
acccgttttc ctcc                                                          14

<210> SEQ ID NO 69
<211> LENGTH: 28
<212> TYPE: DNA
<213> ORGANISM: Artificial Sequence
<220> FEATURE:
<223> OTHER INFORMATION: Synthetic Construct

<400> SEQUENCE: 69 tttttggga ggagatttat agtgaagg                                            28

<210> SEQ ID NO 70
<211> LENGTH: 14
<212> TYPE: DNA
<213> ORGANISM: Artificial Sequence
<220> FEATURE:
<223> OTHER INFORMATION: Synthetic Construct

<400> SEQUENCE: 70
ttgtggggtg ttga                                                          14

<210> SEQ ID NO 71
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 71
acccgttttc ctcc                                                                 14

<210> SEQ ID NO 72
<211> LENGTH: 14
<212> TYPE: DNA
<213> ORGANISM: Artificial Sequence
<220> FEATURE:
<223> OTHER INFORMATION: Synthetic Construct

<400> SEQUENCE: 72
tgtggggtgt tgag                                                                 14

<210> SEQ ID NO 73
<211> LENGTH: 14
<212> TYPE: DNA
<213> ORGANISM: Artificial Sequence
<220> FEATURE:
<223> OTHER INFORMATION: Synthetic Construct

<400> SEQUENCE: 73
acccgttttc ctcc                                                                 14

<210> SEQ ID NO 74
<211> LENGTH: 14
<212> TYPE: DNA
<213> ORGANISM: Artificial Sequence
<220> FEATURE:
<223> OTHER INFORMATION: Synthetic Construct

<400> SEQUENCE: 74
gtggggtgtt gaga                                                                 14

<210> SEQ ID NO 75
<211> LENGTH: 14
<212> TYPE: DNA
<213> ORGANISM: Artificial Sequence
<220> FEATURE:
<223> OTHER INFORMATION: Synthetic Construct

<400> SEQUENCE: 75
acccgttttc ctcc                                                                 14

<210> SEQ ID NO 76
<211> LENGTH: 14
<212> TYPE: DNA
<213> ORGANISM: Artificial Sequence
<220> FEATURE:
<223> OTHER INFORMATION: Synthetic Construct

<400> SEQUENCE: 76
tggggtgttg agat                                                                 14

<210> SEQ ID NO 77
<211> LENGTH: 14
<212> TYPE: DNA
<213> ORGANISM: Artificial Sequence
<220> FEATURE:
<223> OTHER INFORMATION: Synthetic Construct

<400> SEQUENCE: 77
acccgttttc ctcc                                                                 14

<210> SEQ ID NO 78

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 78
ggggtgttga gata                                                           14

<210> SEQ ID NO 79
<211> LENGTH: 14
<212> TYPE: DNA
<213> ORGANISM: Artificial Sequence
<220> FEATURE:
<223> OTHER INFORMATION: Synthetic Construct

<400> SEQUENCE: 79
acccgttttc ctcc                                                           14

<210> SEQ ID NO 80
<211> LENGTH: 14
<212> TYPE: DNA
<213> ORGANISM: Artificial Sequence
<220> FEATURE:
<223> OTHER INFORMATION: Synthetic Construct

<400> SEQUENCE: 80
gggtgttgag ataa                                                           14

<210> SEQ ID NO 81
<211> LENGTH: 14
<212> TYPE: DNA
<213> ORGANISM: Artificial Sequence
<220> FEATURE:
<223> OTHER INFORMATION: Synthetic Construct

<400> SEQUENCE: 81
acccgttttc ctcc                                                           14

<210> SEQ ID NO 82
<211> LENGTH: 14
<212> TYPE: DNA
<213> ORGANISM: Artificial Sequence
<220> FEATURE:
<223> OTHER INFORMATION: Synthetic Construct

<400> SEQUENCE: 82
ggtgttgaga taac                                                           14

<210> SEQ ID NO 83
<211> LENGTH: 14
<212> TYPE: DNA
<213> ORGANISM: Artificial Sequence
<220> FEATURE:
<223> OTHER INFORMATION: Synthetic Construct

<400> SEQUENCE: 83
acccgttttc ctcc                                                           14

<210> SEQ ID NO 84
<211> LENGTH: 14
<212> TYPE: DNA
<213> ORGANISM: Artificial Sequence
<220> FEATURE:
<223> OTHER INFORMATION: Synthetic Construct

<400> SEQUENCE: 84
```

-continued gtgttgagat aacg                                                        14

<210> SEQ ID NO 85
<211> LENGTH: 14
<212> TYPE: DNA
<213> ORGANISM: Artificial Sequence
<220> FEATURE:
<223> OTHER INFORMATION: Synthetic Construct

<400> SEQUENCE: 85
acccgttttc ctcc                                                        14

<210> SEQ ID NO 86
<211> LENGTH: 14
<212> TYPE: DNA
<213> ORGANISM: Artificial Sequence
<220> FEATURE:
<223> OTHER INFORMATION: Synthetic Construct

<400> SEQUENCE: 86
tgttgagata acgt                                                        14

<210> SEQ ID NO 87
<211> LENGTH: 14
<212> TYPE: DNA
<213> ORGANISM: Artificial Sequence
<220> FEATURE:
<223> OTHER INFORMATION: Synthetic Construct

<400> SEQUENCE: 87
acccgttttc ctcc                                                        14

<210> SEQ ID NO 88
<211> LENGTH: 14
<212> TYPE: DNA
<213> ORGANISM: Artificial Sequence
<220> FEATURE:
<223> OTHER INFORMATION: Synthetic Construct

<400> SEQUENCE: 88
gttgagataa cgtg                                                        14

<210> SEQ ID NO 89
<211> LENGTH: 14
<212> TYPE: DNA
<213> ORGANISM: Artificial Sequence
<220> FEATURE:
<223> OTHER INFORMATION: Synthetic Construct

<400> SEQUENCE: 89
acccgttttc ctcc                                                        14

<210> SEQ ID NO 90
<211> LENGTH: 14
<212> TYPE: DNA
<213> ORGANISM: Artificial Sequence
<220> FEATURE:
<223> OTHER INFORMATION: Synthetic Construct

<400> SEQUENCE: 90
ttgagataac gtgt                                                        14

<210> SEQ ID NO 91
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 91
acccgttttc ctcc                                                     14

<210> SEQ ID NO 92
<211> LENGTH: 14
<212> TYPE: DNA
<213> ORGANISM: Artificial Sequence
<220> FEATURE:
<223> OTHER INFORMATION: Synthetic Construct

<400> SEQUENCE: 92
tgagataacg tgtg                                                     14

<210> SEQ ID NO 93
<211> LENGTH: 14
<212> TYPE: DNA
<213> ORGANISM: Artificial Sequence
<220> FEATURE:
<223> OTHER INFORMATION: Synthetic Construct

<400> SEQUENCE: 93
acccgttttc ctcc                                                     14

<210> SEQ ID NO 94
<211> LENGTH: 14
<212> TYPE: DNA
<213> ORGANISM: Artificial Sequence
<220> FEATURE:
<223> OTHER INFORMATION: Synthetic Construct

<400> SEQUENCE: 94
gagataacgt gtgt                                                     14

<210> SEQ ID NO 95
<211> LENGTH: 14
<212> TYPE: DNA
<213> ORGANISM: Artificial Sequence
<220> FEATURE:
<223> OTHER INFORMATION: Synthetic Construct

<400> SEQUENCE: 95
acccgttttc ctcc                                                     14

<210> SEQ ID NO 96
<211> LENGTH: 14
<212> TYPE: DNA
<213> ORGANISM: Artificial Sequence
<220> FEATURE:
<223> OTHER INFORMATION: Synthetic Construct

<400> SEQUENCE: 96
agataacgtg tgtg                                                     14

<210> SEQ ID NO 97
<211> LENGTH: 14
<212> TYPE: DNA
<213> ORGANISM: Artificial Sequence
<220> FEATURE:
<223> OTHER INFORMATION: Synthetic Construct

<400> SEQUENCE: 97
acccgttttc ctcc                                                     14
```

```
<210> SEQ ID NO 98
<211> LENGTH: 14
<212> TYPE: DNA
<213> ORGANISM: Artificial Sequence
<220> FEATURE:
<223> OTHER INFORMATION: Synthetic Construct

<400> SEQUENCE: 98
gataacgtgt gtgt                                                         14

<210> SEQ ID NO 99
<211> LENGTH: 14
<212> TYPE: DNA
<213> ORGANISM: Artificial Sequence
<220> FEATURE:
<223> OTHER INFORMATION: Synthetic Construct

<400> SEQUENCE: 99
acccgttttc ctcc                                                         14

<210> SEQ ID NO 100
<211> LENGTH: 14
<212> TYPE: DNA
<213> ORGANISM: Artificial Sequence
<220> FEATURE:
<223> OTHER INFORMATION: Synthetic Construct

<400> SEQUENCE: 100
ataacgtgtg tgtt                                                         14

<210> SEQ ID NO 101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 101
acccgttttc ctcc                                                         14

<210> SEQ ID NO 102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 102
taacgtgtgt gttt                                                         14

<210> SEQ ID NO 103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 103
acccgttttc ctcc                                                         14

<210> SEQ ID NO 104
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 104
aacgtgtgtg tttg                                                              14

<210> SEQ ID NO 105
<211> LENGTH: 14
<212> TYPE: DNA
<213> ORGANISM: Artificial Sequence
<220> FEATURE:
<223> OTHER INFORMATION: Synthetic Construct

<400> SEQUENCE: 105
acccgttttc ctcc                                                              14

<210> SEQ ID NO 106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 106
acgtgtgtgt ttgt                                                              14

<210> SEQ ID NO 107
<211> LENGTH: 14
<212> TYPE: DNA
<213> ORGANISM: Artificial Sequence
<220> FEATURE:
<223> OTHER INFORMATION: Synthetic Construct

<400> SEQUENCE: 107
acccgttttc ctcc                                                              14

<210> SEQ ID NO 108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 108
cgtgtgtgtt tgta                                                              14

<210> SEQ ID NO 109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 109
acccgttttc ctcc                                                              14

<210> SEQ ID NO 110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 110
gtgtgtgttt gtaa                                                              14

```
<210> SEQ ID NO 111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 111
acccgttttc ctcc                                                       14

<210> SEQ ID NO 112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 112
tgtgtgtttg taat                                                       14

<210> SEQ ID NO 113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 113
acccgttttc ctcc                                                       14

<210> SEQ ID NO 114
<211> LENGTH: 14
<212> TYPE: DNA
<213> ORGANISM: Artificial Sequence
<220> FEATURE:
<223> OTHER INFORMATION: Synthetic Construct

<400> SEQUENCE: 114
gtgtgtttgt aatg                                                       14

<210> SEQ ID NO 115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 115
acccgttttc ctcc                                                       14

<210> SEQ ID NO 116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 116
tgtgtttgta atgt                                                       14

<210> SEQ ID NO 117
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 117
acccgttttc ctcc                                                         14

<210> SEQ ID NO 118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 118
gtgtttgtaa tgtg                                                         14

<210> SEQ ID NO 119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 119
acccgttttc ctcc                                                         14

<210> SEQ ID NO 120
<211> LENGTH: 14
<212> TYPE: DNA
<213> ORGANISM: Artificial Sequence
<220> FEATURE:
<223> OTHER INFORMATION: Synthetic Construct

<400> SEQUENCE: 120
tgtttgtaat gtgt                                                         14

<210> SEQ ID NO 121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 121
acccgttttc ctcc                                                         14

<210> SEQ ID NO 122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 122
gtttgtaatg tgta                                                         14

<210> SEQ ID NO 123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 123
acccgttttc ctcc                                                         14

<210> SEQ ID NO 124
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 124
tttgtaatgt gtat                                                        14

<210> SEQ ID NO 125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 125
acccgttttc ctcc                                                        14

<210> SEQ ID NO 126
<211> LENGTH: 14
<212> TYPE: DNA
<213> ORGANISM: Artificial Sequence
<220> FEATURE:
<223> OTHER INFORMATION: Synthetic Construct

<400> SEQUENCE: 126
ttgtaatgtg tatt                                                        14

<210> SEQ ID NO 127
<211> LENGTH: 14
<212> TYPE: DNA
<213> ORGANISM: Artificial Sequence
<220> FEATURE:
<223> OTHER INFORMATION: Synthetic Construct

<400> SEQUENCE: 127
acccgttttc ctcc                                                        14

<210> SEQ ID NO 128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 128
tgtaatgtgt attt                                                        14

<210> SEQ ID NO 129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 129
acccgttttc ctcc                                                        14

<210> SEQ ID NO 130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 130
```
gtaatgtgta ttta                                                          14

<210> SEQ ID NO 131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 131
acccgttttc ctcc                                                          14

<210> SEQ ID NO 132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 132
taatgtgtat ttaa                                                          14

<210> SEQ ID NO 133
<211> LENGTH: 14
<212> TYPE: DNA
<213> ORGANISM: Artificial Sequence
<220> FEATURE:
<223> OTHER INFORMATION: Synthetic Construct

<400> SEQUENCE: 133
acccgttttc ctcc                                                          14

<210> SEQ ID NO 134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 134
aatgtgtatt taat                                                          14

<210> SEQ ID NO 135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 135
acccgttttc ctcc                                                          14

<210> SEQ ID NO 136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 136
atgtgtattt aatg                                                          14

<210> SEQ ID NO 137
<211> LENGTH: 14
<212> TYPE: DNA
<213> ORGANISM: Artificial Sequence -continued
<220> FEATURE:
<223> OTHER INFORMATION: Synthetic Construct

<400> SEQUENCE: 137
acccgttttc ctcc                                                             14

<210> SEQ ID NO 138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 138
tgtgtattta atgt                                                             14

<210> SEQ ID NO 139
<211> LENGTH: 14
<212> TYPE: DNA
<213> ORGANISM: Artificial Sequence
<220> FEATURE:
<223> OTHER INFORMATION: Synthetic Construct

<400> SEQUENCE: 139
acccgttttc ctcc                                                             14

<210> SEQ ID NO 140
<211> LENGTH: 14
<212> TYPE: DNA
<213> ORGANISM: Artificial Sequence
<220> FEATURE:
<223> OTHER INFORMATION: Synthetic Construct

<400> SEQUENCE: 140
gtgtatttaa tgta                                                             14

<210> SEQ ID NO 141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 141
acccgttttc ctcc                                                             14

<210> SEQ ID NO 142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 142
tgtatttaat gtat                                                             14

<210> SEQ ID NO 143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 143
acccgttttc ctcc                                                             14

```
<210> SEQ ID NO 144
<211> LENGTH: 14
<212> TYPE: DNA
<213> ORGANISM: Artificial Sequence
<220> FEATURE:
<223> OTHER INFORMATION: Synthetic Construct

<400> SEQUENCE: 144
gtatttaatg tatt                                                        14

<210> SEQ ID NO 145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 145
acccgttttc ctcc                                                        14

<210> SEQ ID NO 146
<211> LENGTH: 14
<212> TYPE: DNA
<213> ORGANISM: Artificial Sequence
<220> FEATURE:
<223> OTHER INFORMATION: Synthetic Construct

<400> SEQUENCE: 146
tatttaatgt attt                                                        14

<210> SEQ ID NO 147
<211> LENGTH: 14
<212> TYPE: DNA
<213> ORGANISM: Artificial Sequence
<220> FEATURE:
<223> OTHER INFORMATION: Synthetic Construct

<400> SEQUENCE: 147
acccgttttc ctcc                                                        14

<210> SEQ ID NO 148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 148
atttaatgta ttta                                                        14

<210> SEQ ID NO 149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 149
acccgttttc ctcc                                                        14

<210> SEQ ID NO 150
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 150
tttaatgtat ttag                                                         14

<210> SEQ ID NO 151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 151
acccgttttc ctcc                                                         14

<210> SEQ ID NO 152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 152
ttaatgtatt tagg                                                         14

<210> SEQ ID NO 153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 153
acccgttttc ctcc                                                         14

<210> SEQ ID NO 154
<211> LENGTH: 14
<212> TYPE: DNA
<213> ORGANISM: Artificial Sequence
<220> FEATURE:
<223> OTHER INFORMATION: Synthetic Construct

<400> SEQUENCE: 154
taatgtattt agga                                                         14

<210> SEQ ID NO 155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 155
acccgttttc ctcc                                                         14

<210> SEQ ID NO 156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 156
aatgtattta ggag                                                         14

<210> SEQ ID NO 157

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 157
acccgttttc ctcc                                                         14

<210> SEQ ID NO 158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 158
atgtatttag gaga                                                         14

<210> SEQ ID NO 159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 159
acccgttttc ctcc                                                         14

<210> SEQ ID NO 160
<211> LENGTH: 14
<212> TYPE: DNA
<213> ORGANISM: Artificial Sequence
<220> FEATURE:
<223> OTHER INFORMATION: Synthetic Construct

<400> SEQUENCE: 160
tgtatttagg agag                                                         14

<210> SEQ ID NO 161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 161
acccgttttc ctcc                                                         14

<210> SEQ ID NO 162
<211> LENGTH: 14
<212> TYPE: DNA
<213> ORGANISM: Artificial Sequence
<220> FEATURE:
<223> OTHER INFORMATION: Synthetic Construct

<400> SEQUENCE: 162
gtatttagga gaga                                                         14

<210> SEQ ID NO 163
<211> LENGTH: 14
<212> TYPE: DNA
<213> ORGANISM: Artificial Sequence
<220> FEATURE:
<223> OTHER INFORMATION: Synthetic Construct

<400> SEQUENCE: 163
```

```
acccgttttc ctcc                                                    14

<210> SEQ ID NO 164
<211> LENGTH: 14
<212> TYPE: DNA
<213> ORGANISM: Artificial Sequence
<220> FEATURE:
<223> OTHER INFORMATION: Synthetic Construct

<400> SEQUENCE: 164
tatttaggag agag                                                    14

<210> SEQ ID NO 165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 165
acccgttttc ctcc                                                    14

<210> SEQ ID NO 166
<211> LENGTH: 14
<212> TYPE: DNA
<213> ORGANISM: Artificial Sequence
<220> FEATURE:
<223> OTHER INFORMATION: Synthetic Construct

<400> SEQUENCE: 166
atttaggaga gaga                                                    14

<210> SEQ ID NO 167
<211> LENGTH: 14
<212> TYPE: DNA
<213> ORGANISM: Artificial Sequence
<220> FEATURE:
<223> OTHER INFORMATION: Synthetic Construct

<400> SEQUENCE: 167
acccgttttc ctcc                                                    14

<210> SEQ ID NO 168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 168
tttaggagag agat                                                    14

<210> SEQ ID NO 169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 169
acccgttttc ctcc                                                    14

<210> SEQ ID NO 170
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 170
ttaggagaga gatt                                                         14

<210> SEQ ID NO 171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 171
acccgttttc ctcc                                                         14

<210> SEQ ID NO 172
<211> LENGTH: 14
<212> TYPE: DNA
<213> ORGANISM: Artificial Sequence
<220> FEATURE:
<223> OTHER INFORMATION: Synthetic Construct

<400> SEQUENCE: 172
taggagagag attt                                                         14

<210> SEQ ID NO 173
<211> LENGTH: 14
<212> TYPE: DNA
<213> ORGANISM: Artificial Sequence
<220> FEATURE:
<223> OTHER INFORMATION: Synthetic Construct

<400> SEQUENCE: 173
acccgttttc ctcc                                                         14

<210> SEQ ID NO 174
<211> LENGTH: 14
<212> TYPE: DNA
<213> ORGANISM: Artificial Sequence
<220> FEATURE:
<223> OTHER INFORMATION: Synthetic Construct

<400> SEQUENCE: 174
aggagagaga tttt                                                         14

<210> SEQ ID NO 175
<211> LENGTH: 14
<212> TYPE: DNA
<213> ORGANISM: Artificial Sequence
<220> FEATURE:
<223> OTHER INFORMATION: Synthetic Construct

<400> SEQUENCE: 175
acccgttttc ctcc                                                         14

<210> SEQ ID NO 176
<211> LENGTH: 14
<212> TYPE: DNA
<213> ORGANISM: Artificial Sequence
<220> FEATURE:
<223> OTHER INFORMATION: Synthetic Construct

<400> SEQUENCE: 176
ggagagagat tttg                                                         14
```

```
<210> SEQ ID NO 177
<211> LENGTH: 14
<212> TYPE: DNA
<213> ORGANISM: Artificial Sequence
<220> FEATURE:
<223> OTHER INFORMATION: Synthetic Construct

<400> SEQUENCE: 177
acccgttttc ctcc                                                        14

<210> SEQ ID NO 178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 178
gagagagatt ttgt                                                        14

<210> SEQ ID NO 179
<211> LENGTH: 14
<212> TYPE: DNA
<213> ORGANISM: Artificial Sequence
<220> FEATURE:
<223> OTHER INFORMATION: Synthetic Construct

<400> SEQUENCE: 179
acccgttttc ctcc                                                        14

<210> SEQ ID NO 180
<211> LENGTH: 14
<212> TYPE: DNA
<213> ORGANISM: Artificial Sequence
<220> FEATURE:
<223> OTHER INFORMATION: Synthetic Construct

<400> SEQUENCE: 180
agagagattt tgta                                                        14

<210> SEQ ID NO 181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 181
acccgttttc ctcc                                                        14

<210> SEQ ID NO 182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 182
gagagatttt gtac                                                        14

<210> SEQ ID NO 183
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 183
acccgttttc ctcc                                                    14

<210> SEQ ID NO 184
<211> LENGTH: 14
<212> TYPE: DNA
<213> ORGANISM: Artificial Sequence
<220> FEATURE:
<223> OTHER INFORMATION: Synthetic Construct

<400> SEQUENCE: 184
agagattttg tacg                                                    14

<210> SEQ ID NO 185
<211> LENGTH: 14
<212> TYPE: DNA
<213> ORGANISM: Artificial Sequence
<220> FEATURE:
<223> OTHER INFORMATION: Synthetic Construct

<400> SEQUENCE: 185
acccgttttc ctcc                                                    14

<210> SEQ ID NO 186
<211> LENGTH: 14
<212> TYPE: DNA
<213> ORGANISM: Artificial Sequence
<220> FEATURE:
<223> OTHER INFORMATION: Synthetic Construct

<400> SEQUENCE: 186
gagattttgt acgt                                                    14

<210> SEQ ID NO 187
<211> LENGTH: 14
<212> TYPE: DNA
<213> ORGANISM: Artificial Sequence
<220> FEATURE:
<223> OTHER INFORMATION: Synthetic Construct

<400> SEQUENCE: 187
acccgttttc ctcc                                                    14

<210> SEQ ID NO 188
<211> LENGTH: 14
<212> TYPE: DNA
<213> ORGANISM: Artificial Sequence
<220> FEATURE:
<223> OTHER INFORMATION: Synthetic Construct

<400> SEQUENCE: 188 agatttgta cgtg                                                     14

<210> SEQ ID NO 189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 189
acccgttttc ctcc                                                    14

```
<210> SEQ ID NO 190
<211> LENGTH: 14
<212> TYPE: DNA
<213> ORGANISM: Artificial Sequence
<220> FEATURE:
<223> OTHER INFORMATION: Synthetic Construct

<400> SEQUENCE: 190
gattttgtac gtgt                                                        14

<210> SEQ ID NO 191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 191
acccgttttc ctcc                                                        14

<210> SEQ ID NO 192
<211> LENGTH: 14
<212> TYPE: DNA
<213> ORGANISM: Artificial Sequence
<220> FEATURE:
<223> OTHER INFORMATION: Synthetic Construct

<400> SEQUENCE: 192
attttgtacg tgtt                                                        14

<210> SEQ ID NO 193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 193
acccgttttc ctcc                                                        14

<210> SEQ ID NO 194
<211> LENGTH: 14
<212> TYPE: DNA
<213> ORGANISM: Artificial Sequence
<220> FEATURE:
<223> OTHER INFORMATION: Synthetic Construct

<400> SEQUENCE: 194
ttttgtacgt gttt                                                        14

<210> SEQ ID NO 195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 195
acccgttttc ctcc                                                        14

<210> SEQ ID NO 196
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 196
tttgtacgtg tttt                                                       14

<210> SEQ ID NO 197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 197
acccgttttc ctcc                                                       14

<210> SEQ ID NO 198
<211> LENGTH: 14
<212> TYPE: DNA
<213> ORGANISM: Artificial Sequence
<220> FEATURE:
<223> OTHER INFORMATION: Synthetic Construct

<400> SEQUENCE: 198
ttgtacgtgt tttt                                                       14

<210> SEQ ID NO 199
<211> LENGTH: 14
<212> TYPE: DNA
<213> ORGANISM: Artificial Sequence
<220> FEATURE:
<223> OTHER INFORMATION: Synthetic Construct

<400> SEQUENCE: 199
acccgttttc ctcc                                                       14

<210> SEQ ID NO 200
<211> LENGTH: 14
<212> TYPE: DNA
<213> ORGANISM: Artificial Sequence
<220> FEATURE:
<223> OTHER INFORMATION: Synthetic Construct

<400> SEQUENCE: 200
tgtacgtgtt ttta                                                       14

<210> SEQ ID NO 201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 201
acccgttttc ctcc                                                       14

<210> SEQ ID NO 202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 202
gtacgtgttt ttaa                                                       14

<210> SEQ ID NO 203
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 203
acccgttttc ctcc                                                          14

<210> SEQ ID NO 204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 204
tacgtgtttt taat                                                          14

<210> SEQ ID NO 205
<211> LENGTH: 14
<212> TYPE: DNA
<213> ORGANISM: Artificial Sequence
<220> FEATURE:
<223> OTHER INFORMATION: Synthetic Construct

<400> SEQUENCE: 205
acccgttttc ctcc                                                          14

<210> SEQ ID NO 206
<211> LENGTH: 14
<212> TYPE: DNA
<213> ORGANISM: Artificial Sequence
<220> FEATURE:
<223> OTHER INFORMATION: Synthetic Construct

<400> SEQUENCE: 206
acgtgttttt aatg                                                          14

<210> SEQ ID NO 207
<211> LENGTH: 14
<212> TYPE: DNA
<213> ORGANISM: Artificial Sequence
<220> FEATURE:
<223> OTHER INFORMATION: Synthetic Construct

<400> SEQUENCE: 207
acccgttttc ctcc                                                          14

<210> SEQ ID NO 208
<211> LENGTH: 14
<212> TYPE: DNA
<213> ORGANISM: Artificial Sequence
<220> FEATURE:
<223> OTHER INFORMATION: Synthetic Construct

<400> SEQUENCE: 208
cgtgttttta atga                                                          14

<210> SEQ ID NO 209
<211> LENGTH: 14
<212> TYPE: DNA
<213> ORGANISM: Artificial Sequence
<220> FEATURE:
<223> OTHER INFORMATION: Synthetic Construct

<400> SEQUENCE: 209
```

```
acccgttttc ctcc                                                        14

<210> SEQ ID NO 210
<211> LENGTH: 14
<212> TYPE: DNA
<213> ORGANISM: Artificial Sequence
<220> FEATURE:
<223> OTHER INFORMATION: Synthetic Construct

<400> SEQUENCE: 210
gtgtttttaa tgaa                                                        14

<210> SEQ ID NO 211
<211> LENGTH: 14
<212> TYPE: DNA
<213> ORGANISM: Artificial Sequence
<220> FEATURE:
<223> OTHER INFORMATION: Synthetic Construct

<400> SEQUENCE: 211
tctacgaacg caca                                                        14

<210> SEQ ID NO 212
<211> LENGTH: 24
<212> TYPE: DNA
<213> ORGANISM: Artificial Sequence
<220> FEATURE:
<223> OTHER INFORMATION: Synthetic Construct

<400> SEQUENCE: 212
ggtaggtgga aagagggagg ggtt                                             24

<210> SEQ ID NO 213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 213
tgtttttaat gaaa                                                        14

<210> SEQ ID NO 214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 214
tctacgaacg caca                                                        14

<210> SEQ ID NO 215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 215
gtttttaatg aaag                                                        14

<210> SEQ ID NO 216
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 216
tctacgaacg caca                                                          14

<210> SEQ ID NO 217
<211> LENGTH: 14
<212> TYPE: DNA
<213> ORGANISM: Artificial Sequence
<220> FEATURE:
<223> OTHER INFORMATION: Synthetic Construct

<400> SEQUENCE: 217
tttttaatga aagt                                                          14

<210> SEQ ID NO 218
<211> LENGTH: 14
<212> TYPE: DNA
<213> ORGANISM: Artificial Sequence
<220> FEATURE:
<223> OTHER INFORMATION: Synthetic Construct

<400> SEQUENCE: 218
tctacgaacg caca                                                          14

<210> SEQ ID NO 219
<211> LENGTH: 14
<212> TYPE: DNA
<213> ORGANISM: Artificial Sequence
<220> FEATURE:
<223> OTHER INFORMATION: Synthetic Construct

<400> SEQUENCE: 219
ttttaatgaa agtg                                                          14

<210> SEQ ID NO 220
<211> LENGTH: 14
<212> TYPE: DNA
<213> ORGANISM: Artificial Sequence
<220> FEATURE:
<223> OTHER INFORMATION: Synthetic Construct

<400> SEQUENCE: 220
tctacgaacg caca                                                          14

<210> SEQ ID NO 221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 221
tttaatgaaa gtga                                                          14

<210> SEQ ID NO 222
<211> LENGTH: 14
<212> TYPE: DNA
<213> ORGANISM: Artificial Sequence
<220> FEATURE:
<223> OTHER INFORMATION: Synthetic Construct

<400> SEQUENCE: 222
tctacgaacg caca                                                          14
```

```
<210> SEQ ID NO 223
<211> LENGTH: 14
<212> TYPE: DNA
<213> ORGANISM: Artificial Sequence
<220> FEATURE:
<223> OTHER INFORMATION: Synthetic Construct

<400> SEQUENCE: 223
ttaatgaaag tgaa                                                   14

<210> SEQ ID NO 224
<211> LENGTH: 14
<212> TYPE: DNA
<213> ORGANISM: Artificial Sequence
<220> FEATURE:
<223> OTHER INFORMATION: Synthetic Construct

<400> SEQUENCE: 224
tctacgaacg caca                                                   14

<210> SEQ ID NO 225
<211> LENGTH: 14
<212> TYPE: DNA
<213> ORGANISM: Artificial Sequence
<220> FEATURE:
<223> OTHER INFORMATION: Synthetic Construct

<400> SEQUENCE: 225
taatgaaagt gaaa                                                   14

<210> SEQ ID NO 226
<211> LENGTH: 14
<212> TYPE: DNA
<213> ORGANISM: Artificial Sequence
<220> FEATURE:
<223> OTHER INFORMATION: Synthetic Construct

<400> SEQUENCE: 226
tctacgaacg caca                                                   14

<210> SEQ ID NO 227
<211> LENGTH: 14
<212> TYPE: DNA
<213> ORGANISM: Artificial Sequence
<220> FEATURE:
<223> OTHER INFORMATION: Synthetic Construct

<400> SEQUENCE: 227
aatgaaagtg aaag                                                   14

<210> SEQ ID NO 228
<211> LENGTH: 14
<212> TYPE: DNA
<213> ORGANISM: Artificial Sequence
<220> FEATURE:
<223> OTHER INFORMATION: Synthetic Construct

<400> SEQUENCE: 228
tctacgaacg caca                                                   14

<210> SEQ ID NO 229
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 229
atgaaagtga aagg                                                        14

<210> SEQ ID NO 230
<211> LENGTH: 14
<212> TYPE: DNA
<213> ORGANISM: Artificial Sequence
<220> FEATURE:
<223> OTHER INFORMATION: Synthetic Construct

<400> SEQUENCE: 230
tctacgaacg caca                                                        14

<210> SEQ ID NO 231
<211> LENGTH: 14
<212> TYPE: DNA
<213> ORGANISM: Artificial Sequence
<220> FEATURE:
<223> OTHER INFORMATION: Synthetic Construct

<400> SEQUENCE: 231
tgaaagtgaa aggg                                                        14

<210> SEQ ID NO 232
<211> LENGTH: 14
<212> TYPE: DNA
<213> ORGANISM: Artificial Sequence
<220> FEATURE:
<223> OTHER INFORMATION: Synthetic Construct

<400> SEQUENCE: 232
tctacgaacg caca                                                        14

<210> SEQ ID NO 233
<211> LENGTH: 14
<212> TYPE: DNA
<213> ORGANISM: Artificial Sequence
<220> FEATURE:
<223> OTHER INFORMATION: Synthetic Construct

<400> SEQUENCE: 233
gaaagtgaaa gggg                                                        14

<210> SEQ ID NO 234
<211> LENGTH: 14
<212> TYPE: DNA
<213> ORGANISM: Artificial Sequence
<220> FEATURE:
<223> OTHER INFORMATION: Synthetic Construct

<400> SEQUENCE: 234
tctacgaacg caca                                                        14

<210> SEQ ID NO 235
<211> LENGTH: 14
<212> TYPE: DNA
<213> ORGANISM: Artificial Sequence
<220> FEATURE:
<223> OTHER INFORMATION: Synthetic Construct

<400> SEQUENCE: 235
aaagtgaaag gggg                                                        14

<210> SEQ ID NO 236
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 236
tctacgaacg caca                                                         14

<210> SEQ ID NO 237
<211> LENGTH: 14
<212> TYPE: DNA
<213> ORGANISM: Artificial Sequence
<220> FEATURE:
<223> OTHER INFORMATION: Synthetic Construct

<400> SEQUENCE: 237
aagtgaaagg gggt                                                         14

<210> SEQ ID NO 238
<211> LENGTH: 14
<212> TYPE: DNA
<213> ORGANISM: Artificial Sequence
<220> FEATURE:
<223> OTHER INFORMATION: Synthetic Construct

<400> SEQUENCE: 238
tctacgaacg caca                                                         14

<210> SEQ ID NO 239
<211> LENGTH: 14
<212> TYPE: DNA
<213> ORGANISM: Artificial Sequence
<220> FEATURE:
<223> OTHER INFORMATION: Synthetic Construct

<400> SEQUENCE: 239
agtgaaaggg ggta                                                         14

<210> SEQ ID NO 240
<211> LENGTH: 14
<212> TYPE: DNA
<213> ORGANISM: Artificial Sequence
<220> FEATURE:
<223> OTHER INFORMATION: Synthetic Construct

<400> SEQUENCE: 240
tctacgaacg caca                                                         14

<210> SEQ ID NO 241
<211> LENGTH: 14
<212> TYPE: DNA
<213> ORGANISM: Artificial Sequence
<220> FEATURE:
<223> OTHER INFORMATION: Synthetic Construct

<400> SEQUENCE: 241
gtgaaagggg gtag                                                         14

<210> SEQ ID NO 242
<211> LENGTH: 14
<212> TYPE: DNA
<213> ORGANISM: Artificial Sequence
<220> FEATURE:
<223> OTHER INFORMATION: Synthetic Construct

<400> SEQUENCE: 242
```

```
tctacgaacg caca                                                         14

<210> SEQ ID NO 243
<211> LENGTH: 14
<212> TYPE: DNA
<213> ORGANISM: Artificial Sequence
<220> FEATURE:
<223> OTHER INFORMATION: Synthetic Construct

<400> SEQUENCE: 243
tgaaaggggg tagg                                                         14

<210> SEQ ID NO 244
<211> LENGTH: 14
<212> TYPE: DNA
<213> ORGANISM: Artificial Sequence
<220> FEATURE:
<223> OTHER INFORMATION: Synthetic Construct

<400> SEQUENCE: 244
tctacgaacg caca                                                         14

<210> SEQ ID NO 245
<211> LENGTH: 14
<212> TYPE: DNA
<213> ORGANISM: Artificial Sequence
<220> FEATURE:
<223> OTHER INFORMATION: Synthetic Construct

<400> SEQUENCE: 245 gaaaggggt aggg                                                          14

<210> SEQ ID NO 246
<211> LENGTH: 14
<212> TYPE: DNA
<213> ORGANISM: Artificial Sequence
<220> FEATURE:
<223> OTHER INFORMATION: Synthetic Construct

<400> SEQUENCE: 246
tctacgaacg caca                                                         14

<210> SEQ ID NO 247
<211> LENGTH: 14
<212> TYPE: DNA
<213> ORGANISM: Artificial Sequence
<220> FEATURE:
<223> OTHER INFORMATION: Synthetic Construct

<400> SEQUENCE: 247 aaaggggta gggt                                                          14

<210> SEQ ID NO 248
<211> LENGTH: 14
<212> TYPE: DNA
<213> ORGANISM: Artificial Sequence
<220> FEATURE:
<223> OTHER INFORMATION: Synthetic Construct

<400> SEQUENCE: 248
tctacgaacg caca                                                         14

<210> SEQ ID NO 249
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 249 aaggggtag ggtg                                                        14

<210> SEQ ID NO 250
<211> LENGTH: 14
<212> TYPE: DNA
<213> ORGANISM: Artificial Sequence
<220> FEATURE:
<223> OTHER INFORMATION: Synthetic Construct

<400> SEQUENCE: 250
tctacgaacg caca                                                       14

<210> SEQ ID NO 251
<211> LENGTH: 14
<212> TYPE: DNA
<213> ORGANISM: Artificial Sequence
<220> FEATURE:
<223> OTHER INFORMATION: Synthetic Construct

<400> SEQUENCE: 251 aggggtagg gtgg                                                        14

<210> SEQ ID NO 252
<211> LENGTH: 14
<212> TYPE: DNA
<213> ORGANISM: Artificial Sequence
<220> FEATURE:
<223> OTHER INFORMATION: Synthetic Construct

<400> SEQUENCE: 252
tctacgaacg caca                                                       14

<210> SEQ ID NO 253
<211> LENGTH: 14
<212> TYPE: DNA
<213> ORGANISM: Artificial Sequence
<220> FEATURE:
<223> OTHER INFORMATION: Synthetic Construct

<400> SEQUENCE: 253
gggggtaggg tggg                                                       14

<210> SEQ ID NO 254
<211> LENGTH: 14
<212> TYPE: DNA
<213> ORGANISM: Artificial Sequence
<220> FEATURE:
<223> OTHER INFORMATION: Synthetic Construct

<400> SEQUENCE: 254
tctacgaacg caca                                                       14

<210> SEQ ID NO 255
<211> LENGTH: 14
<212> TYPE: DNA
<213> ORGANISM: Artificial Sequence
<220> FEATURE:
<223> OTHER INFORMATION: Synthetic Construct

<400> SEQUENCE: 255
ggggtagggt gggg                                                       14
```

<210> SEQ ID NO 256
<211> LENGTH: 14
<212> TYPE: DNA
<213> ORGANISM: Artificial Sequence
<220> FEATURE:
<223> OTHER INFORMATION: Synthetic Construct

<400> SEQUENCE: 256
tctacgaacg caca                                                         14

<210> SEQ ID NO 257
<211> LENGTH: 14
<212> TYPE: DNA
<213> ORGANISM: Artificial Sequence
<220> FEATURE:
<223> OTHER INFORMATION: Synthetic Construct

<400> SEQUENCE: 257
gggtagggtg gggg                                                         14

<210> SEQ ID NO 258
<211> LENGTH: 14
<212> TYPE: DNA
<213> ORGANISM: Artificial Sequence
<220> FEATURE:
<223> OTHER INFORMATION: Synthetic Construct

<400> SEQUENCE: 258
tctacgaacg caca                                                         14

<210> SEQ ID NO 259
<211> LENGTH: 14
<212> TYPE: DNA
<213> ORGANISM: Artificial Sequence
<220> FEATURE:
<223> OTHER INFORMATION: Synthetic Construct

<400> SEQUENCE: 259
ggtagggtgg gggt                                                         14

<210> SEQ ID NO 260
<211> LENGTH: 14
<212> TYPE: DNA
<213> ORGANISM: Artificial Sequence
<220> FEATURE:
<223> OTHER INFORMATION: Synthetic Construct

<400> SEQUENCE: 260
tctacgaacg caca                                                         14

<210> SEQ ID NO 261
<211> LENGTH: 14
<212> TYPE: DNA
<213> ORGANISM: Artificial Sequence
<220> FEATURE:
<223> OTHER INFORMATION: Synthetic Construct

<400> SEQUENCE: 261
gtagggtggg ggtt                                                         14

<210> SEQ ID NO 262
<211> LENGTH: 14
<212> TYPE: DNA
<213> ORGANISM: Artificial Sequence
<220> FEATURE:

<223> OTHER INFORMATION: Synthetic Construct

<400> SEQUENCE: 262
tctacgaacg caca                                                              14

<210> SEQ ID NO 263
<211> LENGTH: 14
<212> TYPE: DNA
<213> ORGANISM: Artificial Sequence
<220> FEATURE:
<223> OTHER INFORMATION: Synthetic Construct

<400> SEQUENCE: 263
tagggtgggg gttt                                                              14

<210> SEQ ID NO 264
<211> LENGTH: 14
<212> TYPE: DNA
<213> ORGANISM: Artificial Sequence
<220> FEATURE:
<223> OTHER INFORMATION: Synthetic Construct

<400> SEQUENCE: 264
tctacgaacg caca                                                              14

<210> SEQ ID NO 265
<211> LENGTH: 14
<212> TYPE: DNA
<213> ORGANISM: Artificial Sequence
<220> FEATURE:
<223> OTHER INFORMATION: Synthetic Construct

<400> SEQUENCE: 265
agggtggggg tttt                                                              14

<210> SEQ ID NO 266
<211> LENGTH: 14
<212> TYPE: DNA
<213> ORGANISM: Artificial Sequence
<220> FEATURE:
<223> OTHER INFORMATION: Synthetic Construct

<400> SEQUENCE: 266
tctacgaacg caca                                                              14

<210> SEQ ID NO 267
<211> LENGTH: 14
<212> TYPE: DNA
<213> ORGANISM: Artificial Sequence
<220> FEATURE:
<223> OTHER INFORMATION: Synthetic Construct

<400> SEQUENCE: 267
gggtgggggt tttt                                                              14

<210> SEQ ID NO 268
<211> LENGTH: 14
<212> TYPE: DNA
<213> ORGANISM: Artificial Sequence
<220> FEATURE:
<223> OTHER INFORMATION: Synthetic Construct

<400> SEQUENCE: 268
tctacgaacg caca                                                              14

```
<210> SEQ ID NO 269
<211> LENGTH: 14
<212> TYPE: DNA
<213> ORGANISM: Artificial Sequence
<220> FEATURE:
<223> OTHER INFORMATION: Synthetic Construct

<400> SEQUENCE: 269
ggtgggggtt tttg                                                      14

<210> SEQ ID NO 270
<211> LENGTH: 14
<212> TYPE: DNA
<213> ORGANISM: Artificial Sequence
<220> FEATURE:
<223> OTHER INFORMATION: Synthetic Construct

<400> SEQUENCE: 270
tctacgaacg caca                                                      14

<210> SEQ ID NO 271
<211> LENGTH: 14
<212> TYPE: DNA
<213> ORGANISM: Artificial Sequence
<220> FEATURE:
<223> OTHER INFORMATION: Synthetic Construct

<400> SEQUENCE: 271
gtgggggttt ttgg                                                      14

<210> SEQ ID NO 272
<211> LENGTH: 14
<212> TYPE: DNA
<213> ORGANISM: Artificial Sequence
<220> FEATURE:
<223> OTHER INFORMATION: Synthetic Construct

<400> SEQUENCE: 272
tctacgaacg caca                                                      14

<210> SEQ ID NO 273
<211> LENGTH: 14
<212> TYPE: DNA
<213> ORGANISM: Artificial Sequence
<220> FEATURE:
<223> OTHER INFORMATION: Synthetic Construct

<400> SEQUENCE: 273
tgggggtttt tggg                                                      14

<210> SEQ ID NO 274
<211> LENGTH: 14
<212> TYPE: DNA
<213> ORGANISM: Artificial Sequence
<220> FEATURE:
<223> OTHER INFORMATION: Synthetic Construct

<400> SEQUENCE: 274
tctacgaacg caca                                                      14

<210> SEQ ID NO 275
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 275
gggggttttt gggg                                              14

<210> SEQ ID NO 276
<211> LENGTH: 14
<212> TYPE: DNA
<213> ORGANISM: Artificial Sequence
<220> FEATURE:
<223> OTHER INFORMATION: Synthetic Construct

<400> SEQUENCE: 276
tctacgaacg caca                                              14

<210> SEQ ID NO 277
<211> LENGTH: 14
<212> TYPE: DNA
<213> ORGANISM: Artificial Sequence
<220> FEATURE:
<223> OTHER INFORMATION: Synthetic Construct

<400> SEQUENCE: 277 ggggttttg ggga                                               14

<210> SEQ ID NO 278
<211> LENGTH: 14
<212> TYPE: DNA
<213> ORGANISM: Artificial Sequence
<220> FEATURE:
<223> OTHER INFORMATION: Synthetic Construct

<400> SEQUENCE: 278
tctacgaacg caca                                              14

<210> SEQ ID NO 279
<211> LENGTH: 14
<212> TYPE: DNA
<213> ORGANISM: Artificial Sequence
<220> FEATURE:
<223> OTHER INFORMATION: Synthetic Construct

<400> SEQUENCE: 279 gggttttgg ggag                                               14

<210> SEQ ID NO 280
<211> LENGTH: 14
<212> TYPE: DNA
<213> ORGANISM: Artificial Sequence
<220> FEATURE:
<223> OTHER INFORMATION: Synthetic Construct

<400> SEQUENCE: 280
tctacgaacg caca                                              14

<210> SEQ ID NO 281
<211> LENGTH: 14
<212> TYPE: DNA
<213> ORGANISM: Artificial Sequence
<220> FEATURE:
<223> OTHER INFORMATION: Synthetic Construct

<400> SEQUENCE: 281 ggttttggg gagg                                               14

<210> SEQ ID NO 282
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 282
tctacgaacg caca                                                     14

<210> SEQ ID NO 283
<211> LENGTH: 14
<212> TYPE: DNA
<213> ORGANISM: Artificial Sequence
<220> FEATURE:
<223> OTHER INFORMATION: Synthetic Construct

<400> SEQUENCE: 283
gtttttgggg agga                                                     14

<210> SEQ ID NO 284
<211> LENGTH: 14
<212> TYPE: DNA
<213> ORGANISM: Artificial Sequence
<220> FEATURE:
<223> OTHER INFORMATION: Synthetic Construct

<400> SEQUENCE: 284
tctacgaacg caca                                                     14

<210> SEQ ID NO 285
<211> LENGTH: 14
<212> TYPE: DNA
<213> ORGANISM: Artificial Sequence
<220> FEATURE:
<223> OTHER INFORMATION: Synthetic Construct

<400> SEQUENCE: 285
tttttgggga ggag                                                     14

<210> SEQ ID NO 286
<211> LENGTH: 14
<212> TYPE: DNA
<213> ORGANISM: Artificial Sequence
<220> FEATURE:
<223> OTHER INFORMATION: Synthetic Construct

<400> SEQUENCE: 286
tctacgaacg caca                                                     14

<210> SEQ ID NO 287
<211> LENGTH: 14
<212> TYPE: DNA
<213> ORGANISM: Artificial Sequence
<220> FEATURE:
<223> OTHER INFORMATION: Synthetic Construct

<400> SEQUENCE: 287
ttttggggag gaga                                                     14

<210> SEQ ID NO 288
<211> LENGTH: 14
<212> TYPE: DNA
<213> ORGANISM: Artificial Sequence
<220> FEATURE:
<223> OTHER INFORMATION: Synthetic Construct

<400> SEQUENCE: 288
```
tctacgaacg caca                                              14

<210> SEQ ID NO 289
<211> LENGTH: 14
<212> TYPE: DNA
<213> ORGANISM: Artificial Sequence
<220> FEATURE:
<223> OTHER INFORMATION: Synthetic Construct

<400> SEQUENCE: 289
tttggggagg agat                                              14

<210> SEQ ID NO 290
<211> LENGTH: 14
<212> TYPE: DNA
<213> ORGANISM: Artificial Sequence
<220> FEATURE:
<223> OTHER INFORMATION: Synthetic Construct

<400> SEQUENCE: 290
tctacgaacg caca                                              14

<210> SEQ ID NO 291
<211> LENGTH: 14
<212> TYPE: DNA
<213> ORGANISM: Artificial Sequence
<220> FEATURE:
<223> OTHER INFORMATION: Synthetic Construct

<400> SEQUENCE: 291
ttggggagga gatt                                              14

<210> SEQ ID NO 292
<211> LENGTH: 14
<212> TYPE: DNA
<213> ORGANISM: Artificial Sequence
<220> FEATURE:
<223> OTHER INFORMATION: Synthetic Construct

<400> SEQUENCE: 292
tctacgaacg caca                                              14

<210> SEQ ID NO 293
<211> LENGTH: 14
<212> TYPE: DNA
<213> ORGANISM: Artificial Sequence
<220> FEATURE:
<223> OTHER INFORMATION: Synthetic Construct

<400> SEQUENCE: 293
tggggaggag attt                                              14

<210> SEQ ID NO 294
<211> LENGTH: 14
<212> TYPE: DNA
<213> ORGANISM: Artificial Sequence
<220> FEATURE:
<223> OTHER INFORMATION: Synthetic Construct

<400> SEQUENCE: 294
tctacgaacg caca                                              14

<210> SEQ ID NO 295
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 295
ggggaggaga ttta                                                       14

<210> SEQ ID NO 296
<211> LENGTH: 14
<212> TYPE: DNA
<213> ORGANISM: Artificial Sequence
<220> FEATURE:
<223> OTHER INFORMATION: Synthetic Construct

<400> SEQUENCE: 296
tctacgaacg caca                                                       14

<210> SEQ ID NO 297
<211> LENGTH: 14
<212> TYPE: DNA
<213> ORGANISM: Artificial Sequence
<220> FEATURE:
<223> OTHER INFORMATION: Synthetic Construct

<400> SEQUENCE: 297
gggaggagat ttat                                                       14

<210> SEQ ID NO 298
<211> LENGTH: 14
<212> TYPE: DNA
<213> ORGANISM: Artificial Sequence
<220> FEATURE:
<223> OTHER INFORMATION: Synthetic Construct

<400> SEQUENCE: 298
tctacgaacg caca                                                       14

<210> SEQ ID NO 299
<211> LENGTH: 14
<212> TYPE: DNA
<213> ORGANISM: Artificial Sequence
<220> FEATURE:
<223> OTHER INFORMATION: Synthetic Construct

<400> SEQUENCE: 299
ggaggagatt tata                                                       14

<210> SEQ ID NO 300
<211> LENGTH: 14
<212> TYPE: DNA
<213> ORGANISM: Artificial Sequence
<220> FEATURE:
<223> OTHER INFORMATION: Synthetic Construct

<400> SEQUENCE: 300
tctacgaacg caca                                                       14

<210> SEQ ID NO 301
<211> LENGTH: 14
<212> TYPE: DNA
<213> ORGANISM: Artificial Sequence
<220> FEATURE:
<223> OTHER INFORMATION: Synthetic Construct

<400> SEQUENCE: 301
gaggagattt atag                                                       14
```

```
<210> SEQ ID NO 302
<211> LENGTH: 14
<212> TYPE: DNA
<213> ORGANISM: Artificial Sequence
<220> FEATURE:
<223> OTHER INFORMATION: Synthetic Construct

<400> SEQUENCE: 302
tctacgaacg caca                                                     14

<210> SEQ ID NO 303
<211> LENGTH: 14
<212> TYPE: DNA
<213> ORGANISM: Artificial Sequence
<220> FEATURE:
<223> OTHER INFORMATION: Synthetic Construct

<400> SEQUENCE: 303
aggagattta tagt                                                     14

<210> SEQ ID NO 304
<211> LENGTH: 14
<212> TYPE: DNA
<213> ORGANISM: Artificial Sequence
<220> FEATURE:
<223> OTHER INFORMATION: Synthetic Construct

<400> SEQUENCE: 304
tctacgaacg caca                                                     14

<210> SEQ ID NO 305
<211> LENGTH: 14
<212> TYPE: DNA
<213> ORGANISM: Artificial Sequence
<220> FEATURE:
<223> OTHER INFORMATION: Synthetic Construct

<400> SEQUENCE: 305
ggagatttat agtg                                                     14

<210> SEQ ID NO 306
<211> LENGTH: 14
<212> TYPE: DNA
<213> ORGANISM: Artificial Sequence
<220> FEATURE:
<223> OTHER INFORMATION: Synthetic Construct

<400> SEQUENCE: 306
tctacgaacg caca                                                     14

<210> SEQ ID NO 307
<211> LENGTH: 14
<212> TYPE: DNA
<213> ORGANISM: Artificial Sequence
<220> FEATURE:
<223> OTHER INFORMATION: Synthetic Construct

<400> SEQUENCE: 307
gagatttata gtga                                                     14

<210> SEQ ID NO 308
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 308
tctacgaacg caca                                                     14

<210> SEQ ID NO 309
<211> LENGTH: 14
<212> TYPE: DNA
<213> ORGANISM: Artificial Sequence
<220> FEATURE:
<223> OTHER INFORMATION: Synthetic Construct

<400> SEQUENCE: 309
agatttatag tgaa                                                     14

<210> SEQ ID NO 310
<211> LENGTH: 14
<212> TYPE: DNA
<213> ORGANISM: Artificial Sequence
<220> FEATURE:
<223> OTHER INFORMATION: Synthetic Construct

<400> SEQUENCE: 310
tctacgaacg caca                                                     14

<210> SEQ ID NO 311
<211> LENGTH: 14
<212> TYPE: DNA
<213> ORGANISM: Artificial Sequence
<220> FEATURE:
<223> OTHER INFORMATION: Synthetic Construct

<400> SEQUENCE: 311
gatttatagt gaag                                                     14

<210> SEQ ID NO 312
<211> LENGTH: 14
<212> TYPE: DNA
<213> ORGANISM: Artificial Sequence
<220> FEATURE:
<223> OTHER INFORMATION: Synthetic Construct

<400> SEQUENCE: 312
tctacgaacg caca                                                     14

<210> SEQ ID NO 313
<211> LENGTH: 14
<212> TYPE: DNA
<213> ORGANISM: Artificial Sequence
<220> FEATURE:
<223> OTHER INFORMATION: Synthetic Construct

<400> SEQUENCE: 313
atttatagtg aagg                                                     14

<210> SEQ ID NO 314
<211> LENGTH: 14
<212> TYPE: DNA
<213> ORGANISM: Artificial Sequence
<220> FEATURE:
<223> OTHER INFORMATION: Synthetic Construct

<400> SEQUENCE: 314
ataacaacct cgcc                                                     14

<210> SEQ ID NO 315
```

```
<211> LENGTH: 26
<212> TYPE: DNA
<213> ORGANISM: Artificial Sequence
<220> FEATURE:
<223> OTHER INFORMATION: Synthetic Construct

<400> SEQUENCE: 315
ttttgcgagt tgttttcgtt gggagg                                        26

<210> SEQ ID NO 316
<211> LENGTH: 14
<212> TYPE: DNA
<213> ORGANISM: Artificial Sequence
<220> FEATURE:
<223> OTHER INFORMATION: Synthetic Construct

<400> SEQUENCE: 316
tttatagtga aggg                                                     14

<210> SEQ ID NO 317
<211> LENGTH: 14
<212> TYPE: DNA
<213> ORGANISM: Artificial Sequence
<220> FEATURE:
<223> OTHER INFORMATION: Synthetic Construct

<400> SEQUENCE: 317
ataacaacct cgcc                                                     14

<210> SEQ ID NO 318
<211> LENGTH: 14
<212> TYPE: DNA
<213> ORGANISM: Artificial Sequence
<220> FEATURE:
<223> OTHER INFORMATION: Synthetic Construct

<400> SEQUENCE: 318
ttatagtgaa gggg                                                     14

<210> SEQ ID NO 319
<211> LENGTH: 14
<212> TYPE: DNA
<213> ORGANISM: Artificial Sequence
<220> FEATURE:
<223> OTHER INFORMATION: Synthetic Construct

<400> SEQUENCE: 319
ataacaacct cgcc                                                     14

<210> SEQ ID NO 320
<211> LENGTH: 14
<212> TYPE: DNA
<213> ORGANISM: Artificial Sequence
<220> FEATURE:
<223> OTHER INFORMATION: Synthetic Construct

<400> SEQUENCE: 320
tatagtgaag ggga                                                     14

<210> SEQ ID NO 321
<211> LENGTH: 14
<212> TYPE: DNA
<213> ORGANISM: Artificial Sequence
<220> FEATURE:
<223> OTHER INFORMATION: Synthetic Construct

<400> SEQUENCE: 321
```

```
ataacaacct cgcc                                                       14

<210> SEQ ID NO 322
<211> LENGTH: 14
<212> TYPE: DNA
<213> ORGANISM: Artificial Sequence
<220> FEATURE:
<223> OTHER INFORMATION: Synthetic Construct

<400> SEQUENCE: 322
atagtgaagg ggag                                                       14

<210> SEQ ID NO 323
<211> LENGTH: 14
<212> TYPE: DNA
<213> ORGANISM: Artificial Sequence
<220> FEATURE:
<223> OTHER INFORMATION: Synthetic Construct

<400> SEQUENCE: 323
ataacaacct cgcc                                                       14

<210> SEQ ID NO 324
<211> LENGTH: 14
<212> TYPE: DNA
<213> ORGANISM: Artificial Sequence
<220> FEATURE:
<223> OTHER INFORMATION: Synthetic Construct

<400> SEQUENCE: 324
tagtgaaggg gagg                                                       14

<210> SEQ ID NO 325
<211> LENGTH: 14
<212> TYPE: DNA
<213> ORGANISM: Artificial Sequence
<220> FEATURE:
<223> OTHER INFORMATION: Synthetic Construct

<400> SEQUENCE: 325
ataacaacct cgcc                                                       14

<210> SEQ ID NO 326
<211> LENGTH: 14
<212> TYPE: DNA
<213> ORGANISM: Artificial Sequence
<220> FEATURE:
<223> OTHER INFORMATION: Synthetic Construct

<400> SEQUENCE: 326
agtgaagggg agga                                                       14

<210> SEQ ID NO 327
<211> LENGTH: 14
<212> TYPE: DNA
<213> ORGANISM: Artificial Sequence
<220> FEATURE:
<223> OTHER INFORMATION: Synthetic Construct

<400> SEQUENCE: 327
ataacaacct cgcc                                                       14

<210> SEQ ID NO 328
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 328
gtgaagggga ggaa                                                        14

<210> SEQ ID NO 329
<211> LENGTH: 14
<212> TYPE: DNA
<213> ORGANISM: Artificial Sequence
<220> FEATURE:
<223> OTHER INFORMATION: Synthetic Construct

<400> SEQUENCE: 329
ataacaacct cgcc                                                        14

<210> SEQ ID NO 330
<211> LENGTH: 14
<212> TYPE: DNA
<213> ORGANISM: Artificial Sequence
<220> FEATURE:
<223> OTHER INFORMATION: Synthetic Construct

<400> SEQUENCE: 330
tgaaggggag gaaa                                                        14

<210> SEQ ID NO 331
<211> LENGTH: 14
<212> TYPE: DNA
<213> ORGANISM: Artificial Sequence
<220> FEATURE:
<223> OTHER INFORMATION: Synthetic Construct

<400> SEQUENCE: 331
ataacaacct cgcc                                                        14

<210> SEQ ID NO 332
<211> LENGTH: 14
<212> TYPE: DNA
<213> ORGANISM: Artificial Sequence
<220> FEATURE:
<223> OTHER INFORMATION: Synthetic Construct

<400> SEQUENCE: 332
gaaggggagg aaaa                                                        14

<210> SEQ ID NO 333
<211> LENGTH: 14
<212> TYPE: DNA
<213> ORGANISM: Artificial Sequence
<220> FEATURE:
<223> OTHER INFORMATION: Synthetic Construct

<400> SEQUENCE: 333
ataacaacct cgcc                                                        14

<210> SEQ ID NO 334
<211> LENGTH: 14
<212> TYPE: DNA
<213> ORGANISM: Artificial Sequence
<220> FEATURE:
<223> OTHER INFORMATION: Synthetic Construct

<400> SEQUENCE: 334
aaggggagga aaac                                                        14
```

```
<210> SEQ ID NO 335
<211> LENGTH: 14
<212> TYPE: DNA
<213> ORGANISM: Artificial Sequence
<220> FEATURE:
<223> OTHER INFORMATION: Synthetic Construct

<400> SEQUENCE: 335
ataacaacct cgcc                                                          14

<210> SEQ ID NO 336
<211> LENGTH: 14
<212> TYPE: DNA
<213> ORGANISM: Artificial Sequence
<220> FEATURE:
<223> OTHER INFORMATION: Synthetic Construct

<400> SEQUENCE: 336 agggaggaa aacg                                                           14

<210> SEQ ID NO 337
<211> LENGTH: 14
<212> TYPE: DNA
<213> ORGANISM: Artificial Sequence
<220> FEATURE:
<223> OTHER INFORMATION: Synthetic Construct

<400> SEQUENCE: 337
ataacaacct cgcc                                                          14

<210> SEQ ID NO 338
<211> LENGTH: 14
<212> TYPE: DNA
<213> ORGANISM: Artificial Sequence
<220> FEATURE:
<223> OTHER INFORMATION: Synthetic Construct

<400> SEQUENCE: 338
ggggaggaaa acgg                                                          14

<210> SEQ ID NO 339
<211> LENGTH: 14
<212> TYPE: DNA
<213> ORGANISM: Artificial Sequence
<220> FEATURE:
<223> OTHER INFORMATION: Synthetic Construct

<400> SEQUENCE: 339
ataacaacct cgcc                                                          14

<210> SEQ ID NO 340
<211> LENGTH: 14
<212> TYPE: DNA
<213> ORGANISM: Artificial Sequence
<220> FEATURE:
<223> OTHER INFORMATION: Synthetic Construct

<400> SEQUENCE: 340
gggaggaaaa cggg                                                          14

<210> SEQ ID NO 341
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 341
ataacaacct cgcc                                                              14

<210> SEQ ID NO 342
<211> LENGTH: 14
<212> TYPE: DNA
<213> ORGANISM: Artificial Sequence
<220> FEATURE:
<223> OTHER INFORMATION: Synthetic Construct

<400> SEQUENCE: 342
ggaggaaaac gggt                                                              14

<210> SEQ ID NO 343
<211> LENGTH: 14
<212> TYPE: DNA
<213> ORGANISM: Artificial Sequence
<220> FEATURE:
<223> OTHER INFORMATION: Synthetic Construct

<400> SEQUENCE: 343
ataacaacct cgcc                                                              14

<210> SEQ ID NO 344
<211> LENGTH: 14
<212> TYPE: DNA
<213> ORGANISM: Artificial Sequence
<220> FEATURE:
<223> OTHER INFORMATION: Synthetic Construct

<400> SEQUENCE: 344
gaggaaaacg ggtt                                                              14

<210> SEQ ID NO 345
<211> LENGTH: 14
<212> TYPE: DNA
<213> ORGANISM: Artificial Sequence
<220> FEATURE:
<223> OTHER INFORMATION: Synthetic Construct

<400> SEQUENCE: 345
ataacaacct cgcc                                                              14

<210> SEQ ID NO 346
<211> LENGTH: 14
<212> TYPE: DNA
<213> ORGANISM: Artificial Sequence
<220> FEATURE:
<223> OTHER INFORMATION: Synthetic Construct

<400> SEQUENCE: 346
aggaaaacgg gttt                                                              14

<210> SEQ ID NO 347
<211> LENGTH: 14
<212> TYPE: DNA
<213> ORGANISM: Artificial Sequence
<220> FEATURE:
<223> OTHER INFORMATION: Synthetic Construct

<400> SEQUENCE: 347
ataacaacct cgcc                                                              14

```
<210> SEQ ID NO 348
<211> LENGTH: 14
<212> TYPE: DNA
<213> ORGANISM: Artificial Sequence
<220> FEATURE:
<223> OTHER INFORMATION: Synthetic Construct

<400> SEQUENCE: 348
ggaaaacggg tttt                                                    14

<210> SEQ ID NO 349
<211> LENGTH: 14
<212> TYPE: DNA
<213> ORGANISM: Artificial Sequence
<220> FEATURE:
<223> OTHER INFORMATION: Synthetic Construct

<400> SEQUENCE: 349
ataacaacct cgcc                                                    14

<210> SEQ ID NO 350
<211> LENGTH: 14
<212> TYPE: DNA
<213> ORGANISM: Artificial Sequence
<220> FEATURE:
<223> OTHER INFORMATION: Synthetic Construct

<400> SEQUENCE: 350
gaaaacgggt tttt                                                    14

<210> SEQ ID NO 351
<211> LENGTH: 14
<212> TYPE: DNA
<213> ORGANISM: Artificial Sequence
<220> FEATURE:
<223> OTHER INFORMATION: Synthetic Construct

<400> SEQUENCE: 351
ataacaacct cgcc                                                    14

<210> SEQ ID NO 352
<211> LENGTH: 14
<212> TYPE: DNA
<213> ORGANISM: Artificial Sequence
<220> FEATURE:
<223> OTHER INFORMATION: Synthetic Construct

<400> SEQUENCE: 352
aaaacgggtt tttc                                                    14

<210> SEQ ID NO 353
<211> LENGTH: 14
<212> TYPE: DNA
<213> ORGANISM: Artificial Sequence
<220> FEATURE:
<223> OTHER INFORMATION: Synthetic Construct

<400> SEQUENCE: 353
ataacaacct cgcc                                                    14

<210> SEQ ID NO 354
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 354
aaacgggttt ttcg                                                        14

<210> SEQ ID NO 355
<211> LENGTH: 14
<212> TYPE: DNA
<213> ORGANISM: Artificial Sequence
<220> FEATURE:
<223> OTHER INFORMATION: Synthetic Construct

<400> SEQUENCE: 355
ataacaacct cgcc                                                        14

<210> SEQ ID NO 356
<211> LENGTH: 14
<212> TYPE: DNA
<213> ORGANISM: Artificial Sequence
<220> FEATURE:
<223> OTHER INFORMATION: Synthetic Construct

<400> SEQUENCE: 356
aacgggtttt tcgt                                                        14

<210> SEQ ID NO 357
<211> LENGTH: 14
<212> TYPE: DNA
<213> ORGANISM: Artificial Sequence
<220> FEATURE:
<223> OTHER INFORMATION: Synthetic Construct

<400> SEQUENCE: 357
ataacaacct cgcc                                                        14

<210> SEQ ID NO 358
<211> LENGTH: 14
<212> TYPE: DNA
<213> ORGANISM: Artificial Sequence
<220> FEATURE:
<223> OTHER INFORMATION: Synthetic Construct

<400> SEQUENCE: 358
acgggttttt cgta                                                        14

<210> SEQ ID NO 359
<211> LENGTH: 14
<212> TYPE: DNA
<213> ORGANISM: Artificial Sequence
<220> FEATURE:
<223> OTHER INFORMATION: Synthetic Construct

<400> SEQUENCE: 359
ataacaacct cgcc                                                        14

<210> SEQ ID NO 360
<211> LENGTH: 14
<212> TYPE: DNA
<213> ORGANISM: Artificial Sequence
<220> FEATURE:
<223> OTHER INFORMATION: Synthetic Construct

<400> SEQUENCE: 360
cgggtttttc gtag                                                        14

<210> SEQ ID NO 361
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 361
ataacaacct cgcc                                                             14

<210> SEQ ID NO 362
<211> LENGTH: 14
<212> TYPE: DNA
<213> ORGANISM: Artificial Sequence
<220> FEATURE:
<223> OTHER INFORMATION: Synthetic Construct

<400> SEQUENCE: 362
gggtttttcg taga                                                             14

<210> SEQ ID NO 363
<211> LENGTH: 14
<212> TYPE: DNA
<213> ORGANISM: Artificial Sequence
<220> FEATURE:
<223> OTHER INFORMATION: Synthetic Construct

<400> SEQUENCE: 363
ataacaacct cgcc                                                             14

<210> SEQ ID NO 364
<211> LENGTH: 14
<212> TYPE: DNA
<213> ORGANISM: Artificial Sequence
<220> FEATURE:
<223> OTHER INFORMATION: Synthetic Construct

<400> SEQUENCE: 364 ggttttcgt agag                                                              14

<210> SEQ ID NO 365
<211> LENGTH: 14
<212> TYPE: DNA
<213> ORGANISM: Artificial Sequence
<220> FEATURE:
<223> OTHER INFORMATION: Synthetic Construct

<400> SEQUENCE: 365
ataacaacct cgcc                                                             14

<210> SEQ ID NO 366
<211> LENGTH: 14
<212> TYPE: DNA
<213> ORGANISM: Artificial Sequence
<220> FEATURE:
<223> OTHER INFORMATION: Synthetic Construct

<400> SEQUENCE: 366 gttttcgta gagg                                                              14

<210> SEQ ID NO 367
<211> LENGTH: 14
<212> TYPE: DNA
<213> ORGANISM: Artificial Sequence
<220> FEATURE:
<223> OTHER INFORMATION: Synthetic Construct

<400> SEQUENCE: 367
```
ataacaacct cgcc                                                         14

<210> SEQ ID NO 368
<211> LENGTH: 14
<212> TYPE: DNA
<213> ORGANISM: Artificial Sequence
<220> FEATURE:
<223> OTHER INFORMATION: Synthetic Construct

<400> SEQUENCE: 368
tttttcgtag agga                                                         14

<210> SEQ ID NO 369
<211> LENGTH: 14
<212> TYPE: DNA
<213> ORGANISM: Artificial Sequence
<220> FEATURE:
<223> OTHER INFORMATION: Synthetic Construct

<400> SEQUENCE: 369
ataacaacct cgcc                                                         14

<210> SEQ ID NO 370
<211> LENGTH: 14
<212> TYPE: DNA
<213> ORGANISM: Artificial Sequence
<220> FEATURE:
<223> OTHER INFORMATION: Synthetic Construct

<400> SEQUENCE: 370
ttttcgtaga ggag                                                         14

<210> SEQ ID NO 371
<211> LENGTH: 14
<212> TYPE: DNA
<213> ORGANISM: Artificial Sequence
<220> FEATURE:
<223> OTHER INFORMATION: Synthetic Construct

<400> SEQUENCE: 371
ataacaacct cgcc                                                         14

<210> SEQ ID NO 372
<211> LENGTH: 14
<212> TYPE: DNA
<213> ORGANISM: Artificial Sequence
<220> FEATURE:
<223> OTHER INFORMATION: Synthetic Construct

<400> SEQUENCE: 372
tttcgtagag gagg                                                         14

<210> SEQ ID NO 373
<211> LENGTH: 14
<212> TYPE: DNA
<213> ORGANISM: Artificial Sequence
<220> FEATURE:
<223> OTHER INFORMATION: Synthetic Construct

<400> SEQUENCE: 373
ataacaacct cgcc                                                         14

<210> SEQ ID NO 374
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 374
ttcgtagagg aggt                                                         14

<210> SEQ ID NO 375
<211> LENGTH: 14
<212> TYPE: DNA
<213> ORGANISM: Artificial Sequence
<220> FEATURE:
<223> OTHER INFORMATION: Synthetic Construct

<400> SEQUENCE: 375
ataacaacct cgcc                                                         14

<210> SEQ ID NO 376
<211> LENGTH: 14
<212> TYPE: DNA
<213> ORGANISM: Artificial Sequence
<220> FEATURE:
<223> OTHER INFORMATION: Synthetic Construct

<400> SEQUENCE: 376
tcgtagagga ggta                                                         14

<210> SEQ ID NO 377
<211> LENGTH: 14
<212> TYPE: DNA
<213> ORGANISM: Artificial Sequence
<220> FEATURE:
<223> OTHER INFORMATION: Synthetic Construct

<400> SEQUENCE: 377
ataacaacct cgcc                                                         14

<210> SEQ ID NO 378
<211> LENGTH: 14
<212> TYPE: DNA
<213> ORGANISM: Artificial Sequence
<220> FEATURE:
<223> OTHER INFORMATION: Synthetic Construct

<400> SEQUENCE: 378
cgtagaggag gtag                                                         14

<210> SEQ ID NO 379
<211> LENGTH: 14
<212> TYPE: DNA
<213> ORGANISM: Artificial Sequence
<220> FEATURE:
<223> OTHER INFORMATION: Synthetic Construct

<400> SEQUENCE: 379
ataacaacct cgcc                                                         14

<210> SEQ ID NO 380
<211> LENGTH: 14
<212> TYPE: DNA
<213> ORGANISM: Artificial Sequence
<220> FEATURE:
<223> OTHER INFORMATION: Synthetic Construct

<400> SEQUENCE: 380
gtagaggagg tagg                                                         14
```

<210> SEQ ID NO 381
<211> LENGTH: 14
<212> TYPE: DNA
<213> ORGANISM: Artificial Sequence
<220> FEATURE:
<223> OTHER INFORMATION: Synthetic Construct

<400> SEQUENCE: 381
ataacaacct cgcc                                                         14

<210> SEQ ID NO 382
<211> LENGTH: 14
<212> TYPE: DNA
<213> ORGANISM: Artificial Sequence
<220> FEATURE:
<223> OTHER INFORMATION: Synthetic Construct

<400> SEQUENCE: 382
tagaggaggt aggt                                                         14

<210> SEQ ID NO 383
<211> LENGTH: 14
<212> TYPE: DNA
<213> ORGANISM: Artificial Sequence
<220> FEATURE:
<223> OTHER INFORMATION: Synthetic Construct

<400> SEQUENCE: 383
ataacaacct cgcc                                                         14

<210> SEQ ID NO 384
<211> LENGTH: 14
<212> TYPE: DNA
<213> ORGANISM: Artificial Sequence
<220> FEATURE:
<223> OTHER INFORMATION: Synthetic Construct

<400> SEQUENCE: 384
agaggaggta ggtg                                                         14

<210> SEQ ID NO 385
<211> LENGTH: 14
<212> TYPE: DNA
<213> ORGANISM: Artificial Sequence
<220> FEATURE:
<223> OTHER INFORMATION: Synthetic Construct

<400> SEQUENCE: 385
ataacaacct cgcc                                                         14

<210> SEQ ID NO 386
<211> LENGTH: 14
<212> TYPE: DNA
<213> ORGANISM: Artificial Sequence
<220> FEATURE:
<223> OTHER INFORMATION: Synthetic Construct

<400> SEQUENCE: 386
gaggaggtag gtgg                                                         14

<210> SEQ ID NO 387
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 387
ataacaacct cgcc                                                       14

<210> SEQ ID NO 388
<211> LENGTH: 14
<212> TYPE: DNA
<213> ORGANISM: Artificial Sequence
<220> FEATURE:
<223> OTHER INFORMATION: Synthetic Construct

<400> SEQUENCE: 388
aggaggtagg tgga                                                       14

<210> SEQ ID NO 389
<211> LENGTH: 14
<212> TYPE: DNA
<213> ORGANISM: Artificial Sequence
<220> FEATURE:
<223> OTHER INFORMATION: Synthetic Construct

<400> SEQUENCE: 389
ataacaacct cgcc                                                       14

<210> SEQ ID NO 390
<211> LENGTH: 14
<212> TYPE: DNA
<213> ORGANISM: Artificial Sequence
<220> FEATURE:
<223> OTHER INFORMATION: Synthetic Construct

<400> SEQUENCE: 390
ggaggtaggt ggaa                                                       14

<210> SEQ ID NO 391
<211> LENGTH: 14
<212> TYPE: DNA
<213> ORGANISM: Artificial Sequence
<220> FEATURE:
<223> OTHER INFORMATION: Synthetic Construct

<400> SEQUENCE: 391
ataacaacct cgcc                                                       14

<210> SEQ ID NO 392
<211> LENGTH: 14
<212> TYPE: DNA
<213> ORGANISM: Artificial Sequence
<220> FEATURE:
<223> OTHER INFORMATION: Synthetic Construct

<400> SEQUENCE: 392
gaggtaggtg gaaa                                                       14

<210> SEQ ID NO 393
<211> LENGTH: 14
<212> TYPE: DNA
<213> ORGANISM: Artificial Sequence
<220> FEATURE:
<223> OTHER INFORMATION: Synthetic Construct

<400> SEQUENCE: 393
ataacaacct cgcc                                                       14

<210> SEQ ID NO 394
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 394
aggtaggtgg aaag                                                     14

<210> SEQ ID NO 395
<211> LENGTH: 14
<212> TYPE: DNA
<213> ORGANISM: Artificial Sequence
<220> FEATURE:
<223> OTHER INFORMATION: Synthetic Construct

<400> SEQUENCE: 395
ataacaacct cgcc                                                     14

<210> SEQ ID NO 396
<211> LENGTH: 14
<212> TYPE: DNA
<213> ORGANISM: Artificial Sequence
<220> FEATURE:
<223> OTHER INFORMATION: Synthetic Construct

<400> SEQUENCE: 396
ggtaggtgga aaga                                                     14

<210> SEQ ID NO 397
<211> LENGTH: 14
<212> TYPE: DNA
<213> ORGANISM: Artificial Sequence
<220> FEATURE:
<223> OTHER INFORMATION: Synthetic Construct

<400> SEQUENCE: 397
ataacaacct cgcc                                                     14

<210> SEQ ID NO 398
<211> LENGTH: 14
<212> TYPE: DNA
<213> ORGANISM: Artificial Sequence
<220> FEATURE:
<223> OTHER INFORMATION: Synthetic Construct

<400> SEQUENCE: 398
gtaggtggaa agag                                                     14

<210> SEQ ID NO 399
<211> LENGTH: 14
<212> TYPE: DNA
<213> ORGANISM: Artificial Sequence
<220> FEATURE:
<223> OTHER INFORMATION: Synthetic Construct

<400> SEQUENCE: 399
ataacaacct cgcc                                                     14

<210> SEQ ID NO 400
<211> LENGTH: 14
<212> TYPE: DNA
<213> ORGANISM: Artificial Sequence
<220> FEATURE:
<223> OTHER INFORMATION: Synthetic Construct

<400> SEQUENCE: 400
```
taggtggaaa gagg 14

<210> SEQ ID NO 401
<211> LENGTH: 14
<212> TYPE: DNA
<213> ORGANISM: Artificial Sequence
<220> FEATURE:
<223> OTHER INFORMATION: Synthetic Construct

<400> SEQUENCE: 401
ataacaacct cgcc 14

<210> SEQ ID NO 402
<211> LENGTH: 14
<212> TYPE: DNA
<213> ORGANISM: Artificial Sequence
<220> FEATURE:
<223> OTHER INFORMATION: Synthetic Construct

<400> SEQUENCE: 402
aggtggaaag aggg 14

<210> SEQ ID NO 403
<211> LENGTH: 14
<212> TYPE: DNA
<213> ORGANISM: Artificial Sequence
<220> FEATURE:
<223> OTHER INFORMATION: Synthetic Construct

<400> SEQUENCE: 403
ataacaacct cgcc 14

<210> SEQ ID NO 404
<211> LENGTH: 14
<212> TYPE: DNA
<213> ORGANISM: Artificial Sequence
<220> FEATURE:
<223> OTHER INFORMATION: Synthetic Construct

<400> SEQUENCE: 404
ggtggaaaga ggga 14

<210> SEQ ID NO 405
<211> LENGTH: 14
<212> TYPE: DNA
<213> ORGANISM: Artificial Sequence
<220> FEATURE:
<223> OTHER INFORMATION: Synthetic Construct

<400> SEQUENCE: 405
ataacaacct cgcc 14

<210> SEQ ID NO 406
<211> LENGTH: 14
<212> TYPE: DNA
<213> ORGANISM: Artificial Sequence
<220> FEATURE:
<223> OTHER INFORMATION: Synthetic Construct

<400> SEQUENCE: 406
gtggaaagag ggag 14

<210> SEQ ID NO 407
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 407
ataacaacct cgcc                                                           14

<210> SEQ ID NO 408
<211> LENGTH: 14
<212> TYPE: DNA
<213> ORGANISM: Artificial Sequence
<220> FEATURE:
<223> OTHER INFORMATION: Synthetic Construct

<400> SEQUENCE: 408
tggaaagagg gagg                                                           14

<210> SEQ ID NO 409
<211> LENGTH: 14
<212> TYPE: DNA
<213> ORGANISM: Artificial Sequence
<220> FEATURE:
<223> OTHER INFORMATION: Synthetic Construct

<400> SEQUENCE: 409
ataacaacct cgcc                                                           14

<210> SEQ ID NO 410
<211> LENGTH: 14
<212> TYPE: DNA
<213> ORGANISM: Artificial Sequence
<220> FEATURE:
<223> OTHER INFORMATION: Synthetic Construct

<400> SEQUENCE: 410
ggaaagaggg aggg                                                           14

<210> SEQ ID NO 411
<211> LENGTH: 14
<212> TYPE: DNA
<213> ORGANISM: Artificial Sequence
<220> FEATURE:
<223> OTHER INFORMATION: Synthetic Construct

<400> SEQUENCE: 411
ataacaacct cgcc                                                           14

<210> SEQ ID NO 412
<211> LENGTH: 14
<212> TYPE: DNA
<213> ORGANISM: Artificial Sequence
<220> FEATURE:
<223> OTHER INFORMATION: Synthetic Construct

<400> SEQUENCE: 412
gaaagaggga gggg                                                           14

<210> SEQ ID NO 413
<211> LENGTH: 14
<212> TYPE: DNA
<213> ORGANISM: Artificial Sequence
<220> FEATURE:
<223> OTHER INFORMATION: Synthetic Construct

<400> SEQUENCE: 413
ataacaacct cgcc                                                           14
```

<210> SEQ ID NO 414
<211> LENGTH: 14
<212> TYPE: DNA
<213> ORGANISM: Artificial Sequence
<220> FEATURE:
<223> OTHER INFORMATION: Synthetic Construct

<400> SEQUENCE: 414
aaagagggag gggt                                                         14

<210> SEQ ID NO 415
<211> LENGTH: 14
<212> TYPE: DNA
<213> ORGANISM: Artificial Sequence
<220> FEATURE:
<223> OTHER INFORMATION: Synthetic Construct

<400> SEQUENCE: 415
ataacaacct cgcc                                                         14

<210> SEQ ID NO 416
<211> LENGTH: 14
<212> TYPE: DNA
<213> ORGANISM: Artificial Sequence
<220> FEATURE:
<223> OTHER INFORMATION: Synthetic Construct

<400> SEQUENCE: 416
aagagggagg ggtt                                                         14

<210> SEQ ID NO 417
<211> LENGTH: 14
<212> TYPE: DNA
<213> ORGANISM: Artificial Sequence
<220> FEATURE:
<223> OTHER INFORMATION: Synthetic Construct

<400> SEQUENCE: 417
acgcgaaacc aaat                                                         14

<210> SEQ ID NO 418
<211> LENGTH: 24
<212> TYPE: DNA
<213> ORGANISM: Artificial Sequence
<220> FEATURE:
<223> OTHER INFORMATION: Synthetic Construct

<400> SEQUENCE: 418
aggagtttta gcgcggtttg gaga                                              24

<210> SEQ ID NO 419
<211> LENGTH: 14
<212> TYPE: DNA
<213> ORGANISM: Artificial Sequence
<220> FEATURE:
<223> OTHER INFORMATION: Synthetic Construct

<400> SEQUENCE: 419
agagggaggg gttt                                                         14

<210> SEQ ID NO 420
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 420
acgcgaaacc aaat                                                    14

<210> SEQ ID NO 421
<211> LENGTH: 14
<212> TYPE: DNA
<213> ORGANISM: Artificial Sequence
<220> FEATURE:
<223> OTHER INFORMATION: Synthetic Construct

<400> SEQUENCE: 421
gagggagggg tttg                                                    14

<210> SEQ ID NO 422
<211> LENGTH: 14
<212> TYPE: DNA
<213> ORGANISM: Artificial Sequence
<220> FEATURE:
<223> OTHER INFORMATION: Synthetic Construct

<400> SEQUENCE: 422
acgcgaaacc aaat                                                    14

<210> SEQ ID NO 423
<211> LENGTH: 14
<212> TYPE: DNA
<213> ORGANISM: Artificial Sequence
<220> FEATURE:
<223> OTHER INFORMATION: Synthetic Construct

<400> SEQUENCE: 423
agggaggggt tgt                                                     14

<210> SEQ ID NO 424
<211> LENGTH: 14
<212> TYPE: DNA
<213> ORGANISM: Artificial Sequence
<220> FEATURE:
<223> OTHER INFORMATION: Synthetic Construct

<400> SEQUENCE: 424
acgcgaaacc aaat                                                    14

<210> SEQ ID NO 425
<211> LENGTH: 14
<212> TYPE: DNA
<213> ORGANISM: Artificial Sequence
<220> FEATURE:
<223> OTHER INFORMATION: Synthetic Construct

<400> SEQUENCE: 425
gggaggggtt tgtg                                                    14

<210> SEQ ID NO 426
<211> LENGTH: 14
<212> TYPE: DNA
<213> ORGANISM: Artificial Sequence
<220> FEATURE:
<223> OTHER INFORMATION: Synthetic Construct

<400> SEQUENCE: 426
acgcgaaacc aaat                                                    14
```

```
<210> SEQ ID NO 427
<211> LENGTH: 14
<212> TYPE: DNA
<213> ORGANISM: Artificial Sequence
<220> FEATURE:
<223> OTHER INFORMATION: Synthetic Construct

<400> SEQUENCE: 427 ggagggggttt gtgc                                                      14

<210> SEQ ID NO 428
<211> LENGTH: 14
<212> TYPE: DNA
<213> ORGANISM: Artificial Sequence
<220> FEATURE:
<223> OTHER INFORMATION: Synthetic Construct

<400> SEQUENCE: 428
acgcgaaacc aaat                                                       14

<210> SEQ ID NO 429
<211> LENGTH: 14
<212> TYPE: DNA
<213> ORGANISM: Artificial Sequence
<220> FEATURE:
<223> OTHER INFORMATION: Synthetic Construct

<400> SEQUENCE: 429
gaggggtttg tgcg                                                       14

<210> SEQ ID NO 430
<211> LENGTH: 14
<212> TYPE: DNA
<213> ORGANISM: Artificial Sequence
<220> FEATURE:
<223> OTHER INFORMATION: Synthetic Construct

<400> SEQUENCE: 430
acgcgaaacc aaat                                                       14

<210> SEQ ID NO 431
<211> LENGTH: 14
<212> TYPE: DNA
<213> ORGANISM: Artificial Sequence
<220> FEATURE:
<223> OTHER INFORMATION: Synthetic Construct

<400> SEQUENCE: 431
aggggtttgt gcgt                                                       14

<210> SEQ ID NO 432
<211> LENGTH: 14
<212> TYPE: DNA
<213> ORGANISM: Artificial Sequence
<220> FEATURE:
<223> OTHER INFORMATION: Synthetic Construct

<400> SEQUENCE: 432
acgcgaaacc aaat                                                       14

<210> SEQ ID NO 433
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 433
ggggtttgtg cgtt                                                    14

<210> SEQ ID NO 434
<211> LENGTH: 14
<212> TYPE: DNA
<213> ORGANISM: Artificial Sequence
<220> FEATURE:
<223> OTHER INFORMATION: Synthetic Construct

<400> SEQUENCE: 434
acgcgaaacc aaat                                                    14

<210> SEQ ID NO 435
<211> LENGTH: 14
<212> TYPE: DNA
<213> ORGANISM: Artificial Sequence
<220> FEATURE:
<223> OTHER INFORMATION: Synthetic Construct

<400> SEQUENCE: 435
gggtttgtgc gttc                                                    14

<210> SEQ ID NO 436
<211> LENGTH: 14
<212> TYPE: DNA
<213> ORGANISM: Artificial Sequence
<220> FEATURE:
<223> OTHER INFORMATION: Synthetic Construct

<400> SEQUENCE: 436
acgcgaaacc aaat                                                    14

<210> SEQ ID NO 437
<211> LENGTH: 14
<212> TYPE: DNA
<213> ORGANISM: Artificial Sequence
<220> FEATURE:
<223> OTHER INFORMATION: Synthetic Construct

<400> SEQUENCE: 437
ggtttgtgcg ttcg                                                    14

<210> SEQ ID NO 438
<211> LENGTH: 14
<212> TYPE: DNA
<213> ORGANISM: Artificial Sequence
<220> FEATURE:
<223> OTHER INFORMATION: Synthetic Construct

<400> SEQUENCE: 438
acgcgaaacc aaat                                                    14

<210> SEQ ID NO 439
<211> LENGTH: 14
<212> TYPE: DNA
<213> ORGANISM: Artificial Sequence
<220> FEATURE:
<223> OTHER INFORMATION: Synthetic Construct

<400> SEQUENCE: 439
gtttgtgcgt tcgt                                                    14

<210> SEQ ID NO 440
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 440
acgcgaaacc aaat                                                        14

<210> SEQ ID NO 441
<211> LENGTH: 14
<212> TYPE: DNA
<213> ORGANISM: Artificial Sequence
<220> FEATURE:
<223> OTHER INFORMATION: Synthetic Construct

<400> SEQUENCE: 441
tttgtgcgtt cgta                                                        14

<210> SEQ ID NO 442
<211> LENGTH: 14
<212> TYPE: DNA
<213> ORGANISM: Artificial Sequence
<220> FEATURE:
<223> OTHER INFORMATION: Synthetic Construct

<400> SEQUENCE: 442
acgcgaaacc aaat                                                        14

<210> SEQ ID NO 443
<211> LENGTH: 14
<212> TYPE: DNA
<213> ORGANISM: Artificial Sequence
<220> FEATURE:
<223> OTHER INFORMATION: Synthetic Construct

<400> SEQUENCE: 443
ttgtgcgttc gtag                                                        14

<210> SEQ ID NO 444
<211> LENGTH: 14
<212> TYPE: DNA
<213> ORGANISM: Artificial Sequence
<220> FEATURE:
<223> OTHER INFORMATION: Synthetic Construct

<400> SEQUENCE: 444
acgcgaaacc aaat                                                        14

<210> SEQ ID NO 445
<211> LENGTH: 14
<212> TYPE: DNA
<213> ORGANISM: Artificial Sequence
<220> FEATURE:
<223> OTHER INFORMATION: Synthetic Construct

<400> SEQUENCE: 445
tgtgcgttcg taga                                                        14

<210> SEQ ID NO 446
<211> LENGTH: 14
<212> TYPE: DNA
<213> ORGANISM: Artificial Sequence
<220> FEATURE:
<223> OTHER INFORMATION: Synthetic Construct

<400> SEQUENCE: 446
```
acgcgaaacc aaat                                                         14

<210> SEQ ID NO 447
<211> LENGTH: 14
<212> TYPE: DNA
<213> ORGANISM: Artificial Sequence
<220> FEATURE:
<223> OTHER INFORMATION: Synthetic Construct

<400> SEQUENCE: 447
gtgcgttcgt agag                                                         14

<210> SEQ ID NO 448
<211> LENGTH: 14
<212> TYPE: DNA
<213> ORGANISM: Artificial Sequence
<220> FEATURE:
<223> OTHER INFORMATION: Synthetic Construct

<400> SEQUENCE: 448
acgcgaaacc aaat                                                         14

<210> SEQ ID NO 449
<211> LENGTH: 14
<212> TYPE: DNA
<213> ORGANISM: Artificial Sequence
<220> FEATURE:
<223> OTHER INFORMATION: Synthetic Construct

<400> SEQUENCE: 449
tgcgttcgta gagt                                                         14

<210> SEQ ID NO 450
<211> LENGTH: 14
<212> TYPE: DNA
<213> ORGANISM: Artificial Sequence
<220> FEATURE:
<223> OTHER INFORMATION: Synthetic Construct

<400> SEQUENCE: 450
acgcgaaacc aaat                                                         14

<210> SEQ ID NO 451
<211> LENGTH: 14
<212> TYPE: DNA
<213> ORGANISM: Artificial Sequence
<220> FEATURE:
<223> OTHER INFORMATION: Synthetic Construct

<400> SEQUENCE: 451
gcgttcgtag agtc                                                         14

<210> SEQ ID NO 452
<211> LENGTH: 14
<212> TYPE: DNA
<213> ORGANISM: Artificial Sequence
<220> FEATURE:
<223> OTHER INFORMATION: Synthetic Construct

<400> SEQUENCE: 452
acgcgaaacc aaat                                                         14

<210> SEQ ID NO 453
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 453
cgttcgtaga gtcg                                                         14

<210> SEQ ID NO 454
<211> LENGTH: 14
<212> TYPE: DNA
<213> ORGANISM: Artificial Sequence
<220> FEATURE:
<223> OTHER INFORMATION: Synthetic Construct

<400> SEQUENCE: 454
acgcgaaacc aaat                                                         14

<210> SEQ ID NO 455
<211> LENGTH: 14
<212> TYPE: DNA
<213> ORGANISM: Artificial Sequence
<220> FEATURE:
<223> OTHER INFORMATION: Synthetic Construct

<400> SEQUENCE: 455
gttcgtagag tcgt                                                         14

<210> SEQ ID NO 456
<211> LENGTH: 14
<212> TYPE: DNA
<213> ORGANISM: Artificial Sequence
<220> FEATURE:
<223> OTHER INFORMATION: Synthetic Construct

<400> SEQUENCE: 456
acgcgaaacc aaat                                                         14

<210> SEQ ID NO 457
<211> LENGTH: 14
<212> TYPE: DNA
<213> ORGANISM: Artificial Sequence
<220> FEATURE:
<223> OTHER INFORMATION: Synthetic Construct

<400> SEQUENCE: 457
ttcgtagagt cgtt                                                         14

<210> SEQ ID NO 458
<211> LENGTH: 14
<212> TYPE: DNA
<213> ORGANISM: Artificial Sequence
<220> FEATURE:
<223> OTHER INFORMATION: Synthetic Construct

<400> SEQUENCE: 458
acgcgaaacc aaat                                                         14

<210> SEQ ID NO 459
<211> LENGTH: 14
<212> TYPE: DNA
<213> ORGANISM: Artificial Sequence
<220> FEATURE:
<223> OTHER INFORMATION: Synthetic Construct

<400> SEQUENCE: 459
tcgtagagtc gtta                                                         14
```

<210> SEQ ID NO 460
<211> LENGTH: 14
<212> TYPE: DNA
<213> ORGANISM: Artificial Sequence
<220> FEATURE:
<223> OTHER INFORMATION: Synthetic Construct

<400> SEQUENCE: 460
acgcgaaacc aaat                                                      14

<210> SEQ ID NO 461
<211> LENGTH: 14
<212> TYPE: DNA
<213> ORGANISM: Artificial Sequence
<220> FEATURE:
<223> OTHER INFORMATION: Synthetic Construct

<400> SEQUENCE: 461
cgtagagtcg ttag                                                      14

<210> SEQ ID NO 462
<211> LENGTH: 14
<212> TYPE: DNA
<213> ORGANISM: Artificial Sequence
<220> FEATURE:
<223> OTHER INFORMATION: Synthetic Construct

<400> SEQUENCE: 462
acgcgaaacc aaat                                                      14

<210> SEQ ID NO 463
<211> LENGTH: 14
<212> TYPE: DNA
<213> ORGANISM: Artificial Sequence
<220> FEATURE:
<223> OTHER INFORMATION: Synthetic Construct

<400> SEQUENCE: 463
gtagagtcgt tagg                                                      14

<210> SEQ ID NO 464
<211> LENGTH: 14
<212> TYPE: DNA
<213> ORGANISM: Artificial Sequence
<220> FEATURE:
<223> OTHER INFORMATION: Synthetic Construct

<400> SEQUENCE: 464
acgcgaaacc aaat                                                      14

<210> SEQ ID NO 465
<211> LENGTH: 14
<212> TYPE: DNA
<213> ORGANISM: Artificial Sequence
<220> FEATURE:
<223> OTHER INFORMATION: Synthetic Construct

<400> SEQUENCE: 465
tagagtcgtt aggc                                                      14

<210> SEQ ID NO 466
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 466
acgcgaaacc aaat                                                        14

<210> SEQ ID NO 467
<211> LENGTH: 14
<212> TYPE: DNA
<213> ORGANISM: Artificial Sequence
<220> FEATURE:
<223> OTHER INFORMATION: Synthetic Construct

<400> SEQUENCE: 467
agagtcgtta ggcg                                                        14

<210> SEQ ID NO 468
<211> LENGTH: 14
<212> TYPE: DNA
<213> ORGANISM: Artificial Sequence
<220> FEATURE:
<223> OTHER INFORMATION: Synthetic Construct

<400> SEQUENCE: 468
acgcgaaacc aaat                                                        14

<210> SEQ ID NO 469
<211> LENGTH: 14
<212> TYPE: DNA
<213> ORGANISM: Artificial Sequence
<220> FEATURE:
<223> OTHER INFORMATION: Synthetic Construct

<400> SEQUENCE: 469
gagtcgttag gcgt                                                        14

<210> SEQ ID NO 470
<211> LENGTH: 14
<212> TYPE: DNA
<213> ORGANISM: Artificial Sequence
<220> FEATURE:
<223> OTHER INFORMATION: Synthetic Construct

<400> SEQUENCE: 470
acgcgaaacc aaat                                                        14

<210> SEQ ID NO 471
<211> LENGTH: 14
<212> TYPE: DNA
<213> ORGANISM: Artificial Sequence
<220> FEATURE:
<223> OTHER INFORMATION: Synthetic Construct

<400> SEQUENCE: 471
agtcgttagg cgtt                                                        14

<210> SEQ ID NO 472
<211> LENGTH: 14
<212> TYPE: DNA
<213> ORGANISM: Artificial Sequence
<220> FEATURE:
<223> OTHER INFORMATION: Synthetic Construct

<400> SEQUENCE: 472
acgcgaaacc aaat                                                        14

<210> SEQ ID NO 473
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 473
gtcgttaggc gttt                                                         14

<210> SEQ ID NO 474
<211> LENGTH: 14
<212> TYPE: DNA
<213> ORGANISM: Artificial Sequence
<220> FEATURE:
<223> OTHER INFORMATION: Synthetic Construct

<400> SEQUENCE: 474
acgcgaaacc aaat                                                         14

<210> SEQ ID NO 475
<211> LENGTH: 14
<212> TYPE: DNA
<213> ORGANISM: Artificial Sequence
<220> FEATURE:
<223> OTHER INFORMATION: Synthetic Construct

<400> SEQUENCE: 475
tcgttaggcg tttt                                                         14

<210> SEQ ID NO 476
<211> LENGTH: 14
<212> TYPE: DNA
<213> ORGANISM: Artificial Sequence
<220> FEATURE:
<223> OTHER INFORMATION: Synthetic Construct

<400> SEQUENCE: 476
acgcgaaacc aaat                                                         14

<210> SEQ ID NO 477
<211> LENGTH: 14
<212> TYPE: DNA
<213> ORGANISM: Artificial Sequence
<220> FEATURE:
<223> OTHER INFORMATION: Synthetic Construct

<400> SEQUENCE: 477
cgttaggcgt tttg                                                         14

<210> SEQ ID NO 478
<211> LENGTH: 14
<212> TYPE: DNA
<213> ORGANISM: Artificial Sequence
<220> FEATURE:
<223> OTHER INFORMATION: Synthetic Construct

<400> SEQUENCE: 478
acgcgaaacc aaat                                                         14

<210> SEQ ID NO 479
<211> LENGTH: 14
<212> TYPE: DNA
<213> ORGANISM: Artificial Sequence
<220> FEATURE:
<223> OTHER INFORMATION: Synthetic Construct

<400> SEQUENCE: 479
```
gttaggcgtt ttgc                                              14

<210> SEQ ID NO 480
<211> LENGTH: 14
<212> TYPE: DNA
<213> ORGANISM: Artificial Sequence
<220> FEATURE:
<223> OTHER INFORMATION: Synthetic Construct

<400> SEQUENCE: 480
acgcgaaacc aaat                                              14

<210> SEQ ID NO 481
<211> LENGTH: 14
<212> TYPE: DNA
<213> ORGANISM: Artificial Sequence
<220> FEATURE:
<223> OTHER INFORMATION: Synthetic Construct

<400> SEQUENCE: 481
ttaggcgttt tgcg                                              14

<210> SEQ ID NO 482
<211> LENGTH: 14
<212> TYPE: DNA
<213> ORGANISM: Artificial Sequence
<220> FEATURE:
<223> OTHER INFORMATION: Synthetic Construct

<400> SEQUENCE: 482
acgcgaaacc aaat                                              14

<210> SEQ ID NO 483
<211> LENGTH: 14
<212> TYPE: DNA
<213> ORGANISM: Artificial Sequence
<220> FEATURE:
<223> OTHER INFORMATION: Synthetic Construct

<400> SEQUENCE: 483
taggcgtttt gcga                                              14

<210> SEQ ID NO 484
<211> LENGTH: 14
<212> TYPE: DNA
<213> ORGANISM: Artificial Sequence
<220> FEATURE:
<223> OTHER INFORMATION: Synthetic Construct

<400> SEQUENCE: 484
acgcgaaacc aaat                                              14

<210> SEQ ID NO 485
<211> LENGTH: 14
<212> TYPE: DNA
<213> ORGANISM: Artificial Sequence
<220> FEATURE:
<223> OTHER INFORMATION: Synthetic Construct

<400> SEQUENCE: 485
aggcgttttg cgag                                              14

<210> SEQ ID NO 486
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 486
acgcgaaacc aaat                                                         14

<210> SEQ ID NO 487
<211> LENGTH: 14
<212> TYPE: DNA
<213> ORGANISM: Artificial Sequence
<220> FEATURE:
<223> OTHER INFORMATION: Synthetic Construct

<400> SEQUENCE: 487
ggcgttttgc gagt                                                         14

<210> SEQ ID NO 488
<211> LENGTH: 14
<212> TYPE: DNA
<213> ORGANISM: Artificial Sequence
<220> FEATURE:
<223> OTHER INFORMATION: Synthetic Construct

<400> SEQUENCE: 488
acgcgaaacc aaat                                                         14

<210> SEQ ID NO 489
<211> LENGTH: 14
<212> TYPE: DNA
<213> ORGANISM: Artificial Sequence
<220> FEATURE:
<223> OTHER INFORMATION: Synthetic Construct

<400> SEQUENCE: 489
gcgttttgcg agtt                                                         14

<210> SEQ ID NO 490
<211> LENGTH: 14
<212> TYPE: DNA
<213> ORGANISM: Artificial Sequence
<220> FEATURE:
<223> OTHER INFORMATION: Synthetic Construct

<400> SEQUENCE: 490
acgcgaaacc aaat                                                         14

<210> SEQ ID NO 491
<211> LENGTH: 14
<212> TYPE: DNA
<213> ORGANISM: Artificial Sequence
<220> FEATURE:
<223> OTHER INFORMATION: Synthetic Construct

<400> SEQUENCE: 491
cgttttgcga gttg                                                         14

<210> SEQ ID NO 492
<211> LENGTH: 14
<212> TYPE: DNA
<213> ORGANISM: Artificial Sequence
<220> FEATURE:
<223> OTHER INFORMATION: Synthetic Construct

<400> SEQUENCE: 492
acgcgaaacc aaat                                                         14
```

<210> SEQ ID NO 493
<211> LENGTH: 14
<212> TYPE: DNA
<213> ORGANISM: Artificial Sequence
<220> FEATURE:
<223> OTHER INFORMATION: Synthetic Construct

<400> SEQUENCE: 493
gttttgcgag ttgt                                                    14

<210> SEQ ID NO 494
<211> LENGTH: 14
<212> TYPE: DNA
<213> ORGANISM: Artificial Sequence
<220> FEATURE:
<223> OTHER INFORMATION: Synthetic Construct

<400> SEQUENCE: 494
acgcgaaacc aaat                                                    14

<210> SEQ ID NO 495
<211> LENGTH: 14
<212> TYPE: DNA
<213> ORGANISM: Artificial Sequence
<220> FEATURE:
<223> OTHER INFORMATION: Synthetic Construct

<400> SEQUENCE: 495
ttttgcgagt tgtt                                                    14

<210> SEQ ID NO 496
<211> LENGTH: 14
<212> TYPE: DNA
<213> ORGANISM: Artificial Sequence
<220> FEATURE:
<223> OTHER INFORMATION: Synthetic Construct

<400> SEQUENCE: 496
acgcgaaacc aaat                                                    14

<210> SEQ ID NO 497
<211> LENGTH: 14
<212> TYPE: DNA
<213> ORGANISM: Artificial Sequence
<220> FEATURE:
<223> OTHER INFORMATION: Synthetic Construct

<400> SEQUENCE: 497
tttgcgagtt gttt                                                    14

<210> SEQ ID NO 498
<211> LENGTH: 14
<212> TYPE: DNA
<213> ORGANISM: Artificial Sequence
<220> FEATURE:
<223> OTHER INFORMATION: Synthetic Construct

<400> SEQUENCE: 498
acgcgaaacc aaat                                                    14

<210> SEQ ID NO 499
<211> LENGTH: 14
<212> TYPE: DNA
<213> ORGANISM: Artificial Sequence
<220> FEATURE:

<223> OTHER INFORMATION: Synthetic Construct

<400> SEQUENCE: 499
ttgcgagttg tttt                                                         14

<210> SEQ ID NO 500
<211> LENGTH: 14
<212> TYPE: DNA
<213> ORGANISM: Artificial Sequence
<220> FEATURE:
<223> OTHER INFORMATION: Synthetic Construct

<400> SEQUENCE: 500
acgcgaaacc aaat                                                         14

<210> SEQ ID NO 501
<211> LENGTH: 14
<212> TYPE: DNA
<213> ORGANISM: Artificial Sequence
<220> FEATURE:
<223> OTHER INFORMATION: Synthetic Construct

<400> SEQUENCE: 501
tgcgagttgt tttc                                                         14

<210> SEQ ID NO 502
<211> LENGTH: 14
<212> TYPE: DNA
<213> ORGANISM: Artificial Sequence
<220> FEATURE:
<223> OTHER INFORMATION: Synthetic Construct

<400> SEQUENCE: 502
acgcgaaacc aaat                                                         14

<210> SEQ ID NO 503
<211> LENGTH: 14
<212> TYPE: DNA
<213> ORGANISM: Artificial Sequence
<220> FEATURE:
<223> OTHER INFORMATION: Synthetic Construct

<400> SEQUENCE: 503
gcgagttgtt ttcg                                                         14

<210> SEQ ID NO 504
<211> LENGTH: 14
<212> TYPE: DNA
<213> ORGANISM: Artificial Sequence
<220> FEATURE:
<223> OTHER INFORMATION: Synthetic Construct

<400> SEQUENCE: 504
acgcgaaacc aaat                                                         14

<210> SEQ ID NO 505
<211> LENGTH: 14
<212> TYPE: DNA
<213> ORGANISM: Artificial Sequence
<220> FEATURE:
<223> OTHER INFORMATION: Synthetic Construct

<400> SEQUENCE: 505
cgagttgttt tcgt                                                         14

```
<210> SEQ ID NO 506
<211> LENGTH: 14
<212> TYPE: DNA
<213> ORGANISM: Artificial Sequence
<220> FEATURE:
<223> OTHER INFORMATION: Synthetic Construct

<400> SEQUENCE: 506
acgcgaaacc aaat                                                      14

<210> SEQ ID NO 507
<211> LENGTH: 14
<212> TYPE: DNA
<213> ORGANISM: Artificial Sequence
<220> FEATURE:
<223> OTHER INFORMATION: Synthetic Construct

<400> SEQUENCE: 507
gagttgtttt cgtt                                                      14

<210> SEQ ID NO 508
<211> LENGTH: 14
<212> TYPE: DNA
<213> ORGANISM: Artificial Sequence
<220> FEATURE:
<223> OTHER INFORMATION: Synthetic Construct

<400> SEQUENCE: 508
acgcgaaacc aaat                                                      14

<210> SEQ ID NO 509
<211> LENGTH: 14
<212> TYPE: DNA
<213> ORGANISM: Artificial Sequence
<220> FEATURE:
<223> OTHER INFORMATION: Synthetic Construct

<400> SEQUENCE: 509
agttgttttc gttg                                                      14

<210> SEQ ID NO 510
<211> LENGTH: 14
<212> TYPE: DNA
<213> ORGANISM: Artificial Sequence
<220> FEATURE:
<223> OTHER INFORMATION: Synthetic Construct

<400> SEQUENCE: 510
acgcgaaacc aaat                                                      14

<210> SEQ ID NO 511
<211> LENGTH: 14
<212> TYPE: DNA
<213> ORGANISM: Artificial Sequence
<220> FEATURE:
<223> OTHER INFORMATION: Synthetic Construct

<400> SEQUENCE: 511
gttgttttcg ttgg                                                      14

<210> SEQ ID NO 512
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 512
acgcgaaacc aaat                                                    14

<210> SEQ ID NO 513
<211> LENGTH: 14
<212> TYPE: DNA
<213> ORGANISM: Artificial Sequence
<220> FEATURE:
<223> OTHER INFORMATION: Synthetic Construct

<400> SEQUENCE: 513
ttgttttcgt tggg                                                    14

<210> SEQ ID NO 514
<211> LENGTH: 14
<212> TYPE: DNA
<213> ORGANISM: Artificial Sequence
<220> FEATURE:
<223> OTHER INFORMATION: Synthetic Construct

<400> SEQUENCE: 514
acgcgaaacc aaat                                                    14

<210> SEQ ID NO 515
<211> LENGTH: 14
<212> TYPE: DNA
<213> ORGANISM: Artificial Sequence
<220> FEATURE:
<223> OTHER INFORMATION: Synthetic Construct

<400> SEQUENCE: 515
tgttttcgtt ggga                                                    14

<210> SEQ ID NO 516
<211> LENGTH: 14
<212> TYPE: DNA
<213> ORGANISM: Artificial Sequence
<220> FEATURE:
<223> OTHER INFORMATION: Synthetic Construct

<400> SEQUENCE: 516
acgcgaaacc aaat                                                    14

<210> SEQ ID NO 517
<211> LENGTH: 14
<212> TYPE: DNA
<213> ORGANISM: Artificial Sequence
<220> FEATURE:
<223> OTHER INFORMATION: Synthetic Construct

<400> SEQUENCE: 517
gttttcgttg ggag                                                    14

<210> SEQ ID NO 518
<211> LENGTH: 14
<212> TYPE: DNA
<213> ORGANISM: Artificial Sequence
<220> FEATURE:
<223> OTHER INFORMATION: Synthetic Construct

<400> SEQUENCE: 518
acgcgaaacc aaat                                                    14

<210> SEQ ID NO 519
<211> LENGTH: 14
```

```
<212> TYPE: DNA
<213> ORGANIS: Artificial Sequence
<220> FEATURE:
<223> OTHER INFORMATION: Synthetic Construct

<400> SEQUENCE: 519
ttttcgttgg gagg                                                        14

<210> SEQ ID NO 520
<211> LENGTH: 14
<212> TYPE: DNA
<213> ORGANISM: Artificial Sequence
<220> FEATURE:
<223> OTHER INFORMATION: Synthetic Construct

<400> SEQUENCE: 520
cgaaatccta cttc                                                        14

<210> SEQ ID NO 521
<211> LENGTH: 23
<212> TYPE: DNA
<213> ORGANISM: Artificial Sequence
<220> FEATURE:
<223> OTHER INFORMATION: Synthetic Construct

<400> SEQUENCE: 521 cgttttttt tgggattgt aga                                                23

<210> SEQ ID NO 522
<211> LENGTH: 14
<212> TYPE: DNA
<213> ORGANISM: Artificial Sequence
<220> FEATURE:
<223> OTHER INFORMATION: Synthetic Construct

<400> SEQUENCE: 522
tttcgttggg aggg                                                        14

<210> SEQ ID NO 523
<211> LENGTH: 14
<212> TYPE: DNA
<213> ORGANISM: Artificial Sequence
<220> FEATURE:
<223> OTHER INFORMATION: Synthetic Construct

<400> SEQUENCE: 523
cgaaatccta cttc                                                        14

<210> SEQ ID NO 524
<211> LENGTH: 14
<212> TYPE: DNA
<213> ORGANISM: Artificial Sequence
<220> FEATURE:
<223> OTHER INFORMATION: Synthetic Construct

<400> SEQUENCE: 524
ttcgttggga gggg                                                        14

<210> SEQ ID NO 525
<211> LENGTH: 14
<212> TYPE: DNA
<213> ORGANISM: Artificial Sequence
<220> FEATURE:
<223> OTHER INFORMATION: Synthetic Construct

<400> SEQUENCE: 525
```
cgaaatccta cttc                                                              14

<210> SEQ ID NO 526
<211> LENGTH: 14
<212> TYPE: DNA
<213> ORGANISM: Artificial Sequence
<220> FEATURE:
<223> OTHER INFORMATION: Synthetic Construct

<400> SEQUENCE: 526
tcgttgggag gggc                                                              14

<210> SEQ ID NO 527
<211> LENGTH: 14
<212> TYPE: DNA
<213> ORGANISM: Artificial Sequence
<220> FEATURE:
<223> OTHER INFORMATION: Synthetic Construct

<400> SEQUENCE: 527
cgaaatccta cttc                                                              14

<210> SEQ ID NO 528
<211> LENGTH: 14
<212> TYPE: DNA
<213> ORGANISM: Artificial Sequence
<220> FEATURE:
<223> OTHER INFORMATION: Synthetic Construct

<400> SEQUENCE: 528
cgttgggagg ggcg                                                              14

<210> SEQ ID NO 529
<211> LENGTH: 14
<212> TYPE: DNA
<213> ORGANISM: Artificial Sequence
<220> FEATURE:
<223> OTHER INFORMATION: Synthetic Construct

<400> SEQUENCE: 529
cgaaatccta cttc                                                              14

<210> SEQ ID NO 530
<211> LENGTH: 14
<212> TYPE: DNA
<213> ORGANISM: Artificial Sequence
<220> FEATURE:
<223> OTHER INFORMATION: Synthetic Construct

<400> SEQUENCE: 530
gttgggaggg gcga                                                              14

<210> SEQ ID NO 531
<211> LENGTH: 14
<212> TYPE: DNA
<213> ORGANISM: Artificial Sequence
<220> FEATURE:
<223> OTHER INFORMATION: Synthetic Construct

<400> SEQUENCE: 531
cgaaatccta cttc                                                              14

<210> SEQ ID NO 532
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 532
ttgggagggg cgag                                                        14

<210> SEQ ID NO 533
<211> LENGTH: 14
<212> TYPE: DNA
<213> ORGANISM: Artificial Sequence
<220> FEATURE:
<223> OTHER INFORMATION: Synthetic Construct

<400> SEQUENCE: 533
cgaaatccta cttc                                                        14

<210> SEQ ID NO 534
<211> LENGTH: 14
<212> TYPE: DNA
<213> ORGANISM: Artificial Sequence
<220> FEATURE:
<223> OTHER INFORMATION: Synthetic Construct

<400> SEQUENCE: 534
tgggaggggc gagg                                                        14

<210> SEQ ID NO 535
<211> LENGTH: 14
<212> TYPE: DNA
<213> ORGANISM: Artificial Sequence
<220> FEATURE:
<223> OTHER INFORMATION: Synthetic Construct

<400> SEQUENCE: 535
cgaaatccta cttc                                                        14

<210> SEQ ID NO 536
<211> LENGTH: 14
<212> TYPE: DNA
<213> ORGANISM: Artificial Sequence
<220> FEATURE:
<223> OTHER INFORMATION: Synthetic Construct

<400> SEQUENCE: 536
gggaggggcg aggt                                                        14

<210> SEQ ID NO 537
<211> LENGTH: 14
<212> TYPE: DNA
<213> ORGANISM: Artificial Sequence
<220> FEATURE:
<223> OTHER INFORMATION: Synthetic Construct

<400> SEQUENCE: 537
cgaaatccta cttc                                                        14

<210> SEQ ID NO 538
<211> LENGTH: 14
<212> TYPE: DNA
<213> ORGANISM: Artificial Sequence
<220> FEATURE:
<223> OTHER INFORMATION: Synthetic Construct

<400> SEQUENCE: 538
ggaggggcga ggtt                                                        14
```

```
<210> SEQ ID NO 539
<211> LENGTH: 14
<212> TYPE: DNA
<213> ORGANISM: Artificial Sequence
<220> FEATURE:
<223> OTHER INFORMATION: Synthetic Construct

<400> SEQUENCE: 539
cgaaatccta cttc                                                        14

<210> SEQ ID NO 540
<211> LENGTH: 14
<212> TYPE: DNA
<213> ORGANISM: Artificial Sequence
<220> FEATURE:
<223> OTHER INFORMATION: Synthetic Construct

<400> SEQUENCE: 540
gaggggcgag gttg                                                        14

<210> SEQ ID NO 541
<211> LENGTH: 14
<212> TYPE: DNA
<213> ORGANISM: Artificial Sequence
<220> FEATURE:
<223> OTHER INFORMATION: Synthetic Construct

<400> SEQUENCE: 541
cgaaatccta cttc                                                        14

<210> SEQ ID NO 542
<211> LENGTH: 14
<212> TYPE: DNA
<213> ORGANISM: Artificial Sequence
<220> FEATURE:
<223> OTHER INFORMATION: Synthetic Construct

<400> SEQUENCE: 542
aggggcgagg ttgt                                                        14

<210> SEQ ID NO 543
<211> LENGTH: 14
<212> TYPE: DNA
<213> ORGANISM: Artificial Sequence
<220> FEATURE:
<223> OTHER INFORMATION: Synthetic Construct

<400> SEQUENCE: 543
cgaaatccta cttc                                                        14

<210> SEQ ID NO 544
<211> LENGTH: 14
<212> TYPE: DNA
<213> ORGANISM: Artificial Sequence
<220> FEATURE:
<223> OTHER INFORMATION: Synthetic Construct

<400> SEQUENCE: 544
ggggcgaggt tgtt                                                        14

<210> SEQ ID NO 545
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 545
cgaaatccta cttc                                                        14

<210> SEQ ID NO 546
<211> LENGTH: 14
<212> TYPE: DNA
<213> ORGANISM: Artificial Sequence
<220> FEATURE:
<223> OTHER INFORMATION: Synthetic Construct

<400> SEQUENCE: 546
gggcgaggtt gtta                                                        14

<210> SEQ ID NO 547
<211> LENGTH: 14
<212> TYPE: DNA
<213> ORGANISM: Artificial Sequence
<220> FEATURE:
<223> OTHER INFORMATION: Synthetic Construct

<400> SEQUENCE: 547
cgaaatccta cttc                                                        14

<210> SEQ ID NO 548
<211> LENGTH: 14
<212> TYPE: DNA
<213> ORGANISM: Artificial Sequence
<220> FEATURE:
<223> OTHER INFORMATION: Synthetic Construct

<400> SEQUENCE: 548
ggcgaggttg ttat                                                        14

<210> SEQ ID NO 549
<211> LENGTH: 14
<212> TYPE: DNA
<213> ORGANISM: Artificial Sequence
<220> FEATURE:
<223> OTHER INFORMATION: Synthetic Construct

<400> SEQUENCE: 549
cgaaatccta cttc                                                        14

<210> SEQ ID NO 550
<211> LENGTH: 14
<212> TYPE: DNA
<213> ORGANISM: Artificial Sequence
<220> FEATURE:
<223> OTHER INFORMATION: Synthetic Construct

<400> SEQUENCE: 550
gcgaggttgt tatt                                                        14

<210> SEQ ID NO 551
<211> LENGTH: 14
<212> TYPE: DNA
<213> ORGANISM: Artificial Sequence
<220> FEATURE:
<223> OTHER INFORMATION: Synthetic Construct

<400> SEQUENCE: 551
cgaaatccta cttc                                                        14

<210> SEQ ID NO 552

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 552
cgaggttgtt attt                                                         14

<210> SEQ ID NO 553
<211> LENGTH: 14
<212> TYPE: DNA
<213> ORGANISM: Artificial Sequence
<220> FEATURE:
<223> OTHER INFORMATION: Synthetic Construct

<400> SEQUENCE: 553
cgaaatccta cttc                                                         14

<210> SEQ ID NO 554
<211> LENGTH: 14
<212> TYPE: DNA
<213> ORGANISM: Artificial Sequence
<220> FEATURE:
<223> OTHER INFORMATION: Synthetic Construct

<400> SEQUENCE: 554
gaggttgtta tttg                                                         14

<210> SEQ ID NO 555
<211> LENGTH: 14
<212> TYPE: DNA
<213> ORGANISM: Artificial Sequence
<220> FEATURE:
<223> OTHER INFORMATION: Synthetic Construct

<400> SEQUENCE: 555
cgaaatccta cttc                                                         14

<210> SEQ ID NO 556
<211> LENGTH: 14
<212> TYPE: DNA
<213> ORGANISM: Artificial Sequence
<220> FEATURE:
<223> OTHER INFORMATION: Synthetic Construct

<400> SEQUENCE: 556
aggttgttat ttgt                                                         14

<210> SEQ ID NO 557
<211> LENGTH: 14
<212> TYPE: DNA
<213> ORGANISM: Artificial Sequence
<220> FEATURE:
<223> OTHER INFORMATION: Synthetic Construct

<400> SEQUENCE: 557
cgaaatccta cttc                                                         14

<210> SEQ ID NO 558
<211> LENGTH: 14
<212> TYPE: DNA
<213> ORGANISM: Artificial Sequence
<220> FEATURE:
<223> OTHER INFORMATION: Synthetic Construct

<400> SEQUENCE: 558
```

```
ggttgttatt tgtt                                                   14
```

<210> SEQ ID NO 559
<211> LENGTH: 14
<212> TYPE: DNA
<213> ORGANISM: Artificial Sequence
<220> FEATURE:
<223> OTHER INFORMATION: Synthetic Construct

<400> SEQUENCE: 559

```
cgaaatccta cttc                                                   14
```

<210> SEQ ID NO 560
<211> LENGTH: 14
<212> TYPE: DNA
<213> ORGANISM: Artificial Sequence
<220> FEATURE:
<223> OTHER INFORMATION: Synthetic Construct

<400> SEQUENCE: 560

```
gttgttattt gtta                                                   14
```

<210> SEQ ID NO 561
<211> LENGTH: 14
<212> TYPE: DNA
<213> ORGANISM: Artificial Sequence
<220> FEATURE:
<223> OTHER INFORMATION: Synthetic Construct

<400> SEQUENCE: 561

```
cgaaatccta cttc                                                   14
```

<210> SEQ ID NO 562
<211> LENGTH: 14
<212> TYPE: DNA
<213> ORGANISM: Artificial Sequence
<220> FEATURE:
<223> OTHER INFORMATION: Synthetic Construct

<400> SEQUENCE: 562

```
ttgttatttg ttag                                                   14
```

<210> SEQ ID NO 563
<211> LENGTH: 14
<212> TYPE: DNA
<213> ORGANISM: Artificial Sequence
<220> FEATURE:
<223> OTHER INFORMATION: Synthetic Construct

<400> SEQUENCE: 563

```
cgaaatccta cttc                                                   14
```

<210> SEQ ID NO 564
<211> LENGTH: 14
<212> TYPE: DNA
<213> ORGANISM: Artificial Sequence
<220> FEATURE:
<223> OTHER INFORMATION: Synthetic Construct

<400> SEQUENCE: 564

```
tgttatttgt tagg                                                   14
```

<210> SEQ ID NO 565
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 565
cgaaatccta cttc                                                         14

<210> SEQ ID NO 566
<211> LENGTH: 14
<212> TYPE: DNA
<213> ORGANISM: Artificial Sequence
<220> FEATURE:
<223> OTHER INFORMATION: Synthetic Construct

<400> SEQUENCE: 566
gttatttgtt aggg                                                         14

<210> SEQ ID NO 567
<211> LENGTH: 14
<212> TYPE: DNA
<213> ORGANISM: Artificial Sequence
<220> FEATURE:
<223> OTHER INFORMATION: Synthetic Construct

<400> SEQUENCE: 567
cgaaatccta cttc                                                         14

<210> SEQ ID NO 568
<211> LENGTH: 14
<212> TYPE: DNA
<213> ORGANISM: Artificial Sequence
<220> FEATURE:
<223> OTHER INFORMATION: Synthetic Construct

<400> SEQUENCE: 568
ttatttgtta gggc                                                         14

<210> SEQ ID NO 569
<211> LENGTH: 14
<212> TYPE: DNA
<213> ORGANISM: Artificial Sequence
<220> FEATURE:
<223> OTHER INFORMATION: Synthetic Construct

<400> SEQUENCE: 569
cgaaatccta cttc                                                         14

<210> SEQ ID NO 570
<211> LENGTH: 14
<212> TYPE: DNA
<213> ORGANISM: Artificial Sequence
<220> FEATURE:
<223> OTHER INFORMATION: Synthetic Construct

<400> SEQUENCE: 570
tatttgttag ggcg                                                         14

<210> SEQ ID NO 571
<211> LENGTH: 14
<212> TYPE: DNA
<213> ORGANISM: Artificial Sequence
<220> FEATURE:
<223> OTHER INFORMATION: Synthetic Construct

<400> SEQUENCE: 571
cgaaatccta cttc                                                         14
```

```
<210> SEQ ID NO 572
<211> LENGTH: 14
<212> TYPE: DNA
<213> ORGANISM: Artificial Sequence
<220> FEATURE:
<223> OTHER INFORMATION: Synthetic Construct

<400> SEQUENCE: 572
atttgttagg gcgc                                                        14

<210> SEQ ID NO 573
<211> LENGTH: 14
<212> TYPE: DNA
<213> ORGANISM: Artificial Sequence
<220> FEATURE:
<223> OTHER INFORMATION: Synthetic Construct

<400> SEQUENCE: 573
cgaaatccta cttc                                                        14

<210> SEQ ID NO 574
<211> LENGTH: 14
<212> TYPE: DNA
<213> ORGANISM: Artificial Sequence
<220> FEATURE:
<223> OTHER INFORMATION: Synthetic Construct

<400> SEQUENCE: 574
tttgttaggg cgcg                                                        14

<210> SEQ ID NO 575
<211> LENGTH: 14
<212> TYPE: DNA
<213> ORGANISM: Artificial Sequence
<220> FEATURE:
<223> OTHER INFORMATION: Synthetic Construct

<400> SEQUENCE: 575
cgaaatccta cttc                                                        14

<210> SEQ ID NO 576
<211> LENGTH: 14
<212> TYPE: DNA
<213> ORGANISM: Artificial Sequence
<220> FEATURE:
<223> OTHER INFORMATION: Synthetic Construct

<400> SEQUENCE: 576
ttgttagggc gcga                                                        14

<210> SEQ ID NO 577
<211> LENGTH: 14
<212> TYPE: DNA
<213> ORGANISM: Artificial Sequence
<220> FEATURE:
<223> OTHER INFORMATION: Synthetic Construct

<400> SEQUENCE: 577
cgaaatccta cttc                                                        14

<210> SEQ ID NO 578
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 578
tgttagggcg cgag                                                     14

<210> SEQ ID NO 579
<211> LENGTH: 14
<212> TYPE: DNA
<213> ORGANISM: Artificial Sequence
<220> FEATURE:
<223> OTHER INFORMATION: Synthetic Construct

<400> SEQUENCE: 579
cgaaatccta cttc                                                     14

<210> SEQ ID NO 580
<211> LENGTH: 14
<212> TYPE: DNA
<213> ORGANISM: Artificial Sequence
<220> FEATURE:
<223> OTHER INFORMATION: Synthetic Construct

<400> SEQUENCE: 580
gttagggcgc gagg                                                     14

<210> SEQ ID NO 581
<211> LENGTH: 14
<212> TYPE: DNA
<213> ORGANISM: Artificial Sequence
<220> FEATURE:
<223> OTHER INFORMATION: Synthetic Construct

<400> SEQUENCE: 581
cgaaatccta cttc                                                     14

<210> SEQ ID NO 582
<211> LENGTH: 14
<212> TYPE: DNA
<213> ORGANISM: Artificial Sequence
<220> FEATURE:
<223> OTHER INFORMATION: Synthetic Construct

<400> SEQUENCE: 582
ttagggcgcg agga                                                     14

<210> SEQ ID NO 583
<211> LENGTH: 14
<212> TYPE: DNA
<213> ORGANISM: Artificial Sequence
<220> FEATURE:
<223> OTHER INFORMATION: Synthetic Construct

<400> SEQUENCE: 583
cgaaatccta cttc                                                     14

<210> SEQ ID NO 584
<211> LENGTH: 14
<212> TYPE: DNA
<213> ORGANISM: Artificial Sequence
<220> FEATURE:
<223> OTHER INFORMATION: Synthetic Construct

<400> SEQUENCE: 584
tagggcgcga ggag                                                     14

```
<210> SEQ ID NO 585
<211> LENGTH: 14
<212> TYPE: DNA
<213> ORGANISM: Artificial Sequence
<220> FEATURE:
<223> OTHER INFORMATION: Synthetic Construct

<400> SEQUENCE: 585
cgaaatccta cttc                                                    14

<210> SEQ ID NO 586
<211> LENGTH: 14
<212> TYPE: DNA
<213> ORGANISM: Artificial Sequence
<220> FEATURE:
<223> OTHER INFORMATION: Synthetic Construct

<400> SEQUENCE: 586
agggcgcgag gagt                                                    14

<210> SEQ ID NO 587
<211> LENGTH: 14
<212> TYPE: DNA
<213> ORGANISM: Artificial Sequence
<220> FEATURE:
<223> OTHER INFORMATION: Synthetic Construct

<400> SEQUENCE: 587
cgaaatccta cttc                                                    14

<210> SEQ ID NO 588
<211> LENGTH: 14
<212> TYPE: DNA
<213> ORGANISM: Artificial Sequence
<220> FEATURE:
<223> OTHER INFORMATION: Synthetic Construct

<400> SEQUENCE: 588
gggcgcgagg agtt                                                    14

<210> SEQ ID NO 589
<211> LENGTH: 14
<212> TYPE: DNA
<213> ORGANISM: Artificial Sequence
<220> FEATURE:
<223> OTHER INFORMATION: Synthetic Construct

<400> SEQUENCE: 589
cgaaatccta cttc                                                    14

<210> SEQ ID NO 590
<211> LENGTH: 14
<212> TYPE: DNA
<213> ORGANISM: Artificial Sequence
<220> FEATURE:
<223> OTHER INFORMATION: Synthetic Construct

<400> SEQUENCE: 590
ggcgcgagga gttt                                                    14

<210> SEQ ID NO 591
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 591
cgaaatccta cttc                                                      14

<210> SEQ ID NO 592
<211> LENGTH: 14
<212> TYPE: DNA
<213> ORGANISM: Artificial Sequence
<220> FEATURE:
<223> OTHER INFORMATION: Synthetic Construct

<400> SEQUENCE: 592
gcgcgaggag tttt                                                      14

<210> SEQ ID NO 593
<211> LENGTH: 14
<212> TYPE: DNA
<213> ORGANISM: Artificial Sequence
<220> FEATURE:
<223> OTHER INFORMATION: Synthetic Construct

<400> SEQUENCE: 593
cgaaatccta cttc                                                      14

<210> SEQ ID NO 594
<211> LENGTH: 14
<212> TYPE: DNA
<213> ORGANISM: Artificial Sequence
<220> FEATURE:
<223> OTHER INFORMATION: Synthetic Construct

<400> SEQUENCE: 594
cgcgaggagt ttta                                                      14

<210> SEQ ID NO 595
<211> LENGTH: 14
<212> TYPE: DNA
<213> ORGANISM: Artificial Sequence
<220> FEATURE:
<223> OTHER INFORMATION: Synthetic Construct

<400> SEQUENCE: 595
cgaaatccta cttc                                                      14

<210> SEQ ID NO 596
<211> LENGTH: 14
<212> TYPE: DNA
<213> ORGANISM: Artificial Sequence
<220> FEATURE:
<223> OTHER INFORMATION: Synthetic Construct

<400> SEQUENCE: 596
gcgaggagtt ttag                                                      14

<210> SEQ ID NO 597
<211> LENGTH: 14
<212> TYPE: DNA
<213> ORGANISM: Artificial Sequence
<220> FEATURE:
<223> OTHER INFORMATION: Synthetic Construct

<400> SEQUENCE: 597
cgaaatccta cttc                                                      14

<210> SEQ ID NO 598
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 598
cgaggagttt tagc                                                 14

<210> SEQ ID NO 599
<211> LENGTH: 14
<212> TYPE: DNA
<213> ORGANISM: Artificial Sequence
<220> FEATURE:
<223> OTHER INFORMATION: Synthetic Construct

<400> SEQUENCE: 599
cgaaatccta cttc                                                 14

<210> SEQ ID NO 600
<211> LENGTH: 14
<212> TYPE: DNA
<213> ORGANISM: Artificial Sequence
<220> FEATURE:
<223> OTHER INFORMATION: Synthetic Construct

<400> SEQUENCE: 600
gaggagtttt agcg                                                 14

<210> SEQ ID NO 601
<211> LENGTH: 14
<212> TYPE: DNA
<213> ORGANISM: Artificial Sequence
<220> FEATURE:
<223> OTHER INFORMATION: Synthetic Construct

<400> SEQUENCE: 601
cgaaatccta cttc                                                 14

<210> SEQ ID NO 602
<211> LENGTH: 14
<212> TYPE: DNA
<213> ORGANISM: Artificial Sequence
<220> FEATURE:
<223> OTHER INFORMATION: Synthetic Construct

<400> SEQUENCE: 602
aggagtttta gcgc                                                 14

<210> SEQ ID NO 603
<211> LENGTH: 14
<212> TYPE: DNA
<213> ORGANISM: Artificial Sequence
<220> FEATURE:
<223> OTHER INFORMATION: Synthetic Construct

<400> SEQUENCE: 603
cgaaatccta cttc                                                 14

<210> SEQ ID NO 604
<211> LENGTH: 14
<212> TYPE: DNA
<213> ORGANISM: Artificial Sequence
<220> FEATURE:
<223> OTHER INFORMATION: Synthetic Construct

<400> SEQUENCE: 604
```

| | |
|---|---|
| ggagttttag cgcg | 14 |

<210> SEQ ID NO 605
<211> LENGTH: 14
<212> TYPE: DNA
<213> ORGANISM: Artificial Sequence
<220> FEATURE:
<223> OTHER INFORMATION: Synthetic Construct

<400> SEQUENCE: 605

| | |
|---|---|
| cgaaatccta cttc | 14 |

<210> SEQ ID NO 606
<211> LENGTH: 14
<212> TYPE: DNA
<213> ORGANISM: Artificial Sequence
<220> FEATURE:
<223> OTHER INFORMATION: Synthetic Construct

<400> SEQUENCE: 606

| | |
|---|---|
| gagttttagc gcgg | 14 |

<210> SEQ ID NO 607
<211> LENGTH: 14
<212> TYPE: DNA
<213> ORGANISM: Artificial Sequence
<220> FEATURE:
<223> OTHER INFORMATION: Synthetic Construct

<400> SEQUENCE: 607

| | |
|---|---|
| cgaaatccta cttc | 14 |

<210> SEQ ID NO 608
<211> LENGTH: 14
<212> TYPE: DNA
<213> ORGANISM: Artificial Sequence
<220> FEATURE:
<223> OTHER INFORMATION: Synthetic Construct

<400> SEQUENCE: 608

| | |
|---|---|
| agttttagcg cggt | 14 |

<210> SEQ ID NO 609
<211> LENGTH: 14
<212> TYPE: DNA
<213> ORGANISM: Artificial Sequence
<220> FEATURE:
<223> OTHER INFORMATION: Synthetic Construct

<400> SEQUENCE: 609

| | |
|---|---|
| cgaaatccta cttc | 14 |

<210> SEQ ID NO 610
<211> LENGTH: 14
<212> TYPE: DNA
<213> ORGANISM: Artificial Sequence
<220> FEATURE:
<223> OTHER INFORMATION: Synthetic Construct

<400> SEQUENCE: 610

| | |
|---|---|
| gttttagcgc ggtt | 14 |

<210> SEQ ID NO 611
<211> LENGTH: 14
<212> TYPE: DNA
<213> ORGANISM: Artificial Sequence -continued
<220> FEATURE:
<223> OTHER INFORMATION: Synthetic Construct

<400> SEQUENCE: 611
cgaaatccta cttc                                                        14

<210> SEQ ID NO 612
<211> LENGTH: 14
<212> TYPE: DNA
<213> ORGANISM: Artificial Sequence
<220> FEATURE:
<223> OTHER INFORMATION: Synthetic Construct

<400> SEQUENCE: 612
ttttagcgcg gttt                                                        14

<210> SEQ ID NO 613
<211> LENGTH: 14
<212> TYPE: DNA
<213> ORGANISM: Artificial Sequence
<220> FEATURE:
<223> OTHER INFORMATION: Synthetic Construct

<400> SEQUENCE: 613
cgaaatccta cttc                                                        14

<210> SEQ ID NO 614
<211> LENGTH: 14
<212> TYPE: DNA
<213> ORGANISM: Artificial Sequence
<220> FEATURE:
<223> OTHER INFORMATION: Synthetic Construct

<400> SEQUENCE: 614
tttagcgcgg tttg                                                        14

<210> SEQ ID NO 615
<211> LENGTH: 14
<212> TYPE: DNA
<213> ORGANISM: Artificial Sequence
<220> FEATURE:
<223> OTHER INFORMATION: Synthetic Construct

<400> SEQUENCE: 615
cgaaatccta cttc                                                        14

<210> SEQ ID NO 616
<211> LENGTH: 14
<212> TYPE: DNA
<213> ORGANISM: Artificial Sequence
<220> FEATURE:
<223> OTHER INFORMATION: Synthetic Construct

<400> SEQUENCE: 616
ttagcgcggt ttgg                                                        14

<210> SEQ ID NO 617
<211> LENGTH: 14
<212> TYPE: DNA
<213> ORGANISM: Artificial Sequence
<220> FEATURE:
<223> OTHER INFORMATION: Synthetic Construct

<400> SEQUENCE: 617
cgaaatccta cttc                                                        14

```
<210> SEQ ID NO 618
<211> LENGTH: 14
<212> TYPE: DNA
<213> ORGANISM: Artificial Sequence
<220> FEATURE:
<223> OTHER INFORMATION: Synthetic Construct

<400> SEQUENCE: 618
tagcgcggtt tgga                                                    14

<210> SEQ ID NO 619
<211> LENGTH: 14
<212> TYPE: DNA
<213> ORGANISM: Artificial Sequence
<220> FEATURE:
<223> OTHER INFORMATION: Synthetic Construct

<400> SEQUENCE: 619
cgaaatccta cttc                                                    14

<210> SEQ ID NO 620
<211> LENGTH: 14
<212> TYPE: DNA
<213> ORGANISM: Artificial Sequence
<220> FEATURE:
<223> OTHER INFORMATION: Synthetic Construct

<400> SEQUENCE: 620
agcgcggttt ggag                                                    14

<210> SEQ ID NO 621
<211> LENGTH: 14
<212> TYPE: DNA
<213> ORGANISM: Artificial Sequence
<220> FEATURE:
<223> OTHER INFORMATION: Synthetic Construct

<400> SEQUENCE: 621
cgaaatccta cttc                                                    14

<210> SEQ ID NO 622
<211> LENGTH: 14
<212> TYPE: DNA
<213> ORGANISM: Artificial Sequence
<220> FEATURE:
<223> OTHER INFORMATION: Synthetic Construct

<400> SEQUENCE: 622
gcgcggtttg gaga                                                    14

<210> SEQ ID NO 623
<211> LENGTH: 14
<212> TYPE: DNA
<213> ORGANISM: Artificial Sequence
<220> FEATURE:
<223> OTHER INFORMATION: Synthetic Construct

<400> SEQUENCE: 623 ccgaacctttt aaac                                                   14

<210> SEQ ID NO 624
<211> LENGTH: 25
<212> TYPE: DNA
<213> ORGANISM: Artificial Sequence
<220> FEATURE:
<223> OTHER INFORMATION: Synthetic Construct
```

<400> SEQUENCE: 624
gtgcgcgggc gggcgcgtat atttc                                              25

<210> SEQ ID NO 625
<211> LENGTH: 14
<212> TYPE: DNA
<213> ORGANISM: Artificial Sequence
<220> FEATURE:
<223> OTHER INFORMATION: Synthetic Construct

<400> SEQUENCE: 625
cgcggtttgg agaa                                                          14

<210> SEQ ID NO 626
<211> LENGTH: 14
<212> TYPE: DNA
<213> ORGANISM: Artificial Sequence
<220> FEATURE:
<223> OTHER INFORMATION: Synthetic Construct

<400> SEQUENCE: 626
ccgaaccttt aaac                                                          14

<210> SEQ ID NO 627
<211> LENGTH: 14
<212> TYPE: DNA
<213> ORGANISM: Artificial Sequence
<220> FEATURE:
<223> OTHER INFORMATION: Synthetic Construct

<400> SEQUENCE: 627
gcggtttgga gaat                                                          14

<210> SEQ ID NO 628
<211> LENGTH: 14
<212> TYPE: DNA
<213> ORGANISM: Artificial Sequence
<220> FEATURE:
<223> OTHER INFORMATION: Synthetic Construct

<400> SEQUENCE: 628
ccgaaccttt aaac                                                          14

<210> SEQ ID NO 629
<211> LENGTH: 14
<212> TYPE: DNA
<213> ORGANISM: Artificial Sequence
<220> FEATURE:
<223> OTHER INFORMATION: Synthetic Construct

<400> SEQUENCE: 629
cggtttggag aatt                                                          14

<210> SEQ ID NO 630
<211> LENGTH: 14
<212> TYPE: DNA
<213> ORGANISM: Artificial Sequence
<220> FEATURE:
<223> OTHER INFORMATION: Synthetic Construct

<400> SEQUENCE: 630
ccgaaccttt aaac                                                          14

<210> SEQ ID NO 631

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 631
ggtttggaga attt                                                  14

<210> SEQ ID NO 632
<211> LENGTH: 14
<212> TYPE: DNA
<213> ORGANISM: Artificial Sequence
<220> FEATURE:
<223> OTHER INFORMATION: Synthetic Construct

<400> SEQUENCE: 632
ccgaaccttt aaac                                                  14

<210> SEQ ID NO 633
<211> LENGTH: 14
<212> TYPE: DNA
<213> ORGANISM: Artificial Sequence
<220> FEATURE:
<223> OTHER INFORMATION: Synthetic Construct

<400> SEQUENCE: 633
gtttggagaa tttg                                                  14

<210> SEQ ID NO 634
<211> LENGTH: 14
<212> TYPE: DNA
<213> ORGANISM: Artificial Sequence
<220> FEATURE:
<223> OTHER INFORMATION: Synthetic Construct

<400> SEQUENCE: 634
ccgaaccttt aaac                                                  14

<210> SEQ ID NO 635
<211> LENGTH: 14
<212> TYPE: DNA
<213> ORGANISM: Artificial Sequence
<220> FEATURE:
<223> OTHER INFORMATION: Synthetic Construct

<400> SEQUENCE: 635
tttggagaat ttgg                                                  14

<210> SEQ ID NO 636
<211> LENGTH: 14
<212> TYPE: DNA
<213> ORGANISM: Artificial Sequence
<220> FEATURE:
<223> OTHER INFORMATION: Synthetic Construct

<400> SEQUENCE: 636
ccgaaccttt aaac                                                  14

<210> SEQ ID NO 637
<211> LENGTH: 14
<212> TYPE: DNA
<213> ORGANISM: Artificial Sequence
<220> FEATURE:
<223> OTHER INFORMATION: Synthetic Construct

<400> SEQUENCE: 637
```
ttggagaatt tggt                                                          14

<210> SEQ ID NO 638
<211> LENGTH: 14
<212> TYPE: DNA
<213> ORGANISM: Artificial Sequence
<220> FEATURE:
<223> OTHER INFORMATION: Synthetic Construct

<400> SEQUENCE: 638
ccgaaccttt aaac                                                          14

<210> SEQ ID NO 639
<211> LENGTH: 14
<212> TYPE: DNA
<213> ORGANISM: Artificial Sequence
<220> FEATURE:
<223> OTHER INFORMATION: Synthetic Construct

<400> SEQUENCE: 639
tggagaattt ggtt                                                          14

<210> SEQ ID NO 640
<211> LENGTH: 14
<212> TYPE: DNA
<213> ORGANISM: Artificial Sequence
<220> FEATURE:
<223> OTHER INFORMATION: Synthetic Construct

<400> SEQUENCE: 640
ccgaaccttt aaac                                                          14

<210> SEQ ID NO 641
<211> LENGTH: 14
<212> TYPE: DNA
<213> ORGANISM: Artificial Sequence
<220> FEATURE:
<223> OTHER INFORMATION: Synthetic Construct

<400> SEQUENCE: 641
ggagaatttg gttt                                                          14

<210> SEQ ID NO 642
<211> LENGTH: 14
<212> TYPE: DNA
<213> ORGANISM: Artificial Sequence
<220> FEATURE:
<223> OTHER INFORMATION: Synthetic Construct

<400> SEQUENCE: 642
ccgaacsttt aaac                                                          14

<210> SEQ ID NO 643
<211> LENGTH: 14
<212> TYPE: DNA
<213> ORGANISM: Artificial Sequence
<220> FEATURE:
<223> OTHER INFORMATION: Synthetic Construct

<400> SEQUENCE: 643
gagaatttgg tttc                                                          14

<210> SEQ ID NO 644
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 644
ccgaaccttt aaac                                                   14

<210> SEQ ID NO 645
<211> LENGTH: 14
<212> TYPE: DNA
<213> ORGANISM: Artificial Sequence
<220> FEATURE:
<223> OTHER INFORMATION: Synthetic Construct

<400> SEQUENCE: 645
agaatttggt ttcg                                                   14

<210> SEQ ID NO 646
<211> LENGTH: 14
<212> TYPE: DNA
<213> ORGANISM: Artificial Sequence
<220> FEATURE:
<223> OTHER INFORMATION: Synthetic Construct

<400> SEQUENCE: 646
ccgaaccttt aaac                                                   14

<210> SEQ ID NO 647
<211> LENGTH: 14
<212> TYPE: DNA
<213> ORGANISM: Artificial Sequence
<220> FEATURE:
<223> OTHER INFORMATION: Synthetic Construct

<400> SEQUENCE: 647
gaatttggtt tcgc                                                   14

<210> SEQ ID NO 648
<211> LENGTH: 14
<212> TYPE: DNA
<213> ORGANISM: Artificial Sequence
<220> FEATURE:
<223> OTHER INFORMATION: Synthetic Construct

<400> SEQUENCE: 648
ccgaaccttt aaac                                                   14

<210> SEQ ID NO 649
<211> LENGTH: 14
<212> TYPE: DNA
<213> ORGANISM: Artificial Sequence
<220> FEATURE:
<223> OTHER INFORMATION: Synthetic Construct

<400> SEQUENCE: 649
aatttggttt cgcg                                                   14

<210> SEQ ID NO 650
<211> LENGTH: 14
<212> TYPE: DNA
<213> ORGANISM: Artificial Sequence
<220> FEATURE:
<223> OTHER INFORMATION: Synthetic Construct

<400> SEQUENCE: 650
ccgaaccttt aaac                                                   14
```

```
<210> SEQ ID NO 651
<211> LENGTH: 14
<212> TYPE: DNA
<213> ORGANISM: Artificial Sequence
<220> FEATURE:
<223> OTHER INFORMATION: Synthetic Construct

<400> SEQUENCE: 651
atttggtttc gcgt                                                    14

<210> SEQ ID NO 652
<211> LENGTH: 14
<212> TYPE: DNA
<213> ORGANISM: Artificial Sequence
<220> FEATURE:
<223> OTHER INFORMATION: Synthetic Construct

<400> SEQUENCE: 652
ccgaaccttt aaac                                                    14

<210> SEQ ID NO 653
<211> LENGTH: 14
<212> TYPE: DNA
<213> ORGANISM: Artificial Sequence
<220> FEATURE:
<223> OTHER INFORMATION: Synthetic Construct

<400> SEQUENCE: 653
tttggtttcg cgta                                                    14

<210> SEQ ID NO 654
<211> LENGTH: 14
<212> TYPE: DNA
<213> ORGANISM: Artificial Sequence
<220> FEATURE:
<223> OTHER INFORMATION: Synthetic Construct

<400> SEQUENCE: 654
ccgaaccttt aaac                                                    14

<210> SEQ ID NO 655
<211> LENGTH: 14
<212> TYPE: DNA
<213> ORGANISM: Artificial Sequence
<220> FEATURE:
<223> OTHER INFORMATION: Synthetic Construct

<400> SEQUENCE: 655
ttggtttcgc gtag                                                    14

<210> SEQ ID NO 656
<211> LENGTH: 14
<212> TYPE: DNA
<213> ORGANISM: Artificial Sequence
<220> FEATURE:
<223> OTHER INFORMATION: Synthetic Construct

<400> SEQUENCE: 656
ccgaaccttt aaac                                                    14

<210> SEQ ID NO 657
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 657
tggtttcgcg tagc                                                    14

<210> SEQ ID NO 658
<211> LENGTH: 14
<212> TYPE: DNA
<213> ORGANISM: Artificial Sequence
<220> FEATURE:
<223> OTHER INFORMATION: Synthetic Construct

<400> SEQUENCE: 658
ccgaaccttt aaac                                                    14

<210> SEQ ID NO 659
<211> LENGTH: 14
<212> TYPE: DNA
<213> ORGANISM: Artificial Sequence
<220> FEATURE:
<223> OTHER INFORMATION: Synthetic Construct

<400> SEQUENCE: 659
ggtttcgcgt agcg                                                    14

<210> SEQ ID NO 660
<211> LENGTH: 14
<212> TYPE: DNA
<213> ORGANISM: Artificial Sequence
<220> FEATURE:
<223> OTHER INFORMATION: Synthetic Construct

<400> SEQUENCE: 660
ccgaaccttt aaac                                                    14

<210> SEQ ID NO 661
<211> LENGTH: 14
<212> TYPE: DNA
<213> ORGANISM: Artificial Sequence
<220> FEATURE:
<223> OTHER INFORMATION: Synthetic Construct

<400> SEQUENCE: 661
gtttcgcgta gcgt                                                    14

<210> SEQ ID NO 662
<211> LENGTH: 14
<212> TYPE: DNA
<213> ORGANISM: Artificial Sequence
<220> FEATURE:
<223> OTHER INFORMATION: Synthetic Construct

<400> SEQUENCE: 662
ccgaaccttt aaac                                                    14

<210> SEQ ID NO 663
<211> LENGTH: 14
<212> TYPE: DNA
<213> ORGANISM: Artificial Sequence
<220> FEATURE:
<223> OTHER INFORMATION: Synthetic Construct

<400> SEQUENCE: 663
tttcgcgtag cgtt                                                    14

-continued

```
<210> SEQ ID NO 664
<211> LENGTH: 14
<212> TYPE: DNA
<213> ORGANISM: Artificial Sequence
<220> FEATURE:
<223> OTHER INFORMATION: Synthetic Construct

<400> SEQUENCE: 664
ccgaaccttt aaac                                                       14

<210> SEQ ID NO 665
<211> LENGTH: 14
<212> TYPE: DNA
<213> ORGANISM: Artificial Sequence
<220> FEATURE:
<223> OTHER INFORMATION: Synthetic Construct

<400> SEQUENCE: 665
ttcgcgtagc gttt                                                       14

<210> SEQ ID NO 666
<211> LENGTH: 14
<212> TYPE: DNA
<213> ORGANISM: Artificial Sequence
<220> FEATURE:
<223> OTHER INFORMATION: Synthetic Construct

<400> SEQUENCE: 666
ccgaaccttt aaac                                                       14

<210> SEQ ID NO 667
<211> LENGTH: 14
<212> TYPE: DNA
<213> ORGANISM: Artificial Sequence
<220> FEATURE:
<223> OTHER INFORMATION: Synthetic Construct

<400> SEQUENCE: 667
tcgcgtagcg tttg                                                       14

<210> SEQ ID NO 668
<211> LENGTH: 14
<212> TYPE: DNA
<213> ORGANISM: Artificial Sequence
<220> FEATURE:
<223> OTHER INFORMATION: Synthetic Construct

<400> SEQUENCE: 668
ccgaaccttt aaac                                                       14

<210> SEQ ID NO 669
<211> LENGTH: 14
<212> TYPE: DNA
<213> ORGANISM: Artificial Sequence
<220> FEATURE:
<223> OTHER INFORMATION: Synthetic Construct

<400> SEQUENCE: 669
cgcgtagcgt ttgg                                                       14

<210> SEQ ID NO 670
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 670
ccgaaccttt aaac                                                          14

<210> SEQ ID NO 671
<211> LENGTH: 14
<212> TYPE: DNA
<213> ORGANISM: Artificial Sequence
<220> FEATURE:
<223> OTHER INFORMATION: Synthetic Construct

<400> SEQUENCE: 671
gcgtagcgtt tggt                                                          14

<210> SEQ ID NO 672
<211> LENGTH: 14
<212> TYPE: DNA
<213> ORGANISM: Artificial Sequence
<220> FEATURE:
<223> OTHER INFORMATION: Synthetic Construct

<400> SEQUENCE: 672
ccgaaccttt aaac                                                          14

<210> SEQ ID NO 673
<211> LENGTH: 14
<212> TYPE: DNA
<213> ORGANISM: Artificial Sequence
<220> FEATURE:
<223> OTHER INFORMATION: Synthetic Construct

<400> SEQUENCE: 673
cgtagcgttt ggtt                                                          14

<210> SEQ ID NO 674
<211> LENGTH: 14
<212> TYPE: DNA
<213> ORGANISM: Artificial Sequence
<220> FEATURE:
<223> OTHER INFORMATION: Synthetic Construct

<400> SEQUENCE: 674
ccgaaccttt aaac                                                          14

<210> SEQ ID NO 675
<211> LENGTH: 14
<212> TYPE: DNA
<213> ORGANISM: Artificial Sequence
<220> FEATURE:
<223> OTHER INFORMATION: Synthetic Construct

<400> SEQUENCE: 675
gtagcgtttg gtta                                                          14

<210> SEQ ID NO 676
<211> LENGTH: 14
<212> TYPE: DNA
<213> ORGANISM: Artificial Sequence
<220> FEATURE:
<223> OTHER INFORMATION: Synthetic Construct

<400> SEQUENCE: 676
ccgaaccttt aaac                                                          14

<210> SEQ ID NO 677
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 677
tagcgtttgg ttat                                                         14

<210> SEQ ID NO 678
<211> LENGTH: 14
<212> TYPE: DNA
<213> ORGANISM: Artificial Sequence
<220> FEATURE:
<223> OTHER INFORMATION: Synthetic Construct

<400> SEQUENCE: 678
ccgaaccttt aaac                                                         14

<210> SEQ ID NO 679
<211> LENGTH: 14
<212> TYPE: DNA
<213> ORGANISM: Artificial Sequence
<220> FEATURE:
<223> OTHER INFORMATION: Synthetic Construct

<400> SEQUENCE: 679
agcgtttggt tatt                                                         14

<210> SEQ ID NO 680
<211> LENGTH: 14
<212> TYPE: DNA
<213> ORGANISM: Artificial Sequence
<220> FEATURE:
<223> OTHER INFORMATION: Synthetic Construct

<400> SEQUENCE: 680
ccgaaccttt aaac                                                         14

<210> SEQ ID NO 681
<211> LENGTH: 14
<212> TYPE: DNA
<213> ORGANISM: Artificial Sequence
<220> FEATURE:
<223> OTHER INFORMATION: Synthetic Construct

<400> SEQUENCE: 681
gcgtttggtt attc                                                         14

<210> SEQ ID NO 682
<211> LENGTH: 14
<212> TYPE: DNA
<213> ORGANISM: Artificial Sequence
<220> FEATURE:
<223> OTHER INFORMATION: Synthetic Construct

<400> SEQUENCE: 682
ccgaaccttt aaac                                                         14

<210> SEQ ID NO 683
<211> LENGTH: 14
<212> TYPE: DNA
<213> ORGANISM: Artificial Sequence
<220> FEATURE:
<223> OTHER INFORMATION: Synthetic Construct

<400> SEQUENCE: 683
```
cgtttggtta ttcg                                                       14

<210> SEQ ID NO 684
<211> LENGTH: 14
<212> TYPE: DNA
<213> ORGANISM: Artificial Sequence
<220> FEATURE:
<223> OTHER INFORMATION: Synthetic Construct

<400> SEQUENCE: 684
ccgaaccttt aaac                                                       14

<210> SEQ ID NO 685
<211> LENGTH: 14
<212> TYPE: DNA
<213> ORGANISM: Artificial Sequence
<220> FEATURE:
<223> OTHER INFORMATION: Synthetic Construct

<400> SEQUENCE: 685
gtttggttat tcgt                                                       14

<210> SEQ ID NO 686
<211> LENGTH: 14
<212> TYPE: DNA
<213> ORGANISM: Artificial Sequence
<220> FEATURE:
<223> OTHER INFORMATION: Synthetic Construct

<400> SEQUENCE: 686
ccgaaccttt aaac                                                       14

<210> SEQ ID NO 687
<211> LENGTH: 14
<212> TYPE: DNA
<213> ORGANISM: Artificial Sequence
<220> FEATURE:
<223> OTHER INFORMATION: Synthetic Construct

<400> SEQUENCE: 687
tttggttatt cgtt                                                       14

<210> SEQ ID NO 688
<211> LENGTH: 14
<212> TYPE: DNA
<213> ORGANISM: Artificial Sequence
<220> FEATURE:
<223> OTHER INFORMATION: Synthetic Construct

<400> SEQUENCE: 688
ccgaaccttt aaac                                                       14

<210> SEQ ID NO 689
<211> LENGTH: 14
<212> TYPE: DNA
<213> ORGANISM: Artificial Sequence
<220> FEATURE:
<223> OTHER INFORMATION: Synthetic Construct

<400> SEQUENCE: 689
ttggttattc gttt                                                       14

<210> SEQ ID NO 690
<211> LENGTH: 14
<212> TYPE: DNA
<213> ORGANISM: Artificial Sequence
<220> FEATURE:
<223> OTHER INFORMATION: Synthetic Construct

<400> SEQUENCE: 690
ccgaaccttt aaac                                                          14

<210> SEQ ID NO 691
<211> LENGTH: 14
<212> TYPE: DNA
<213> ORGANISM: Artificial Sequence
<220> FEATURE:
<223> OTHER INFORMATION: Synthetic Construct

<400> SEQUENCE: 691
tggttattcg tttt                                                          14

<210> SEQ ID NO 692
<211> LENGTH: 14
<212> TYPE: DNA
<213> ORGANISM: Artificial Sequence
<220> FEATURE:
<223> OTHER INFORMATION: Synthetic Construct

<400> SEQUENCE: 692
ccgaaccttt aaac                                                          14

<210> SEQ ID NO 693
<211> LENGTH: 14
<212> TYPE: DNA
<213> ORGANISM: Artificial Sequence
<220> FEATURE:
<223> OTHER INFORMATION: Synthetic Construct

<400> SEQUENCE: 693
ggttattcgt tttt                                                          14

<210> SEQ ID NO 694
<211> LENGTH: 14
<212> TYPE: DNA
<213> ORGANISM: Artificial Sequence
<220> FEATURE:
<223> OTHER INFORMATION: Synthetic Construct

<400> SEQUENCE: 694
ccgaaccttt aaac                                                          14

<210> SEQ ID NO 695
<211> LENGTH: 14
<212> TYPE: DNA
<213> ORGANISM: Artificial Sequence
<220> FEATURE:
<223> OTHER INFORMATION: Synthetic Construct

<400> SEQUENCE: 695
gttattcgtt tttt                                                          14

<210> SEQ ID NO 696
<211> LENGTH: 14
<212> TYPE: DNA
<213> ORGANISM: Artificial Sequence
<220> FEATURE:
<223> OTHER INFORMATION: Synthetic Construct

<400> SEQUENCE: 696
ccgaaccttt aaac                                                          14

```
<210> SEQ ID NO 697
<211> LENGTH: 14
<212> TYPE: DNA
<213> ORGANISM: Artificial Sequence
<220> FEATURE:
<223> OTHER INFORMATION: Synthetic Construct

<400> SEQUENCE: 697
ttattcgttt tttt                                                         14

<210> SEQ ID NO 698
<211> LENGTH: 14
<212> TYPE: DNA
<213> ORGANISM: Artificial Sequence
<220> FEATURE:
<223> OTHER INFORMATION: Synthetic Construct

<400> SEQUENCE: 698
ccgaaccttt aaac                                                         14

<210> SEQ ID NO 699
<211> LENGTH: 14
<212> TYPE: DNA
<213> ORGANISM: Artificial Sequence
<220> FEATURE:
<223> OTHER INFORMATION: Synthetic Construct

<400> SEQUENCE: 699
tattcgtttt tttt                                                         14

<210> SEQ ID NO 700
<211> LENGTH: 14
<212> TYPE: DNA
<213> ORGANISM: Artificial Sequence
<220> FEATURE:
<223> OTHER INFORMATION: Synthetic Construct

<400> SEQUENCE: 700
ccgaaccttt aaac                                                         14

<210> SEQ ID NO 701
<211> LENGTH: 14
<212> TYPE: DNA
<213> ORGANISM: Artificial Sequence
<220> FEATURE:
<223> OTHER INFORMATION: Synthetic Construct

<400> SEQUENCE: 701
attcgttttt tttt                                                         14

<210> SEQ ID NO 702
<211> LENGTH: 14
<212> TYPE: DNA
<213> ORGANISM: Artificial Sequence
<220> FEATURE:
<223> OTHER INFORMATION: Synthetic Construct

<400> SEQUENCE: 702
ccgaaccttt aaac                                                         14

<210> SEQ ID NO 703
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 703 ttcgttttttt tttg                                                14

<210> SEQ ID NO 704
<211> LENGTH: 14
<212> TYPE: DNA
<213> ORGANISM: Artificial Sequence
<220> FEATURE:
<223> OTHER INFORMATION: Synthetic Construct

<400> SEQUENCE: 704
ccgaaccttt aaac                                                 14

<210> SEQ ID NO 705
<211> LENGTH: 14
<212> TYPE: DNA
<213> ORGANISM: Artificial Sequence
<220> FEATURE:
<223> OTHER INFORMATION: Synthetic Construct

<400> SEQUENCE: 705 tcgtttttttt ttgg                                                14

<210> SEQ ID NO 706
<211> LENGTH: 14
<212> TYPE: DNA
<213> ORGANISM: Artificial Sequence
<220> FEATURE:
<223> OTHER INFORMATION: Synthetic Construct

<400> SEQUENCE: 706
ccgaaccttt aaac                                                 14

<210> SEQ ID NO 707
<211> LENGTH: 14
<212> TYPE: DNA
<213> ORGANISM: Artificial Sequence
<220> FEATURE:
<223> OTHER INFORMATION: Synthetic Construct

<400> SEQUENCE: 707
cgtttttttt tggg                                                 14

<210> SEQ ID NO 708
<211> LENGTH: 14
<212> TYPE: DNA
<213> ORGANISM: Artificial Sequence
<220> FEATURE:
<223> OTHER INFORMATION: Synthetic Construct

<400> SEQUENCE: 708
ccgaaccttt aaac                                                 14

<210> SEQ ID NO 709
<211> LENGTH: 14
<212> TYPE: DNA
<213> ORGANISM: Artificial Sequence
<220> FEATURE:
<223> OTHER INFORMATION: Synthetic Construct

<400> SEQUENCE: 709 gtttttttt gggg                                                  14

<210> SEQ ID NO 710

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 710
ccgaaccttt aaac                                                    14

<210> SEQ ID NO 711
<211> LENGTH: 14
<212> TYPE: DNA
<213> ORGANISM: Artificial Sequence
<220> FEATURE:
<223> OTHER INFORMATION: Synthetic Construct

<400> SEQUENCE: 711
tttttttttg ggga                                                    14

<210> SEQ ID NO 712
<211> LENGTH: 14
<212> TYPE: DNA
<213> ORGANISM: Artificial Sequence
<220> FEATURE:
<223> OTHER INFORMATION: Synthetic Construct

<400> SEQUENCE: 712
ccgaaccttt aaac                                                    14

<210> SEQ ID NO 713
<211> LENGTH: 14
<212> TYPE: DNA
<213> ORGANISM: Artificial Sequence
<220> FEATURE:
<223> OTHER INFORMATION: Synthetic Construct

<400> SEQUENCE: 713 tttttttgg ggat                                                     14

<210> SEQ ID NO 714
<211> LENGTH: 14
<212> TYPE: DNA
<213> ORGANISM: Artificial Sequence
<220> FEATURE:
<223> OTHER INFORMATION: Synthetic Construct

<400> SEQUENCE: 714
ccgaaccttt aaac                                                    14

<210> SEQ ID NO 715
<211> LENGTH: 14
<212> TYPE: DNA
<213> ORGANISM: Artificial Sequence
<220> FEATURE:
<223> OTHER INFORMATION: Synthetic Construct

<400> SEQUENCE: 715
tttttttggg gatt                                                    14

<210> SEQ ID NO 716
<211> LENGTH: 14
<212> TYPE: DNA
<213> ORGANISM: Artificial Sequence
<220> FEATURE:
<223> OTHER INFORMATION: Synthetic Construct

<400> SEQUENCE: 716
``` ccgaacctttt aaac                                              14

<210> SEQ ID NO 717
<211> LENGTH: 14
<212> TYPE: DNA
<213> ORGANISM: Artificial Sequence
<220> FEATURE:
<223> OTHER INFORMATION: Synthetic Construct

<400> SEQUENCE: 717
tttttggggg attg                                               14

<210> SEQ ID NO 718
<211> LENGTH: 14
<212> TYPE: DNA
<213> ORGANISM: Artificial Sequence
<220> FEATURE:
<223> OTHER INFORMATION: Synthetic Construct

<400> SEQUENCE: 718 ccgaacctttt aaac                                              14

<210> SEQ ID NO 719
<211> LENGTH: 14
<212> TYPE: DNA
<213> ORGANISM: Artificial Sequence
<220> FEATURE:
<223> OTHER INFORMATION: Synthetic Construct

<400> SEQUENCE: 719
tttttgggga ttgt                                               14

<210> SEQ ID NO 720
<211> LENGTH: 14
<212> TYPE: DNA
<213> ORGANISM: Artificial Sequence
<220> FEATURE:
<223> OTHER INFORMATION: Synthetic Construct

<400> SEQUENCE: 720 ccgaacctttt aaac                                              14

<210> SEQ ID NO 721
<211> LENGTH: 14
<212> TYPE: DNA
<213> ORGANISM: Artificial Sequence
<220> FEATURE:
<223> OTHER INFORMATION: Synthetic Construct

<400> SEQUENCE: 721
ttttggggat tgta                                               14

<210> SEQ ID NO 722
<211> LENGTH: 14
<212> TYPE: DNA
<213> ORGANISM: Artificial Sequence
<220> FEATURE:
<223> OTHER INFORMATION: Synthetic Construct

<400> SEQUENCE: 722 ccgaacctttt aaac                                              14

<210> SEQ ID NO 723
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 723
tttggggatt gtag                                                   14

<210> SEQ ID NO 724
<211> LENGTH: 14
<212> TYPE: DNA
<213> ORGANISM: Artificial Sequence
<220> FEATURE:
<223> OTHER INFORMATION: Synthetic Construct

<400> SEQUENCE: 724
ccgaaccttt aaac                                                   14

<210> SEQ ID NO 725
<211> LENGTH: 14
<212> TYPE: DNA
<213> ORGANISM: Artificial Sequence
<220> FEATURE:
<223> OTHER INFORMATION: Synthetic Construct

<400> SEQUENCE: 725
ttggggattg taga                                                   14

<210> SEQ ID NO 726
<211> LENGTH: 14
<212> TYPE: DNA
<213> ORGANISM: Artificial Sequence
<220> FEATURE:
<223> OTHER INFORMATION: Synthetic Construct

<400> SEQUENCE: 726
atctaaaacc gaaa                                                   14

<210> SEQ ID NO 727
<211> LENGTH: 23
<212> TYPE: DNA
<213> ORGANISM: Artificial Sequence
<220> FEATURE:
<223> OTHER INFORMATION: Synthetic Construct

<400> SEQUENCE: 727
attatagaaa gaaaatgaat gtt                                         23

<210> SEQ ID NO 728
<211> LENGTH: 14
<212> TYPE: DNA
<213> ORGANISM: Artificial Sequence
<220> FEATURE:
<223> OTHER INFORMATION: Synthetic Construct

<400> SEQUENCE: 728
tggggattgt agag                                                   14

<210> SEQ ID NO 729
<211> LENGTH: 14
<212> TYPE: DNA
<213> ORGANISM: Artificial Sequence
<220> FEATURE:
<223> OTHER INFORMATION: Synthetic Construct

<400> SEQUENCE: 729
atctaaaacc gaaa                                                   14
```

```
<210> SEQ ID NO 730
<211> LENGTH: 14
<212> TYPE: DNA
<213> ORGANISM: Artificial Sequence
<220> FEATURE:
<223> OTHER INFORMATION: Synthetic Construct

<400> SEQUENCE: 730
ggggattgta gaga                                                       14

<210> SEQ ID NO 731
<211> LENGTH: 14
<212> TYPE: DNA
<213> ORGANISM: Artificial Sequence
<220> FEATURE:
<223> OTHER INFORMATION: Synthetic Construct

<400> SEQUENCE: 731
atctaaaacc gaaa                                                       14

<210> SEQ ID NO 732
<211> LENGTH: 14
<212> TYPE: DNA
<213> ORGANISM: Artificial Sequence
<220> FEATURE:
<223> OTHER INFORMATION: Synthetic Construct

<400> SEQUENCE: 732
gggattgtag agaa                                                       14

<210> SEQ ID NO 733
<211> LENGTH: 14
<212> TYPE: DNA
<213> ORGANISM: Artificial Sequence
<220> FEATURE:
<223> OTHER INFORMATION: Synthetic Construct

<400> SEQUENCE: 733
atctaaaacc gaaa                                                       14

<210> SEQ ID NO 734
<211> LENGTH: 14
<212> TYPE: DNA
<213> ORGANISM: Artificial Sequence
<220> FEATURE:
<223> OTHER INFORMATION: Synthetic Construct

<400> SEQUENCE: 734
ggattgtaga gaag                                                       14

<210> SEQ ID NO 735
<211> LENGTH: 14
<212> TYPE: DNA
<213> ORGANISM: Artificial Sequence
<220> FEATURE:
<223> OTHER INFORMATION: Synthetic Construct

<400> SEQUENCE: 735
atctaaaacc gaaa                                                       14

<210> SEQ ID NO 736
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 736
gattgtagag aagt        14

<210> SEQ ID NO 737
<211> LENGTH: 14
<212> TYPE: DNA
<213> ORGANISM: Artificial Sequence
<220> FEATURE:
<223> OTHER INFORMATION: Synthetic Construct

<400> SEQUENCE: 737
atctaaaacc gaaa        14

<210> SEQ ID NO 738
<211> LENGTH: 14
<212> TYPE: DNA
<213> ORGANISM: Artificial Sequence
<220> FEATURE:
<223> OTHER INFORMATION: Synthetic Construct

<400> SEQUENCE: 738
attgtagaga agta        14

<210> SEQ ID NO 739
<211> LENGTH: 14
<212> TYPE: DNA
<213> ORGANISM: Artificial Sequence
<220> FEATURE:
<223> OTHER INFORMATION: Synthetic Construct

<400> SEQUENCE: 739
atctaaaacc gaaa        14

<210> SEQ ID NO 740
<211> LENGTH: 14
<212> TYPE: DNA
<213> ORGANISM: Artificial Sequence
<220> FEATURE:
<223> OTHER INFORMATION: Synthetic Construct

<400> SEQUENCE: 740
ttgtagagaa gtag        14

<210> SEQ ID NO 741
<211> LENGTH: 14
<212> TYPE: DNA
<213> ORGANISM: Artificial Sequence
<220> FEATURE:
<223> OTHER INFORMATION: Synthetic Construct

<400> SEQUENCE: 741
atctaaaacc gaaa        14

<210> SEQ ID NO 742
<211> LENGTH: 14
<212> TYPE: DNA
<213> ORGANISM: Artificial Sequence
<220> FEATURE:
<223> OTHER INFORMATION: Synthetic Construct

<400> SEQUENCE: 742
tgtagagaag tagg        14

```
<210> SEQ ID NO 743
<211> LENGTH: 14
<212> TYPE: DNA
<213> ORGANISM: Artificial Sequence
<220> FEATURE:
<223> OTHER INFORMATION: Synthetic Construct

<400> SEQUENCE: 743
atctaaaacc gaaa                                                       14

<210> SEQ ID NO 744
<211> LENGTH: 14
<212> TYPE: DNA
<213> ORGANISM: Artificial Sequence
<220> FEATURE:
<223> OTHER INFORMATION: Synthetic Construct

<400> SEQUENCE: 744
gtagagaagt agga                                                       14

<210> SEQ ID NO 745
<211> LENGTH: 14
<212> TYPE: DNA
<213> ORGANISM: Artificial Sequence
<220> FEATURE:
<223> OTHER INFORMATION: Synthetic Construct

<400> SEQUENCE: 745
atctaaaacc gaaa                                                       14

<210> SEQ ID NO 746
<211> LENGTH: 14
<212> TYPE: DNA
<213> ORGANISM: Artificial Sequence
<220> FEATURE:
<223> OTHER INFORMATION: Synthetic Construct

<400> SEQUENCE: 746
tagagaagta ggat                                                       14

<210> SEQ ID NO 747
<211> LENGTH: 14
<212> TYPE: DNA
<213> ORGANISM: Artificial Sequence
<220> FEATURE:
<223> OTHER INFORMATION: Synthetic Construct

<400> SEQUENCE: 747
atctaaaacc gaaa                                                       14

<210> SEQ ID NO 748
<211> LENGTH: 14
<212> TYPE: DNA
<213> ORGANISM: Artificial Sequence
<220> FEATURE:
<223> OTHER INFORMATION: Synthetic Construct

<400> SEQUENCE: 748
agagaagtag gatt                                                       14

<210> SEQ ID NO 749
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 749
atctaaaacc gaaa                                                      14

<210> SEQ ID NO 750
<211> LENGTH: 14
<212> TYPE: DNA
<213> ORGANISM: Artificial Sequence
<220> FEATURE:
<223> OTHER INFORMATION: Synthetic Construct

<400> SEQUENCE: 750
gagaagtagg attt                                                      14

<210> SEQ ID NO 751
<211> LENGTH: 14
<212> TYPE: DNA
<213> ORGANISM: Artificial Sequence
<220> FEATURE:
<223> OTHER INFORMATION: Synthetic Construct

<400> SEQUENCE: 751
atctaaaacc gaaa                                                      14

<210> SEQ ID NO 752
<211> LENGTH: 14
<212> TYPE: DNA
<213> ORGANISM: Artificial Sequence
<220> FEATURE:
<223> OTHER INFORMATION: Synthetic Construct

<400> SEQUENCE: 752
agaagtagga tttc                                                      14

<210> SEQ ID NO 753
<211> LENGTH: 14
<212> TYPE: DNA
<213> ORGANISM: Artificial Sequence
<220> FEATURE:
<223> OTHER INFORMATION: Synthetic Construct

<400> SEQUENCE: 753
atctaaaacc gaaa                                                      14

<210> SEQ ID NO 754
<211> LENGTH: 14
<212> TYPE: DNA
<213> ORGANISM: Artificial Sequence
<220> FEATURE:
<223> OTHER INFORMATION: Synthetic Construct

<400> SEQUENCE: 754
gaagtaggat ttcg                                                      14

<210> SEQ ID NO 755
<211> LENGTH: 14
<212> TYPE: DNA
<213> ORGANISM: Artificial Sequence
<220> FEATURE:
<223> OTHER INFORMATION: Synthetic Construct

<400> SEQUENCE: 755
atctaaaacc gaaa                                                      14

<210> SEQ ID NO 756
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 756
aagtaggatt tcgg                                                       14

<210> SEQ ID NO 757
<211> LENGTH: 14
<212> TYPE: DNA
<213> ORGANISM: Artificial Sequence
<220> FEATURE:
<223> OTHER INFORMATION: Synthetic Construct

<400> SEQUENCE: 757
atctaaaacc gaaa                                                       14

<210> SEQ ID NO 758
<211> LENGTH: 14
<212> TYPE: DNA
<213> ORGANISM: Artificial Sequence
<220> FEATURE:
<223> OTHER INFORMATION: Synthetic Construct

<400> SEQUENCE: 758
agtaggattt cggg                                                       14

<210> SEQ ID NO 759
<211> LENGTH: 14
<212> TYPE: DNA
<213> ORGANISM: Artificial Sequence
<220> FEATURE:
<223> OTHER INFORMATION: Synthetic Construct

<400> SEQUENCE: 759
atctaaaacc gaaa                                                       14

<210> SEQ ID NO 760
<211> LENGTH: 14
<212> TYPE: DNA
<213> ORGANISM: Artificial Sequence
<220> FEATURE:
<223> OTHER INFORMATION: Synthetic Construct

<400> SEQUENCE: 760
gtaggatttc gggt                                                       14

<210> SEQ ID NO 761
<211> LENGTH: 14
<212> TYPE: DNA
<213> ORGANISM: Artificial Sequence
<220> FEATURE:
<223> OTHER INFORMATION: Synthetic Construct

<400> SEQUENCE: 761
atctaaaacc gaaa                                                       14

<210> SEQ ID NO 762
<211> LENGTH: 14
<212> TYPE: DNA
<213> ORGANISM: Artificial Sequence
<220> FEATURE:
<223> OTHER INFORMATION: Synthetic Construct

<400> SEQUENCE: 762
```
taggatttcg ggtt                                                    14

<210> SEQ ID NO 763
<211> LENGTH: 14
<212> TYPE: DNA
<213> ORGANISM: Artificial Sequence
<220> FEATURE:
<223> OTHER INFORMATION: Synthetic Construct

<400> SEQUENCE: 763
atctaaaacc gaaa                                                    14

<210> SEQ ID NO 764
<211> LENGTH: 14
<212> TYPE: DNA
<213> ORGANISM: Artificial Sequence
<220> FEATURE:
<223> OTHER INFORMATION: Synthetic Construct

<400> SEQUENCE: 764
aggatttcgg gtta                                                    14

<210> SEQ ID NO 765
<211> LENGTH: 14
<212> TYPE: DNA
<213> ORGANISM: Artificial Sequence
<220> FEATURE:
<223> OTHER INFORMATION: Synthetic Construct

<400> SEQUENCE: 765
atctaaaacc gaaa                                                    14

<210> SEQ ID NO 766
<211> LENGTH: 14
<212> TYPE: DNA
<213> ORGANISM: Artificial Sequence
<220> FEATURE:
<223> OTHER INFORMATION: Synthetic Construct

<400> SEQUENCE: 766
ggatttcggg ttat                                                    14

<210> SEQ ID NO 767
<211> LENGTH: 14
<212> TYPE: DNA
<213> ORGANISM: Artificial Sequence
<220> FEATURE:
<223> OTHER INFORMATION: Synthetic Construct

<400> SEQUENCE: 767
atctaaaacc gaaa                                                    14

<210> SEQ ID NO 768
<211> LENGTH: 14
<212> TYPE: DNA
<213> ORGANISM: Artificial Sequence
<220> FEATURE:
<223> OTHER INFORMATION: Synthetic Construct

<400> SEQUENCE: 768
gatttcgggt tatg                                                    14

<210> SEQ ID NO 769
<211> LENGTH: 14
<212> TYPE: DNA
<213> ORGANISM: Artificial Sequence
<220> FEATURE:
<223> OTHER INFORMATION: Synthetic Construct

<400> SEQUENCE: 769
atctaaaacc gaaa                                                                 14

<210> SEQ ID NO 770
<211> LENGTH: 14
<212> TYPE: DNA
<213> ORGANISM: Artificial Sequence
<220> FEATURE:
<223> OTHER INFORMATION: Synthetic Construct

<400> SEQUENCE: 770
atttcgggtt atgg                                                                 14

<210> SEQ ID NO 771
<211> LENGTH: 14
<212> TYPE: DNA
<213> ORGANISM: Artificial Sequence
<220> FEATURE:
<223> OTHER INFORMATION: Synthetic Construct

<400> SEQUENCE: 771
atctaaaacc gaaa                                                                 14

<210> SEQ ID NO 772
<211> LENGTH: 14
<212> TYPE: DNA
<213> ORGANISM: Artificial Sequence
<220> FEATURE:
<223> OTHER INFORMATION: Synthetic Construct

<400> SEQUENCE: 772
tttcgggtta tggg                                                                 14

<210> SEQ ID NO 773
<211> LENGTH: 14
<212> TYPE: DNA
<213> ORGANISM: Artificial Sequence
<220> FEATURE:
<223> OTHER INFORMATION: Synthetic Construct

<400> SEQUENCE: 773
atctaaaacc gaaa                                                                 14

<210> SEQ ID NO 774
<211> LENGTH: 14
<212> TYPE: DNA
<213> ORGANISM: Artificial Sequence
<220> FEATURE:
<223> OTHER INFORMATION: Synthetic Construct

<400> SEQUENCE: 774
ttcgggttat gggt                                                                 14

<210> SEQ ID NO 775
<211> LENGTH: 14
<212> TYPE: DNA
<213> ORGANISM: Artificial Sequence
<220> FEATURE:
<223> OTHER INFORMATION: Synthetic Construct

<400> SEQUENCE: 775
atctaaaacc gaaa                                                                 14

```
<210> SEQ ID NO 776
<211> LENGTH: 14
<212> TYPE: DNA
<213> ORGANISM: Artificial Sequence
<220> FEATURE:
<223> OTHER INFORMATION: Synthetic Construct

<400> SEQUENCE: 776
tcgggttatg ggtg                                                    14

<210> SEQ ID NO 777
<211> LENGTH: 14
<212> TYPE: DNA
<213> ORGANISM: Artificial Sequence
<220> FEATURE:
<223> OTHER INFORMATION: Synthetic Construct

<400> SEQUENCE: 777
atctaaaacc gaaa                                                    14

<210> SEQ ID NO 778
<211> LENGTH: 14
<212> TYPE: DNA
<213> ORGANISM: Artificial Sequence
<220> FEATURE:
<223> OTHER INFORMATION: Synthetic Construct

<400> SEQUENCE: 778
cgggttatgg gtga                                                    14

<210> SEQ ID NO 779
<211> LENGTH: 14
<212> TYPE: DNA
<213> ORGANISM: Artificial Sequence
<220> FEATURE:
<223> OTHER INFORMATION: Synthetic Construct

<400> SEQUENCE: 779
atctaaaacc gaaa                                                    14

<210> SEQ ID NO 780
<211> LENGTH: 14
<212> TYPE: DNA
<213> ORGANISM: Artificial Sequence
<220> FEATURE:
<223> OTHER INFORMATION: Synthetic Construct

<400> SEQUENCE: 780
gggttatggg tgag                                                    14

<210> SEQ ID NO 781
<211> LENGTH: 14
<212> TYPE: DNA
<213> ORGANISM: Artificial Sequence
<220> FEATURE:
<223> OTHER INFORMATION: Synthetic Construct

<400> SEQUENCE: 781
atctaaaacc gaaa                                                    14

<210> SEQ ID NO 782
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 782
ggttatgggt gagt                                                        14

<210> SEQ ID NO 783
<211> LENGTH: 14
<212> TYPE: DNA
<213> ORGANISM: Artificial Sequence
<220> FEATURE:
<223> OTHER INFORMATION: Synthetic Construct

<400> SEQUENCE: 783
atctaaaacc gaaa                                                        14

<210> SEQ ID NO 784
<211> LENGTH: 14
<212> TYPE: DNA
<213> ORGANISM: Artificial Sequence
<220> FEATURE:
<223> OTHER INFORMATION: Synthetic Construct

<400> SEQUENCE: 784
gttatgggtg agtg                                                        14

<210> SEQ ID NO 785
<211> LENGTH: 14
<212> TYPE: DNA
<213> ORGANISM: Artificial Sequence
<220> FEATURE:
<223> OTHER INFORMATION: Synthetic Construct

<400> SEQUENCE: 785
atctaaaacc gaaa                                                        14

<210> SEQ ID NO 786
<211> LENGTH: 14
<212> TYPE: DNA
<213> ORGANISM: Artificial Sequence
<220> FEATURE:
<223> OTHER INFORMATION: Synthetic Construct

<400> SEQUENCE: 786
ttatgggtga gtgc                                                        14

<210> SEQ ID NO 787
<211> LENGTH: 14
<212> TYPE: DNA
<213> ORGANISM: Artificial Sequence
<220> FEATURE:
<223> OTHER INFORMATION: Synthetic Construct

<400> SEQUENCE: 787
atctaaaacc gaaa                                                        14

<210> SEQ ID NO 788
<211> LENGTH: 14
<212> TYPE: DNA
<213> ORGANISM: Artificial Sequence
<220> FEATURE:
<223> OTHER INFORMATION: Synthetic Construct

<400> SEQUENCE: 788
tatgggtgag tgcg                                                        14

<210> SEQ ID NO 789
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 789
atctaaaacc gaaa                                                        14

<210> SEQ ID NO 790
<211> LENGTH: 14
<212> TYPE: DNA
<213> ORGANISM: Artificial Sequence
<220> FEATURE:
<223> OTHER INFORMATION: Synthetic Construct

<400> SEQUENCE: 790
atgggtgagt gcgc                                                        14

<210> SEQ ID NO 791
<211> LENGTH: 14
<212> TYPE: DNA
<213> ORGANISM: Artificial Sequence
<220> FEATURE:
<223> OTHER INFORMATION: Synthetic Construct

<400> SEQUENCE: 791
atctaaaacc gaaa                                                        14

<210> SEQ ID NO 792
<211> LENGTH: 14
<212> TYPE: DNA
<213> ORGANISM: Artificial Sequence
<220> FEATURE:
<223> OTHER INFORMATION: Synthetic Construct

<400> SEQUENCE: 792
tgggtgagtg cgcg                                                        14

<210> SEQ ID NO 793
<211> LENGTH: 14
<212> TYPE: DNA
<213> ORGANISM: Artificial Sequence
<220> FEATURE:
<223> OTHER INFORMATION: Synthetic Construct

<400> SEQUENCE: 793
atctaaaacc gaaa                                                        14

<210> SEQ ID NO 794
<211> LENGTH: 14
<212> TYPE: DNA
<213> ORGANISM: Artificial Sequence
<220> FEATURE:
<223> OTHER INFORMATION: Synthetic Construct

<400> SEQUENCE: 794
gggtgagtgc gcgg                                                        14

<210> SEQ ID NO 795
<211> LENGTH: 14
<212> TYPE: DNA
<213> ORGANISM: Artificial Sequence
<220> FEATURE:
<223> OTHER INFORMATION: Synthetic Construct

<400> SEQUENCE: 795
```
atctaaaacc gaaa                                          14

<210> SEQ ID NO 796
<211> LENGTH: 14
<212> TYPE: DNA
<213> ORGANISM: Artificial Sequence
<220> FEATURE:
<223> OTHER INFORMATION: Synthetic Construct

<400> SEQUENCE: 796
ggtgagtgcg cggg                                          14

<210> SEQ ID NO 797
<211> LENGTH: 14
<212> TYPE: DNA
<213> ORGANISM: Artificial Sequence
<220> FEATURE:
<223> OTHER INFORMATION: Synthetic Construct

<400> SEQUENCE: 797
atctaaaacc gaaa                                          14

<210> SEQ ID NO 798
<211> LENGTH: 14
<212> TYPE: DNA
<213> ORGANISM: Artificial Sequence
<220> FEATURE:
<223> OTHER INFORMATION: Synthetic Construct

<400> SEQUENCE: 798
gtgagtgcgc gggc                                          14

<210> SEQ ID NO 799
<211> LENGTH: 14
<212> TYPE: DNA
<213> ORGANISM: Artificial Sequence
<220> FEATURE:
<223> OTHER INFORMATION: Synthetic Construct

<400> SEQUENCE: 799
atctaaaacc gaaa                                          14

<210> SEQ ID NO 800
<211> LENGTH: 14
<212> TYPE: DNA
<213> ORGANISM: Artificial Sequence
<220> FEATURE:
<223> OTHER INFORMATION: Synthetic Construct

<400> SEQUENCE: 800
tgagtgcgcg ggcg                                          14

<210> SEQ ID NO 801
<211> LENGTH: 14
<212> TYPE: DNA
<213> ORGANISM: Artificial Sequence
<220> FEATURE:
<223> OTHER INFORMATION: Synthetic Construct

<400> SEQUENCE: 801
atctaaaacc gaaa                                          14

<210> SEQ ID NO 802
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 802
gagtgcgcgg gcgg                                                        14

<210> SEQ ID NO 803
<211> LENGTH: 14
<212> TYPE: DNA
<213> ORGANISM: Artificial Sequence
<220> FEATURE:
<223> OTHER INFORMATION: Synthetic Construct

<400> SEQUENCE: 803
atctaaaacc gaaa                                                        14

<210> SEQ ID NO 804
<211> LENGTH: 14
<212> TYPE: DNA
<213> ORGANISM: Artificial Sequence
<220> FEATURE:
<223> OTHER INFORMATION: Synthetic Construct

<400> SEQUENCE: 804
agtgcgcggg cggg                                                        14

<210> SEQ ID NO 805
<211> LENGTH: 14
<212> TYPE: DNA
<213> ORGANISM: Artificial Sequence
<220> FEATURE:
<223> OTHER INFORMATION: Synthetic Construct

<400> SEQUENCE: 805
atctaaaacc gaaa                                                        14

<210> SEQ ID NO 806
<211> LENGTH: 14
<212> TYPE: DNA
<213> ORGANISM: Artificial Sequence
<220> FEATURE:
<223> OTHER INFORMATION: Synthetic Construct

<400> SEQUENCE: 806
gtgcgcgggc gggc                                                        14

<210> SEQ ID NO 807
<211> LENGTH: 14
<212> TYPE: DNA
<213> ORGANISM: Artificial Sequence
<220> FEATURE:
<223> OTHER INFORMATION: Synthetic Construct

<400> SEQUENCE: 807
atctaaaacc gaaa                                                        14

<210> SEQ ID NO 808
<211> LENGTH: 14
<212> TYPE: DNA
<213> ORGANISM: Artificial Sequence
<220> FEATURE:
<223> OTHER INFORMATION: Synthetic Construct

<400> SEQUENCE: 808
tgcgcgggcg ggcg                                                        14
```

```
<210> SEQ ID NO 809
<211> LENGTH: 14
<212> TYPE: DNA
<213> ORGANISM: Artificial Sequence
<220> FEATURE:
<223> OTHER INFORMATION: Synthetic Construct

<400> SEQUENCE: 809
atctaaaacc gaaa                                                         14

<210> SEQ ID NO 810
<211> LENGTH: 14
<212> TYPE: DNA
<213> ORGANISM: Artificial Sequence
<220> FEATURE:
<223> OTHER INFORMATION: Synthetic Construct

<400> SEQUENCE: 810
gcgcgggcgg gcgc                                                         14

<210> SEQ ID NO 811
<211> LENGTH: 14
<212> TYPE: DNA
<213> ORGANISM: Artificial Sequence
<220> FEATURE:
<223> OTHER INFORMATION: Synthetic Construct

<400> SEQUENCE: 811
atctaaaacc gaaa                                                         14

<210> SEQ ID NO 812
<211> LENGTH: 14
<212> TYPE: DNA
<213> ORGANISM: Artificial Sequence
<220> FEATURE:
<223> OTHER INFORMATION: Synthetic Construct

<400> SEQUENCE: 812
cgcgggcggg cgcg                                                         14

<210> SEQ ID NO 813
<211> LENGTH: 14
<212> TYPE: DNA
<213> ORGANISM: Artificial Sequence
<220> FEATURE:
<223> OTHER INFORMATION: Synthetic Construct

<400> SEQUENCE: 813
atctaaaacc gaaa                                                         14

<210> SEQ ID NO 814
<211> LENGTH: 14
<212> TYPE: DNA
<213> ORGANISM: Artificial Sequence
<220> FEATURE:
<223> OTHER INFORMATION: Synthetic Construct

<400> SEQUENCE: 814
gcgggcgggc gcgt                                                         14

<210> SEQ ID NO 815
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 815
atctaaaacc gaaa                                                                14

<210> SEQ ID NO 816
<211> LENGTH: 14
<212> TYPE: DNA
<213> ORGANISM: Artificial Sequence
<220> FEATURE:
<223> OTHER INFORMATION: Synthetic Construct

<400> SEQUENCE: 816
cgggcgggcg cgta                                                                14

<210> SEQ ID NO 817
<211> LENGTH: 14
<212> TYPE: DNA
<213> ORGANISM: Artificial Sequence
<220> FEATURE:
<223> OTHER INFORMATION: Synthetic Construct

<400> SEQUENCE: 817
atctaaaacc gaaa                                                                14

<210> SEQ ID NO 818
<211> LENGTH: 14
<212> TYPE: DNA
<213> ORGANISM: Artificial Sequence
<220> FEATURE:
<223> OTHER INFORMATION: Synthetic Construct

<400> SEQUENCE: 818
gggcgggcgc gtat                                                                14

<210> SEQ ID NO 819
<211> LENGTH: 14
<212> TYPE: DNA
<213> ORGANISM: Artificial Sequence
<220> FEATURE:
<223> OTHER INFORMATION: Synthetic Construct

<400> SEQUENCE: 819
atctaaaacc gaaa                                                                14

<210> SEQ ID NO 820
<211> LENGTH: 14
<212> TYPE: DNA
<213> ORGANISM: Artificial Sequence
<220> FEATURE:
<223> OTHER INFORMATION: Synthetic Construct

<400> SEQUENCE: 820
ggcgggcgcg tata                                                                14

<210> SEQ ID NO 821
<211> LENGTH: 14
<212> TYPE: DNA
<213> ORGANISM: Artificial Sequence
<220> FEATURE:
<223> OTHER INFORMATION: Synthetic Construct

<400> SEQUENCE: 821
atctaaaacc gaaa                                                                14

```
<210> SEQ ID NO 822
<211> LENGTH: 14
<212> TYPE: DNA
<213> ORGANISM: Artificial Sequence
<220> FEATURE:
<223> OTHER INFORMATION: Synthetic Construct

<400> SEQUENCE: 822
gcgggcgcgt atat                                                     14

<210> SEQ ID NO 823
<211> LENGTH: 14
<212> TYPE: DNA
<213> ORGANISM: Artificial Sequence
<220> FEATURE:
<223> OTHER INFORMATION: Synthetic Construct

<400> SEQUENCE: 823
atctaaaacc gaaa                                                     14

<210> SEQ ID NO 824
<211> LENGTH: 14
<212> TYPE: DNA
<213> ORGANISM: Artificial Sequence
<220> FEATURE:
<223> OTHER INFORMATION: Synthetic Construct

<400> SEQUENCE: 824
cgggcgcgta tatt                                                     14

<210> SEQ ID NO 825
<211> LENGTH: 14
<212> TYPE: DNA
<213> ORGANISM: Artificial Sequence
<220> FEATURE:
<223> OTHER INFORMATION: Synthetic Construct

<400> SEQUENCE: 825
atctaaaacc gaaa                                                     14

<210> SEQ ID NO 826
<211> LENGTH: 14
<212> TYPE: DNA
<213> ORGANISM: Artificial Sequence
<220> FEATURE:
<223> OTHER INFORMATION: Synthetic Construct

<400> SEQUENCE: 826
gggcgcgtat attt                                                     14

<210> SEQ ID NO 827
<211> LENGTH: 14
<212> TYPE: DNA
<213> ORGANISM: Artificial Sequence
<220> FEATURE:
<223> OTHER INFORMATION: Synthetic Construct

<400> SEQUENCE: 827
atctaaaacc gaaa                                                     14

<210> SEQ ID NO 828
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 828
ggcgcgtata tttc                                                    14

<210> SEQ ID NO 829
<211> LENGTH: 14
<212> TYPE: DNA
<213> ORGANISM: Artificial Sequence
<220> FEATURE:
<223> OTHER INFORMATION: Synthetic Construct

<400> SEQUENCE: 829
cgaaaaacga aaaa                                                    14

<210> SEQ ID NO 830
<211> LENGTH: 24
<212> TYPE: DNA
<213> ORGANISM: Artificial Sequence
<220> FEATURE:
<223> OTHER INFORMATION: Synthetic Construct

<400> SEQUENCE: 830
gttttgtttt tttcgcgttt ggcg                                         24

<210> SEQ ID NO 831
<211> LENGTH: 14
<212> TYPE: DNA
<213> ORGANISM: Artificial Sequence
<220> FEATURE:
<223> OTHER INFORMATION: Synthetic Construct

<400> SEQUENCE: 831
gcgcgtatat ttcg                                                    14

<210> SEQ ID NO 832
<211> LENGTH: 14
<212> TYPE: DNA
<213> ORGANISM: Artificial Sequence
<220> FEATURE:
<223> OTHER INFORMATION: Synthetic Construct

<400> SEQUENCE: 832
cgaaaaacga aaaa                                                    14

<210> SEQ ID NO 833
<211> LENGTH: 14
<212> TYPE: DNA
<213> ORGANISM: Artificial Sequence
<220> FEATURE:
<223> OTHER INFORMATION: Synthetic Construct

<400> SEQUENCE: 833
cgcgtatatt tcgt                                                    14

<210> SEQ ID NO 834
<211> LENGTH: 14
<212> TYPE: DNA
<213> ORGANISM: Artificial Sequence
<220> FEATURE:
<223> OTHER INFORMATION: Synthetic Construct

<400> SEQUENCE: 834
cgaaaaacga aaaa                                                    14

<210> SEQ ID NO 835
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 835
gcgtatattt cgtt                                                    14

<210> SEQ ID NO 836
<211> LENGTH: 14
<212> TYPE: DNA
<213> ORGANISM: Artificial Sequence
<220> FEATURE:
<223> OTHER INFORMATION: Synthetic Construct

<400> SEQUENCE: 836
cgaaaaacga aaaa                                                    14

<210> SEQ ID NO 837
<211> LENGTH: 14
<212> TYPE: DNA
<213> ORGANISM: Artificial Sequence
<220> FEATURE:
<223> OTHER INFORMATION: Synthetic Construct

<400> SEQUENCE: 837
cgtatatttc gttt                                                    14

<210> SEQ ID NO 838
<211> LENGTH: 14
<212> TYPE: DNA
<213> ORGANISM: Artificial Sequence
<220> FEATURE:
<223> OTHER INFORMATION: Synthetic Construct

<400> SEQUENCE: 838
cgaaaaacga aaaa                                                    14

<210> SEQ ID NO 839
<211> LENGTH: 14
<212> TYPE: DNA
<213> ORGANISM: Artificial Sequence
<220> FEATURE:
<223> OTHER INFORMATION: Synthetic Construct

<400> SEQUENCE: 839
gtatatttcg ttta                                                    14

<210> SEQ ID NO 840
<211> LENGTH: 14
<212> TYPE: DNA
<213> ORGANISM: Artificial Sequence
<220> FEATURE:
<223> OTHER INFORMATION: Synthetic Construct

<400> SEQUENCE: 840
cgaaaaacga aaaa                                                    14

<210> SEQ ID NO 841
<211> LENGTH: 14
<212> TYPE: DNA
<213> ORGANISM: Artificial Sequence
<220> FEATURE:
<223> OTHER INFORMATION: Synthetic Construct

<400> SEQUENCE: 841
```
tatatttcgt ttaa					14

<210> SEQ ID NO 842
<211> LENGTH: 14
<212> TYPE: DNA
<213> ORGANISM: Artificial Sequence
<220> FEATURE:
<223> OTHER INFORMATION: Synthetic Construct

<400> SEQUENCE: 842
cgaaaaacga aaaa					14

<210> SEQ ID NO 843
<211> LENGTH: 14
<212> TYPE: DNA
<213> ORGANISM: Artificial Sequence
<220> FEATURE:
<223> OTHER INFORMATION: Synthetic Construct

<400> SEQUENCE: 843
atatttcgtt taaa					14

<210> SEQ ID NO 844
<211> LENGTH: 14
<212> TYPE: DNA
<213> ORGANISM: Artificial Sequence
<220> FEATURE:
<223> OTHER INFORMATION: Synthetic Construct

<400> SEQUENCE: 844
cgaaaaacga aaaa					14

<210> SEQ ID NO 845
<211> LENGTH: 14
<212> TYPE: DNA
<213> ORGANISM: Artificial Sequence
<220> FEATURE:
<223> OTHER INFORMATION: Synthetic Construct

<400> SEQUENCE: 845
tatttcgttt aaag					14

<210> SEQ ID NO 846
<211> LENGTH: 14
<212> TYPE: DNA
<213> ORGANISM: Artificial Sequence
<220> FEATURE:
<223> OTHER INFORMATION: Synthetic Construct

<400> SEQUENCE: 846
cgaaaaacga aaaa					14

<210> SEQ ID NO 847
<211> LENGTH: 14
<212> TYPE: DNA
<213> ORGANISM: Artificial Sequence
<220> FEATURE:
<223> OTHER INFORMATION: Synthetic Construct

<400> SEQUENCE: 847
atttcgttta aagg					14

<210> SEQ ID NO 848
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 848
cgaaaaacga aaaa                                                    14

<210> SEQ ID NO 849
<211> LENGTH: 14
<212> TYPE: DNA
<213> ORGANISM: Artificial Sequence
<220> FEATURE:
<223> OTHER INFORMATION: Synthetic Construct

<400> SEQUENCE: 849
tttcgtttaa aggt                                                    14

<210> SEQ ID NO 850
<211> LENGTH: 14
<212> TYPE: DNA
<213> ORGANISM: Artificial Sequence
<220> FEATURE:
<223> OTHER INFORMATION: Synthetic Construct

<400> SEQUENCE: 850
cgaaaaacga aaaa                                                    14

<210> SEQ ID NO 851
<211> LENGTH: 14
<212> TYPE: DNA
<213> ORGANISM: Artificial Sequence
<220> FEATURE:
<223> OTHER INFORMATION: Synthetic Construct

<400> SEQUENCE: 851
ttcgtttaaa ggtt                                                    14

<210> SEQ ID NO 852
<211> LENGTH: 14
<212> TYPE: DNA
<213> ORGANISM: Artificial Sequence
<220> FEATURE:
<223> OTHER INFORMATION: Synthetic Construct

<400> SEQUENCE: 852
cgaaaaacga aaaa                                                    14

<210> SEQ ID NO 853
<211> LENGTH: 14
<212> TYPE: DNA
<213> ORGANISM: Artificial Sequence
<220> FEATURE:
<223> OTHER INFORMATION: Synthetic Construct

<400> SEQUENCE: 853
tcgtttaaag gttc                                                    14

<210> SEQ ID NO 854
<211> LENGTH: 14
<212> TYPE: DNA
<213> ORGANISM: Artificial Sequence
<220> FEATURE:
<223> OTHER INFORMATION: Synthetic Construct

<400> SEQUENCE: 854
cgaaaaacga aaaa                                                    14
```

```
<210> SEQ ID NO 855
<211> LENGTH: 14
<212> TYPE: DNA
<213> ORGANISM: Artificial Sequence
<220> FEATURE:
<223> OTHER INFORMATION: Synthetic Construct

<400> SEQUENCE: 855
cgtttaaagg ttcg                                                      14

<210> SEQ ID NO 856
<211> LENGTH: 14
<212> TYPE: DNA
<213> ORGANISM: Artificial Sequence
<220> FEATURE:
<223> OTHER INFORMATION: Synthetic Construct

<400> SEQUENCE: 856
cgaaaaacga aaaa                                                      14

<210> SEQ ID NO 857
<211> LENGTH: 14
<212> TYPE: DNA
<213> ORGANISM: Artificial Sequence
<220> FEATURE:
<223> OTHER INFORMATION: Synthetic Construct

<400> SEQUENCE: 857
gtttaaaggt tcgg                                                      14

<210> SEQ ID NO 858
<211> LENGTH: 14
<212> TYPE: DNA
<213> ORGANISM: Artificial Sequence
<220> FEATURE:
<223> OTHER INFORMATION: Synthetic Construct

<400> SEQUENCE: 858
cgaaaaacga aaaa                                                      14

<210> SEQ ID NO 859
<211> LENGTH: 14
<212> TYPE: DNA
<213> ORGANISM: Artificial Sequence
<220> FEATURE:
<223> OTHER INFORMATION: Synthetic Construct

<400> SEQUENCE: 859
tttaaaggtt cggt                                                      14

<210> SEQ ID NO 860
<211> LENGTH: 14
<212> TYPE: DNA
<213> ORGANISM: Artificial Sequence
<220> FEATURE:
<223> OTHER INFORMATION: Synthetic Construct

<400> SEQUENCE: 860
cgaaaaacga aaaa                                                      14

<210> SEQ ID NO 861
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 861
ttaaaggttc ggtt                                                    14

<210> SEQ ID NO 862
<211> LENGTH: 14
<212> TYPE: DNA
<213> ORGANISM: Artificial Sequence
<220> FEATURE:
<223> OTHER INFORMATION: Synthetic Construct

<400> SEQUENCE: 862
cgaaaaacga aaaa                                                    14

<210> SEQ ID NO 863
<211> LENGTH: 14
<212> TYPE: DNA
<213> ORGANISM: Artificial Sequence
<220> FEATURE:
<223> OTHER INFORMATION: Synthetic Construct

<400> SEQUENCE: 863
taaaggttcg gttt                                                    14

<210> SEQ ID NO 864
<211> LENGTH: 14
<212> TYPE: DNA
<213> ORGANISM: Artificial Sequence
<220> FEATURE:
<223> OTHER INFORMATION: Synthetic Construct

<400> SEQUENCE: 864
cgaaaaacga aaaa                                                    14

<210> SEQ ID NO 865
<211> LENGTH: 14
<212> TYPE: DNA
<213> ORGANISM: Artificial Sequence
<220> FEATURE:
<223> OTHER INFORMATION: Synthetic Construct

<400> SEQUENCE: 865
aaaggttcgg tttc                                                    14

<210> SEQ ID NO 866
<211> LENGTH: 14
<212> TYPE: DNA
<213> ORGANISM: Artificial Sequence
<220> FEATURE:
<223> OTHER INFORMATION: Synthetic Construct

<400> SEQUENCE: 866
cgaaaaacga aaaa                                                    14

<210> SEQ ID NO 867
<211> LENGTH: 14
<212> TYPE: DNA
<213> ORGANISM: Artificial Sequence
<220> FEATURE:
<223> OTHER INFORMATION: Synthetic Construct

<400> SEQUENCE: 867
aaggttcggt ttcg                                                    14

<210> SEQ ID NO 868
```

<211> LENGTH: 14
<212> TYPE: DNA
<213> ORGANISM: Artificial Sequence
<220> FEATURE:
<223> OTHER INFORMATION: Synthetic Construct

<400> SEQUENCE: 868
cgaaaaacga aaaa                                                         14

<210> SEQ ID NO 869
<211> LENGTH: 14
<212> TYPE: DNA
<213> ORGANISM: Artificial Sequence
<220> FEATURE:
<223> OTHER INFORMATION: Synthetic Construct

<400> SEQUENCE: 869
aggttcggtt tcgg                                                         14

<210> SEQ ID NO 870
<211> LENGTH: 14
<212> TYPE: DNA
<213> ORGANISM: Artificial Sequence
<220> FEATURE:
<223> OTHER INFORMATION: Synthetic Construct

<400> SEQUENCE: 870
cgaaaaacga aaaa                                                         14

<210> SEQ ID NO 871
<211> LENGTH: 14
<212> TYPE: DNA
<213> ORGANISM: Artificial Sequence
<220> FEATURE:
<223> OTHER INFORMATION: Synthetic Construct

<400> SEQUENCE: 871
ggttcggttt cggg                                                         14

<210> SEQ ID NO 872
<211> LENGTH: 14
<212> TYPE: DNA
<213> ORGANISM: Artificial Sequence
<220> FEATURE:
<223> OTHER INFORMATION: Synthetic Construct

<400> SEQUENCE: 872
cgaaaaacga aaaa                                                         14

<210> SEQ ID NO 873
<211> LENGTH: 14
<212> TYPE: DNA
<213> ORGANISM: Artificial Sequence
<220> FEATURE:
<223> OTHER INFORMATION: Synthetic Construct

<400> SEQUENCE: 873
gttcggtttc ggga                                                         14

<210> SEQ ID NO 874
<211> LENGTH: 14
<212> TYPE: DNA
<213> ORGANISM: Artificial Sequence
<220> FEATURE:
<223> OTHER INFORMATION: Synthetic Construct

<400> SEQUENCE: 874

```
cgaaaaacga aaaa                                                  14

<210> SEQ ID NO 875
<211> LENGTH: 14
<212> TYPE: DNA
<213> ORGANISM: Artificial Sequence
<220> FEATURE:
<223> OTHER INFORMATION: Synthetic Construct

<400> SEQUENCE: 875
ttcggtttcg ggaa                                                  14

<210> SEQ ID NO 876
<211> LENGTH: 14
<212> TYPE: DNA
<213> ORGANISM: Artificial Sequence
<220> FEATURE:
<223> OTHER INFORMATION: Synthetic Construct

<400> SEQUENCE: 876
cgaaaaacga aaaa                                                  14

<210> SEQ ID NO 877
<211> LENGTH: 14
<212> TYPE: DNA
<213> ORGANISM: Artificial Sequence
<220> FEATURE:
<223> OTHER INFORMATION: Synthetic Construct

<400> SEQUENCE: 877
tcggtttcgg gaat                                                  14

<210> SEQ ID NO 878
<211> LENGTH: 14
<212> TYPE: DNA
<213> ORGANISM: Artificial Sequence
<220> FEATURE:
<223> OTHER INFORMATION: Synthetic Construct

<400> SEQUENCE: 878
cgaaaaacga aaaa                                                  14

<210> SEQ ID NO 879
<211> LENGTH: 14
<212> TYPE: DNA
<213> ORGANISM: Artificial Sequence
<220> FEATURE:
<223> OTHER INFORMATION: Synthetic Construct

<400> SEQUENCE: 879
cggtttcggg aatg                                                  14

<210> SEQ ID NO 880
<211> LENGTH: 14
<212> TYPE: DNA
<213> ORGANISM: Artificial Sequence
<220> FEATURE:
<223> OTHER INFORMATION: Synthetic Construct

<400> SEQUENCE: 880
cgaaaaacga aaaa                                                  14

<210> SEQ ID NO 881
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 881
ggtttcggga atgg                                                         14

<210> SEQ ID NO 882
<211> LENGTH: 14
<212> TYPE: DNA
<213> ORGANISM: Artificial Sequence
<220> FEATURE:
<223> OTHER INFORMATION: Synthetic Construct

<400> SEQUENCE: 882
cgaaaaacga aaaa                                                         14

<210> SEQ ID NO 883
<211> LENGTH: 14
<212> TYPE: DNA
<213> ORGANISM: Artificial Sequence
<220> FEATURE:
<223> OTHER INFORMATION: Synthetic Construct

<400> SEQUENCE: 883
gtttcgggaa tggg                                                         14

<210> SEQ ID NO 884
<211> LENGTH: 14
<212> TYPE: DNA
<213> ORGANISM: Artificial Sequence
<220> FEATURE:
<223> OTHER INFORMATION: Synthetic Construct

<400> SEQUENCE: 884
cgaaaaacga aaaa                                                         14

<210> SEQ ID NO 885
<211> LENGTH: 14
<212> TYPE: DNA
<213> ORGANISM: Artificial Sequence
<220> FEATURE:
<223> OTHER INFORMATION: Synthetic Construct

<400> SEQUENCE: 885
tttcgggaat gggt                                                         14

<210> SEQ ID NO 886
<211> LENGTH: 14
<212> TYPE: DNA
<213> ORGANISM: Artificial Sequence
<220> FEATURE:
<223> OTHER INFORMATION: Synthetic Construct

<400> SEQUENCE: 886
cgaaaaacga aaaa                                                         14

<210> SEQ ID NO 887
<211> LENGTH: 14
<212> TYPE: DNA
<213> ORGANISM: Artificial Sequence
<220> FEATURE:
<223> OTHER INFORMATION: Synthetic Construct

<400> SEQUENCE: 887
ttcgggaatg ggta                                                         14
```

<210> SEQ ID NO 888
<211> LENGTH: 14
<212> TYPE: DNA
<213> ORGANISM: Artificial Sequence
<220> FEATURE:
<223> OTHER INFORMATION: Synthetic Construct

<400> SEQUENCE: 888
cgaaaaacga aaaa                                                        14

<210> SEQ ID NO 889
<211> LENGTH: 14
<212> TYPE: DNA
<213> ORGANISM: Artificial Sequence
<220> FEATURE:
<223> OTHER INFORMATION: Synthetic Construct

<400> SEQUENCE: 889
tcgggaatgg gtat                                                        14

<210> SEQ ID NO 890
<211> LENGTH: 14
<212> TYPE: DNA
<213> ORGANISM: Artificial Sequence
<220> FEATURE:
<223> OTHER INFORMATION: Synthetic Construct

<400> SEQUENCE: 890
cgaaaaacga aaaa                                                        14

<210> SEQ ID NO 891
<211> LENGTH: 14
<212> TYPE: DNA
<213> ORGANISM: Artificial Sequence
<220> FEATURE:
<223> OTHER INFORMATION: Synthetic Construct

<400> SEQUENCE: 891
cgggaatggg tatt                                                        14

<210> SEQ ID NO 892
<211> LENGTH: 14
<212> TYPE: DNA
<213> ORGANISM: Artificial Sequence
<220> FEATURE:
<223> OTHER INFORMATION: Synthetic Construct

<400> SEQUENCE: 892
cgaaaaacga aaaa                                                        14

<210> SEQ ID NO 893
<211> LENGTH: 14
<212> TYPE: DNA
<213> ORGANISM: Artificial Sequence
<220> FEATURE:
<223> OTHER INFORMATION: Synthetic Construct

<400> SEQUENCE: 893
gggaatgggt atta                                                        14

<210> SEQ ID NO 894
<211> LENGTH: 14
<212> TYPE: DNA
<213> ORGANISM: Artificial Sequence
<220> FEATURE:

<223> OTHER INFORMATION: Synthetic Construct

<400> SEQUENCE: 894
cgaaaaacga aaaa                    14

<210> SEQ ID NO 895
<211> LENGTH: 14
<212> TYPE: DNA
<213> ORGANISM: Artificial Sequence
<220> FEATURE:
<223> OTHER INFORMATION: Synthetic Construct

<400> SEQUENCE: 895
ggaatgggta ttat                    14

<210> SEQ ID NO 896
<211> LENGTH: 14
<212> TYPE: DNA
<213> ORGANISM: Artificial Sequence
<220> FEATURE:
<223> OTHER INFORMATION: Synthetic Construct

<400> SEQUENCE: 896
cgaaaaacga aaaa                    14

<210> SEQ ID NO 897
<211> LENGTH: 14
<212> TYPE: DNA
<213> ORGANISM: Artificial Sequence
<220> FEATURE:
<223> OTHER INFORMATION: Synthetic Construct

<400> SEQUENCE: 897
gaatgggtat tata                    14

<210> SEQ ID NO 898
<211> LENGTH: 14
<212> TYPE: DNA
<213> ORGANISM: Artificial Sequence
<220> FEATURE:
<223> OTHER INFORMATION: Synthetic Construct

<400> SEQUENCE: 898
cgaaaaacga aaaa                    14

<210> SEQ ID NO 899
<211> LENGTH: 14
<212> TYPE: DNA
<213> ORGANISM: Artificial Sequence
<220> FEATURE:
<223> OTHER INFORMATION: Synthetic Construct

<400> SEQUENCE: 899
aatgggtatt atag                    14

<210> SEQ ID NO 900
<211> LENGTH: 14
<212> TYPE: DNA
<213> ORGANISM: Artificial Sequence
<220> FEATURE:
<223> OTHER INFORMATION: Synthetic Construct

<400> SEQUENCE: 900
cgaaaaacga aaaa                    14

```
<210> SEQ ID NO 901
<211> LENGTH: 14
<212> TYPE: DNA
<213> ORGANISM: Artificial Sequence
<220> FEATURE:
<223> OTHER INFORMATION: Synthetic Construct

<400> SEQUENCE: 901
atgggtatta taga                                                         14

<210> SEQ ID NO 902
<211> LENGTH: 14
<212> TYPE: DNA
<213> ORGANISM: Artificial Sequence
<220> FEATURE:
<223> OTHER INFORMATION: Synthetic Construct

<400> SEQUENCE: 902
cgaaaaacga aaaa                                                         14

<210> SEQ ID NO 903
<211> LENGTH: 14
<212> TYPE: DNA
<213> ORGANISM: Artificial Sequence
<220> FEATURE:
<223> OTHER INFORMATION: Synthetic Construct

<400> SEQUENCE: 903
tgggtattat agaa                                                         14

<210> SEQ ID NO 904
<211> LENGTH: 14
<212> TYPE: DNA
<213> ORGANISM: Artificial Sequence
<220> FEATURE:
<223> OTHER INFORMATION: Synthetic Construct

<400> SEQUENCE: 904
cgaaaaacga aaaa                                                         14

<210> SEQ ID NO 905
<211> LENGTH: 14
<212> TYPE: DNA
<213> ORGANISM: Artificial Sequence
<220> FEATURE:
<223> OTHER INFORMATION: Synthetic Construct

<400> SEQUENCE: 905
gggtattata gaaa                                                         14

<210> SEQ ID NO 906
<211> LENGTH: 14
<212> TYPE: DNA
<213> ORGANISM: Artificial Sequence
<220> FEATURE:
<223> OTHER INFORMATION: Synthetic Construct

<400> SEQUENCE: 906
cgaaaaacga aaaa                                                         14

<210> SEQ ID NO 907
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 907
ggtattatag aaag                                                        14

<210> SEQ ID NO 908
<211> LENGTH: 14
<212> TYPE: DNA
<213> ORGANISM: Artificial Sequence
<220> FEATURE:
<223> OTHER INFORMATION: Synthetic Construct

<400> SEQUENCE: 908
cgaaaaacga aaaa                                                        14

<210> SEQ ID NO 909
<211> LENGTH: 14
<212> TYPE: DNA
<213> ORGANISM: Artificial Sequence
<220> FEATURE:
<223> OTHER INFORMATION: Synthetic Construct

<400> SEQUENCE: 909
gtattataga aaga                                                        14

<210> SEQ ID NO 910
<211> LENGTH: 14
<212> TYPE: DNA
<213> ORGANISM: Artificial Sequence
<220> FEATURE:
<223> OTHER INFORMATION: Synthetic Construct

<400> SEQUENCE: 910
cgaaaaacga aaaa                                                        14

<210> SEQ ID NO 911
<211> LENGTH: 14
<212> TYPE: DNA
<213> ORGANISM: Artificial Sequence
<220> FEATURE:
<223> OTHER INFORMATION: Synthetic Construct

<400> SEQUENCE: 911
tattatagaa agaa                                                        14

<210> SEQ ID NO 912
<211> LENGTH: 14
<212> TYPE: DNA
<213> ORGANISM: Artificial Sequence
<220> FEATURE:
<223> OTHER INFORMATION: Synthetic Construct

<400> SEQUENCE: 912
cgaaaaacga aaaa                                                        14

<210> SEQ ID NO 913
<211> LENGTH: 14
<212> TYPE: DNA
<213> ORGANISM: Artificial Sequence
<220> FEATURE:
<223> OTHER INFORMATION: Synthetic Construct

<400> SEQUENCE: 913
attatagaaa gaaa                                                        14

<210> SEQ ID NO 914
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 914
cgaaaaacga aaaa                                                    14

<210> SEQ ID NO 915
<211> LENGTH: 14
<212> TYPE: DNA
<213> ORGANISM: Artificial Sequence
<220> FEATURE:
<223> OTHER INFORMATION: Synthetic Construct

<400> SEQUENCE: 915
ttatagaaag aaaa                                                    14

<210> SEQ ID NO 916
<211> LENGTH: 14
<212> TYPE: DNA
<213> ORGANISM: Artificial Sequence
<220> FEATURE:
<223> OTHER INFORMATION: Synthetic Construct

<400> SEQUENCE: 916
cgaaaaacga aaaa                                                    14

<210> SEQ ID NO 917
<211> LENGTH: 14
<212> TYPE: DNA
<213> ORGANISM: Artificial Sequence
<220> FEATURE:
<223> OTHER INFORMATION: Synthetic Construct

<400> SEQUENCE: 917
tatagaaaga aaat                                                    14

<210> SEQ ID NO 918
<211> LENGTH: 14
<212> TYPE: DNA
<213> ORGANISM: Artificial Sequence
<220> FEATURE:
<223> OTHER INFORMATION: Synthetic Construct

<400> SEQUENCE: 918
cgaaaaacga aaaa                                                    14

<210> SEQ ID NO 919
<211> LENGTH: 14
<212> TYPE: DNA
<213> ORGANISM: Artificial Sequence
<220> FEATURE:
<223> OTHER INFORMATION: Synthetic Construct

<400> SEQUENCE: 919
atagaaagaa aatg                                                    14

<210> SEQ ID NO 920
<211> LENGTH: 14
<212> TYPE: DNA
<213> ORGANISM: Artificial Sequence
<220> FEATURE:
<223> OTHER INFORMATION: Synthetic Construct

<400> SEQUENCE: 920
```

```
cgaaaaacga aaaa                                                   14
```

<210> SEQ ID NO 921
<211> LENGTH: 14
<212> TYPE: DNA
<213> ORGANISM: Artificial Sequence
<220> FEATURE:
<223> OTHER INFORMATION: Synthetic Construct

<400> SEQUENCE: 921

```
tagaaagaaa atga                                                   14
```

<210> SEQ ID NO 922
<211> LENGTH: 14
<212> TYPE: DNA
<213> ORGANISM: Artificial Sequence
<220> FEATURE:
<223> OTHER INFORMATION: Synthetic Construct

<400> SEQUENCE: 922

```
cgaaaaacga aaaa                                                   14
```

<210> SEQ ID NO 923
<211> LENGTH: 14
<212> TYPE: DNA
<213> ORGANISM: Artificial Sequence
<220> FEATURE:
<223> OTHER INFORMATION: Synthetic Construct

<400> SEQUENCE: 923

```
agaaagaaaa tgaa                                                   14
```

<210> SEQ ID NO 924
<211> LENGTH: 14
<212> TYPE: DNA
<213> ORGANISM: Artificial Sequence
<220> FEATURE:
<223> OTHER INFORMATION: Synthetic Construct

<400> SEQUENCE: 924

```
cgaaaaacga aaaa                                                   14
```

<210> SEQ ID NO 925
<211> LENGTH: 14
<212> TYPE: DNA
<213> ORGANISM: Artificial Sequence
<220> FEATURE:
<223> OTHER INFORMATION: Synthetic Construct

<400> SEQUENCE: 925

```
gaaagaaat gaat                                                    14
```

<210> SEQ ID NO 926
<211> LENGTH: 14
<212> TYPE: DNA
<213> ORGANISM: Artificial Sequence
<220> FEATURE:
<223> OTHER INFORMATION: Synthetic Construct

<400> SEQUENCE: 926

```
cgaaaaacga aaaa                                                   14
```

<210> SEQ ID NO 927
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 927
aaagaaaatg aatg                                                  14

<210> SEQ ID NO 928
<211> LENGTH: 14
<212> TYPE: DNA
<213> ORGANISM: Artificial Sequence
<220> FEATURE:
<223> OTHER INFORMATION: Synthetic Construct

<400> SEQUENCE: 928
cgaaaaacga aaaa                                                  14

<210> SEQ ID NO 929
<211> LENGTH: 14
<212> TYPE: DNA
<213> ORGANISM: Artificial Sequence
<220> FEATURE:
<223> OTHER INFORMATION: Synthetic Construct

<400> SEQUENCE: 929
aagaaaatga atgt                                                  14

<210> SEQ ID NO 930
<211> LENGTH: 14
<212> TYPE: DNA
<213> ORGANISM: Artificial Sequence
<220> FEATURE:
<223> OTHER INFORMATION: Synthetic Construct

<400> SEQUENCE: 930
cgaaaaacga aaaa                                                  14

<210> SEQ ID NO 931
<211> LENGTH: 14
<212> TYPE: DNA
<213> ORGANISM: Artificial Sequence
<220> FEATURE:
<223> OTHER INFORMATION: Synthetic Construct

<400> SEQUENCE: 931
agaaaatgaa tgtt                                                  14

<210> SEQ ID NO 932
<211> LENGTH: 14
<212> TYPE: DNA
<213> ORGANISM: Artificial Sequence
<220> FEATURE:
<223> OTHER INFORMATION: Synthetic Construct

<400> SEQUENCE: 932
ccccatcgcc atcg                                                  14

<210> SEQ ID NO 933
<211> LENGTH: 25
<212> TYPE: DNA
<213> ORGANISM: Artificial Sequence
<220> FEATURE:
<223> OTHER INFORMATION: Synthetic Construct

<400> SEQUENCE: 933 cggattttt ttttgggag agagg                                        25
```

<210> SEQ ID NO 934
<211> LENGTH: 14
<212> TYPE: DNA
<213> ORGANISM: Artificial Sequence
<220> FEATURE:
<223> OTHER INFORMATION: Synthetic Construct

<400> SEQUENCE: 934
gaaaatgaat gttt                                                        14

<210> SEQ ID NO 935
<211> LENGTH: 14
<212> TYPE: DNA
<213> ORGANISM: Artificial Sequence
<220> FEATURE:
<223> OTHER INFORMATION: Synthetic Construct

<400> SEQUENCE: 935
ccccatcgcc atcg                                                        14

<210> SEQ ID NO 936
<211> LENGTH: 14
<212> TYPE: DNA
<213> ORGANISM: Artificial Sequence
<220> FEATURE:
<223> OTHER INFORMATION: Synthetic Construct

<400> SEQUENCE: 936
aaaatgaatg tttt                                                        14

<210> SEQ ID NO 937
<211> LENGTH: 14
<212> TYPE: DNA
<213> ORGANISM: Artificial Sequence
<220> FEATURE:
<223> OTHER INFORMATION: Synthetic Construct

<400> SEQUENCE: 937
ccccatcgcc atcg                                                        14

<210> SEQ ID NO 938
<211> LENGTH: 14
<212> TYPE: DNA
<213> ORGANISM: Artificial Sequence
<220> FEATURE:
<223> OTHER INFORMATION: Synthetic Construct

<400> SEQUENCE: 938
aaatgaatgt tttt                                                        14

<210> SEQ ID NO 939
<211> LENGTH: 14
<212> TYPE: DNA
<213> ORGANISM: Artificial Sequence
<220> FEATURE:
<223> OTHER INFORMATION: Synthetic Construct

<400> SEQUENCE: 939
ccccatcgcc atcg                                                        14

<210> SEQ ID NO 940
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 940
aatgaatgtt tttc                                            14

<210> SEQ ID NO 941
<211> LENGTH: 14
<212> TYPE: DNA
<213> ORGANISM: Artificial Sequence
<220> FEATURE:
<223> OTHER INFORMATION: Synthetic Construct

<400> SEQUENCE: 941
ccccatcgcc atcg                                            14

<210> SEQ ID NO 942
<211> LENGTH: 14
<212> TYPE: DNA
<213> ORGANISM: Artificial Sequence
<220> FEATURE:
<223> OTHER INFORMATION: Synthetic Construct

<400> SEQUENCE: 942
atgaatgttt ttcg                                            14

<210> SEQ ID NO 943
<211> LENGTH: 14
<212> TYPE: DNA
<213> ORGANISM: Artificial Sequence
<220> FEATURE:
<223> OTHER INFORMATION: Synthetic Construct

<400> SEQUENCE: 943
ccccatcgcc atcg                                            14

<210> SEQ ID NO 944
<211> LENGTH: 14
<212> TYPE: DNA
<213> ORGANISM: Artificial Sequence
<220> FEATURE:
<223> OTHER INFORMATION: Synthetic Construct

<400> SEQUENCE: 944
tgaatgtttt tcgg                                            14

<210> SEQ ID NO 945
<211> LENGTH: 14
<212> TYPE: DNA
<213> ORGANISM: Artificial Sequence
<220> FEATURE:
<223> OTHER INFORMATION: Synthetic Construct

<400> SEQUENCE: 945
ccccatcgcc atcg                                            14

<210> SEQ ID NO 946
<211> LENGTH: 14
<212> TYPE: DNA
<213> ORGANISM: Artificial Sequence
<220> FEATURE:
<223> OTHER INFORMATION: Synthetic Construct

<400> SEQUENCE: 946
gaatgttttt cggt                                            14

<210> SEQ ID NO 947
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 947
ccccatcgcc atcg                                                       14

<210> SEQ ID NO 948
<211> LENGTH: 14
<212> TYPE: DNA
<213> ORGANISM: Artificial Sequence
<220> FEATURE:
<223> OTHER INFORMATION: Synthetic Construct

<400> SEQUENCE: 948 aatgttttc ggtt                                                        14

<210> SEQ ID NO 949
<211> LENGTH: 14
<212> TYPE: DNA
<213> ORGANISM: Artificial Sequence
<220> FEATURE:
<223> OTHER INFORMATION: Synthetic Construct

<400> SEQUENCE: 949
ccccatcgcc atcg                                                       14

<210> SEQ ID NO 950
<211> LENGTH: 14
<212> TYPE: DNA
<213> ORGANISM: Artificial Sequence
<220> FEATURE:
<223> OTHER INFORMATION: Synthetic Construct

<400> SEQUENCE: 950
atgtttttcg gttt                                                       14

<210> SEQ ID NO 951
<211> LENGTH: 14
<212> TYPE: DNA
<213> ORGANISM: Artificial Sequence
<220> FEATURE:
<223> OTHER INFORMATION: Synthetic Construct

<400> SEQUENCE: 951
ccccatcgcc atcg                                                       14

<210> SEQ ID NO 952
<211> LENGTH: 14
<212> TYPE: DNA
<213> ORGANISM: Artificial Sequence
<220> FEATURE:
<223> OTHER INFORMATION: Synthetic Construct

<400> SEQUENCE: 952 tgttttcgg tttt                                                        14

<210> SEQ ID NO 953
<211> LENGTH: 14
<212> TYPE: DNA
<213> ORGANISM: Artificial Sequence
<220> FEATURE:
<223> OTHER INFORMATION: Synthetic Construct

<400> SEQUENCE: 953
```
ccccatcgcc atcg    14

<210> SEQ ID NO 954
<211> LENGTH: 14
<212> TYPE: DNA
<213> ORGANISM: Artificial Sequence
<220> FEATURE:
<223> OTHER INFORMATION: Synthetic Construct

<400> SEQUENCE: 954 gttttcggt ttta    14

<210> SEQ ID NO 955
<211> LENGTH: 14
<212> TYPE: DNA
<213> ORGANISM: Artificial Sequence
<220> FEATURE:
<223> OTHER INFORMATION: Synthetic Construct

<400> SEQUENCE: 955
ccccatcgcc atcg    14

<210> SEQ ID NO 956
<211> LENGTH: 14
<212> TYPE: DNA
<213> ORGANISM: Artificial Sequence
<220> FEATURE:
<223> OTHER INFORMATION: Synthetic Construct

<400> SEQUENCE: 956
tttttcggtt ttag    14

<210> SEQ ID NO 957
<211> LENGTH: 14
<212> TYPE: DNA
<213> ORGANISM: Artificial Sequence
<220> FEATURE:
<223> OTHER INFORMATION: Synthetic Construct

<400> SEQUENCE: 957
ccccatcgcc atcg    14

<210> SEQ ID NO 958
<211> LENGTH: 14
<212> TYPE: DNA
<213> ORGANISM: Artificial Sequence
<220> FEATURE:
<223> OTHER INFORMATION: Synthetic Construct

<400> SEQUENCE: 958
ttttcggttt taga    14

<210> SEQ ID NO 959
<211> LENGTH: 14
<212> TYPE: DNA
<213> ORGANISM: Artificial Sequence
<220> FEATURE:
<223> OTHER INFORMATION: Synthetic Construct

<400> SEQUENCE: 959
ccccatcgcc atcg    14

<210> SEQ ID NO 960
<211> LENGTH: 14
<212> TYPE: DNA

-continued

```
<213> ORGANISM: Artificial Sequence
<220> FEATURE:
<223> OTHER INFORMATION: Synthetic Construct

<400> SEQUENCE: 960
tttcggtttt agat                                                14

<210> SEQ ID NO 961
<211> LENGTH: 14
<212> TYPE: DNA
<213> ORGANISM: Artificial Sequence
<220> FEATURE:
<223> OTHER INFORMATION: Synthetic Construct

<400> SEQUENCE: 961
ccccatcgcc atcg                                                14

<210> SEQ ID NO 962
<211> LENGTH: 14
<212> TYPE: DNA
<213> ORGANISM: Artificial Sequence
<220> FEATURE:
<223> OTHER INFORMATION: Synthetic Construct

<400> SEQUENCE: 962
ttcggtttta gatt                                                14

<210> SEQ ID NO 963
<211> LENGTH: 14
<212> TYPE: DNA
<213> ORGANISM: Artificial Sequence
<220> FEATURE:
<223> OTHER INFORMATION: Synthetic Construct

<400> SEQUENCE: 963
ccccatcgcc atcg                                                14

<210> SEQ ID NO 964
<211> LENGTH: 14
<212> TYPE: DNA
<213> ORGANISM: Artificial Sequence
<220> FEATURE:
<223> OTHER INFORMATION: Synthetic Construct

<400> SEQUENCE: 964
tcggttttag attg                                                14

<210> SEQ ID NO 965
<211> LENGTH: 14
<212> TYPE: DNA
<213> ORGANISM: Artificial Sequence
<220> FEATURE:
<223> OTHER INFORMATION: Synthetic Construct

<400> SEQUENCE: 965
ccccatcgcc atcg                                                14

<210> SEQ ID NO 966
<211> LENGTH: 14
<212> TYPE: DNA
<213> ORGANISM: Artificial Sequence
<220> FEATURE:
<223> OTHER INFORMATION: Synthetic Construct

<400> SEQUENCE: 966
cggttttaga ttgc                                                14
```

<210> SEQ ID NO 967
<211> LENGTH: 14
<212> TYPE: DNA
<213> ORGANISM: Artificial Sequence
<220> FEATURE:
<223> OTHER INFORMATION: Synthetic Construct

<400> SEQUENCE: 967
ccccatcgcc atcg                                                        14

<210> SEQ ID NO 968
<211> LENGTH: 14
<212> TYPE: DNA
<213> ORGANISM: Artificial Sequence
<220> FEATURE:
<223> OTHER INFORMATION: Synthetic Construct

<400> SEQUENCE: 968
ggttttagat tgcg                                                        14

<210> SEQ ID NO 969
<211> LENGTH: 14
<212> TYPE: DNA
<213> ORGANISM: Artificial Sequence
<220> FEATURE:
<223> OTHER INFORMATION: Synthetic Construct

<400> SEQUENCE: 969
ccccatcgcc atcg                                                        14

<210> SEQ ID NO 970
<211> LENGTH: 14
<212> TYPE: DNA
<213> ORGANISM: Artificial Sequence
<220> FEATURE:
<223> OTHER INFORMATION: Synthetic Construct

<400> SEQUENCE: 970
gttttagatt gcgt                                                        14

<210> SEQ ID NO 971
<211> LENGTH: 14
<212> TYPE: DNA
<213> ORGANISM: Artificial Sequence
<220> FEATURE:
<223> OTHER INFORMATION: Synthetic Construct

<400> SEQUENCE: 971
ccccatcgcc atcg                                                        14

<210> SEQ ID NO 972
<211> LENGTH: 14
<212> TYPE: DNA
<213> ORGANISM: Artificial Sequence
<220> FEATURE:
<223> OTHER INFORMATION: Synthetic Construct

<400> SEQUENCE: 972
ttttagattg cgtt                                                        14

<210> SEQ ID NO 973
<211> LENGTH: 14
<212> TYPE: DNA
<213> ORGANISM: Artificial Sequence
<220> FEATURE:

<223> OTHER INFORMATION: Synthetic Construct

<400> SEQUENCE: 973
ccccatcgcc atcg                                                                14

<210> SEQ ID NO 974
<211> LENGTH: 14
<212> TYPE: DNA
<213> ORGANISM: Artificial Sequence
<220> FEATURE:
<223> OTHER INFORMATION: Synthetic Construct

<400> SEQUENCE: 974
tttagattgc gttt                                                                14

<210> SEQ ID NO 975
<211> LENGTH: 14
<212> TYPE: DNA
<213> ORGANISM: Artificial Sequence
<220> FEATURE:
<223> OTHER INFORMATION: Synthetic Construct

<400> SEQUENCE: 975
ccccatcgcc atcg                                                                14

<210> SEQ ID NO 976
<211> LENGTH: 14
<212> TYPE: DNA
<213> ORGANISM: Artificial Sequence
<220> FEATURE:
<223> OTHER INFORMATION: Synthetic Construct

<400> SEQUENCE: 976
ttagattgcg tttt                                                                14

<210> SEQ ID NO 977
<211> LENGTH: 14
<212> TYPE: DNA
<213> ORGANISM: Artificial Sequence
<220> FEATURE:
<223> OTHER INFORMATION: Synthetic Construct

<400> SEQUENCE: 977
ccccatcgcc atcg                                                                14

<210> SEQ ID NO 978
<211> LENGTH: 14
<212> TYPE: DNA
<213> ORGANISM: Artificial Sequence
<220> FEATURE:
<223> OTHER INFORMATION: Synthetic Construct

<400> SEQUENCE: 978
tagattgcgt tttt                                                                14

<210> SEQ ID NO 979
<211> LENGTH: 14
<212> TYPE: DNA
<213> ORGANISM: Artificial Sequence
<220> FEATURE:
<223> OTHER INFORMATION: Synthetic Construct

<400> SEQUENCE: 979
ccccatcgcc atcg                                                                14

```
<210> SEQ ID NO 980
<211> LENGTH: 14
<212> TYPE: DNA
<213> ORGANISM: Artificial Sequence
<220> FEATURE:
<223> OTHER INFORMATION: Synthetic Construct

<400> SEQUENCE: 980
agattgcgtt tttt                                                         14

<210> SEQ ID NO 981
<211> LENGTH: 14
<212> TYPE: DNA
<213> ORGANISM: Artificial Sequence
<220> FEATURE:
<223> OTHER INFORMATION: Synthetic Construct

<400> SEQUENCE: 981
ccccatcgcc atcg                                                         14

<210> SEQ ID NO 982
<211> LENGTH: 14
<212> TYPE: DNA
<213> ORGANISM: Artificial Sequence
<220> FEATURE:
<223> OTHER INFORMATION: Synthetic Construct

<400> SEQUENCE: 982
gattgcgttt tttt                                                         14

<210> SEQ ID NO 983
<211> LENGTH: 14
<212> TYPE: DNA
<213> ORGANISM: Artificial Sequence
<220> FEATURE:
<223> OTHER INFORMATION: Synthetic Construct

<400> SEQUENCE: 983
ccccatcgcc atcg                                                         14

<210> SEQ ID NO 984
<211> LENGTH: 14
<212> TYPE: DNA
<213> ORGANISM: Artificial Sequence
<220> FEATURE:
<223> OTHER INFORMATION: Synthetic Construct

<400> SEQUENCE: 984
attgcgtttt tttt                                                         14

<210> SEQ ID NO 985
<211> LENGTH: 14
<212> TYPE: DNA
<213> ORGANISM: Artificial Sequence
<220> FEATURE:
<223> OTHER INFORMATION: Synthetic Construct

<400> SEQUENCE: 985
ccccatcgcc atcg                                                         14

<210> SEQ ID NO 986
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 986
ttgcgttttt ttta                                                      14

<210> SEQ ID NO 987
<211> LENGTH: 14
<212> TYPE: DNA
<213> ORGANISM: Artificial Sequence
<220> FEATURE:
<223> OTHER INFORMATION: Synthetic Construct

<400> SEQUENCE: 987
ccccatcgcc atcg                                                      14

<210> SEQ ID NO 988
<211> LENGTH: 14
<212> TYPE: DNA
<213> ORGANISM: Artificial Sequence
<220> FEATURE:
<223> OTHER INFORMATION: Synthetic Construct

<400> SEQUENCE: 988 tgcgttttt ttag                                                       14

<210> SEQ ID NO 989
<211> LENGTH: 14
<212> TYPE: DNA
<213> ORGANISM: Artificial Sequence
<220> FEATURE:
<223> OTHER INFORMATION: Synthetic Construct

<400> SEQUENCE: 989
ccccatcgcc atcg                                                      14

<210> SEQ ID NO 990
<211> LENGTH: 14
<212> TYPE: DNA
<213> ORGANISM: Artificial Sequence
<220> FEATURE:
<223> OTHER INFORMATION: Synthetic Construct

<400> SEQUENCE: 990
gcgttttttt tagt                                                      14

<210> SEQ ID NO 991
<211> LENGTH: 14
<212> TYPE: DNA
<213> ORGANISM: Artificial Sequence
<220> FEATURE:
<223> OTHER INFORMATION: Synthetic Construct

<400> SEQUENCE: 991
ccccatcgcc atcg                                                      14

<210> SEQ ID NO 992
<211> LENGTH: 14
<212> TYPE: DNA
<213> ORGANISM: Artificial Sequence
<220> FEATURE:
<223> OTHER INFORMATION: Synthetic Construct

<400> SEQUENCE: 992 cgttttttt agtt                                                       14

<210> SEQ ID NO 993
<211> LENGTH: 14
```

-continued

```
<212> TYPE: DNA
<213> ORGANISM: Artificial Sequence
<220> FEATURE:
<223> OTHER INFORMATION: Synthetic Construct

<400> SEQUENCE: 993
ccccatcgcc atcg                                                       14

<210> SEQ ID NO 994
<211> LENGTH: 14
<212> TYPE: DNA
<213> ORGANISM: Artificial Sequence
<220> FEATURE:
<223> OTHER INFORMATION: Synthetic Construct

<400> SEQUENCE: 994 gttttttta gttt                                                        14

<210> SEQ ID NO 995
<211> LENGTH: 14
<212> TYPE: DNA
<213> ORGANISM: Artificial Sequence
<220> FEATURE:
<223> OTHER INFORMATION: Synthetic Construct

<400> SEQUENCE: 995
ccccatcgcc atcg                                                       14

<210> SEQ ID NO 996
<211> LENGTH: 14
<212> TYPE: DNA
<213> ORGANISM: Artificial Sequence
<220> FEATURE:
<223> OTHER INFORMATION: Synthetic Construct

<400> SEQUENCE: 996 tttttttag tttt                                                        14

<210> SEQ ID NO 997
<211> LENGTH: 14
<212> TYPE: DNA
<213> ORGANISM: Artificial Sequence
<220> FEATURE:
<223> OTHER INFORMATION: Synthetic Construct

<400> SEQUENCE: 997
ccccatcgcc atcg                                                       14

<210> SEQ ID NO 998
<211> LENGTH: 14
<212> TYPE: DNA
<213> ORGANISM: Artificial Sequence
<220> FEATURE:
<223> OTHER INFORMATION: Synthetic Construct

<400> SEQUENCE: 998
tttttttagt tttg                                                       14

<210> SEQ ID NO 999
<211> LENGTH: 14
<212> TYPE: DNA
<213> ORGANISM: Artificial Sequence
<220> FEATURE:
<223> OTHER INFORMATION: Synthetic Construct

<400> SEQUENCE: 999
```
ccccatcgcc atcg						14

<210> SEQ ID NO 1000
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1000 tttttagtt ttgt						14

<210> SEQ ID NO 1001
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1001
ccccatcgcc atcg						14

<210> SEQ ID NO 1002
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1002 ttttagttt tgtt						14

<210> SEQ ID NO 1003
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1003
ccccatcgcc atcg						14

<210> SEQ ID NO 1004
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1004
ttttagtttt gttt						14

<210> SEQ ID NO 1005
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1005
ccccatcgcc atcg						14

<210> SEQ ID NO 1006
<211> LENGTH: 14
<212> TYPE: DNA
<213> ORGANISM: Artificial Sequence -continued
<220> FEATURE:
<223> OTHER INFORMATION: Synthetic Construct

<400> SEQUENCE: 1006
tttagttttg tttt                                                             14

<210> SEQ ID NO 1007
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1007
ccccatcgcc atcg                                                             14

<210> SEQ ID NO 1008
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1008
ttagttttgt tttt                                                             14

<210> SEQ ID NO 1009
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1009
ccccatcgcc atcg                                                             14

<210> SEQ ID NO 1010
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1010
tagttttgtt tttt                                                             14

<210> SEQ ID NO 1011
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1011
ccccatcgcc atcg                                                             14

<210> SEQ ID NO 1012
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1012
agttttgttt tttt                                                             14

```
<210> SEQ ID NO 1013
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1013
ccccatcgcc atcg                                                         14

<210> SEQ ID NO 1014
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1014
gttttgtttt tttc                                                         14

<210> SEQ ID NO 1015
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1015
ccccatcgcc atcg                                                         14

<210> SEQ ID NO 1016
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1016
ttttgttttt ttcg                                                         14

<210> SEQ ID NO 1017
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1017
ccccatcgcc atcg                                                         14

<210> SEQ ID NO 1018
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1018 tttgttttt tcgc                                                          14

<210> SEQ ID NO 1019
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1019
ccccatcgcc atcg                                                    14

<210> SEQ ID NO 1020
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1020
ttgttttttt cgcg                                                    14

<210> SEQ ID NO 1021
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1021
ccccatcgcc atcg                                                    14

<210> SEQ ID NO 1022
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1022 tgttttttc gcgt                                                     14

<210> SEQ ID NO 1023
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1023
ccccatcgcc atcg                                                    14

<210> SEQ ID NO 1024
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1024
gtttttttcg cgtt                                                    14

<210> SEQ ID NO 1025
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1025
ccccatcgcc atcg                                                    14

<210> SEQ ID NO 1026
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1026
tttttttcgc gttt                                                    14

<210> SEQ ID NO 1027
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1027
ccccatcgcc atcg                                                    14

<210> SEQ ID NO 1028
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1028 tttttttcgcg tttg                                                   14

<210> SEQ ID NO 1029
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1029
ccccatcgcc atcg                                                    14

<210> SEQ ID NO 1030
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1030
tttttcgcgt ttgg                                                    14

<210> SEQ ID NO 1031
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1031
ccccatcgcc atcg                                                    14

<210> SEQ ID NO 1032
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1032
```
ttttcgcgtt tggc                                                      14

<210> SEQ ID NO 1033
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1033
ccccatcgcc atcg                                                      14

<210> SEQ ID NO 1034
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1034
tttcgcgttt ggcg                                                      14

<210> SEQ ID NO 1035
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1035
ctcccgaccc acta                                                      14

<210> SEQ ID NO 1036
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1036
cgagggaggg tgttcgattg ttta                                           24

<210> SEQ ID NO 1037
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1037
ttcgcgtttg gcgt                                                      14

<210> SEQ ID NO 1038
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1038
ctcccgaccc acta                                                      14

<210> SEQ ID NO 1039
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1039
tcgcgtttgg cgtt                                                      14

<210> SEQ ID NO 1040
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1040
ctcccgaccc acta                                                      14

<210> SEQ ID NO 1041
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1041
cgcgtttggc gttt                                                      14

<210> SEQ ID NO 1042
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1042
ctcccgaccc acta                                                      14

<210> SEQ ID NO 1043
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1043
gcgtttggcg tttt                                                      14

<210> SEQ ID NO 1044
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1044
ctcccgaccc acta                                                      14

<210> SEQ ID NO 1045
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1045
cgtttggcgt tttt                                                      14
```

<210> SEQ ID NO 1046
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1046
ctcccgaccc acta                                                       14

<210> SEQ ID NO 1047
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1047
gtttggcgtt tttc                                                       14

<210> SEQ ID NO 1048
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1048
ctcccgaccc acta                                                       14

<210> SEQ ID NO 1049
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1049
tttggcgttt ttcg                                                       14

<210> SEQ ID NO 1050
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1050
ctcccgaccc acta                                                       14

<210> SEQ ID NO 1051
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1051
ttggcgtttt tcgt                                                       14

<210> SEQ ID NO 1052
<211> LENGTH: 14
<212> TYPE: DNA
<213> ORGANISM: Artificial Sequence
<220> FEATURE:

<223> OTHER INFORMATION: Synthetic Construct

<400> SEQUENCE: 1052
ctcccgaccc acta                                                        14

<210> SEQ ID NO 1053
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1053
tggcgttttt cgtt                                                        14

<210> SEQ ID NO 1054
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1054
ctcccgaccc acta                                                        14

<210> SEQ ID NO 1055
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1055 ggcgttttc gttt                                                         14

<210> SEQ ID NO 1056
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1056
ctcccgaccc acta                                                        14

<210> SEQ ID NO 1057
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1057 gcgttttcg tttt                                                         14

<210> SEQ ID NO 1058
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1058
ctcccgaccc acta                                                        14

```
<210> SEQ ID NO 1059
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1059 cgttttcgt tttt                                                        14

<210> SEQ ID NO 1060
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1060
ctcccgaccc acta                                                       14

<210> SEQ ID NO 1061
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1061 gttttcgtt tttc                                                        14

<210> SEQ ID NO 1062
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1062
ctcccgaccc acta                                                       14

<210> SEQ ID NO 1063
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1063
tttttcgttt ttcg                                                       14

<210> SEQ ID NO 1064
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1064
ctcccgaccc acta                                                       14

<210> SEQ ID NO 1065
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 1065
ttttcgtttt tcgt                                                              14

<210> SEQ ID NO 1066
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1066
ctcccgaccc acta                                                              14

<210> SEQ ID NO 1067
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1067
tttcgttttt cgtt                                                              14

<210> SEQ ID NO 1068
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1068
ctcccgaccc acta                                                              14

<210> SEQ ID NO 1069
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1069 ttcgttttte gttt                                                              14

<210> SEQ ID NO 1070
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1070
ctcccgaccc acta                                                              14

<210> SEQ ID NO 1071
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1071 tcgttttteg tttt                                                              14

<210> SEQ ID NO 1072
<211> LENGTH: 14

<212> TYPE: DNA
<213> ORGANISM: Artificial Sequence
<220> FEATURE:
<223> OTHER INFORMATION: Synthetic Construct

<400> SEQUENCE: 1072
ctcccgaccc acta                                            14

<210> SEQ ID NO 1073
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1073 cgttttcgt tttt                                             14

<210> SEQ ID NO 1074
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1074
ctcccgaccc acta                                            14

<210> SEQ ID NO 1075
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1075
gtttttcgtt tttt                                            14

<210> SEQ ID NO 1076
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1076
ctcccgaccc acta                                            14

<210> SEQ ID NO 1077
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1077
tttttcgttt tttt                                            14

<210> SEQ ID NO 1078
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1078
ctcccgaccc acta                                                              14

<210> SEQ ID NO 1079
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1079
ttttcgtttt tttg                                                              14

<210> SEQ ID NO 1080
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1080
ctcccgaccc acta                                                              14

<210> SEQ ID NO 1081
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1081
tttcgttttt ttgt                                                              14

<210> SEQ ID NO 1082
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1082
ctcccgaccc acta                                                              14

<210> SEQ ID NO 1083
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1083 ttcgttttt tgtt                                                               14

<210> SEQ ID NO 1084
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1084
ctcccgaccc acta                                                              14

<210> SEQ ID NO 1085
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1085
tcgttttttt gttt                                                      14

<210> SEQ ID NO 1086
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1086
ctcccgaccc acta                                                      14

<210> SEQ ID NO 1087
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1087
cgtttttttg tttt                                                      14

<210> SEQ ID NO 1088
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1088
ctcccgaccc acta                                                      14

<210> SEQ ID NO 1089
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1089
gtttttttgt tttc                                                      14

<210> SEQ ID NO 1090
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1090
ctcccgaccc acta                                                      14

<210> SEQ ID NO 1091
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1091
tttttttgtt ttcg                                                      14
```

```
<210> SEQ ID NO 1092
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1092
ctcccgaccc acta                                                        14

<210> SEQ ID NO 1093
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1093 tttttgttt tcgg                                                         14

<210> SEQ ID NO 1094
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1094
ctcccgaccc acta                                                        14

<210> SEQ ID NO 1095
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1095
tttttgtttt cgga                                                        14

<210> SEQ ID NO 1096
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1096
ctcccgaccc acta                                                        14

<210> SEQ ID NO 1097
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1097
ttttgttttc ggat                                                        14

<210> SEQ ID NO 1098
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1098
ctcccgaccc acta                                                       14

<210> SEQ ID NO 1099
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1099
tttgttttcg gatt                                                       14

<210> SEQ ID NO 1100
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1100
ctcccgaccc acta                                                       14

<210> SEQ ID NO 1101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1101
ttgttttcgg attt                                                       14

<210> SEQ ID NO 1102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1102
ctcccgaccc acta                                                       14

<210> SEQ ID NO 1103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1103
tgttttcgga tttt                                                       14

<210> SEQ ID NO 1104
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1104
ctcccgaccc acta                                                       14

<210> SEQ ID NO 1105
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1105
gttttcggat tttt                                                       14

<210> SEQ ID NO 1106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1106
ctcccgaccc acta                                                       14

<210> SEQ ID NO 1107
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1107
ttttcggatt tttt                                                       14

<210> SEQ ID NO 1108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1108
ctcccgaccc acta                                                       14

<210> SEQ ID NO 1109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1109
tttcggattt tttt                                                       14

<210> SEQ ID NO 1110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1110
ctcccgaccc acta                                                       14

<210> SEQ ID NO 1111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1111
```
ttcggatttt tttt                                                          14

<210> SEQ ID NO 1112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1112
ctcccgaccc acta                                                          14

<210> SEQ ID NO 1113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1113
tcggattttt tttt                                                          14

<210> SEQ ID NO 1114
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1114
ctcccgaccc acta                                                          14

<210> SEQ ID NO 1115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1115
cggatttttt tttt                                                          14

<210> SEQ ID NO 1116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1116
ctcccgaccc acta                                                          14

<210> SEQ ID NO 1117
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1117
ggattttttt tttt                                                          14

<210> SEQ ID NO 1118
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1118
ctcccgaccc acta                                                        14

<210> SEQ ID NO 1119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1119
gatttttttt tttg                                                        14

<210> SEQ ID NO 1120
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1120
ctcccgaccc acta                                                        14

<210> SEQ ID NO 1121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1121
attttttttt ttgg                                                        14

<210> SEQ ID NO 1122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1122
ctcccgaccc acta                                                        14

<210> SEQ ID NO 1123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1123
tttttttttt tggg                                                        14

<210> SEQ ID NO 1124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1124
ctcccgaccc acta                                                        14
```

<210> SEQ ID NO 1125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1125
tttttttttt ggga                                                       14

<210> SEQ ID NO 1126
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1126
ctcccgaccc acta                                                       14

<210> SEQ ID NO 1127
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1127 ttttttttg ggag                                                        14

<210> SEQ ID NO 1128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1128
ctcccgaccc acta                                                       14

<210> SEQ ID NO 1129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1129
ttttttttgg gaga                                                       14

<210> SEQ ID NO 1130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1130
ctcccgaccc acta                                                       14

<210> SEQ ID NO 1131
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 1131
tttttttggg agag                                                    14

<210> SEQ ID NO 1132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1132
ctcccgaccc acta                                                    14

<210> SEQ ID NO 1133
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1133 tttttggga gaga                                                     14

<210> SEQ ID NO 1134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1134
ctcccgaccc acta                                                    14

<210> SEQ ID NO 1135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1135
tttttgggag agag                                                    14

<210> SEQ ID NO 1136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1136
ctcccgaccc acta                                                    14

<210> SEQ ID NO 1137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1137
ttttgggaga gagg                                                    14
```

```
<210> SEQ ID NO 1138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1138
aaccgacgca aaaa                                                      14

<210> SEQ ID NO 1139
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1139 tgggggttg cgtttgggcg ttgat                                           25

<210> SEQ ID NO 1140
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1140
tttgggagag aggc                                                      14

<210> SEQ ID NO 1141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1141
aaccgacgca aaaa                                                      14

<210> SEQ ID NO 1142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1142
ttgggagaga ggcg                                                      14

<210> SEQ ID NO 1143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1143
aaccgacgca aaaa                                                      14

<210> SEQ ID NO 1144
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1144
tgggagagag gcga                                                    14

<210> SEQ ID NO 1145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1145
aaccgacgca aaaa                                                    14

<210> SEQ ID NO 1146
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1146
gggagagagg cgat                                                    14

<210> SEQ ID NO 1147
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1147
aaccgacgca aaaa                                                    14

<210> SEQ ID NO 1148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1148
ggagagaggc gatg                                                    14

<210> SEQ ID NO 1149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1149
aaccgacgca aaaa                                                    14

<210> SEQ ID NO 1150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1150
gagagaggcg atgg                                                    14

<210> SEQ ID NO 1151
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 1151
aaccgacgca aaaa                                                       14

<210> SEQ ID NO 1152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1152
agagaggcga tggc                                                       14

<210> SEQ ID NO 1153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1153
aaccgacgca aaaa                                                       14

<210> SEQ ID NO 1154
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1154
gagaggcgat ggcg                                                       14

<210> SEQ ID NO 1155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1155
aaccgacgca aaaa                                                       14

<210> SEQ ID NO 1156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1156
agaggcgatg gcga                                                       14

<210> SEQ ID NO 1157
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1157
```

```
aaccgacgca aaaa                                                    14

<210> SEQ ID NO 1158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1158
gaggcgatgg cgat                                                    14

<210> SEQ ID NO 1159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1159
aaccgacgca aaaa                                                    14

<210> SEQ ID NO 1160
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1160
aggcgatggc gatg                                                    14

<210> SEQ ID NO 1161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1161
aaccgacgca aaaa                                                    14

<210> SEQ ID NO 1162
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1162
ggcgatggcg atgg                                                    14

<210> SEQ ID NO 1163
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1163
aaccgacgca aaaa                                                    14

<210> SEQ ID NO 1164
<211> LENGTH: 14
<212> TYPE: DNA
<213> ORGANISM: Artificial Sequence
```

-continued

```
<220> FEATURE:
<223> OTHER INFORMATION: Synthetic Construct

<400> SEQUENCE: 1164
gcgatggcga tggg                                                       14

<210> SEQ ID NO 1165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1165
aaccgacgca aaaa                                                       14

<210> SEQ ID NO 1166
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1166
cgatggcgat gggg                                                       14

<210> SEQ ID NO 1167
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1167
aaccgacgca aaaa                                                       14

<210> SEQ ID NO 1168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1168
gatggcgatg gggt                                                       14

<210> SEQ ID NO 1169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1169
aaccgacgca aaaa                                                       14

<210> SEQ ID NO 1170
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1170
atggcgatgg ggtg                                                       14
```

```
<210> SEQ ID NO 1171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1171
aaccgacgca aaaa                                                         14

<210> SEQ ID NO 1172
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1172
tggcgatggg gtgg                                                         14

<210> SEQ ID NO 1173
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1173
aaccgacgca aaaa                                                         14

<210> SEQ ID NO 1174
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1174
ggcgatgggg tggt                                                         14

<210> SEQ ID NO 1175
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1175
aaccgacgca aaaa                                                         14

<210> SEQ ID NO 1176
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1176
gcgatggggt ggta                                                         14

<210> SEQ ID NO 1177
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1177
aaccgacgca aaaa                                                          14

<210> SEQ ID NO 1178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1178
cgatggggtg gtat                                                          14

<210> SEQ ID NO 1179
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1179
aaccgacgca aaaa                                                          14

<210> SEQ ID NO 1180
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1180
gatggggtgg tatt                                                          14

<210> SEQ ID NO 1181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1181
aaccgacgca aaaa                                                          14

<210> SEQ ID NO 1182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1182
atggggtggt attt                                                          14

<210> SEQ ID NO 1183
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1183
aaccgacgca aaaa                                                          14

<210> SEQ ID NO 1184
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1184
tggggtggta tttg                                                    14

<210> SEQ ID NO 1185
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1185
aaccgacgca aaaa                                                    14

<210> SEQ ID NO 1186
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1186
ggggtggtat ttgg                                                    14

<210> SEQ ID NO 1187
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1187
aaccgacgca aaaa                                                    14

<210> SEQ ID NO 1188
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1188
gggtggtatt tgga                                                    14

<210> SEQ ID NO 1189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1189
aaccgacgca aaaa                                                    14

<210> SEQ ID NO 1190
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1190
```
ggtggtattt ggag                                                14

<210> SEQ ID NO 1191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1191
aaccgacgca aaaa                                                14

<210> SEQ ID NO 1192
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1192
gtggtatttg gagg                                                14

<210> SEQ ID NO 1193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1193
aaccgacgca aaaa                                                14

<210> SEQ ID NO 1194
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1194
tggtatttgg aggc                                                14

<210> SEQ ID NO 1195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1195
aaccgacgca aaaa                                                14

<210> SEQ ID NO 1196
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1196
ggtatttgga ggcg                                                14

<210> SEQ ID NO 1197
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1197
aaccgacgca aaaa                                                          14

<210> SEQ ID NO 1198
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1198
gtatttggag gcga                                                          14

<210> SEQ ID NO 1199
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1199
aaccgacgca aaaa                                                          14

<210> SEQ ID NO 1200
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1200
tatttggagg cgag                                                          14

<210> SEQ ID NO 1201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1201
aaccgacgca aaaa                                                          14

<210> SEQ ID NO 1202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1202
atttggaggc gagg                                                          14

<210> SEQ ID NO 1203
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1203
aaccgacgca aaaa                                                          14
```

<210> SEQ ID NO 1204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1204
tttggaggcg aggg                                                        14

<210> SEQ ID NO 1205
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1205
aaccgacgca aaaa                                                        14

<210> SEQ ID NO 1206
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1206
ttggaggcga ggga                                                        14

<210> SEQ ID NO 1207
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1207
aaccgacgca aaaa                                                        14

<210> SEQ ID NO 1208
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1208
tggaggcgag ggag                                                        14

<210> SEQ ID NO 1209
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1209
aaccgacgca aaaa                                                        14

<210> SEQ ID NO 1210
<211> LENGTH: 14
<212> TYPE: DNA
<213> ORGANISM: Artificial Sequence
<220> FEATURE:

<223> OTHER INFORMATION: Synthetic Construct

<400> SEQUENCE: 1210
ggaggcgagg gagg                                                        14

<210> SEQ ID NO 1211
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1211
aaccgacgca aaaa                                                        14

<210> SEQ ID NO 1212
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1212
gaggcgaggg aggg                                                        14

<210> SEQ ID NO 1213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1213
aaccgacgca aaaa                                                        14

<210> SEQ ID NO 1214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1214
aggcgaggga gggt                                                        14

<210> SEQ ID NO 1215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1215
aaccgacgca aaaa                                                        14

<210> SEQ ID NO 1216
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1216
ggcgagggag ggtg                                                        14

```
<210> SEQ ID NO 1217
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1217
aaccgacgca aaaa                                                    14

<210> SEQ ID NO 1218
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1218
gcgagggagg gtgt                                                    14

<210> SEQ ID NO 1219
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1219
aaccgacgca aaaa                                                    14

<210> SEQ ID NO 1220
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1220
cgagggaggg tgtt                                                    14

<210> SEQ ID NO 1221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1221
ccaaataccg cccc                                                    14

<210> SEQ ID NO 1222
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1222
ttgggggttc ggtttatcgt gttg                                         24

<210> SEQ ID NO 1223
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 1223
gagggagggt gttc                                                         14

<210> SEQ ID NO 1224
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1224
ccaaataccg cccc                                                         14

<210> SEQ ID NO 1225
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1225
agggagggtg ttcg                                                         14

<210> SEQ ID NO 1226
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1226
ccaaataccg cccc                                                         14

<210> SEQ ID NO 1227
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1227
gggagggtgt tcga                                                         14

<210> SEQ ID NO 1228
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1228
ccaaataccg cccc                                                         14

<210> SEQ ID NO 1229
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1229
ggagggtgtt cgat                                                         14

<210> SEQ ID NO 1230
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 1230
ccaaataccg cccc                                                     14

<210> SEQ ID NO 1231
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1231
gagggtgttc gatt                                                     14

<210> SEQ ID NO 1232
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1232
ccaaataccg cccc                                                     14

<210> SEQ ID NO 1233
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1233
agggtgttcg attg                                                     14

<210> SEQ ID NO 1234
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1234
ccaaataccg cccc                                                     14

<210> SEQ ID NO 1235
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1235
gggtgttcga ttgt                                                     14

<210> SEQ ID NO 1236
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1236
```
ccaaataccg cccc                                               14

<210> SEQ ID NO 1237
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1237
ggtgttcgat tgtt                                               14

<210> SEQ ID NO 1238
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1238
ccaaataccg cccc                                               14

<210> SEQ ID NO 1239
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1239
gtgttcgatt gttt                                               14

<210> SEQ ID NO 1240
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1240
ccaaataccg cccc                                               14

<210> SEQ ID NO 1241
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1241
tgttcgattg ttta                                               14

<210> SEQ ID NO 1242
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1242
ccaaataccg cccc                                               14

<210> SEQ ID NO 1243
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1243
gttcgattgt ttat                                                          14

<210> SEQ ID NO 1244
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1244
ccaaataccg cccc                                                          14

<210> SEQ ID NO 1245
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1245
ttcgattgtt tata                                                          14

<210> SEQ ID NO 1246
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1246
ccaaataccg cccc                                                          14

<210> SEQ ID NO 1247
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1247
tcgattgttt atag                                                          14

<210> SEQ ID NO 1248
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1248
ccaaataccg cccc                                                          14

<210> SEQ ID NO 1249
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1249
cgattgttta tagt                                                          14
```

```
<210> SEQ ID NO 1250
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1250
ccaaataccg cccc                                                        14

<210> SEQ ID NO 1251
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1251
gattgtttat agtg                                                        14

<210> SEQ ID NO 1252
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1252
ccaaataccg cccc                                                        14

<210> SEQ ID NO 1253
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1253
attgtttata gtgg                                                        14

<210> SEQ ID NO 1254
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1254
ccaaataccg cccc                                                        14

<210> SEQ ID NO 1255
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1255
ttgtttatag tggg                                                        14

<210> SEQ ID NO 1256
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1256
ccaaataccg cccc                                                        14

<210> SEQ ID NO 1257
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1257
tgtttatagt gggt                                                        14

<210> SEQ ID NO 1258
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1258
ccaaataccg cccc                                                        14

<210> SEQ ID NO 1259
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1259
gtttatagtg ggtc                                                        14

<210> SEQ ID NO 1260
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1260
ccaaataccg cccc                                                        14

<210> SEQ ID NO 1261
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1261
tttatagtgg gtcg                                                        14

<210> SEQ ID NO 1262
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1262
ccaaataccg cccc                                                        14

<210> SEQ ID NO 1263
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1263
ttatagtggg tcgg                                                        14

<210> SEQ ID NO 1264
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1264
ccaaataccg cccc                                                        14

<210> SEQ ID NO 1265
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1265
tatagtgggt cggg                                                        14

<210> SEQ ID NO 1266
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1266
ccaaataccg cccc                                                        14

<210> SEQ ID NO 1267
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1267
atagtgggtc ggga                                                        14

<210> SEQ ID NO 1268
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1268
ccaaataccg cccc                                                        14

<210> SEQ ID NO 1269
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1269
```
tagtgggtcg ggag                                                          14

<210> SEQ ID NO 1270
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1270
ccaaataccg cccc                                                          14

<210> SEQ ID NO 1271
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1271
agtgggtcgg gagg                                                          14

<210> SEQ ID NO 1272
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1272
ccaaataccg cccc                                                          14

<210> SEQ ID NO 1273
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1273
gtgggtcggg aggg                                                          14

<210> SEQ ID NO 1274
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1274
ccaaataccg cccc                                                          14

<210> SEQ ID NO 1275
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1275
tgggtcggga gggt                                                          14

<210> SEQ ID NO 1276
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1276
ccaaataccg cccc                                                        14

<210> SEQ ID NO 1277
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1277
gggtcgggag ggtg                                                        14

<210> SEQ ID NO 1278
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1278
ccaaataccg cccc                                                        14

<210> SEQ ID NO 1279
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1279
ggtcgggagg gtgg                                                        14

<210> SEQ ID NO 1280
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1280
ccaaataccg cccc                                                        14

<210> SEQ ID NO 1281
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1281
gtcgggaggg tggg                                                        14

<210> SEQ ID NO 1282
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1282
ccaaataccg cccc                                                        14
```

<210> SEQ ID NO 1283
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1283
tcgggagggt gggg                                                       14

<210> SEQ ID NO 1284
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1284
ccaaataccg cccc                                                       14

<210> SEQ ID NO 1285
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1285
cgggagggtg gggg                                                       14

<210> SEQ ID NO 1286
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1286
ccaaataccg cccc                                                       14

<210> SEQ ID NO 1287
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1287
gggagggtgg gggg                                                       14

<210> SEQ ID NO 1288
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1288
ccaaataccg cccc                                                       14

<210> SEQ ID NO 1289
<211> LENGTH: 14
<212> TYPE: DNA
<213> ORGANISM: Artificial Sequence
<220> FEATURE:

<223> OTHER INFORMATION: Synthetic Construct

<400> SEQUENCE: 1289 ggagggtgggg gggt                                                    14

<210> SEQ ID NO 1290
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1290
ccaaataccg cccc                                                     14

<210> SEQ ID NO 1291
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1291
gagggtgggg ggtt                                                     14

<210> SEQ ID NO 1292
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1292
ccaaataccg cccc                                                     14

<210> SEQ ID NO 1293
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1293
agggtggggg gttg                                                     14

<210> SEQ ID NO 1294
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1294
ccaaataccg cccc                                                     14

<210> SEQ ID NO 1295
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1295 gggtggggggg ttgc                                                    14

```
<210> SEQ ID NO 1296
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1296
ccaaataccg cccc                                                        14

<210> SEQ ID NO 1297
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1297 ggtgggggt tgcg                                                         14

<210> SEQ ID NO 1298
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1298
ccaaataccg cccc                                                        14

<210> SEQ ID NO 1299
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1299 gtgggggtt gcgt                                                         14

<210> SEQ ID NO 1300
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1300
ccaaataccg cccc                                                        14

<210> SEQ ID NO 1301
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1301 tgggggttg cgtt                                                         14

<210> SEQ ID NO 1302
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1302
ccaaataccg cccc                                                    14

<210> SEQ ID NO 1303
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1303 gggggttgc gttt                                                     14

<210> SEQ ID NO 1304
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1304
ccaaataccg cccc                                                    14

<210> SEQ ID NO 1305
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1305
gggggttgcg tttg                                                    14

<210> SEQ ID NO 1306
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1306
ccaaataccg cccc                                                    14

<210> SEQ ID NO 1307
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1307
ggggttgcgt ttgg                                                    14

<210> SEQ ID NO 1308
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1308
ccaaataccg cccc                                                    14

<210> SEQ ID NO 1309
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 1309
gggttgcgtt tggg                                                         14

<210> SEQ ID NO 1310
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1310
ccaaataccg cccc                                                         14

<210> SEQ ID NO 1311
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1311
ggttgcgttt gggc                                                         14

<210> SEQ ID NO 1312
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1312
ccaaataccg cccc                                                         14

<210> SEQ ID NO 1313
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1313
gttgcgtttg ggcg                                                         14

<210> SEQ ID NO 1314
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1314
ccaaataccg cccc                                                         14

<210> SEQ ID NO 1315
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1315
```
ttgcgtttgg gcgt 14

<210> SEQ ID NO 1316
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1316
ccaaataccg cccc 14

<210> SEQ ID NO 1317
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1317
tgcgtttggg cgtt 14

<210> SEQ ID NO 1318
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1318
ccaaataccg cccc 14

<210> SEQ ID NO 1319
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1319
gcgtttgggc gttg 14

<210> SEQ ID NO 1320
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1320
ccaaataccg cccc 14

<210> SEQ ID NO 1321
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1321
cgtttgggcg ttga 14

<210> SEQ ID NO 1322
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1322
ccaaataccg cccc                                                          14

<210> SEQ ID NO 1323
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1323
gtttgggcgt tgat                                                          14

<210> SEQ ID NO 1324
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1324
tataatcgcc tcgc                                                          14

<210> SEQ ID NO 1325
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1325
attaagagat ttaggattcg aata                                               24

<210> SEQ ID NO 1326
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1326
tttgggcgtt gatt                                                          14

<210> SEQ ID NO 1327
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1327
tataatcgcc tcgc                                                          14

<210> SEQ ID NO 1328
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1328
ttgggcgttg attt                                                          14
```

```
<210> SEQ ID NO 1329
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1329
tataatcgcc tcgc                                                        14

<210> SEQ ID NO 1330
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1330
tgggcgttga tttt                                                        14

<210> SEQ ID NO 1331
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1331
tataatcgcc tcgc                                                        14

<210> SEQ ID NO 1332
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1332
gggcgttgat tttt                                                        14

<210> SEQ ID NO 1333
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1333
tataatcgcc tcgc                                                        14

<210> SEQ ID NO 1334
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1334
ggcgttgatt tttt                                                        14

<210> SEQ ID NO 1335
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1335
tataatcgcc tcgc                                              14

<210> SEQ ID NO 1336
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1336
gcgttgattt tttg                                              14

<210> SEQ ID NO 1337
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1337
tataatcgcc tcgc                                              14

<210> SEQ ID NO 1338
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1338
cgttgatttt ttgc                                              14

<210> SEQ ID NO 1339
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1339
tataatcgcc tcgc                                              14

<210> SEQ ID NO 1340
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1340
gttgattttt tgcg                                              14

<210> SEQ ID NO 1341
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1341
tataatcgcc tcgc                                              14

<210> SEQ ID NO 1342
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1342 ttgattttttt gcgt                                                  14

<210> SEQ ID NO 1343
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1343
tataatcgcc tcgc                                                   14

<210> SEQ ID NO 1344
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1344 tgatttttttg cgtc                                                  14

<210> SEQ ID NO 1345
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1345
tataatcgcc tcgc                                                   14

<210> SEQ ID NO 1346
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1346 gatttttttgc gtcg                                                  14

<210> SEQ ID NO 1347
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1347
tataatcgcc tcgc                                                   14

<210> SEQ ID NO 1348
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1348
```
attttttgcg tcgg                                                          14

<210> SEQ ID NO 1349
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1349
tataatcgcc tcgc                                                          14

<210> SEQ ID NO 1350
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1350 tttttgcgt cggt                                                           14

<210> SEQ ID NO 1351
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1351
tataatcgcc tcgc                                                          14

<210> SEQ ID NO 1352
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1352
tttttgcgtc ggtt                                                          14

<210> SEQ ID NO 1353
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1353
tataatcgcc tcgc                                                          14

<210> SEQ ID NO 1354
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1354
ttttgcgtcg gttt                                                          14

<210> SEQ ID NO 1355
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1355
tataatcgcc tcgc                                                      14

<210> SEQ ID NO 1356
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1356
tttgcgtcgg tttt                                                      14

<210> SEQ ID NO 1357
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1357
tataatcgcc tcgc                                                      14

<210> SEQ ID NO 1358
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1358
ttgcgtcggt ttta                                                      14

<210> SEQ ID NO 1359
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1359
tataatcgcc tcgc                                                      14

<210> SEQ ID NO 1360
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1360
tgcgtcggtt ttag                                                      14

<210> SEQ ID NO 1361
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1361
tataatcgcc tcgc                                                      14
```

<210> SEQ ID NO 1362
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1362
gcgtcggttt tagg                                                14

<210> SEQ ID NO 1363
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1363
tataatcgcc tcgc                                                14

<210> SEQ ID NO 1364
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1364
cgtcggtttt agga                                                14

<210> SEQ ID NO 1365
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1365
tataatcgcc tcgc                                                14

<210> SEQ ID NO 1366
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1366
gtcggtttta ggat                                                14

<210> SEQ ID NO 1367
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1367
tataatcgcc tcgc                                                14

<210> SEQ ID NO 1368
<211> LENGTH: 14
<212> TYPE: DNA
<213> ORGANISM: Artificial Sequence
<220> FEATURE:

<223> OTHER INFORMATION: Synthetic Construct

<400> SEQUENCE: 1368
tcggttttag gatt                                                              14

<210> SEQ ID NO 1369
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1369
tataatcgcc tcgc                                                              14

<210> SEQ ID NO 1370
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1370
cggttttagg attt                                                              14

<210> SEQ ID NO 1371
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1371
tataatcgcc tcgc                                                              14

<210> SEQ ID NO 1372
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1372
ggttttagga ttta                                                              14

<210> SEQ ID NO 1373
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1373
tataatcgcc tcgc                                                              14

<210> SEQ ID NO 1374
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1374
gttttaggat ttaa                                                              14

```
<210> SEQ ID NO 1375
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1375
tataatcgcc tcgc                                                       14

<210> SEQ ID NO 1376
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1376
ttttaggatt taag                                                       14

<210> SEQ ID NO 1377
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1377
tataatcgcc tcgc                                                       14

<210> SEQ ID NO 1378
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1378
tttaggattt aagt                                                       14

<210> SEQ ID NO 1379
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1379
tataatcgcc tcgc                                                       14

<210> SEQ ID NO 1380
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1380
ttaggattta agtt                                                       14

<210> SEQ ID NO 1381
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1381
tataatcgcc tcgc                                                    14

<210> SEQ ID NO 1382
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1382
taggatttaa gttt                                                    14

<210> SEQ ID NO 1383
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1383
tataatcgcc tcgc                                                    14

<210> SEQ ID NO 1384
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1384
aggatttaag tttg                                                    14

<210> SEQ ID NO 1385
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1385
tataatcgcc tcgc                                                    14

<210> SEQ ID NO 1386
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1386
ggatttaagt ttgg                                                    14

<210> SEQ ID NO 1387
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1387
tataatcgcc tcgc                                                    14

<210> SEQ ID NO 1388
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 1388
gatttaagtt tggg                                                        14

<210> SEQ ID NO 1389
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1389
tataatcgcc tcgc                                                        14

<210> SEQ ID NO 1390
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1390
atttaagttt gggg                                                        14

<210> SEQ ID NO 1391
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1391
tataatcgcc tcgc                                                        14

<210> SEQ ID NO 1392
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1392
tttaagtttg gggg                                                        14

<210> SEQ ID NO 1393
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1393
tataatcgcc tcgc                                                        14

<210> SEQ ID NO 1394
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1394
```

```
ttaagtttgg gggt                                                    14

<210> SEQ ID NO 1395
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1395
tataatcgcc tcgc                                                    14

<210> SEQ ID NO 1396
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1396
taagtttggg ggtt                                                    14

<210> SEQ ID NO 1397
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1397
tataatcgcc tcgc                                                    14

<210> SEQ ID NO 1398
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1398
aagtttgggg gttc                                                    14

<210> SEQ ID NO 1399
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1399
tataatcgcc tcgc                                                    14

<210> SEQ ID NO 1400
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1400
agtttggggg ttcg                                                    14

<210> SEQ ID NO 1401
<211> LENGTH: 14
<212> TYPE: DNA
<213> ORGANISM: Artificial Sequence
```

-continued

<220> FEATURE:
<223> OTHER INFORMATION: Synthetic Construct

<400> SEQUENCE: 1401
tataatcgcc tcgc                                                    14

<210> SEQ ID NO 1402
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1402
gtttgggggt tcgg                                                    14

<210> SEQ ID NO 1403
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1403
tataatcgcc tcgc                                                    14

<210> SEQ ID NO 1404
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1404
tttgggggtt cggt                                                    14

<210> SEQ ID NO 1405
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1405
tataatcgcc tcgc                                                    14

<210> SEQ ID NO 1406
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1406
ttgggggttc ggtt                                                    14

<210> SEQ ID NO 1407
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1407
tataatcgcc tcgc                                                    14

```
<210> SEQ ID NO 1408
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1408
tgggggttcg gttt                                                       14

<210> SEQ ID NO 1409
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1409
tataatcgcc tcgc                                                       14

<210> SEQ ID NO 1410
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1410
gggggttcgg ttta                                                       14

<210> SEQ ID NO 1411
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1411
tataatcgcc tcgc                                                       14

<210> SEQ ID NO 1412
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1412
ggggttcggt ttat                                                       14

<210> SEQ ID NO 1413
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1413
tataatcgcc tcgc                                                       14

<210> SEQ ID NO 1414
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1414
gggttcggtt tatc                                                        14

<210> SEQ ID NO 1415
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1415
tataatcgcc tcgc                                                        14

<210> SEQ ID NO 1416
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1416
ggttcggttt atcg                                                        14

<210> SEQ ID NO 1417
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1417
tataatcgcc tcgc                                                        14

<210> SEQ ID NO 1418
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1418
gttcggttta tcgt                                                        14

<210> SEQ ID NO 1419
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1419
tataatcgcc tcgc                                                        14

<210> SEQ ID NO 1420
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1420
ttcggtttat cgtg                                                        14

<210> SEQ ID NO 1421
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1421
tataatcgcc tcgc                                                        14

<210> SEQ ID NO 1422
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1422
tcggtttatc gtgt                                                        14

<210> SEQ ID NO 1423
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1423
tataatcgcc tcgc                                                        14

<210> SEQ ID NO 1424
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1424
cggtttatcg tgtt                                                        14

<210> SEQ ID NO 1425
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1425
tataatcgcc tcgc                                                        14

<210> SEQ ID NO 1426
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1426
ggtttatcgt gttg                                                        14

<210> SEQ ID NO 1427
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1427
```

```
aaacataaaa acgt                                              14

<210> SEQ ID NO 1428
<211> LENGTH: 27
<212> TYPE: DNA
<213> ORGANISM: Artificial Sequence
<220> FEATURE:
<223> OTHER INFORMATION: Synthetic Construct

<400> SEQUENCE: 1428
gggagatttt tgtttttcg agttttt                                 27
```

METHOD FOR DETECTING METHYLATION OF COLORECTAL CANCER SPECIFIC METHYLATION MARKER GENE FOR COLORECTAL CANCER DIAGNOSIS

CROSS-REFERENCE TO RELATED APPLICATIONS

This is a continuation-in-part application under 35 U.S.C. § 120 of U.S. patent application Ser. No. 15/010,379 filed on Jan. 29, 2016, which in turn is a continuation-in-part application of U.S. patent application Ser. No. 13/994,732 filed Jun. 15, 2013, now U.S. Pat. No. 9,315,870, which in turn is a U.S. national stage under the provisions of 35 U.S.C. § 371 of International Patent Application No. PCT/KR11/09710 filed Dec. 16, 2011, which in turn claims priority of Korean Patent Application No. 10-2010-129208 filed Dec. 16, 2010. The disclosures of such U.S. patent applications, international patent application, and Korean priority patent application are hereby incorporated herein by reference in their respective entireties, for all purposes.

SEQUENCE LISTING

The instant application contains a Sequence Listing which has been submitted in ASCII format via EFS-Web and is hereby incorporated by reference in its entirety. Said ASCII copy, created on Aug. 8, 2017, is named 214CIP2_SeqID_2_REV_ST25.txt and is 278,918 bytes in size.

TECHNICAL FIELD

The present disclosure relates to a method for detecting the methylation of colorectal cancer-specific marker genes for colorectal cancer diagnosis, and more particularly to a method of detecting the methylation of a colorectal cancer-specific marker gene, which are methylated specifically in colorectal cancer cells, to provide information for diagnosing colorectal cancer.

BACKGROUND ART

In current clinical practice, the diagnosis of cancer is confirmed by performing tissue biopsy after history taking, physical examination and clinical assessment, followed by radiographic testing and endoscopy if cancer is suspected. However, the diagnosis of cancer by the existing clinical practices is possible only when the number of cancer cells is more than a billion and the diameter of cancer is more than 1 cm. In this case, the cancer cells already have metastatic ability, and at least half thereof have already metastasized. Meanwhile, tumor markers for monitoring substances that are directly or indirectly produced from cancers are used in cancer screening, but they cause confusion due to limitations in accuracy, since up to about half thereof appear normal even in the presence of cancer, and they often appear positive even in the absence of cancer. Furthermore, the anticancer agents that are mainly used in cancer therapy have the problem that they show an effect only when the volume of cancer is small.

Recently, genetic analysis has been actively attempted to diagnose cancer. The simplest typical method is to detect the presence of ABL: BCR fusion genes (the genetic characteristic of leukemia) in blood by PCR. The method has an accuracy rate of more than 95%, and after the diagnosis and therapy of chronic myelocytic leukemia using this simple and easy genetic analysis, this method is being used for the assessment of the result and follow-up study. However, this method has a shortcoming in that it can be applied only to some blood cancers.

Furthermore, another method has been attempted, in which the presence of genes expressed by cancer cells is detected by RT-PCR and blotting, thereby diagnosing cancer cells present in blood cells. However, this method has shortcomings in that it can be applied only to some cancers, including prostate cancer and melanoma, has a high false positive rate. In addition, it is difficult to standardize detection and reading in this method, and its utility is also limited (Kopreski, M. S. et al., *Clin. Cancer Res.*, 5:1961, 1999; Miyashiro, I. et al., *Clin. Chem.*, 47:505, 2001).

Recently, genetic testing that uses a DNA in serum or blood plasma has been actively attempted. This is a method of detecting a cancer-related gene that is isolated from cancer cells and released into blood and present in the form of a free DNA in serum. It is found that the concentration of DNA in serum is increased by a factor of 5-10 times in actual cancer patients as compared to that of normal persons, and such increased DNA is released mostly from cancer cells. The analysis of cancer-specific gene abnormalities, such as the mutation, deletion and functional loss of oncogenes and tumor-suppressor genes, using such DNAs isolated from cancer cells, allows the diagnosis of cancer. In this effort, there has been an active attempt to diagnose lung cancer, head and neck cancer, breast cancer, colorectal cancer, and liver cancer by examining the promoter methylation of mutated K-Ras oncogenes, p53 tumor-suppressor genes and p16 genes in serum, and the labeling and instability of microsatellite (Chen, X. Q. et al., *Clin. Cancer Res.*, 5:2297, 1999; Esteller, M. et al., *Cancer Res.*, 59:67, 1999; Sanchez-Cespedes, M. et al., *Cancer Res.*, 60:892, 2000; Sozzi, G. et al., *Clin. Cancer Res.*, 5:2689, 1999).

Meanwhile, in samples other than blood, the DNA of cancer cells can also be detected. A method has been attempted in which the presence of cancer cells or oncogenes in sputum or bronchoalveolar lavage of lung cancer patients is detected by a gene or antibody test (Palmisano, W. A. et al., *Cancer Res.*, 60:5954, 2000; Sueoka, E. et al., *Cancer Res.*, 59:1404, 1999). Additionally, other methods of detecting the presence of oncogenes in feces of colorectal cancer patients (Ahlquist, D. A. et al., *Gastroenterol.*, 119: 1219-27, 2000) and detecting promoter methylation abnormalities in urine and prostate fluid (Goessl, C. et al., *Cancer Res.*, 60:5941, 2000) have been attempted. However, in order to accurately diagnose cancers that cause a large number of gene abnormalities and show various mutations characteristic of each cancer, a method in which a large number of genes are simultaneously analyzed in an accurate and automatic manner is required. However, such a method has not yet been established.

Accordingly, methods of diagnosing cancer by measuring DNA methylation have recently been proposed. When the promoter CpG island of a certain gene is hyper-methylated, the expression of such a gene is silenced. This is interpreted to be a main mechanism by which the function of this gene is lost even when there is no mutation in the protein-coding sequence of the gene in a living body. In addition, this is analyzed as a factor by which the function of a number of tumor-suppressor genes in human cancer is lost. Thus, analysis of the methylation of the promoter CpG island of tumor-suppressor genes is very helpful in cancer research. An active attempt has been made to analyze the methylation of the promoter CpG island by methods such as methylation-specific PCR (hereinafter, referred to as "MSP") or automatic base sequencing and to use the analysis results for the diagnosis and screening of cancer.

A significant number of diseases are caused by genetic abnormalities, and the most frequent form of genetic abnormality is a change in the coding sequence of a gene. This genetic change is referred to as mutation. When any gene has a mutation, the structure and function of a protein encoded by the gene change, resulting in abnormalities and deletions, and this mutant protein causes disease. However, an abnormality in the expression of a specific gene can cause disease even in the absence of a mutation in the gene. A typical example thereof is methylation in which a methyl group is attached to the transcription regulatory region of a gene, that is, the cytosine base of the promoter CpG islands, and in this case, the expression of the gene is silenced. This is known as epigenetic change. This is transmitted to offspring and results in the loss of the expression of the relevant protein in the same manner as mutation. Most typically, the expression of tumor suppressor genes is silenced by the methylation of promoter CpG islands in cancer cells, resulting in carcinogenesis (Robertson, K. D. et al., *Carcinogensis*, 21:461, 2000).

During a cancer-causing process, methylation is found in promoter CpG islands, and the restriction on the corresponding gene expression occurs. Particularly, if methylation occurs in the promoter CpG islands of tumor-suppressor genes that regulate cell cycle or apoptosis, restore DNA, are involved in the adhesion of cells and the interaction between cells, and/or suppress cell invasion and metastasis, such methylation blocks the expression and function of such genes in the same manner as the mutations of a coding sequence, thereby promoting the development and progression of cancer. In addition, partial methylation also occurs in the CpG islands according to aging.

An interesting fact is that, in the case of genes whose mutations are attributed to the development of cancer in congenital cancer but do not occur in acquired cancer, the methylation of promoter CpG islands occurs instead of mutation. Typical examples include the promoter methylation of genes, such as acquired renal cancer VHL (von Hippel Lindau), breast cancer BRCA1, colorectal cancer MLH1, and stomach cancer E-CAD. In addition, in about half of all cancers, the promoter methylation of p16 or the mutation of Rb occurs, and the remaining cancers show the mutation of p53 or the promoter methylation of p73, p 14 and the like.

An important fact is that an epigenetic change caused by promoter methylation causes a genetic change (i.e., the mutation of a coding sequence), and the development of cancer is progressed by the combination of such genetic and epigenetic changes. In a MLH1 gene as an example, there is the circumstance in which the function of one allele of the MLH1 gene in colorectal cancer cells is lost due to its mutation or deletion, and the remaining one allele does not function due to promoter methylation. In addition, if the function of MLH1, which is a DNA restoring gene, is lost due to promoter methylation, the occurrence of mutation in other important genes is facilitated to promote the development of cancer.

Most cancers show three common characteristics with respect to CpG, namely, hypermethylation of the promoter CpG islands of tumor-suppressor genes, hypomethylation of the remaining CpG base sites, and an increase in the activity of methylation enzyme, namely, DNA cytosine methyltransferase (DNMT) (Singal, R. & Ginder, G. D., *Blood*, 93:4059, 1999; Robertson, K. et al., *Carcinogensis*, 21:461, 2000; Malik, K. & Brown, K. W., *Brit. J. Cancer*, 83:1583, 2000).

When promoter CpG islands are methylated, the reason why the expression of the corresponding genes is blocked is not clearly established, but is presumed to be because a methyl CpG-binding protein (MECP) or a methyl CpG-binding domain protein (MBD), and histone deacetylase, bind to methylated cytosine, thereby causing a change in the chromatin structure of chromosomes and a change in histone protein.

It is unsettled whether the methylation of promoter CpG islands directly causes the development of cancer or is a secondary change after the development of cancer. However, it is clear that the promoter methylation of tumor-related genes is an important index to cancer, and thus can be used in many applications, including the diagnosis and early detection of cancer, the prediction of the risk of the development of cancer, the prognosis of cancer, follow-up examination after treatment, and the prediction of a response to anticancer therapy. Recently, an attempt to examine the promoter methylation of tumor-related genes in blood, sputum, saliva, feces or urine and to use the examined results for the diagnosis and treatment of various cancers, has been actively conducted (Esteller, M. et al., *Cancer Res.*, 59:67, 1999; Sanchez-Cespedez, M. et al., *Cancer Res.*, 60:892, 2000; Ahlquist, D. A. et al., *Gastroenterol.*, 119:1219, 2000).

In order to maximize the accuracy of cancer diagnosis using promoter methylation, analyze the development of cancer according to each stage and discriminate a change according to cancer and aging, an examination that can accurately analyze the methylation of all the cytosine bases of promoter CpG islands is required. Currently, a standard method for this examination is a bisulfite genome-sequencing method, in which a sample DNA is treated with sodium bisulfite, and all regions of the CpG islands of a target gene to be examined is amplified by PCR, and then, the base sequence of the amplified regions is analyzed. However, this examination has the problem that there are limitations to the number of genes or samples that can be examined at a given time. Other problems are that automation is difficult, and much time and expense are required.

In the Johns Hopkins School of Medicine, the MD Anderson Cancer Center, Charité-Universitätsmedizin Berlin, etc., studies on promoter methylation of cancer-related genes have been actively conducted. The fundamental data thus obtained are interchanged through the DNA Methylation Society (DMS) and stored in MethDB (http://www.methdb.de). Meanwhile, EpiGenX Pharmaceuticals, Inc. is now developing therapeutic agents associated with the methylation of CpG islands, and Epigenomics, Inc. is now conducting studies to apply promoter methylation to cancer diagnosis by examining the promoter methylation using various techniques, such as DNA chips and MALDI-TOF.

Accordingly, the present inventors have made extensive efforts to develop an effective colon-cancer-specific methylation marker which makes it possible to diagnose cancer and the risk of carcinogenesis at an early stage and predict cancer prognosis. As a result, the present inventors have found that GPM6A (NM_005277, Glycoprotein M6A) gene is methylated specifically in colorectal cancer cells and that colorectal cancer can be diagnosed by measuring the degree of methylation using this gene as a biomarker, thereby completing the present disclosure.

DISCLOSURE OF INVENTION

It is a main object of the present disclosure to provide a colorectal cancer-specific methylation biomarker, which is methylated specifically in colorectal cancer cells and can be effectively used for diagnosis of colorectal cancer.

Another object of the present disclosure is to provide a method for detecting colorectal cancer, the method comprising identifying the degree of methylation of the biomarker.

Still another object of the present disclosure is to provide a nucleic acid chip for diagnosing colorectal cancer, which comprises a probe capable of hybridizing with a fragment comprising the CpG island of the colorectal cancer-specific methylation biomarker.

To achieve the above objects, the present disclosure provides a biomarker for diagnosing colorectal cancer, which comprises either the methylated CpG island of the promoter of GPM6A (NM_201591, glycoprotein M6A) gene or the methylated CpG island of a first intron of GPM6A (NM_201591, glycoprotein M6A) gene.

The present disclosure also provides a method for detecting the methylation of a biomarker for colorectal cancer diagnosis, the method comprising the steps of:
(a) isolating DNAs from a clinical sample;
(b) detecting the methylation of the CpG island of the promoter of GPM6A (NM_201591, glycoprotein M6A) gene or the CpG island of a first intron of GPM6A (NM_201591, glycoprotein M6A) gene from the isolated DNAs.

The present disclosure also provides a method for detecting CpG methylation of GPM6A (glycoprotein M6A) gene, the method comprising the steps of:
(a) isolating genomic DNA from a clinical sample;
(b) treating the genomic DNA or a fragment thereof with bisulfite;
(c) amplifying a methylated CpG of GPM6A gene in the bisulfite-treated genomic DNA or fragment thereof from step (b) by using primer(s) to amplify a methylated CpG of the bisulfite-treated GPM6A gene; and
(d) determining whether the CpG of GPM6A was methylated based on whether the DNA was amplified in step (c).

The present disclosure also provides a nucleic acid chip for diagnosing colorectal cancer, which comprises a probe capable of hybridizing with a fragment comprising either the CpG island of the promoter of GPM6A (NM_201591, glycoprotein M6A) gene or the CpG island of a first intron of GPM6A (NM_201591, glycoprotein M6A) gene.

The present disclosure also provides a kit for diagnosing colorectal cancer, which contains: a PCR primer pair for amplifying a fragment comprising the methylated CpG island of a first intron of GPM6A (NM_201591, glycoprotein M6A) gene; and a sequencing primer for pyrosequencing a PCR product amplified by the primer pair.

The present disclosure also provides a kit for detecting CpG methylation of GPM6A (glycoprotein M6A) gene, comprising primer(s) to amplify a methylated CpG of the GPM6A gene.

Other features and embodiments of the present disclosure will be more apparent from the following detailed descriptions and the appended claims.

BEST MODE FOR CARRYING OUT THE INVENTION

Figure 1:
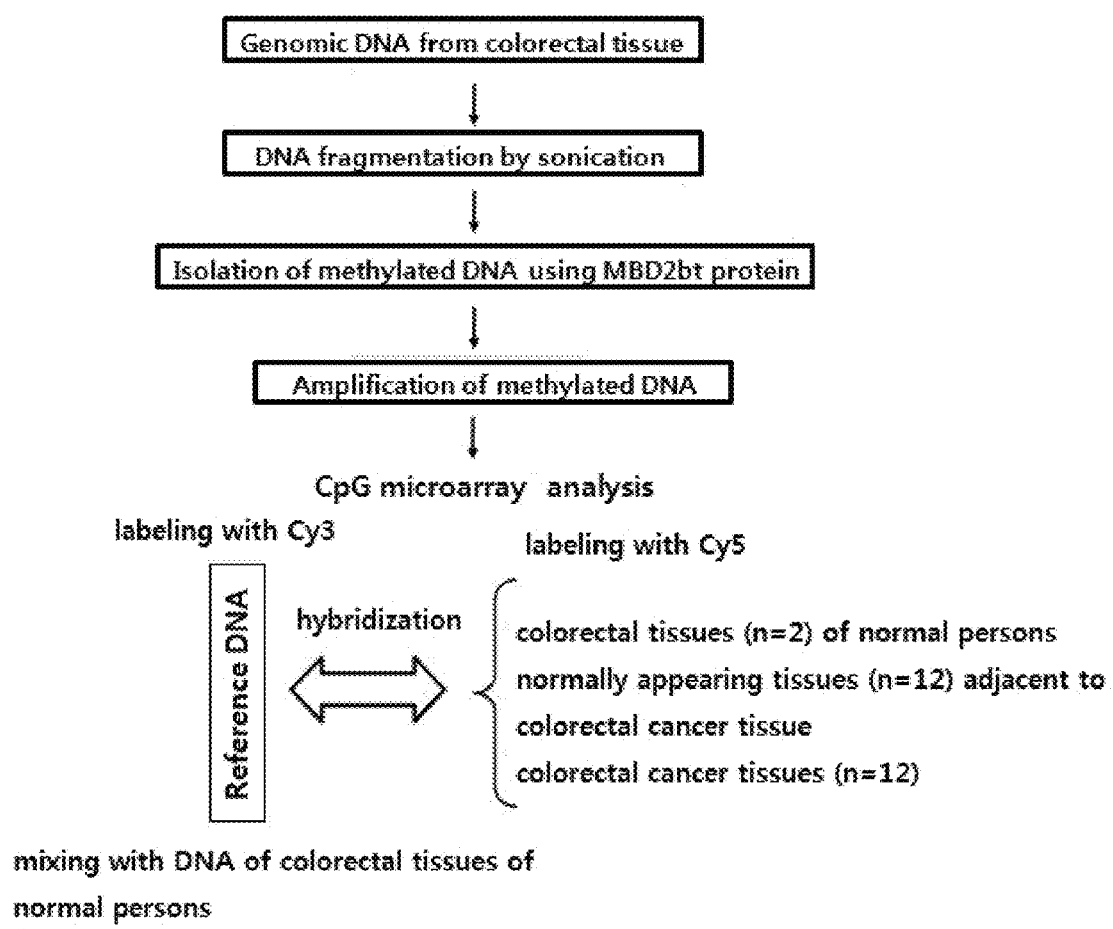
FIG. 1 is a schematic diagram showing a process of discovering a methylation biomarker for colorectal cancer diagnosis from the tissue cells of a normal person and a colorectal cancer patient by a CpG microassay.

Unless defined otherwise, all technical and scientific terms used herein have the same meaning as commonly understood by one of ordinary skill in the art to which the invention pertains. Generally, the nomenclature used herein is well known and is commonly employed in the art.

In one aspect, the present disclosure is directed to a biomarker for diagnosing colorectal cancer, which comprises either the methylated CpG island of the promoter of GPM6A (NM_201591, glycoprotein M6A) gene or the methylated CpG island of a first intron of GPM6A (NM_201591, glycoprotein M6A) gene.

In the present disclosure, the CpG island may be located in the intron region of the gene. Herein, the intron region of the GPM6A gene may be located between +501 and +1200 nucleotides (nt) from the transcription start site and may comprise a nucleotide sequence of SEQ ID NO: 1.

In another aspect, the present disclosure is directed to a method for detecting the methylation of a biomarker for colorectal cancer diagnosis, the method comprising the steps of:
(a) isolating DNA from a clinical sample;
(b) detecting the methylation of the CpG island of the promoter of GPM6A (NM_201591, glycoprotein M6A) gene or the CpG island of a first intron of GPM6A (NM_201591, glycoprotein M6A) gene from the isolated DNA.

In the present disclosure, step (b) of detecting the methylation of the CpG island of a first intron of GPM6A (NM_201591, glycoprotein M6A) gene may be performed by detecting the methylation of the region shown by SEQ ID NO: 1.

In the present disclosure, step (b) may be performed by detecting the methylation based on the presence/absence or a change in the base sequence of product amplified by using primers capable of amplifying a fragment comprising the CpG island of the first intron of GPM6A (NM_201591, glycoprotein M6A) gene.

In the present disclosure, step (b) may be performed by a method selected from the group consisting of PCR, methylation-specific PCR, real-time methylation-specific PCR, PCR assay using a methylation DNA-specific binding protein, quantitative PCR, DNA chip-based assay, pyrosequencing, and bisulfate sequencing.

In the present disclosure, the clinical sample may be selected from the group consisting of a tissue, cell, blood, blood plasma, feces, and urine from a patient suspected of cancer or a subject to be diagnosed.

In the present disclosure, 4 biomarker candidate genes showing the greatest difference in the degree of methylation between normal persons and colorectal cancer patients were screened, and among these genes, SDC2, SIM1 and SORCS3 genes were confirmed for diagnosis of colorectal cancer. A method for screening methylation marker genes according to the present disclosure comprises the steps of: (a) isolating genomic DNAs from transformed cells and non-transformed cells; (b) reacting the isolated genomic DNAs with a methylated DNA-binding protein, thereby isolating methylated DNAs; and (c) amplifying the methylated DNAs, hybridizing the amplified DNAs to a CpG microarray, and then selecting genes showing the greatest difference in the degree of methylation between the normal cells and the cancer cells, thereby ensuring methylation marker genes.

The above method for screening biomarker genes can find genes which are differentially methylated in colorectal cancer as well as at various dysplasic stages of the tissue that progresses to colorectal cancer. The screened genes can be used for colorectal cancer screening, risk-assessment, prognosis, disease identification, the diagnosis of disease stages, and the selection of therapeutic targets.

The identification of genes that are methylated in colorectal cancer and abnormalities at various stages of colorectal cancer makes it possible to diagnose colorectal cancer at an early stage in an accurate and effective manner and allows methylation profiling of multiple genes and the identification of new targets for therapeutic intervention. Furthermore, the methylation data according to the present disclosure may be combined with other non-methylation related biomarker detection methods to obtain a more accurate system for colorectal cancer diagnosis.

According to the method of the present disclosure, the progression of colorectal cancer at various stages or phases can be diagnosed by determining the methylation stage of one or more nucleic acid biomarkers obtained from a sample. By comparing the methylation stage of a nucleic acid isolated from a sample at each stage of colorectal cancer with the methylation stage of one or more nucleic acids isolated from a sample in which there is no cell proliferative disorder of colon tissue, a specific stage of colorectal cancer in the sample can be detected. Herein, the methylation stage may be hypermethylation.

In one embodiment of the present disclosure, nucleic acid may be methylated in the regulatory region of a gene. In another embodiment, a gene which is involved in cell transformation can be diagnosed by detecting methylation outside of the regulatory region of the gene, because methylation proceeds inwards from the outside of the gene.

In yet another embodiment of the present disclosure, cells that are likely to form colorectal cancer can be diagnosed at an early stage using the methylation marker genes. When genes confirmed to be methylated in cancer cells are methylated in cells that appear normal clinically or morphologically, this indicates that the normally appearing cells progress to cancer. Thus, colorectal cancer can be diagnosed at an early stage by detecting the methylation of colorectal cancer-specific genes in cells that appear normal.

The use of the methylation marker gene of the present disclosure allows for detection of a cellular proliferative disorder (dysplasia) of colon tissue in a sample. The detection method comprises bringing a sample comprising at least one nucleic acid isolated from a subject into contact with at least one agent capable of determining the methylation state of the nucleic acid. The method comprises detecting the methylation of at least one region in at least one nucleic acid, wherein the methylation of the nucleic acid differs from the methylation state of the same region of a nucleic acid present in a sample in which there is no abnormal growth (dysplastic progression) of colon cells.

In yet another embodiment of the present disclosure, the likelihood of progression of tissue to colorectal cancer can be evaluated by examining the frequency of the methylation of a gene which is specifically methylated in colorectal cancer, and determining the methylation frequency of tissue that is likely to progress to colorectal cancer.

Thus, in still another aspect, the present disclosure is directed to a method for detecting the methylation of colorectal cancer-specific methylation marker gene for colorectal cancer diagnosis, the method comprising the steps of:
(a) preparing a clinical sample containing DNA; and
(b) detecting the methylation of the CpG island of a first intron of GPM6A (NM_005277, glycoprotein M6A) gene in the DNA of the clinical sample.

In the present disclosure, step (b) may be performed by detecting the methylation of the CpG island in the intron region of the gene. Herein, the intron region of the GPM6A gene may be located between +501 and +1200 nucleotides (nt) from the transcription start site and may comprise a nucleotide sequence of SEQ ID NO: 1.

In the present disclosure, step (b) may be performed by a method selected from the group consisting of PCR, methylation-specific PCR, real-time methylation-specific PCR, PCR assay using a methylation DNA-specific binding protein, quantitative PCR, DNA chip-based assay, pyrosequencing, and bisulfate sequencing. In addition, the clinical sample may be selected from the group consisting of a tissue, cell, blood, blood plasma, feces, and urine from a patient suspected of cancer or a subject to be diagnosed, but is not limited thereto.

In one embodiment of the present disclosure, the method for detecting the methylation of a gene may comprise: (a) preparing a clinical sample containing DNA; (b) isolating DNA from the clinical sample; (c) amplifying the isolated DNA using primers capable of amplifying a fragment comprising the CpG island of a first intron of GPM6A (NM_005277, glycoprotein M6A) gene; and (d) determining whether the intron was methylated based on whether the DNA was amplified in step (c).

In yet another aspect, the present disclosure is directed to a nucleic acid chip for diagnosing colorectal cancer, which comprises a probe capable of hybridizing with a fragment comprising the CpG island of a first intron of GPM6A (NM_201591, glycoprotein M6A) gene.

In the present disclosure, the CpG island may be located in the intron region of the gene. Herein, the intron region of the GPM6A gene may be located between +501 and +1200 nucleotides (nt) from the transcription start site and may comprise a nucleotide sequence of SEQ ID NO: 1.

In a further another aspect, the present disclosure is directed to a kit for diagnosing colorectal cancer, which contains: a PCR primer pair for amplifying a fragment comprising the methylated CpG island of a first intron of GPM6A (NM_201591, glycoprotein M6A) gene; and a sequencing primer for pyrosequencing a PCR product amplified by the primer pair.

In the present disclosure, the PCR primer pair may be a primer pair comprising base sequences shown by SEQ ID NOS: 16 and 17 or SEQ ID NO: 18 and 19, and the sequencing primer may comprise a base sequence shown by SEQ ID NO: 15.

In yet another embodiment of the present disclosure, the abnormal growth (dysplasia) of colorectal tissue cells in a sample can be diagnosed by detecting the methylation state of CpG island of a first intron of GPM6A (NM_201591, glycoprotein M6A) gene using a kit.

In the present disclosure, the probe may be selected from the group consisting of the base sequences shown by SEQ ID NOS: 2 to 6, and specific examples thereof are as follows.

The probe capable of hybridizing with the CpG island of a first intron of GPM6A:

1)
(SEQ ID NO: 2)
gtatttggga aataaagaaa 2)
(SEQ ID NO: 3)
gactaagaga cccaggatcc gaatagcgag 3)
(SEQ ID NO: 4)
gttcccacgt tttcatgttc tctttgggga gcaagttgaa 4)
(SEQ ID NO: 5)
ggcgtccaca ctggctcggg tcactggacg gtggagttcg gcgcagttca 5)
(SEQ ID NO: 6)
agtttccagg cagggtccgc ttattcggtg cttagcggag gcagcttgga atagctccag The use of the diagnostic kit or nucleic acid chip of the present disclosure makes it possible to determine the abnormal growth (dysplastic progression) of colon tissue cells in a sample. The method comprises determining the methylation state of at least one nucleic acid isolated from a sample, wherein the methylation state of the at least one nucleic acid is compared with the methylation stage of a nucleic acid isolated from a sample in which there is no abnormal growth (dysplastic progression) of colorectal cells.

In another embodiment of the present disclosure, transformed colorectal cancer cells can be detected by examining the methylation of the marker gene using said nucleic acid chip.

In still another embodiment of the present disclosure, colorectal cancer can be diagnosed by examining the methylation of the marker gene using said nucleic acid chip.

In yet another embodiment of the present disclosure, the likelihood of progression to colorectal cancer can be diagnosed by examining the methylation of the marker gene in a sample showing a normal phenotype using said kit or nucleic acid chip. The sample that is used in the present disclosure may be solid or liquid tissue, cells, feces, urine, serum, or blood plasma.

Major terms which are used herein are defined as follows.

As used herein, the term "cell transformation" refers to the change in characteristics of a cell from one form to another form such as from normal to abnormal, non-tumorous to tumorous, undifferentiated to differentiated, stem cell to non-stem cell. In addition, the transformation can be recognized by the morphology, phenotype, biochemical characteristics and the like of a cell.

As used herein, the term "early detection" of cancer refers to discovering the likelihood of cancer prior to metastasis, and preferably before observation of a morphological change in a tissue or cell. Furthermore, the term "early detection" of cell transformation refers to the high probability of a cell to undergo transformation in its early stages before the cell is morphologically designated as being transformed.

As used herein, the term "hypermethylation" refers to the methylation of a CpG island.

As used herein, the term "sample" or "clinical sample" is referred to in its broadest sense, and includes any biological sample obtained from an individual, body fluid, a cell line, a tissue culture, depending on the type of assay that is to be performed. Methods for obtaining tissue biopsies and body fluids from mammals are well known in the art. A tissue biopsy of the colon is a preferred source.

Biomarker for Colorectal Cancer—Use of Cancer Cells for Comparison with Normal Cells In the present disclosure, "normal" cells refer to those that do not show any abnormal morphological or cytological changes. "Tumor" cells are cancer cells. "Non-tumor" cells are those cells that are part of the diseased tissue but are not considered to be the tumor portion.

In one aspect, the present disclosure is based on the discovery of the relationship between colorectal cancer and the hypermethylation of GPM6A (NM_005277, glycoprotein M6A) gene.

In another embodiment of the present disclosure, a cellular proliferative disorder of colorectal tissue cell can be diagnosed at an early stage by determining the methylation stage of at least one nucleic acid from a subject using the kit or nucleic acid chip of the present disclosure. Herein, the methylation stage of the at least one nucleic acid may be compared with the methylation state of at least one nucleic acid isolated from a subject not having a cellular proliferative disorder of colon tissue. The nucleic acid is preferably a CpG-containing nucleic acid such as a CpG island.

In another embodiment of the present disclosure, a cellular proliferative disorder of colon tissue can be diagnosed by determining the methylation of at least one nucleic acid from a subject using the kit or nucleic acid chip of the present disclosure. Herein, the nucleic acid may be a CpG island gene of GPM6A (NM_005277, glycoprotein M6A) gene. In this embodiment, the methylation of the at least one nucleic acid may be compared with the methylation state of at least one nucleic acid isolated from a subject having no predisposition to a cellular proliferative disorder of colon tissue.

As used herein, "predisposition" refers to the property of being susceptible to a cellular proliferative disorder. A subject having a predisposition to a cellular proliferative disorder has no cellular proliferative disorder, but is a subject having an increased likelihood of having a cellular proliferative disorder.

In another aspect, the present disclosure provides a method for diagnosing a cellular proliferative disorder of colon tissue, the method comprising brining a sample comprising a nucleic acid into contact with an agent capable of determining the methylation state of the sample, and determining the methylation of at least one region of the at least one nucleic acid. Herein, the methylation of the at least one region in the at least one nucleic acid differs from the methylation stage of the same region in a nucleic acid present in a subject in which there is no abnormal growth of cells.

The method of the present disclosure comprises a step of determining the methylation of at least one region of at least one nucleic acid isolated from a subject.

The term "nucleic acid" or "nucleic acid sequence" as used herein refers to an oligonucleotide, nucleotide or polynucleotide, or fragments thereof, or single-stranded or double-stranded DNA or RNA of genomic or synthetic origin, sense- or antisense-strand DNA or RNA of genomic or synthetic origin, peptide nucleic acid (PNA), or any DNA-like or RNA-like material of natural or synthetic origin. It will apparent to those of skill in the art that, when the nucleic acid is RNA, the deoxynucleotides A, G, C, and T are replaced by the ribonucleotides A, G, C, and U, respectively.

Any nucleic acid may be used in the present disclosure, given the presence of differently methylated CpG islands can be detected therein. The CpG island is a CpG-rich region in a nucleic acid sequence.

Methylation

In the present disclosure, any nucleic acid sample, in purified or nonpurified form, can be used, provided it contains or is suspected of containing a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten-fold relative to the rest of the genome. CpG islands have an average G*C content of about 60%, compared with the 40% average in bulk DNA. The islands take the form of stretches of DNA typically about one to two kilobases long. There are about 45,000 islands in the human genome.

In many genes, the CpG islands begin just upstream of a promoter and extend downstream into the transcribed region. Methylation of a CpG island at a promoter usually suppresses expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns.

Typically, the CpG-containing nucleic acid is DNA. However, the inventive method may employ, for example, samples that contain DNA, or DNA and RNA containing mRNA, wherein DNA or RNA may be single-stranded or double-stranded, or a DNA-RNA hybrid may be included in the sample.

A mixture of nucleic acids may also be used. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. Nucleic acids contained in a sample used for detection of methylated CpG islands may be extracted by a variety of techniques such as that described by Sambrook, et al. (Molecular Cloning: A Laboratory Manual, Cold Spring Harbor, N.Y., 1989).

Nucleic acids isolated from a subject are obtained in a biological sample from the subject. If it is desired to detect colorectal cancer or stages of colorectal cancer progression, the nucleic acid may be isolated from colon tissue by scraping or biopsy. Such samples may be obtained by various medical procedures known to those of skill in the art.

In one aspect of the invention, the state of methylation in nucleic acids of the sample obtained from a subject is hypermethylation compared with the same regions of the nucleic acid in a subject not having a cellular proliferative disorder of colon tissue. Hypermethylation as used herein refers to the presence of methylated alleles in one or more nucleic acids. Nucleic acids from a subject not having a cellular proliferative disorder of colon tissue contain no detectable methylated alleles when the same nucleic acids are examined.

Method for Detection of Methylation

Methylation-Specific PCR

When genomic DNA is treated with bisulfite, cytosine in the 5'-CpG'-3 region remains intact, if it was methylated, but the cytosine changes to uracil, if it was unmethylated. Accordingly, based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

Real-Time Methylation Specific PCR

Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using Sybergreen. Thus, the real-time methylation-specific PCR allows selective quantitative analysis of methylated DNA. Herein, a standard curve is plotted using an in vitro methylated DNA sample, and a gene containing no 5'-CpG-3' sequence in the base sequence is also amplified as a negative control group for standardization to quantitatively analyze the degree of methylation.

Primer(s) that could amplify a methylated CpG of GPM6A might be used, and primer(s) comprises at least one or more CpG dinucleotide in a region which hybridizes to the methylated CpG of GPM6A. Specifically, the primer(s) for amplifying a methylated CpG of GPM6A comprise sequence(s) having a homology of 50% or more, specifically at least 81%, 82%, 83%, 84%, 85%, 86%, 87%, 88%, 89%, 90%, 91%, 92%, 93%, 94%, 95%, 96%, 97%, 98% or 99%, with one or more sequence(s) selected from the group consisting of SEQ ID NOs: 24-25, 27-68, 70-211, 213-314, 316-417, 419-520, 522-623, 625-726, 728-829, 831-932, 934-1035, 1037-1138, 1140-1221, 1223-1324, 1326-1427.

If required, probe(s) capable of hybridizing with a methylated CpG of GPM6A might be used. The probe(s) capable of hybridizing with a methylated CpG of GPM6A comprise at least one or more CpG dinucleotide in a region which hybridizes to the methylated CpG of GPM6A. Specifically, probe(s) might comprise sequence(s) having a homology of 50% or more, specifically at least 81%, 82%, 83%, 84%, 85%, 86%, 87%, 88%, 89%, 90%, 91%, 92%, 93%, 94%, 95%, 96%, 97%, 98% or 99%, with one or more sequence(s) selected from the group consisting of SEQ ID NOs: 26, 69, 212, 315, 418, 521, 624, 727, 830, 933, 1036, 1139, 1222, 1325 and 1428.

Pyrosequencing

The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

PCR Using Methylated DNA-Specific Binding Protein, Quantitative PCR, and DNA Chip Assay When a protein binding specifically only to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, McrBt.

Detection of Differential Methylation-Methylation-Sensitive Restriction Endonuclease Detection of differential methylation can be accomplished by bringing a nucleic acid sample into contact with a methylation-sensitive restriction endonuclease that cleaves only unmethylated CpG sites.

In a separate reaction, the sample is further brought into contact with an isoschizomer of the methylation-sensitive restriction enzyme that cleaves both methylated and unmethylated CpG-sites, thereby cleaving the methylated nucleic acid.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination. Examples of other methylation-sensitive restriction enzymes include, but are not limited to SacII and EagI.

The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

Primers of the present disclosure are designed to be "substantially" complementary to each strand of the locus to be amplified and include the appropriate G or C nucleotides as discussed above. This means that the primers must be sufficiently complementary to hybridize with their respective strands under polymerization reaction conditions. Primers of the present disclosure are used in the amplification process, which is an enzymatic chain reaction (e.g., PCR) in which that a target locus exponentially increases through a number of reaction steps. Typically, one primer is homologous with the negative (−) strand of the locus (antisense primer), and the other primer is homologous with the positive (+) strand (sense primer). After the primers have been annealed to denatured nucleic acid, the nucleic acid chain is extended by an enzyme such as DNA Polymerase I (Klenow), and reactants such as nucleotides, and, as a result, + and − strands containing the target locus sequence are newly synthesized. When the newly synthesized target locus is used as a template and subjected to repeated cycles of denaturing, primer annealing, and extension, exponential synthesis of the target locus sequence occurs. The resulting reaction product is a discrete nucleic acid duplex with termini corresponding to the ends of specific primers employed.

The amplification reaction is PCR which is commonly used in the art. However, alternative methods such as real-time PCR or linear amplification using isothermal enzyme may also be used. In addition, multiplex amplification reactions may also be used.

Detection of Differential Methylation—Bisulfite Sequencing Method

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfite sequencing for detection of methylated nucleic acid.

Kit

The present disclosure provides a kit useful for the detection of a cellular proliferative disorder in a subject.

The present disclosure provides a kit useful for detecting CpG methylation of GPM6A (glycoprotein M6A) gene, comprising primer(s) to amplify a methylated CpG of the GPM6A gene.

Primer(s) that could amplify a methylated CpG of GPM6A might be used, and primer(s) comprises at least one or more CpG dinucleotide in a region which hybridizes to the methylated CpG of GPM6A. Specifically, the primer(s) for amplifying a methylated CpG of GPM6A comprise sequence(s) having a homology of 50% or more, specifically at least 81%, 82%, 83%, 84%, 85%, 86%, 87%, 88%, 89%, 90%, 91%, 92%, 93%, 94%, 95%, 96%, 97%, 98% or 99%, with one or more sequence(s) selected from the group consisting of SEQ ID NOs: 24-25, 27-68, 70-211, 213-314, 316-417, 419-520, 522-623, 625-726, 728-829, 831-932, 934-1035, 1037-1138, 1140-1221, 1223-1324, 1326-1427.

If required, probe(s) capable of hybridizing with a methylated CpG of GPM6A might be used. The probe(s) capable of hybridizing with a methylated CpG of GPM6A comprise at least one or more CpG dinucleotide in a region which hybridizes to the methylated CpG of GPM6A. Specifically, probe(s) might comprise sequence(s) having a homology of 50% or more, specifically at least 81%, 82%, 83%, 84%, 85%, 86%, 87%, 88%, 89%, 90%, 91%, 92%, 93%, 94%, 95%, 96%, 97%, 98% or 99%, with one or more sequence(s) selected from the group consisting of SEQ ID NOs: 26, 69, 212, 315, 418, 521, 624, 727, 830, 933, 1036, 1139, 1222, 1325 and 1428.

The kit of the present disclosure comprises a carrier means compartmentalized to receive a sample therein, one or more containers comprising a second container containing PCR primers for amplification of a 5'-CpG-3' base sequence, and a third container containing a sequencing primer for pyrosequencing an amplified PCR product.

Carrier means are suited for containing one or more containers such as vials, tubes, and the like, each of the containers comprising one of the separate elements to be used in the method. In view of the description provided herein of the inventive method, those of skill in the art can readily determine the apportionment of the necessary reagents among the containers.

Substrates

After the target nucleic acid region has been amplified, the nucleic acid amplification product can be hybridized to a known gene probe attached to a solid support (substrate) to detect the presence of the nucleic acid sequence.

As used herein, the term "substrate", when used in reference to a substance, structure, surface or material, means a composition comprising a nonbiological, synthetic, nonliving, planar or round surface that is not heretofore known to comprise a specific binding, hybridization or catalytic recognition site or a plurality of different recognition sites or a number of different recognition sites which exceeds the number of different molecular species comprising the surface, structure or material. Examples of the substrate include, but are not limited to, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes silicon, silicates, glass, metals and ceramics; and wood, paper, cardboard, cotton, wool, cloth, woven and nonwoven fibers, materials and fabrics; and amphibious surfaces.

It is known in the art that several types of membranes have adhesion to nucleic acid sequences. Specific non-limiting examples of these membranes include nitrocellulose or other membranes used for detection of gene expression such as polyvinylchloride, diazotized paper and other commercially available membranes such as GENE-SCREEN™, ZETAPROBE™ (Biorad) and NYTRAN™. Beads, glass, wafer and metal substrates are also included. Methods for attaching nucleic acids to these objects are well known in the art. Alternatively, screening can be done in a liquid phase.

Hybridization Conditions

In nucleic acid hybridization reactions, the conditions used to achieve a particular level of stringency will vary depending on the nature of the nucleic acids being hybridized. For example, the length, degree of complementarity, nucleotide sequence composition (e.g., GC/AT content), and nucleic acid type (e.g., RNA/DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at room temperature (hybridization conditions); 0.2×SSC/0.1% SDS at room temperature (low stringency conditions); 0.2×SSC/0.1% SDS at 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary depending on the particular hybridization reaction involved, and can be determined empirically. In general, conditions of high stringency are used for the hybridization of the probe of interest.

Label

The probe of interest can be detectably labeled, for example, with a radioisotope, a fluorescent compound, a bioluminescent compound, a chemiluminescent compound, a metal chelator, or an enzyme. Appropriate labeling with such probes is widely known in the art and can be performed by any conventional method.

EXAMPLES

Hereinafter, the present disclosure will be described in further detail with reference to examples. It will be obvious to a person having ordinary skill in the art that these examples are illustrative purposes only and are not to be construed to limit the scope of the present disclosure.

Example 1: Discovery of Colorectal Cancer-Specific Methylated Genes

In order to screen biomarkers which are methylated specifically in colorectal cancer, 500 ng of each of genomic DNAs from 2 normal persons and genomic DNAs from the cancer tissue and adjacent normal tissue from 12 colorectal cancer patients was sonicated (Vibra Cell, SONICS), thus constructing about 200-300-bp-genomic DNA fragments.

To obtain only methylated DNA from the genomic DNA, a methyl binding domain (Methyl binding domain; MBD) (Fraga et al., *Nucleic Acid Res.*, 31: 1765, 2003) known to bind to methylated DNA was used. Specifically, 2 µg of 6ΔHis-tagged MBD2bt was pre-incubated with 500 ng of the genomic DNA of *E. coli* JM110 (No. 2638, Biological Resource Center, Korea Research Institute of Bioscience & Biotechnology), and then bound to Ni-NTA magnetic beads (Qiagen, USA). 500 ng of each of the sonicated genomic DNAs isolated from the normal persons and the colorectal cancer patient patients was allowed to react with the beads in the presence of binding buffer solution (10 mM Tris-HCl (pH 7.5), 50 mM NaCl, 1 mM EDTA, 1 mM DTT, 3 mM $MgCl_2$, 0.1% Triton-X100, 5% glycerol, 25 mg/ml BSA) at 4° C. for 20 minutes. Then, the beads were washed three times with 500 µL of a binding buffer solution containing 700 mM NaCl, and then methylated DNA bound to the MBD2bt was isolated using the QiaQuick PCR purification kit (Qiagen, USA).

Then, the methylated DNAs bound to the MBD2bt were amplified using a genomic DNA amplification kit (Sigma, USA, Cat. No. WGA2), and 4 µg of the amplified DNAs were labeled with Cy5 using a BioPrime Total Genomic Labeling system I (Invitrogen Corp., USA). To indirectly compare the degree of methylation between the normal person and the colorectal cancer patient, a reference DNA was constructed. Herein, the reference DNA was constructed by mixing the genomic DNAs from the 12 colorectal cancer patients with each other in the same amount, amplifying the genomic DNA mixture using a genomic DNA amplification kit (Sigma, USA, Cat. No. WGA2), and labeling 4 μg of the amplified genomic DNA with Cy3 using a BioPrime Total Genomic Labeling system I (Invitrogen Corp., USA). The reference DNA was mixed with each of the DNAs of the normal persons and the colorectal cancer patients, and then hybridized to 244K human CpG microarrays (Agilent, USA) (see FIG. 1). After the hybridization, the DNA mixture was subjected to a series of washing processes, and then scanned using an Agilent scanner. The calculation of signal values from the microarray images was performed by calculating the relative difference in signal strength between the normal person sample and the colorectal cancer patient sample using Feature Extraction program v. 9.5.3.1 (Agilent).

Figure 2:
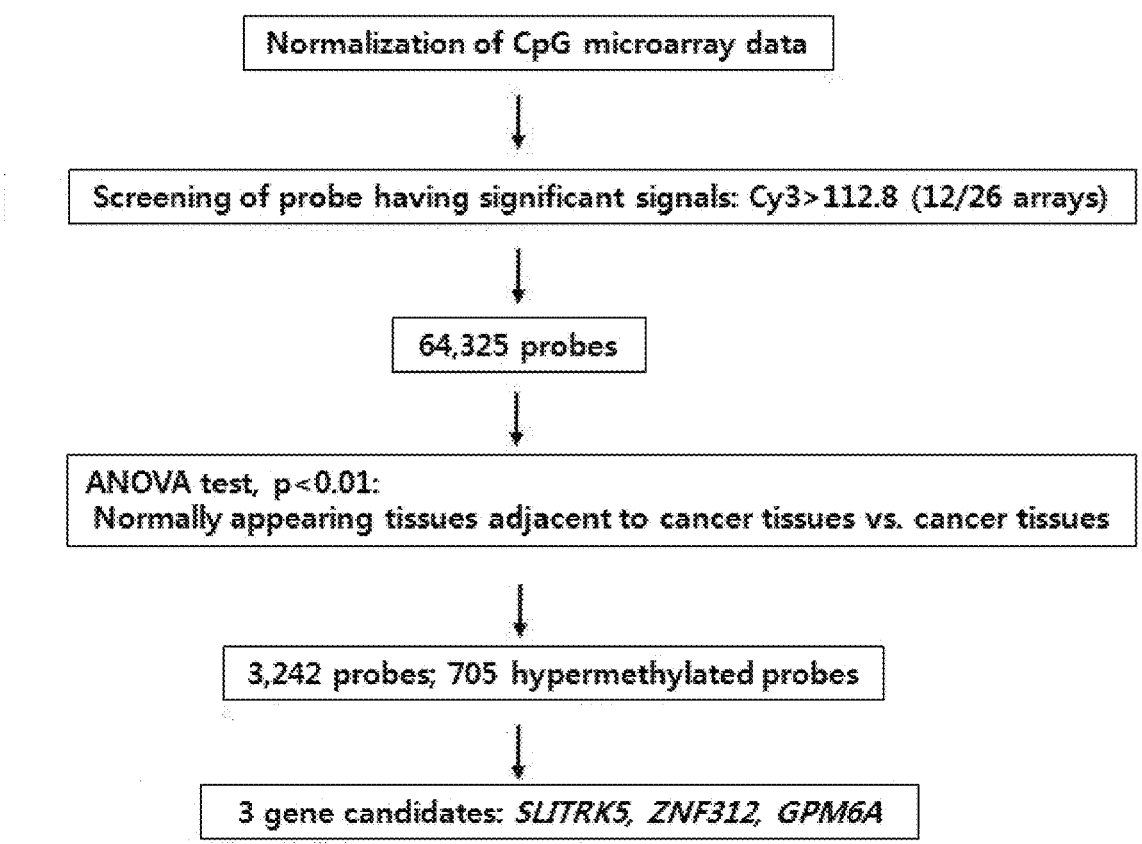
FIG. 2 is a schematic diagram showing a process of screening colorectal cancer-specific hypermethylated genes from the CpG microarray data of colorectal cancer.

In order to screen probes having reliable hybridization signals, 64,325 probes having a Cy3 signal value of more than 112.8 in at least 21 arrays among a total of 26 arrays were screened by the cross gene error model using Gene-Spring 7.3 program (Agilent, USA). In order to screen probes hypermethylated specifically in colorectal cancer from the above probes, the normally appearing tissue adjacent to the colorectal cancer tissue and the colorectal cancer tissue are compared with each other, and in order to screen probes showing differential methylation, the ANOVA test was performed, thereby screening 3,242 probes (p<0.01). From these probes, 705 probes hypermethylated in the colorectal cancer tissue were further screened, and from these probes, 3 biomarker gene candidates (SLITRK5, ZNF312, GPM6A) showing hypermethylation in two or more adjacent probes present within a distance of about 400 bp were selected (see FIG. 2).

The 4 biomarker candidate genes analyzed using the above analysis method are listed in Table 1 below. In addition, the nucleotide sequence corresponding to the probe of each of the 4 genes showing hypermethylation in the CpG microarray was analyzed using MethPrimer (http://itsa.uc-stedu/~urolab/methprimer/index1.html), thereby confirming CpG islands in the probes.

TABLE 1

List of methylation biomarker candidate genes for colorectal cancer diagnosis

| Candidate genes | Probe locations[a] | GenBank No. | Description |
|---|---|---|---|
| SLITRK5 | +1,811, +2,046 | NM_015567 | SLIT and NTRK-like family, member 5 |
| ZNF312 | +2,558, +2,646 | NM_018008 | zinc finger protein 312 |
| GPM6A | +554, +786 | NM_005277 | Glycoprotein M6A |

[a]base pairs (bp) from the transcription start site (+1)

Example 2: Measurement of Methylation of Biomarker Genes in Cancer Cell Lines

In order to additionally confirm the methylation state of the biomarker candidate genes selected in Example 1, pyrosequencing for the promoter and intron region of each gene was performed.

In order to modify unmethylated cytosine to uracil using bisulfite, total genomic DNA was isolated from each of the colorectal cancer cell lines Caco-2 (KCLB No. 30037.1) and HCT116 (KCLB No. 10247), and 200 ng of the genomic DNA was treated with bisulfite using the EZ DNA methylation-gold kit (Zymo Research, USA). When the DNA was treated with bisulfite, unmethylated cytosine was modified to uracil, and the methylated cytosine remained without changes. The DNA treated with bisulfite was eluted in 20 μl of sterile distilled water and subjected to pyrosequencing.

PCR and sequencing primers for performing pyrosequencing for the 3 genes were designed using PSQ assay design program (Biotage, USA). The PCR and sequencing primers for measuring the methylation of each gene are shown in Tables 2 and 3 below.

TABLE 2

PCR primers

| Genes | Primers | Sequences (5'3')[a] | SEQ ID NOS | CpG location[b] | Size of amplicon (bp) |
|---|---|---|---|---|---|
| SLITRK5 | forward | TGTTGATTTTTGGTGTATTGA | 7 | +1949, +1960, +1963, +1989 | 253 |
| SLITRK5 | reverse | AACACATCAACRTCCTAATTACATA | 8 | +1949, +1960, +1963, +1989 | 253 |
| ZNF312 | forward | TGTTTGGTGTAGGGGGAAGT | 9 | +2521, +2527, +2535, +2546 | 224 |
| ZNF312 | reverse | CCCRAAAAAATTATTTTACCTCCA | 10 | +2521, +2527, +2535, +2546 | 224 |
| GPM6A | forward | GGGAAATAAAGAAAGATTAAGAGA | 11 | +560, +567, +572, +598 | 121 |
| GPM6A | reverse | ACCCCRTTTCAACTTACTC | 12 | +560, +567, +572, +598 | 121 |

[a]Y = C or T; R = A or G
[b]distances (nucleotides) from the transcription start site (+1): the positions of CpG regions on the genomic DNA used in the measurement of methylation

TABLE 3

Sequences of sequencing primers for methylation marker genes

| Genes | Sequences (5'→3')[a] | SEQ ID NOS |
|---|---|---|
| SLITRK5 | ATTTTAGTGGTTTAAAGATG | 13 |
| ZNF312 | TGGGTGTATTGAGAGATTT | 14 |
| GPM6A | AAGATTAAGAGATTTAGGAT | 15 |

[a]Y = C or T; R = A or G 20 ng of the genomic DNA treated with bisulfite was amplified by PCR. In the PCR amplification, a PCR reaction solution (20 ng of the genomic DNA treated with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index. The methylation index was calculated by determining the average rate of cytosine binding to each CpG island.

Figure 3:
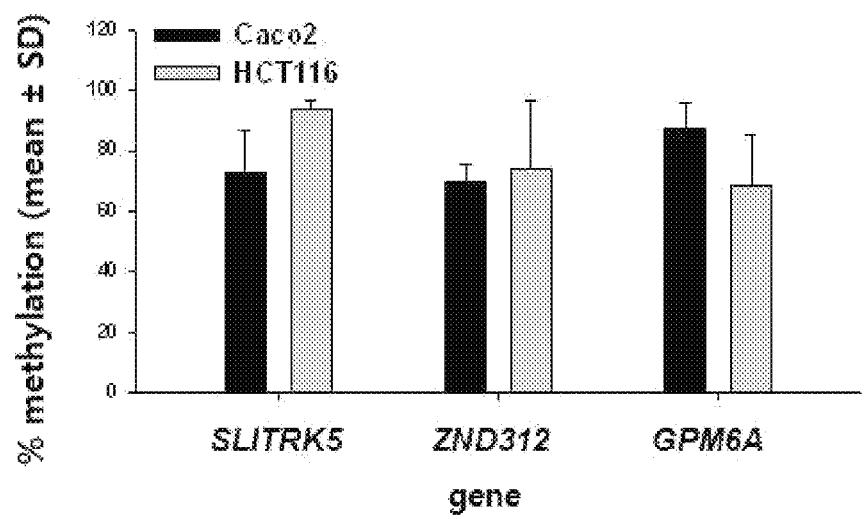
FIG. 3 is a graphic diagram showing the results of measuring the degree of methylation of 3 biomarker candidate genes in a colorectal cancer cell line and the colon tissues of normal persons by pyrosequencing.
Figure 3:
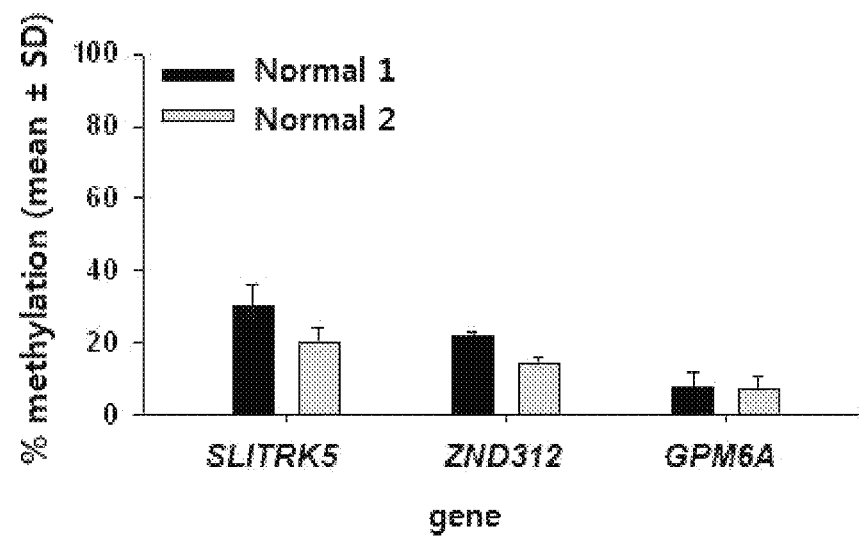

As described above, the degrees of methylation of the biomarker candidate genes in the colorectal cancer cell lines were measured using the pyrosequencing method. As a result, as can be seen in FIG. 3A, the 3 marker genes were all methylated at high levels of 50% in at least one of the cell lines. The 3 genes showed high levels of methylation in the colorectal cancer cell lines, suggesting that these genes are useful as biomarkers for colorectal cancer diagnosis. In order to verify whether these genes are used as biomarkers, the following test was additionally performed using a tissue sample.

Example 3: Measurement of Methylation of Biomarker Candidate Genes in Colon Tissue of Normal Persons In order for the 3 biomarker candidate gene to have utility as biomarkers for colorectal cancer diagnosis, these genes should show low levels of methylation in the colon tissue of normal persons other than patients, but should show high levels of methylation in colorectal cancer tissue.

To verify whether these genes satisfy these requirements, genomic DNA was isolated from two normal person's colorectal tissues (Biochain) using the QIAamp DNA minikit (QIAGEN, USA), and 200 ng of the isolated genomic DNA was treated with bisulfite using the EZ DNA methylation-gold kit (Zymo Research, USA). The treated DNA was eluted in 20 µl of sterile distilled water and subjected to pyrosequencing.

20 ng of the genomic DNA treated with bisulfite was amplified by PCR. In the PCR amplification, a PCR reaction solution (20 ng of the genomic DNA treated with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index thereof. The methylation index was calculated by determining the average rate of cytosine binding to each CpG region.

As a result, as can be seen in FIG. 3B, the GPM6A gene among the 3 genes showed the lowest methylation level in the normal tissue. Thus, in order to verify whether the GPM6A gene is useful as a biomarker, the following test was performed using the tissue of colorectal cancer patients.

Example 4: Measurement of Methylation of Biomarker Genes in Tissue of Colorectal Cancer Patients In order to verify whether the GPM6A gene showing low level of methylation in the colon tissue of normal persons is useful as a biomarker for colorectal cancer diagnosis, genomic DNAs were isolated from colorectal cancer tissues isolated from 96 colorectal cancer patients (the Biochip Research Center in Yonsei University, appointed by the Korean Ministry of Health and Welfare) and the normally appearing tissues adjacent thereto.

200 ng of each of the isolated genomic DNAs was treated with bisulfite using the EZ DNA methylation-gold kit (Zymo Research, USA). Each of the treated DNAs was eluted in 20 µl of sterile distilled water and subjected to pyrosequencing.

20 ng of the genomic DNA treated with bisulfite was amplified by PCR. In the PCR amplification, a PCR reaction solution (20 ng of the genomic DNA treated with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction solution was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system. After the pyrosequencing, the methylation degree of the DNA was measured by calculating the methylation index thereof. The methylation index was calculated by determining the average rate of cytosine binding to each CpG region.

Figure 4:
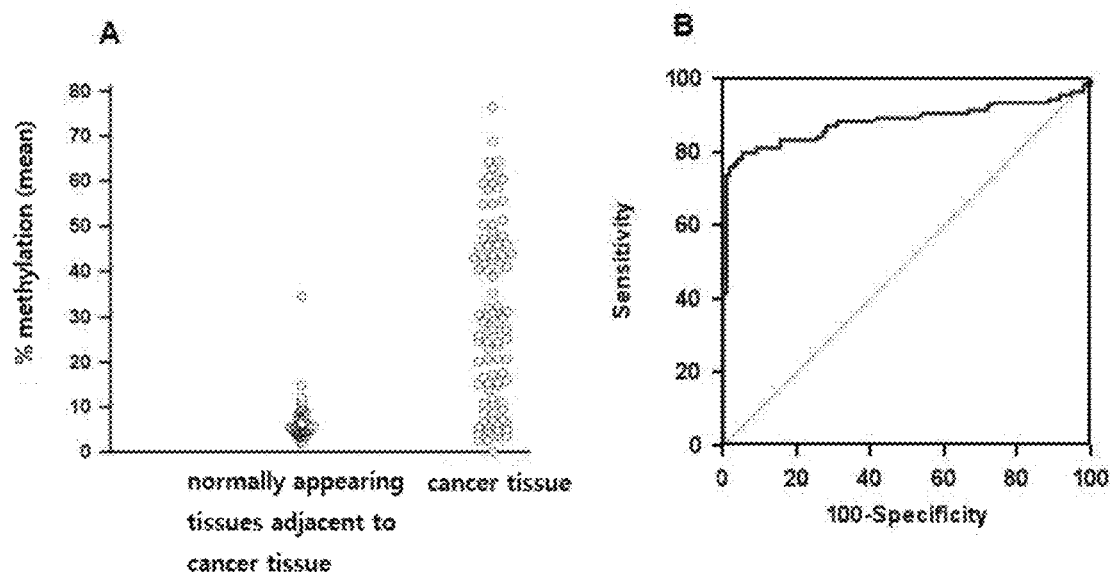
FIG. 4 is a graphic diagram showing the results of measuring the degrees of methylation of GPM6A methylation biomarker in colorectal cancer tissue and adjacent normal tissue by pyrosequencing, and the results of measuring the sensitivity and specificity of GPM6A methylation biomarker for colorectal cancer by ROC curve analysis.

The degree of methylation of the GPM6A gene was measured. As a result, as can be seen in FIG. 4A, the GPM6A gene showed higher levels of methylation in the colorectal cancer tissues of 72 patients (80.2%) of the 96 patients compared to those in the normally appearing tissues. Table 4 below shows the average values of the methylation levels of the GPM6A biomarker gene in the colorectal cancer tissues and the normally appearing tissues adjacent thereto. In order to confirm whether the level of methylation of the genes statistically significantly differs between the colorectal cancer tissue and the normally appearing tissue, the Chi-Square test was performed. As a result, it could be seen that all the three genes showed statistically significant levels ($p<0.01$) (see Table 4).

TABLE 4

Results of quantitative analysis of methylation of GPM6A biomarker

| Average methylation level (%, average ± standard deviation) | | |
|---|---|---|
| Normally appearing tissues | Colorectal cancer tissues | P values[a] |
| 6.8 ± 5.7 | 30.3 ± 19.6 | <0.0001 |

[a]p values obtained through the Chi-Square test

Example 5: Evaluation of the Ability of GPM6A Biomarker to Diagnose Colorectal Cancer For the GPM6A gene confirmed to be useful as colorectal cancer markers in Example 4, receiver operating characteristic (ROC) analysis was performed using MedCalc program (MEDCALC, Belgium) in order to evaluate the ability of the genes to diagnose colorectal cancer.

As a result, as shown in FIG. 4B, the sensitivity and specificity of the GPM6A gene for colorectal cancer were, respectively, 80.2% and 94.8%. This suggests that the GPM6A gene has a very excellent ability to diagnose colorectal cancer. Table 5 shows the results of ROC curve analysis of the GPM6A gene for colorectal cancer diagnosis.

TABLE 5

Results of ROC curve analysis for colorectal cancer diagnosis of the GPM6A methylation biomarker gene

| AUC (95% C.I) | 0.884 (0.830-0.926) |
|---|---|
| Cut-off[a] | >10.31 |
| p value | 0.0001 |
| Sensitivity (%) (95% C.I) | 80.2 (70.8-87.6) |
| Specificity (%) (95% C.I) | 94.8 (88.3-98.3) |

[a]methylation index critera for distinction between normal and cancer samples

Additionally, the GPM6A gene was evaluated for its ability to diagnose colorectal cancer in a fecal sample.

Figure 5:
FIG. 5 shows the results of verifying the methylation of a GPM6A biomarker gene in the fecal tissues of normal persons and colorectal cancer patients by methylation-specific PCR.
Figure 5:
Figure 5:

Specifically, measurement of the methylation was performed on two kinds of colorectal cancer cell lines using a nested methylation-specific PCR (MSP) technique, and it was confirmed that all the two kinds of colorectal cancer cell lines were methylated as shown in FIG. 5A. This result is identical to the result of pyrosequencing performed in the above Example 2. Genomic DNAs were isolated from the fecal samples of 4 normal persons and 8 colorectal cancer patients (the Biochip Research Center in Yonsei University, appointed by the Korean Ministry of Health and Welfare). 4 µg of each of the isolated genomic DNAs was treated with bisulfite using the EZ DNA methylation-gold kit (Zymo Research, USA). Each of the treated DNAs was eluted in 20 µl of sterile distilled water and subjected to a nested MSP test. The primer sequences used in the nested MSP test are shown in Table 6 below.

TABLE 6

Primer sequences used in MSP test of GPM6A gene

| Methylation | Primers | Primer sequences (5'→3') | Size of amplified product (bp) | SEQ ID NOS |
|---|---|---|---|---|
| Methylation | Outer-F | TTAAAAGGGCGTTTATATTGGTTCG | 233 | 16 |
| | Outer-R | CCTCGCTCTTCGAAATAACTCGTA | | 17 |
| | Inner-F | TAGGGTTCGTTTATTCGGTGTTTAGC | 156 | 18 |
| | Inner-R | CCTCGCTCTTCGAAATAACTCGTA | | 19 |
| Non-methylation | Outer-F | TAAAAGGGTGTTTATATTGGTTTGG | 233 | 20 |
| | Outer-R | CCCTCACTCTTCAAAATAACTCATA | | 21 |
| | Inner-F | GGTAGGGTTTGTTTATTTGGTGTTTAGTG | 160 | 22 |
| | Inner-R | TCCCTCACTCTTCAAAATAACTCATA | | 23 |

1 µg of the genomic DNA treated with bisulfite was amplified by PCR. In the PCR amplification, a PCR reaction solution (20 µg of the genomic DNA treated with bisulfite, 5 µl of 10×PCR buffer (Enzynomics, Korea), 5 units of Taq polymerase (Enzynomics, Korea), 4 µl of 2.5 mM Dntp (Solgent, Korea), and 2 µl (10 pmole/µl) of PCR primers) was used, and the PCR reaction was performed under the following conditions: predenaturation at 95° C. for 5 min, and then 30 cycles of denaturation at 95° C. for 40 sec, annealing at 60° C. for 45 sec and extension at 72° C. for 40 sec, followed by final extension at 72° C. for 5 min. ½ of the PCR product was taken and amplified by PCR for 45 cycles in the same manner as above. The amplification of the PCR products was confirmed by electrophoresis on 2.0% agarose gel.

As a result, as shown in FIG. 5B, it was observed that the GPM6A gene was not methylated in the tissues of the 4 normal persons, but was methylated in 5 (62.5%) of the 8 colorectal cancer patients. This suggests that the GPM6A gene is useful for the diagnosis of colorectal cancer in feces.

Example 6: Evaluation of the Ability of GPM6A Biomarker Gene to Diagnose Colorectal Cancer by Using qMSP In order to analyze the ability of GPM6A gene to diagnose colorectal cancer, 695 sets of primers and probes, which could amplify whole CpG island of GMB6A gene and detect specific methylation sites were designed (Table 7), and methylation specific real time PCR (qMSP) was performed. To achieve the purpose, genome DNA was isolated from cancer tissues and normal tissues adjacent to cancer tissues detached by surgery from 20 colorectal cancer patients respectively. Treating bisulfite to the isolated genome DNA (2.0 ug) by using EZ DNA methylation-Gold kit (Zymo Research, USA) was followed by eluting with 10 µl water, and then was subjected to methylation specific real time PCR (qMSP). qMSP was performed by using bisulfite treated genome DNA as a template and methylation specific primers and probes designed according to Table 7. qMSP was performed by using Rotor-Gene Q PCR equipment (Qiagen). Total 20 µl PCR reaction solution (template DNA, 2 µl; 5× AptaTaq DNA Master (Roche Diagnostics), 4 µl; PCR primers, 2 µl (2 pmole/µl), TaqMan probe, 2 µl (2 pmole/µl); D.W. 10 µl) was prepared. Total 40 times of PCR was performed with a PCR condition that treatment at 95° C. for 5 minutes is followed by treatment at 95° C. for 15 seconds under the proper annealing temperature (58° C.–61° C.) for 1 minute. The amplification of the PCR product was confirmed by measuring the Ct (cycling threshold) value. Methylated and non-methylated control DNA were tested with sample DNA by using EpiTect PCR control DNA set (Quagen, cat. no. 59695). COL2A1 gene was used as an internal control (Kristensen et al., 2008). The methylation level of respective samples were measured with PMR value and the PMR value was calculated as follows:

$$PMR = 2^{-\Delta\Delta Ct} \times 100, \Delta\Delta Ct = [(Ct_{(GPM6A)} - Ct_{(COL2A1)sample})] - [Ct_{(GPM6A)} - Ct_{(COL2A1)Methyl\ DNA})]$$

The sensitivity and sensitivity for set of respective primers and probes were calculated with ROC curve analysis (MedCalc program, Belgium) by using PMR value of cancer tissues and normal tissues adjacent to cancer tissues (Table 8).

TABLE 7

Sequences of primer and probes for qMSP of GPM6A gene

| Set | Primer | Sequences (5'→3') | Size of amplification product (bp) | SEQ ID NOs: |
|---|---|---|---|---|
| 1 | F1 | ATTATTTTGGTTAT | 100 | 24 |
|  | R1 | AAAAACACGTACAA |  | 25 |
|  | P1 | GTATTTAGGAGAGAGATT |  | 26 |
| 2 | F2 | TTATTTTGGTTATC | 99 | 27 |
|  | R1 | AAAAACACGTACAA |  | 28 |
|  | P1 | GTATTTAGGAGAGAGATT |  | 26 |
| 3 | F3 | TATTTTGGTTATCG | 98 | 29 |
|  | R1 | AAAAACACGTACAA |  | 30 |
|  | P1 | GTATTTAGGAGAGAGATT |  | 26 |
| 4 | F4 | ATTTTGGTTATCGA | 97 | 31 |
|  | R1 | AAAAACACGTACAA |  | 32 |
|  | P1 | GTATTTAGGAGAGAGATT |  | 26 |
| 5 | F5 | TTTTGGTTATCGAG | 96 | 33 |
|  | R1 | AAAAACACGTACAA |  | 34 |
|  | P1 | GTATTTAGGAGAGAGATT |  | 26 |
| 6 | F6 | TTTGGTTATCGAGT | 95 | 35 |
|  | R1 | AAAAACACGTACAA |  | 36 |
|  | P1 | GTATTTAGGAGAGAGATT |  | 26 |
| 7 | F7 | TTGGTTATCGAGTC | 94 | 37 |
|  | R1 | AAAAACACGTACAA |  | 38 |
|  | P1 | GTATTTAGGAGAGAGATT |  | 26 |
| 8 | F8 | TGGTTATCGAGTCG | 93 | 39 |
|  | R1 | AAAAACACGTACAA |  | 40 |
|  | P1 | GTATTTAGGAGAGAGATT |  | 26 |
| 9 | F9 | GGTTATCGAGTCGG | 92 | 41 |
|  | R1 | AAAAACACGTACAA |  | 42 |
|  | P1 | GTATTTAGGAGAGAGATT |  | 26 |
| 10 | F10 | GTTATCGAGTCGGT | 91 | 43 |
|  | R1 | AAAAACACGTACAA |  | 44 |
|  | P1 | GTATTTAGGAGAGAGATT |  | 26 |
| 11 | F11 | TTATCGAGTCGGTT | 90 | 45 |
|  | R1 | AAAAACACGTACAA |  | 46 |
|  | P1 | GTATTTAGGAGAGAGATT |  | 26 |
| 12 | F12 | TATCGAGTCGGTTG | 89 | 47 |
|  | R1 | AAAAACACGTACAA |  | 48 |
|  | P1 | GTATTTAGGAGAGAGATT |  | 26 |
| 13 | F13 | ATCGAGTCGGTTGT | 88 | 49 |
|  | R1 | AAAAACACGTACAA |  | 50 |
|  | P1 | GTATTTAGGAGAGAGATT |  | 26 |
| 14 | F14 | TCGAGTCGGTTGTG | 87 | Si |
|  | R1 | AAAAACACGTACAA |  | 52 |
|  | P1 | GTATTTAGGAGAGAGATT |  | 26 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 15 | F15 | CGAGTCGGTTGTGG | 86 | 53 |
|  | R1 | AAAAACACGTACAA |  | 54 |
|  | P1 | GTATTTAGGAGAGAGATT |  | 26 |
| 16 | F16 | GAGTCGGTTGTGGG | 85 | 55 |
|  | R1 | AAAAACACGTACAA |  | 56 |
|  | P1 | GTATTTAGGAGAGAGATT |  | 26 |
| 17 | F17 | AGTCGGTTGTGGGG | 84 | 57 |
|  | R1 | AAAAACACGTACAA |  | 58 |
|  | P1 | GTATTTAGGAGAGAGATT |  | 26 |
| 18 | F18 | GTCGGTTGTGGGGT | 83 | 59 |
|  | R1 | AAAAACACGTACAA |  | 60 |
|  | P1 | GTATTTAGGAGAGAGATT |  | 26 |
| 19 | F19 | TCGGTTGTGGGGTG | 82 | 61 |
|  | R1 | AAAAACACGTACAA |  | 62 |
|  | P1 | GTATTTAGGAGAGAGATT |  | 26 |
| 20 | F20 | CGGTTGTGGGGTGT | 81 | 63 |
|  | R1 | AAAAACACGTACAA |  | 64 |
|  | P1 | GTATTTAGGAGAGAGATT |  | 26 |
| 21 | F21 | GGTTGTGGGGTGTT | 80 | 65 |
|  | R1 | AAAAACACGTACAA |  | 66 |
|  | P1 | GTATTTAGGAGAGAGATT |  | 26 |
| 22 | F22 | GTTGTGGGGTGTTG | 150 | 67 |
|  | R2 | ACCCGTTTTCCTCC |  | 68 |
|  | P2 | TTTTTGGGGAGGAGATTTATAGTGAAGG |  | 69 |
| 23 | F23 | TTGTGGGGTGTTGA | 149 | 70 |
|  | R2 | ACCCGTTTTCCTCC |  | 71 |
|  | P2 | TTTTTGGGGAGGAGATTTATAGTGAAGG |  | 69 |
| 24 | F24 | TGTGGGGTGTTGAG | 148 | 72 |
|  | R2 | ACCCGTTTTCCTCC |  | 73 |
|  | P2 | TTTTTGGGGAGGAGATTTATAGTGAAGG |  | 69 |
| 25 | F25 | GTGGGGTGTTGAGA | 147 | 74 |
|  | R2 | ACCCGTTTTCCTCC |  | 75 |
|  | P2 | TTTTTGGGGAGGAGATTTATAGTGAAGG |  | 69 |
| 26 | F26 | TGGGGTGTTGAGAT | 146 | 76 |
|  | R2 | ACCCGTTTTCCTCC |  | 77 |
|  | P2 | TTTTTGGGGAGGAGATTTATAGTGAAGG |  | 69 |
| 27 | F27 | GGGGTGTTGAGATA | 145 | 78 |
|  | R2 | ACCCGTTTTCCTCC |  | 79 |
|  | P2 | TTTTTGGGGAGGAGATTTATAGTGAAGG |  | 69 |
| 28 | F28 | GGGTGTTGAGATAA | 144 | 80 |
|  | R2 | ACCCGTTTTCCTCC |  | 81 |
|  | P2 | TTTTTGGGGAGGAGATTTATAGTGAAGG |  | 69 |
| 29 | F29 | GGTGTTGAGATAAC | 143 | 82 |
|  | R2 | ACCCGTTTTCCTCC |  | 83 |
|  | P2 | TTTTTGGGGAGGAGATTTATAGTGAAGG |  | 69 |
| 30 | F30 | GTGTTGAGATAACG | 142 | 84 |
|  | R2 | ACCCGTTTTCCTCC |  | 85 |
|  | P2 | TTTTTGGGGAGGAGATTTATAGTGAAGG |  | 69 |
| 31 | F31 | TGTTGAGATAACGT | 141 | 86 |
|  | R2 | ACCCGTTTTCCTCC |  | 87 |
|  | P2 | TTTTTGGGGAGGAGATTTATAGTGAAGG |  | 69 |
| 32 | F32 | GTTGAGATAACGTG | 40 | 88 |
|  | R2 | ACCCGTTTTCCTCC |  | 89 |
|  | P2 | TTTTTGGGGAGGAGATTTATAGTGAAGG |  | 69 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 33 | F33 | TTGAGATAACGTGT | 139 | 90 |
|  | R2 | ACCCGTTTTCCTCC |  | 91 |
|  | P2 | TTTTTGGGGAGGAGATTTATAGTGAAGG |  | 69 |
| 34 | F34 | TGAGATAACGTGTG | 138 | 92 |
|  | R2 | ACCCGTTTTCCTCC |  | 93 |
|  | P2 | TTTTTGGGGAGGAGATTTATAGTGAAGG |  | 69 |
| 35 | F35 | GAGATAACGTGTGT | 137 | 94 |
|  | R2 | ACCCGTTTTCCTCC |  | 95 |
|  | P2 | TTTTTGGGGAGGAGATTTATAGTGAAGG |  | 69 |
| 36 | F36 | AGATAACGTGTGTG | 136 | 96 |
|  | R2 | ACCCGTTTTCCTCC |  | 97 |
|  | P2 | TTTTTGGGGAGGAGATTTATAGTGAAGG |  | 69 |
| 37 | F37 | GATAACGTGTGTGT | 135 | 98 |
|  | R2 | ACCCGTTTTCCTCC |  | 99 |
|  | P2 | TTTTTGGGGAGGAGATTTATAGTGAAGG |  | 69 |
| 38 | F38 | ATAACGTGTGTGTT | 134 | 100 |
|  | R2 | ACCCGTTTTCCTCC |  | 101 |
|  | P2 | TTTTTGGGGAGGAGATTTATAGTGAAGG |  | 69 |
| 39 | F39 | TAACGTGTGTGTTT | 133 | 102 |
|  | R2 | ACCCGTTTTCCTCC |  | 103 |
|  | P2 | TTTTTGGGGAGGAGATTTATAGTGAAGG |  | 69 |
| 40 | F40 | AACGTGTGTGTTTG | 132 | 104 |
|  | R2 | ACCCGTTTTCCTCC |  | 105 |
|  | P2 | TTTTTGGGGAGGAGATTTATAGTGAAGG |  | 69 |
| 41 | F41 | ACGTGTGTGTTTGT | 131 | 106 |
|  | R2 | ACCCGTTTTCCTCC |  | 107 |
|  | P2 | TTTTTGGGGAGGAGATTTATAGTGAAGG |  | 69 |
| 42 | F42 | CGTGTGTGTTTGTA | 130 | 108 |
|  | R2 | ACCCGTTTTCCTCC |  | 109 |
|  | P2 | TTTTTGGGGAGGAGATTTATAGTGAAGG |  | 69 |
| 43 | F43 | GTGTGTGTTTGTAA | 129 | 110 |
|  | R2 | ACCCGTTTTCCTCC |  | 111 |
|  | P2 | TTTTTGGGGAGGAGATTTATAGTGAAGG |  | 69 |
| 44 | F44 | TGTGTGTTTGTAAT | 128 | 112 |
|  | R2 | ACCCGTTTTCCTCC |  | 113 |
|  | P2 | TTTTTGGGGAGGAGATTTATAGTGAAGG |  | 69 |
| 45 | F45 | GTGTGTTTGTAATG | 127 | 114 |
|  | R2 | ACCCGTTTTCCTCC |  | 115 |
|  | P2 | TTTTTGGGGAGGAGATTTATAGTGAAGG |  | 69 |
| 46 | F46 | TGTGTTTGTAATGT | 126 | 116 |
|  | R2 | ACCCGTTTTCCTCC |  | 117 |
|  | P2 | TTTTTGGGGAGGAGATTTATAGTGAAGG |  | 69 |
| 47 | F47 | GTGTTTGTAATGTG | 125 | 118 |
|  | R2 | ACCCGTTTTCCTCC |  | 119 |
|  | P2 | TTTTTGGGGAGGAGATTTATAGTGAAGG |  | 69 |
| 48 | F48 | TGTTTGTAATGTGT | 124 | 120 |
|  | R2 | ACCCGTTTTCCTCC |  | 121 |
|  | P2 | TTTTTGGGGAGGAGATTTATAGTGAAGG |  | 69 |
| 49 | F49 | GTTTGTAATGTGTA | 123 | 122 |
|  | R2 | ACCCGTTTTCCTCC |  | 123 |
|  | P2 | TTTTTGGGGAGGAGATTTATAGTGAAGG |  | 69 |
| 50 | F50 | TTTGTAATGTGTAT | 122 | 124 |
|  | R2 | ACCCGTTTTCCTCC |  | 125 |
|  | P2 | TTTTTGGGGAGGAGATTTATAGTGAAGG |  | 69 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 51 | F51 | TTGTAATGTGTATT | 121 | 126 |
|  | R2 | ACCCGTTTTCCTCC |  | 127 |
|  | P2 | TTTTTGGGGAGGAGATTTATAGTGAAGG |  | 69 |
| 52 | F52 | TGTAATGTGTATTT | 120 | 128 |
|  | R2 | ACCCGTTTTCCTCC |  | 129 |
|  | P2 | TTTTTGGGGAGGAGATTTATAGTGAAGG |  | 69 |
| 53 | F53 | GTAATGTGTATTTA | 119 | 130 |
|  | R2 | ACCCGTTTTCCTCC |  | 131 |
|  | P2 | TTTTTGGGGAGGAGATTTATAGTGAAGG |  | 69 |
| 54 | F54 | TAATGTGTATTTAA | 118 | 132 |
|  | R2 | ACCCGTTTTCCTCC |  | 133 |
|  | P2 | TTTTTGGGGAGGAGATTTATAGTGAAGG |  | 69 |
| 55 | F55 | AATGTGTATTTAAT | 117 | 134 |
|  | R2 | ACCCGTTTTCCTCC |  | 135 |
|  | P2 | TTTTTGGGGAGGAGATTTATAGTGAAGG |  | 69 |
| 56 | F56 | ATGTGTATTTAATG | 116 | 136 |
|  | R2 | ACCCGTTTTCCTCC |  | 137 |
|  | P2 | TTTTTGGGGAGGAGATTTATAGTGAAGG |  | 69 |
| 57 | F57 | TGTGTATTTAATGT | 115 | 138 |
|  | R2 | ACCCGTTTTCCTCC |  | 139 |
|  | P2 | TTTTTGGGGAGGAGATTTATAGTGAAGG |  | 69 |
| 58 | F58 | GTGTATTTAATGTA | 114 | 140 |
|  | R2 | ACCCGTTTTCCTCC |  | 141 |
|  | P2 | TTTTTGGGGAGGAGATTTATAGTGAAGG |  | 69 |
| 59 | F59 | TGTATTTAATGTAT | 113 | 142 |
|  | R2 | ACCCGTTTTCCTCC |  | 143 |
|  | P2 | TTTTTGGGGAGGAGATTTATAGTGAAGG |  | 69 |
| 60 | F60 | GTATTTAATGTATT | 112 | 144 |
|  | R2 | ACCCGTTTTCCTCC |  | 145 |
|  | P2 | TTTTTGGGGAGGAGATTTATAGTGAAGG |  | 69 |
| 61 | F61 | TATTTAATGTATTT | 111 | 146 |
|  | R2 | ACCCGTTTTCCTCC |  | 147 |
|  | P2 | TTTTTGGGGAGGAGATTTATAGTGAAGG |  | 69 |
| 62 | F62 | ATTTAATGTATTTA | 110 | 148 |
|  | R2 | ACCCGTTTTCCTCC |  | 149 |
|  | P2 | TTTTTGGGGAGGAGATTTATAGTGAAGG |  | 69 |
| 63 | F63 | TTTAATGTATTTAG | 109 | 150 |
|  | R2 | ACCCGTTTTCCTCC |  | 151 |
|  | P2 | TTTTTGGGGAGGAGATTTATAGTGAAGG |  | 69 |
| 64 | F64 | TTAATGTATTTAGG | 108 | 152 |
|  | R2 | ACCCGTTTTCCTCC |  | 153 |
|  | P2 | TTTTTGGGGAGGAGATTTATAGTGAAGG |  | 69 |
| 65 | F65 | TAATGTATTTAGGA | 07 | 154 |
|  | R2 | ACCCGTTTTCCTCC |  | 155 |
|  | P2 | TTTTTGGGGAGGAGATTTATAGTGAAGG |  | 69 |
| 66 | F66 | AATGTATTTAGGAG | 106 | 156 |
|  | R2 | ACCCGTTTTCCTCC |  | 157 |
|  | P2 | TTTTTGGGGAGGAGATTTATAGTGAAGG |  | 69 |
| 67 | F67 | ATGTATTTAGGAGA | 105 | 158 |
|  | R2 | ACCCGTTTTCCTCC |  | 159 |
|  | P2 | TTTTTGGGGAGGAGATTTATAGTGAAGG |  | 69 |
| 68 | F68 | TGTATTTAGGAGAG | 104 | 160 |
|  | R2 | ACCCGTTTTCCTCC |  | 161 |
|  | P2 | TTTTTGGGGAGGAGATTTATAGTGAAGG |  | 69 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 69 | F69 | GTATTTAGGAGAGA | 103 | 162 |
|  | R2 | ACCCGTTTTCCTCC |  | 163 |
|  | P2 | TTTTTGGGGAGGAGATTTATAGTGAAGG |  | 69 |
| 70 | F70 | TATTTAGGAGAGAG | 102 | 164 |
|  | R2 | ACCCGTTTTCCTCC |  | 165 |
|  | P2 | TTTTTGGGGAGGAGATTTATAGTGAAGG |  | 69 |
| 71 | F71 | ATTTAGGAGAGAGA | 101 | 166 |
|  | R2 | ACCCGTTTTCCTCC |  | 167 |
|  | P2 | TTTTTGGGGAGGAGATTTATAGTGAAGG |  | 69 |
| 72 | F72 | TTTAGGAGAGAGAT | 100 | 168 |
|  | R2 | ACCCGTTTTCCTCC |  | 169 |
|  | P2 | TTTTTGGGGAGGAGATTTATAGTGAAGG |  | 69 |
| 73 | F73 | TTAGGAGAGAGATT | 99 | 170 |
|  | R2 | ACCCGTTTTCCTCC |  | 171 |
|  | P2 | TTTTTGGGGAGGAGATTTATAGTGAAGG |  | 69 |
| 74 | F74 | TAGGAGAGAGATTT | 98 | 172 |
|  | R2 | ACCCGTTTTCCTCC |  | 173 |
|  | P2 | TTTTTGGGGAGGAGATTTATAGTGAAGG |  | 69 |
| 75 | F75 | AGGAGAGAGATTTT | 97 | 174 |
|  | R2 | ACCCGTTTTCCTCC |  | 175 |
|  | P2 | TTTTTGGGGAGGAGATTTATAGTGAAGG |  | 69 |
| 76 | F76 | GGAGAGAGATTTTG | 96 | 176 |
|  | R2 | ACCCGTTTTCCTCC |  | 177 |
|  | P2 | TTTTTGGGGAGGAGATTTATAGTGAAGG |  | 69 |
| 77 | F77 | GAGAGAGATTTTGT | 95 | 178 |
|  | R2 | ACCCGTTTTCCTCC |  | 179 |
|  | P2 | TTTTTGGGGAGGAGATTTATAGTGAAGG |  | 69 |
| 78 | F78 | AGAGAGATTTTGTA | 94 | 180 |
|  | R2 | ACCCGTTTTCCTCC |  | 181 |
|  | P2 | TTTTTGGGGAGGAGATTTATAGTGAAGG |  | 69 |
| 79 | F79 | GAGAGATTTTGTAC | 93 | 182 |
|  | R2 | ACCCGTTTTCCTCC |  | 183 |
|  | P2 | TTTTTGGGGAGGAGATTTATAGTGAAGG |  | 69 |
| 80 | F80 | AGAGATTTTGTACG | 92 | 184 |
|  | R2 | ACCCGTTTTCCTCC |  | 185 |
|  | P2 | TTTTTGGGGAGGAGATTTATAGTGAAGG |  | 69 |
| 81 | F81 | GAGATTTTGTACGT | 91 | 186 |
|  | R2 | ACCCGTTTTCCTCC |  | 187 |
|  | P2 | TTTTTGGGGAGGAGATTTATAGTGAAGG |  | 69 |
| 82 | F82 | AGATTTTGTACGTG | 90 | 188 |
|  | R2 | ACCCGTTTTCCTCC |  | 189 |
|  | P2 | TTTTTGGGGAGGAGATTTATAGTGAAGG |  | 69 |
| 83 | F83 | GATTTTGTACGTGT | 89 | 190 |
|  | R2 | ACCCGTTTTCCTCC |  | 191 |
|  | P2 | TTTTTGGGGAGGAGATTTATAGTGAAGG |  | 69 |
| 84 | F84 | ATTTTGTACGTGTT | 88 | 192 |
|  | R2 | ACCCGTTTTCCTCC |  | 193 |
|  | P2 | TTTTTGGGGAGGAGATTTATAGTGAAGG |  | 69 |
| 85 | F85 | TTTTGTACGTGTTT | 87 | 194 |
|  | R2 | ACCCGTTTTCCTCC |  | 195 |
|  | P2 | TTTTTGGGGAGGAGATTTATAGTGAAGG |  | 69 |
| 86 | F86 | TTTGTACGTGTTTT | 86 | 196 |
|  | R2 | ACCCGTTTTCCTCC |  | 197 |
|  | P2 | TTTTTGGGGAGGAGATTTATAGTGAAGG |  | 69 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 87 | F87 | TTGTACGTGTTTTT | 85 | 198 |
| | R2 | ACCCGTTTTCCTCC | | 199 |
| | P2 | TTTTTGGGGAGGAGATTTATAGTGAAGG | | 69 |
| 88 | F88 | TGTACGTGTTTTTA | 84 | 200 |
| | R2 | ACCCGTTTTCCTCC | | 201 |
| | P2 | TTTTTGGGGAGGAGATTTATAGTGAAGG | | 69 |
| 89 | F89 | GTACGTGTTTTTAA | 83 | 202 |
| | R2 | ACCCGTTTTCCTCC | | 203 |
| | P2 | TTTTTGGGGAGGAGATTTATAGTGAAGG | | 69 |
| 90 | F90 | TACGTGTTTTTAAT | 82 | 204 |
| | R2 | ACCCGTTTTCCTCC | | 205 |
| | P2 | TTTTTGGGGAGGAGATTTATAGTGAAGG | | 69 |
| 91 | F91 | ACGTGTTTTTAATG | 81 | 206 |
| | R2 | ACCCGTTTTCCTCC | | 207 |
| | P2 | TTTTTGGGGAGGAGATTTATAGTGAAGG | | 69 |
| 92 | F92 | CGTGTTTTTAATGA | 80 | 208 |
| | R2 | ACCCGTTTTCCTCC | | 209 |
| | P2 | TTTTTGGGGAGGAGATTTATAGTGAAGG | | 69 |
| 93 | F93 | GTGTTTTTAATGAA | 130 | 210 |
| | R3 | TCTACGAACGCACA | | 211 |
| | P3 | GGTAGGTGGAAAGAGGGAGGGGTT | | 212 |
| 94 | F94 | TGTTTTTAATGAAA | 129 | 213 |
| | R3 | TCTACGAACGCACA | | 214 |
| | P3 | GGTAGGTGGAAAGAGGGAGGGGTT | | 212 |
| 95 | F95 | GTTTTTAATGAAAG | 128 | 215 |
| | R3 | TCTACGAACGCACA | | 216 |
| | P3 | GGTAGGTGGAAAGAGGGAGGGGTT | | 212 |
| 96 | F96 | TTTTTAATGAAAGT | 127 | 217 |
| | R3 | TCTACGAACGCACA | | 218 |
| | P3 | GGTAGGTGGAAAGAGGGAGGGGTT | | 212 |
| 97 | F97 | TTTTAATGAAAGTG | 126 | 219 |
| | R3 | TCTACGAACGCACA | | 220 |
| | P3 | GGTAGGTGGAAAGAGGGAGGGGTT | | 212 |
| 98 | F98 | TTTAATGAAAGTGA | 125 | 221 |
| | R3 | TCTACGAACGCACA | | 222 |
| | P3 | GGTAGGTGGAAAGAGGGAGGGGTT | | 212 |
| 99 | F99 | TTAATGAAAGTGAA | 124 | 223 |
| | R3 | TCTACGAACGCACA | | 224 |
| | P3 | GGTAGGTGGAAAGAGGGAGGGGTT | | 212 |
| 100 | F100 | TAATGAAAGTGAAA | 123 | 225 |
| | R3 | TCTACGAACGCACA | | 226 |
| | P3 | GGTAGGTGGAAAGAGGGAGGGGTT | | 212 |
| 101 | F101 | AATGAAAGTGAAAG | 122 | 227 |
| | R3 | TCTACGAACGCACA | | 228 |
| | P3 | GGTAGGTGGAAAGAGGGAGGGGTT | | 212 |
| 102 | F102 | ATGAAAGTGAAAGG | 121 | 229 |
| | R3 | TCTACGAACGCACA | | 230 |
| | P3 | GGTAGGTGGAAAGAGGGAGGGGTT | | 212 |
| 103 | F103 | TGAAAGTGAAAGGG | | 231 |
| | R3 | TCTACGAACGCACA | 120 | 232 |
| | P3 | GGTAGGTGGAAAGAGGGAGGGGTT | | 212 |
| 104 | F104 | GAAAGTGAAAGGGG | 119 | 233 |
| | R3 | TCTACGAACGCACA | | 234 |
| | P3 | GGTAGGTGGAAAGAGGGAGGGGTT | | 212 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 105 | F105 | AAAGTGAAAGGGGG | 118 | 235 |
| | R3 | TCTACGAACGCACA | | 236 |
| | P3 | GGTAGGTGGAAAGAGGGAGGGGTT | | 212 |
| 106 | F106 | AAGTGAAAGGGGGT | 117 | 237 |
| | R3 | TCTACGAACGCACA | | 238 |
| | P3 | GGTAGGTGGAAAGAGGGAGGGGTT | | 212 |
| 107 | F107 | AGTGAAAGGGGGTA | 116 | 239 |
| | R3 | TCTACGAACGCACA | | 240 |
| | P3 | GGTAGGTGGAAAGAGGGAGGGGTT | | 212 |
| 108 | F108 | GTGAAAGGGGGTAG | 115 | 241 |
| | R3 | TCTACGAACGCACA | | 242 |
| | P3 | GGTAGGTGGAAAGAGGGAGGGGTT | | 212 |
| 109 | F109 | TGAAAGGGGGTAGG | 114 | 243 |
| | R3 | TCTACGAACGCACA | | 244 |
| | P3 | GGTAGGTGGAAAGAGGGAGGGGTT | | 212 |
| 110 | F110 | GAAAGGGGGTAGGG | 113 | 245 |
| | R3 | TCTACGAACGCACA | | 246 |
| | P3 | GGTAGGTGGAAAGAGGGAGGGGTT | | 212 |
| 111 | F111 | AAAGGGGGTAGGGT | 112 | 247 |
| | R3 | TCTACGAACGCACA | | 248 |
| | P3 | GGTAGGTGGAAAGAGGGAGGGGTT | | 212 |
| 112 | F112 | AAGGGGGTAGGGTG | 111 | 249 |
| | R3 | TCTACGAACGCACA | | 250 |
| | P3 | GGTAGGTGGAAAGAGGGAGGGGTT | | 212 |
| 113 | F113 | AGGGGGTAGGGTGG | 110 | 251 |
| | R3 | TCTACGAACGCACA | | 252 |
| | P3 | GGTAGGTGGAAAGAGGGAGGGGTT | | 212 |
| 114 | F114 | GGGGGTAGGGTGGG | 109 | 253 |
| | R3 | TCTACGAACGCACA | | 254 |
| | P3 | GGTAGGTGGAAAGAGGGAGGGGTT | | 212 |
| 115 | F115 | GGGGTAGGGTGGGG | 108 | 255 |
| | R3 | TCTACGAACGCACA | | 256 |
| | P3 | GGTAGGTGGAAAGAGGGAGGGGTT | | 212 |
| 116 | F116 | GGGTAGGGTGGGGG | 107 | 257 |
| | R3 | TCTACGAACGCACA | | 258 |
| | P3 | GGTAGGTGGAAAGAGGGAGGGGTT | | 212 |
| 117 | F117 | GGTAGGGTGGGGGT | 106 | 259 |
| | R3 | TCTACGAACGCACA | | 260 |
| | P3 | GGTAGGTGGAAAGAGGGAGGGGTT | | 212 |
| 118 | F118 | GTAGGGTGGGGGTT | 105 | 261 |
| | R3 | TCTACGAACGCACA | | 262 |
| | P3 | GGTAGGTGGAAAGAGGGAGGGGTT | | 212 |
| 119 | F119 | TAGGGTGGGGGTTT | 104 | 263 |
| | R3 | TCTACGAACGCACA | | 264 |
| | P3 | GGTAGGTGGAAAGAGGGAGGGGTT | | 212 |
| 120 | F120 | AGGGTGGGGGTTTT | 103 | 265 |
| | R3 | TCTACGAACGCACA | | 266 |
| | P3 | GGTAGGTGGAAAGAGGGAGGGGTT | | 212 |
| 121 | F121 | GGGTGGGGGTTTTT | 102 | 267 |
| | R3 | TCTACGAACGCACA | | 268 |
| | P3 | GGTAGGTGGAAAGAGGGAGGGGTT | | 212 |
| 122 | F122 | GGTGGGGGTTTTTG | 101 | 269 |
| | R3 | TCTACGAACGCACA | | 270 |
| | P3 | GGTAGGTGGAAAGAGGGAGGGGTT | | 212 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 123 | F123 | GTGGGGGTTTTTGG | 100 | 271 |
|  | R3 | TCTACGAACGCACA |  | 272 |
|  | P3 | GGTAGGTGGAAAGAGGGAGGGGTT |  | 212 |
| 124 | F124 | TGGGGGTTTTTGGG | 99 | 273 |
|  | R3 | TCTACGAACGCACA |  | 274 |
|  | P3 | GGTAGGTGGAAAGAGGGAGGGGTT |  | 212 |
| 125 | F125 | GGGGGTTTTTGGGG | 98 | 275 |
|  | R3 | TCTACGAACGCACA |  | 276 |
|  | P3 | GGTAGGTGGAAAGAGGGAGGGGTT |  | 212 |
| 126 | F126 | GGGGTTTTTGGGGA | 97 | 277 |
|  | R3 | TCTACGAACGCACA |  | 278 |
|  | P3 | GGTAGGTGGAAAGAGGGAGGGGTT |  | 212 |
| 127 | F127 | GGGTTTTTGGGGAG | 96 | 279 |
|  | R3 | TCTACGAACGCACA |  | 280 |
|  | P3 | GGTAGGTGGAAAGAGGGAGGGGTT |  | 212 |
| 128 | F128 | GGTTTTTGGGGAGG | 95 | 281 |
|  | R3 | TCTACGAACGCACA |  | 282 |
|  | P3 | GGTAGGTGGAAAGAGGGAGGGGTT |  | 212 |
| 129 | F129 | GTTTTTGGGGAGGA | 94 | 283 |
|  | R3 | TCTACGAACGCACA |  | 284 |
|  | P3 | GGTAGGTGGAAAGAGGGAGGGGTT |  | 212 |
| 130 | F130 | TTTTTGGGGAGGAG | 93 | 285 |
|  | R3 | TCTACGAACGCACA |  | 286 |
|  | P3 | GGTAGGTGGAAAGAGGGAGGGGTT |  | 212 |
| 131 | F131 | TTTTGGGGAGGAGA | 92 | 287 |
|  | R3 | TCTACGAACGCACA |  | 288 |
|  | P3 | GGTAGGTGGAAAGAGGGAGGGGTT |  | 212 |
| 132 | F132 | TTTGGGGAGGAGAT | 91 | 289 |
|  | R3 | TCTACGAACGCACA |  | 290 |
|  | P3 | GGTAGGTGGAAAGAGGGAGGGGTT |  | 212 |
| 133 | F133 | TTGGGGAGGAGATT | 90 | 291 |
|  | R3 | TCTACGAACGCACA |  | 292 |
|  | P3 | GGTAGGTGGAAAGAGGGAGGGGTT |  | 212 |
| 134 | F134 | TGGGGAGGAGATTT | 89 | 293 |
|  | R3 | TCTACGAACGCACA |  | 294 |
|  | P3 | GGTAGGTGGAAAGAGGGAGGGGTT |  | 212 |
| 135 | F135 | GGGGAGGAGATTTA | 88 | 295 |
|  | R3 | TCTACGAACGCACA |  | 296 |
|  | P3 | GGTAGGTGGAAAGAGGGAGGGGTT |  | 212 |
| 136 | F136 | GGGAGGAGATTTAT | 87 | 297 |
|  | R3 | TCTACGAACGCACA |  | 298 |
|  | P3 | GGTAGGTGGAAAGAGGGAGGGGTT |  | 212 |
| 137 | F137 | GGAGGAGATTTATA | 86 | 299 |
|  | R3 | TCTACGAACGCACA |  | 300 |
|  | P3 | GGTAGGTGGAAAGAGGGAGGGGTT |  | 212 |
| 138 | F138 | GAGGAGATTTATAG | 85 | 301 |
|  | R3 | TCTACGAACGCACA |  | 302 |
|  | P3 | GGTAGGTGGAAAGAGGGAGGGGTT |  | 212 |
| 139 | F139 | AGGAGATTTATAGT | 84 | 303 |
|  | R3 | TCTACGAACGCACA |  | 304 |
|  | P3 | GGTAGGTGGAAAGAGGGAGGGGTT |  | 212 |
| 140 | F140 | GGAGATTTATAGTG | 83 | 305 |
|  | R3 | TCTACGAACGCACA |  | 306 |
|  | P3 | GGTAGGTGGAAAGAGGGAGGGGTT |  | 212 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 141 | F141 | GAGATTTATAGTGA | 82 | 307 |
|  | R3 | TCTACGAACGCACA |  | 308 |
|  | P3 | GGTAGGTGGAAAGAGGGAGGGGTT |  | 212 |
| 142 | F142 | AGATTTATAGTGAA | 81 | 309 |
|  | R3 | TCTACGAACGCACA |  | 310 |
|  | P3 | GGTAGGTGGAAAGAGGGAGGGGTT |  | 212 |
| 143 | F143 | GATTTATAGTGAAG | 80 | 311 |
|  | R3 | TCTACGAACGCACA |  | 312 |
|  | P3 | GGTAGGTGGAAAGAGGGAGGGGTT |  | 212 |
| 144 | F144 | ATTTATAGTGAAGG | 130 | 313 |
|  | R4 | ATAACAACCTCGCC |  | 314 |
|  | P4 | TTTTGCGAGTTGTTTTCGTTGGGAGG |  | 315 |
| 145 | F145 | TTTATAGTGAAGGG | 129 | 316 |
|  | R4 | ATAACAACCTCGCC |  | 317 |
|  | P4 | TTTTGCGAGTTGTTTTCGTTGGGAGG |  | 315 |
| 146 | F146 | TTATAGTGAAGGGG | 128 | 318 |
|  | R4 | ATAACAACCTCGCC |  | 319 |
|  | P4 | TTTTGCGAGTTGTTTTCGTTGGGAGG |  | 315 |
| 147 | F147 | TATAGTGAAGGGGA | 127 | 320 |
|  | R4 | ATAACAACCTCGCC |  | 321 |
|  | P4 | TTTTGCGAGTTGTTTTCGTTGGGAGG |  | 315 |
| 148 | F148 | ATAGTGAAGGGGAG | 126 | 322 |
|  | R4 | ATAACAACCTCGCC |  | 323 |
|  | P4 | TTTTGCGAGTTGTTTTCGTTGGGAGG |  | 315 |
| 149 | F149 | TAGTGAAGGGGAGG | 125 | 324 |
|  | R4 | ATAACAACCTCGCC |  | 325 |
|  | P4 | TTTTGCGAGTTGTTTTCGTTGGGAGG |  | 315 |
| 150 | F150 | AGTGAAGGGGAGGA | 124 | 326 |
|  | R4 | ATAACAACCTCGCC |  | 327 |
|  | P4 | TTTTGCGAGTTGTTTTCGTTGGGAGG |  | 315 |
| 151 | F151 | GTGAAGGGGAGGAA | 123 | 328 |
|  | R4 | ATAACAACCTCGCC |  | 329 |
|  | P4 | TTTTGCGAGTTGTTTTCGTTGGGAGG |  | 315 |
| 152 | F152 | TGAAGGGGAGGAAA | 122 | 330 |
|  | R4 | ATAACAACCTCGCC |  | 331 |
|  | P4 | TTTTGCGAGTTGTTTTCGTTGGGAGG |  | 315 |
| 153 | F153 | GAAGGGGAGGAAAA | 121 | 332 |
|  | R4 | ATAACAACCTCGCC |  | 333 |
|  | P4 | TTTTGCGAGTTGTTTTCGTTGGGAGG |  | 315 |
| 154 | F154 | AAGGGGAGGAAAAC | 120 | 334 |
|  | R4 | ATAACAACCTCGCC |  | 335 |
|  | P4 | TTTTGCGAGTTGTTTTCGTTGGGAGG |  | 315 |
| 155 | F155 | AGGGGAGGAAAACG | 119 | 336 |
|  | R4 | ATAACAACCTCGCC |  | 337 |
|  | P4 | TTTTGCGAGTTGTTTTCGTTGGGAGG |  | 315 |
| 156 | F156 | GGGGAGGAAAACGG | 118 | 338 |
|  | R4 | ATAACAACCTCGCC |  | 339 |
|  | P4 | TTTTGCGAGTTGTTTTCGTTGGGAGG |  | 315 |
| 157 | F157 | GGGAGGAAAACGGG | 117 | 340 |
|  | R4 | ATAACAACCTCGCC |  | 341 |
|  | P4 | TTTTGCGAGTTGTTTTCGTTGGGAGG |  | 315 |
| 158 | F158 | GGAGGAAAACGGGT | 116 | 342 |
|  | R4 | ATAACAACCTCGCC |  | 343 |
|  | P4 | TTTTGCGAGTTGTTTTCGTTGGGAGG |  | 315 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 159 | F159 | GAGGAAAACGGGTT | 115 | 344 |
|  | R4 | ATAACAACCTCGCC |  | 345 |
|  | P4 | TTTTGCGAGTTGTTTTCGTTGGGAGG |  | 315 |
| 160 | F160 | AGGAAAACGGGTTT | 114 | 346 |
|  | R4 | ATAACAACCTCGCC |  | 347 |
|  | P4 | TTTTGCGAGTTGTTTTCGTTGGGAGG |  | 315 |
| 161 | F161 | GGAAAACGGGTTTT | 113 | 348 |
|  | R4 | ATAACAACCTCGCC |  | 349 |
|  | P4 | TTTTGCGAGTTGTTTTCGTTGGGAGG |  | 315 |
| 162 | F162 | GAAAACGGGTTTTT | 112 | 350 |
|  | R4 | ATAACAACCTCGCC |  | 351 |
|  | P4 | TTTTGCGAGTTGTTTTCGTTGGGAGG |  | 315 |
| 163 | F163 | AAAACGGGTTTTTC | 111 | 352 |
|  | R4 | ATAACAACCTCGCC |  | 353 |
|  | P4 | TTTTGCGAGTTGTTTTCGTTGGGAGG |  | 315 |
| 164 | F164 | AAACGGGTTTTTCG | 110 | 354 |
|  | R4 | ATAACAACCTCGCC |  | 355 |
|  | P4 | TTTTGCGAGTTGTTTTCGTTGGGAGG |  | 315 |
| 165 | F165 | AACGGGTTTTTCGT | 109 | 356 |
|  | R4 | ATAACAACCTCGCC |  | 357 |
|  | P4 | TTTTGCGAGTTGTTTTCGTTGGGAGG |  | 315 |
| 166 | F166 | ACGGGTTTTTCGTA | 108 | 358 |
|  | R4 | ATAACAACCTCGCC |  | 359 |
|  | P4 | TTTTGCGAGTTGTTTTCGTTGGGAGG |  | 315 |
| 167 | F167 | CGGGTTTTTCGTAG | 107 | 360 |
|  | R4 | ATAACAACCTCGCC |  | 361 |
|  | P4 | TTTTGCGAGTTGTTTTCGTTGGGAGG |  | 315 |
| 168 | F168 | GGGTTTTTCGTAGA | 106 | 362 |
|  | R4 | ATAACAACCTCGCC |  | 363 |
|  | P4 | TTTTGCGAGTTGTTTTCGTTGGGAGG |  | 315 |
| 169 | F169 | GGTTTTTCGTAGAG | 105 | 364 |
|  | R4 | ATAACAACCTCGCC |  | 365 |
|  | P4 | TTTTGCGAGTTGTTTTCGTTGGGAGG |  | 315 |
| 170 | F170 | GTTTTTCGTAGAGG | 104 | 366 |
|  | R4 | ATAACAACCTCGCC |  | 367 |
|  | P4 | TTTTGCGAGTTGTTTTCGTTGGGAGG |  | 315 |
| 171 | F171 | TTTTTCGTAGAGGA | 103 | 368 |
|  | R4 | ATAACAACCTCGCC |  | 369 |
|  | P4 | TTTTGCGAGTTGTTTTCGTTGGGAGG |  | 315 |
| 172 | F172 | TTTTCGTAGAGGAG | 102 | 370 |
|  | R4 | ATAACAACCTCGCC |  | 371 |
|  | P4 | TTTTGCGAGTTGTTTTCGTTGGGAGG |  | 315 |
| 173 | F173 | TTTCGTAGAGGAGG | 101 | 372 |
|  | R4 | ATAACAACCTCGCC |  | 373 |
|  | P4 | TTTTGCGAGTTGTTTTCGTTGGGAGG |  | 315 |
| 174 | F174 | TTCGTAGAGGAGGT | 100 | 374 |
|  | R4 | ATAACAACCTCGCC |  | 375 |
|  | P4 | TTTTGCGAGTTGTTTTCGTTGGGAGG |  | 315 |
| 175 | F175 | TCGTAGAGGAGGTA | 99 | 376 |
|  | R4 | ATAACAACCTCGCC |  | 377 |
|  | P4 | TTTTGCGAGTTGTTTTCGTTGGGAGG |  | 315 |
| 176 | F176 | CGTAGAGGAGGTAG | 98 | 378 |
|  | R4 | ATAACAACCTCGCC |  | 379 |
|  | P4 | TTTTGCGAGTTGTTTTCGTTGGGAGG |  | 315 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 177 | F177 | GTAGAGGAGGTAGG | 97 | 380 |
|  | R4 | ATAACAACCTCGCC |  | 381 |
|  | P4 | TTTTGCGAGTTGTTTTCGTTGGGAGG |  | 315 |
| 178 | F178 | TAGAGGAGGTAGGT | 96 | 382 |
|  | R4 | ATAACAACCTCGCC |  | 383 |
|  | P4 | TTTTGCGAGTTGTTTTCGTTGGGAGG |  | 315 |
| 179 | F179 | AGAGGAGGTAGGTG | 95 | 384 |
|  | R4 | ATAACAACCTCGCC |  | 385 |
|  | P4 | TTTTGCGAGTTGTTTTCGTTGGGAGG |  | 315 |
| 180 | F180 | GAGGAGGTAGGTGG | 94 | 386 |
|  | R4 | ATAACAACCTCGCC |  | 387 |
|  | P4 | TTTTGCGAGTTGTTTTCGTTGGGAGG |  | 315 |
| 181 | F181 | AGGAGGTAGGTGGA | 93 | 388 |
|  | R4 | ATAACAACCTCGCC |  | 389 |
|  | P4 | TTTTGCGAGTTGTTTTCGTTGGGAGG |  | 315 |
| 182 | F182 | GGAGGTAGGTGGAA | 92 | 390 |
|  | R4 | ATAACAACCTCGCC |  | 391 |
|  | P4 | TTTTGCGAGTTGTTTTCGTTGGGAGG |  | 315 |
| 183 | F183 | GAGGTAGGTGGAAA | 91 | 392 |
|  | R4 | ATAACAACCTCGCC |  | 393 |
|  | P4 | TTTTGCGAGTTGTTTTCGTTGGGAGG |  | 315 |
| 184 | F184 | AGGTAGGTGGAAAG | 90 | 394 |
|  | R4 | ATAACAACCTCGCC |  | 395 |
|  | P4 | TTTTGCGAGTTGTTTTCGTTGGGAGG |  | 315 |
| 185 | F185 | GGTAGGTGGAAAGA | 89 | 396 |
|  | R4 | ATAACAACCTCGCC |  | 397 |
|  | P4 | TTTTGCGAGTTGTTTTCGTTGGGAGG |  | 315 |
| 186 | F186 | GTAGGTGGAAAGAG | 88 | 398 |
|  | R4 | ATAACAACCTCGCC |  | 399 |
|  | P4 | TTTTGCGAGTTGTTTTCGTTGGGAGG |  | 315 |
| 187 | F187 | TAGGTGGAAAGAGG | 87 | 400 |
|  | R4 | ATAACAACCTCGCC |  | 401 |
|  | P4 | TTTTGCGAGTTGTTTTCGTTGGGAGG |  | 315 |
| 188 | F188 | AGGTGGAAAGAGGG | 86 | 402 |
|  | R4 | ATAACAACCTCGCC |  | 403 |
|  | P4 | TTTTGCGAGTTGTTTTCGTTGGGAGG |  | 315 |
| 189 | F189 | GGTGGAAAGAGGGA | 85 | 404 |
|  | R4 | ATAACAACCTCGCC |  | 405 |
|  | P4 | TTTTGCGAGTTGTTTTCGTTGGGAGG |  | 315 |
| 190 | F190 | GTGGAAAGAGGGAG | 84 | 406 |
|  | R4 | ATAACAACCTCGCC |  | 407 |
|  | P4 | TTTTGCGAGTTGTTTTCGTTGGGAGG |  | 315 |
| 191 | F191 | TGGAAAGAGGGAGG | 83 | 408 |
|  | R4 | ATAACAACCTCGCC |  | 409 |
|  | P4 | TTTTGCGAGTTGTTTTCGTTGGGAGG |  | 315 |
| 192 | F192 | GGAAAGAGGGAGGG | 82 | 410 |
|  | R4 | ATAACAACCTCGCC |  | 411 |
|  | P4 | TTTTGCGAGTTGTTTTCGTTGGGAGG |  | 315 |
| 193 | F193 | GAAAGAGGGAGGGG | 81 | 412 |
|  | R4 | ATAACAACCTCGCC |  | 413 |
|  | P4 | TTTTGCGAGTTGTTTTCGTTGGGAGG |  | 315 |
| 194 | F194 | AAAGAGGGAGGGGT | 80 | 414 |
|  | R4 | ATAACAACCTCGCC |  | 415 |
|  | P4 | TTTTGCGAGTTGTTTTCGTTGGGAGG |  | 315 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 195 | F195 | AAGAGGGAGGGGTT | 130 | 416 |
|  | R5 | ACGCGAAACCAAAT |  | 417 |
|  | P5 | AGGAGTTTTAGCGCGGTTTGGAGA |  | 418 |
| 196 | F196 | AGAGGGAGGGGTTT | 129 | 419 |
|  | R5 | ACGCGAAACCAAAT |  | 420 |
|  | P5 | AGGAGTTTTAGCGCGGTTTGGAGA |  | 418 |
| 197 | F197 | GAGGGAGGGGTTTG | 128 | 421 |
|  | R5 | ACGCGAAACCAAAT |  | 422 |
|  | P5 | AGGAGTTTTAGCGCGGTTTGGAGA |  | 418 |
| 198 | F198 | AGGGAGGGGTTTGT | 127 | 423 |
|  | R5 | ACGCGAAACCAAAT |  | 424 |
|  | P5 | AGGAGTTTTAGCGCGGTTTGGAGA |  | 418 |
| 199 | F199 | GGGAGGGGTTTGTG | 126 | 425 |
|  | R5 | ACGCGAAACCAAAT |  | 426 |
|  | P5 | AGGAGTTTTAGCGCGGTTTGGAGA |  | 418 |
| 200 | F200 | GGAGGGGTTTGTGC | 125 | 427 |
|  | R5 | ACGCGAAACCAAAT |  | 428 |
|  | P5 | AGGAGTTTTAGCGCGGTTTGGAGA |  | 418 |
| 201 | F201 | GAGGGGTTTGTGCG | 124 | 429 |
|  | R5 | ACGCGAAACCAAAT |  | 430 |
|  | P5 | AGGAGTTTTAGCGCGGTTTGGAGA |  | 418 |
| 202 | F202 | AGGGGTTTGTGCGT | 123 | 431 |
|  | R5 | ACGCGAAACCAAAT |  | 432 |
|  | P5 | AGGAGTTTTAGCGCGGTTTGGAGA |  | 418 |
| 203 | F203 | GGGGTTTGTGCGTT | 122 | 433 |
|  | R5 | ACGCGAAACCAAAT |  | 434 |
|  | P5 | AGGAGTTTTAGCGCGGTTTGGAGA |  | 418 |
| 204 | F204 | GGGTTTGTGCGTTC | 121 | 435 |
|  | R5 | ACGCGAAACCAAAT |  | 436 |
|  | P5 | AGGAGTTTTAGCGCGGTTTGGAGA |  | 418 |
| 205 | F205 | GGTTTGTGCGTTCG | 120 | 437 |
|  | R5 | ACGCGAAACCAAAT |  | 438 |
|  | P5 | AGGAGTTTTAGCGCGGTTTGGAGA |  | 418 |
| 206 | F206 | GTTTGTGCGTTCGT | 119 | 439 |
|  | R5 | ACGCGAAACCAAAT |  | 440 |
|  | P5 | AGGAGTTTTAGCGCGGTTTGGAGA |  | 418 |
| 207 | F207 | TTTGTGCGTTCGTA | 118 | 441 |
|  | R5 | ACGCGAAACCAAAT |  | 442 |
|  | P5 | AGGAGTTTTAGCGCGGTTTGGAGA |  | 418 |
| 208 | F208 | TTGTGCGTTCGTAG | 117 | 443 |
|  | R5 | ACGCGAAACCAAAT |  | 444 |
|  | P5 | AGGAGTTTTAGCGCGGTTTGGAGA |  | 418 |
| 209 | F209 | TGTGCGTTCGTAGA | 116 | 445 |
|  | R5 | ACGCGAAACCAAAT |  | 446 |
|  | P5 | AGGAGTTTTAGCGCGGTTTGGAGA |  | 418 |
| 210 | F210 | GTGCGTTCGTAGAG | 115 | 447 |
|  | R5 | ACGCGAAACCAAAT |  | 448 |
|  | P5 | AGGAGTTTTAGCGCGGTTTGGAGA |  | 418 |
| 211 | F211 | TGCGTTCGTAGAGT | 114 | 449 |
|  | R5 | ACGCGAAACCAAAT |  | 450 |
|  | P5 | AGGAGTTTTAGCGCGGTTTGGAGA |  | 418 |
| 212 | F212 | GCGTTCGTAGAGTC | 113 | 451 |
|  | R5 | ACGCGAAACCAAAT |  | 452 |
|  | P5 | AGGAGTTTTAGCGCGGTTTGGAGA |  | 418 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 213 | F213 | CGTTCGTAGAGTCG | 112 | 453 |
|  | R5 | ACGCGAAACCAAAT |  | 454 |
|  | P5 | AGGAGTTTTAGCGCGGTTTGGAGA |  | 418 |
| 214 | F214 | GTTCGTAGAGTCGT | 111 | 455 |
|  | R5 | ACGCGAAACCAAAT |  | 456 |
|  | P5 | AGGAGTTTTAGCGCGGTTTGGAGA |  | 418 |
| 215 | F215 | TTCGTAGAGTCGTT | 110 | 457 |
|  | R5 | ACGCGAAACCAAAT |  | 458 |
|  | P5 | AGGAGTTTTAGCGCGGTTTGGAGA |  | 418 |
| 216 | F216 | TCGTAGAGTCGTTA | 109 | 459 |
|  | R5 | ACGCGAAACCAAAT |  | 460 |
|  | P5 | AGGAGTTTTAGCGCGGTTTGGAGA |  | 418 |
| 217 | F217 | CGTAGAGTCGTTAG | 108 | 461 |
|  | R5 | ACGCGAAACCAAAT |  | 462 |
|  | P5 | AGGAGTTTTAGCGCGGTTTGGAGA |  | 418 |
| 218 | F218 | GTAGAGTCGTTAGG | 107 | 463 |
|  | R5 | ACGCGAAACCAAAT |  | 464 |
|  | P5 | AGGAGTTTTAGCGCGGTTTGGAGA |  | 418 |
| 219 | F219 | TAGAGTCGTTAGGC | 106 | 465 |
|  | R5 | ACGCGAAACCAAAT |  | 466 |
|  | P5 | AGGAGTTTTAGCGCGGTTTGGAGA |  | 418 |
| 220 | F220 | AGAGTCGTTAGGCG | 105 | 467 |
|  | R5 | ACGCGAAACCAAAT |  | 468 |
|  | P5 | AGGAGTTTTAGCGCGGTTTGGAGA |  | 418 |
| 221 | F221 | GAGTCGTTAGGCGT | 104 | 469 |
|  | R5 | ACGCGAAACCAAAT |  | 470 |
|  | P5 | AGGAGTTTTAGCGCGGTTTGGAGA |  | 418 |
| 222 | F222 | AGTCGTTAGGCGTT | 103 | 471 |
|  | R5 | ACGCGAAACCAAAT |  | 472 |
|  | P5 | AGGAGTTTTAGCGCGGTTTGGAGA |  | 418 |
| 223 | F223 | GTCGTTAGGCGTTT | 102 | 473 |
|  | R5 | ACGCGAAACCAAAT |  | 474 |
|  | P5 | AGGAGTTTTAGCGCGGTTTGGAGA |  | 418 |
| 224 | F224 | TCGTTAGGCGTTTT | 101 | 475 |
|  | R5 | ACGCGAAACCAAAT |  | 476 |
|  | P5 | AGGAGTTTTAGCGCGGTTTGGAGA |  | 418 |
| 225 | F225 | CGTTAGGCGTTTTG | 100 | 477 |
|  | R5 | ACGCGAAACCAAAT |  | 478 |
|  | P5 | AGGAGTTTTAGCGCGGTTTGGAGA |  | 418 |
| 226 | F226 | GTTAGGCGTTTTGC | 99 | 479 |
|  | R5 | ACGCGAAACCAAAT |  | 480 |
|  | P5 | AGGAGTTTTAGCGCGGTTTGGAGA |  | 418 |
| 227 | F227 | TTAGGCGTTTTGCG | 98 | 481 |
|  | R5 | ACGCGAAACCAAAT |  | 482 |
|  | P5 | AGGAGTTTTAGCGCGGTTTGGAGA |  | 418 |
| 228 | F228 | TAGGCGTTTTGCGA | 97 | 483 |
|  | R5 | ACGCGAAACCAAAT |  | 484 |
|  | P5 | AGGAGTTTTAGCGCGGTTTGGAGA |  | 418 |
| 229 | F229 | AGGCGTTTTGCGAG | 96 | 485 |
|  | R5 | ACGCGAAACCAAAT |  | 486 |
|  | P5 | AGGAGTTTTAGCGCGGTTTGGAGA |  | 418 |
| 230 | F230 | GGCGTTTTGCGAGT | 95 | 487 |
|  | R5 | ACGCGAAACCAAAT |  | 488 |
|  | P5 | AGGAGTTTTAGCGCGGTTTGGAGA |  | 418 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 231 | F231 | GCGTTTTGCGAGTT | 94 | 489 |
|  | R5 | ACGCGAAACCAAAT |  | 490 |
|  | P5 | AGGAGTTTTAGCGCGGTTTGGAGA |  | 418 |
| 232 | F232 | CGTTTTGCGAGTTG | 93 | 491 |
|  | R5 | ACGCGAAACCAAAT |  | 492 |
|  | P5 | AGGAGTTTTAGCGCGGTTTGGAGA |  | 418 |
| 233 | F233 | GTTTTGCGAGTTGT | 92 | 493 |
|  | R5 | ACGCGAAACCAAAT |  | 494 |
|  | P5 | AGGAGTTTTAGCGCGGTTTGGAGA |  | 418 |
| 234 | F234 | TTTTGCGAGTTGTT | 91 | 495 |
|  | R5 | ACGCGAAACCAAAT |  | 496 |
|  | P5 | AGGAGTTTTAGCGCGGTTTGGAGA |  | 418 |
| 235 | F235 | TTTGCGAGTTGTTT | 90 | 497 |
|  | R5 | ACGCGAAACCAAAT |  | 498 |
|  | P5 | AGGAGTTTTAGCGCGGTTTGGAGA |  | 418 |
| 236 | F236 | TTGCGAGTTGTTTT | 89 | 499 |
|  | R5 | ACGCGAAACCAAAT |  | 500 |
|  | P5 | AGGAGTTTTAGCGCGGTTTGGAGA |  | 418 |
| 237 | F237 | TGCGAGTTGTTTTC | 88 | 501 |
|  | R5 | ACGCGAAACCAAAT |  | 502 |
|  | P5 | AGGAGTTTTAGCGCGGTTTGGAGA |  | 418 |
| 238 | F238 | GCGAGTTGTTTTCG | 87 | 503 |
|  | R5 | ACGCGAAACCAAAT |  | 504 |
|  | P5 | AGGAGTTTTAGCGCGGTTTGGAGA |  | 418 |
| 239 | F239 | CGAGTTGTTTTCGT | 86 | 505 |
|  | R5 | ACGCGAAACCAAAT |  | 506 |
|  | P5 | AGGAGTTTTAGCGCGGTTTGGAGA |  | 418 |
| 240 | F240 | GAGTTGTTTTCGTT | 85 | 507 |
|  | R5 | ACGCGAAACCAAAT |  | 508 |
|  | P5 | AGGAGTTTTAGCGCGGTTTGGAGA |  | 418 |
| 241 | F241 | AGTTGTTTTCGTTG | 84 | 509 |
|  | R5 | ACGCGAAACCAAAT |  | 510 |
|  | P5 | AGGAGTTTTAGCGCGGTTTGGAGA |  | 418 |
| 242 | F242 | GTTGTTTTCGTTGG | 83 | 511 |
|  | R5 | ACGCGAAACCAAAT |  | 512 |
|  | P5 | AGGAGTTTTAGCGCGGTTTGGAGA |  | 418 |
| 243 | F243 | TTGTTTTCGTTGGG | 82 | 513 |
|  | R5 | ACGCGAAACCAAAT |  | 514 |
|  | P5 | AGGAGTTTTAGCGCGGTTTGGAGA |  | 418 |
| 244 | F244 | TGTTTTCGTTGGGA | 81 | 515 |
|  | R5 | ACGCGAAACCAAAT |  | 516 |
|  | P5 | AGGAGTTTTAGCGCGGTTTGGAGA |  | 418 |
| 245 | F245 | GTTTTCGTTGGGAG | 80 | 517 |
|  | R5 | ACGCGAAACCAAAT |  | 518 |
|  | P5 | AGGAGTTTTAGCGCGGTTTGGAGA |  | 418 |
| 246 | F246 | TTTTCGTTGGGAGG | 130 | 519 |
|  | R6 | CGAAATCCTACTTC |  | 520 |
|  | P6 | CGTTTTTTTTTGGGGATTGTAGA |  | 521 |
| 247 | F247 | TTTCGTTGGGAGGG | 129 | 522 |
|  | R6 | CGAAATCCTACTTC |  | 523 |
|  | P6 | CGTTTTTTTTTGGGGATTGTAGA |  | 521 |
| 248 | F248 | TTCGTTGGGAGGGG | 128 | 524 |
|  | R6 | CGAAATCCTACTTC |  | 525 |
|  | P6 | CGTTTTTTTTTGGGGATTGTAGA |  | 521 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 249 | F249 | TCGTTGGGAGGGGC | 127 | 526 |
|  | R6 | CGAAATCCTACTTC |  | 527 |
|  | P6 | CGTTTTTTTTTGGGGATTGTAGA |  | 521 |
| 250 | F250 | CGTTGGGAGGGGCG | 126 | 528 |
|  | R6 | CGAAATCCTACTTC |  | 529 |
|  | P6 | CGTTTTTTTTTGGGGATTGTAGA |  | 521 |
| 251 | F251 | GTTGGGAGGGGCGA | 125 | 530 |
|  | R6 | CGAAATCCTACTTC |  | 531 |
|  | P6 | CGTTTTTTTTTGGGGATTGTAGA |  | 521 |
| 252 | F252 | TTGGGAGGGGCGAG | 124 | 532 |
|  | R6 | CGAAATCCTACTTC |  | 533 |
|  | P6 | CGTTTTTTTTTGGGGATTGTAGA |  | 521 |
| 253 | F253 | TGGGAGGGGCGAGG | 123 | 534 |
|  | R6 | CGAAATCCTACTTC |  | 535 |
|  | P6 | CGTTTTTTTTTGGGGATTGTAGA |  | 521 |
| 254 | F254 | GGGAGGGGCGAGGT | 122 | 536 |
|  | R6 | CGAAATCCTACTTC |  | 537 |
|  | P6 | CGTTTTTTTTTGGGGATTGTAGA |  | 521 |
| 255 | F255 | GGAGGGGCGAGGTT | 121 | 538 |
|  | R6 | CGAAATCCTACTTC |  | 539 |
|  | P6 | CGTTTTTTTTTGGGGATTGTAGA |  | 521 |
| 256 | F256 | GAGGGGCGAGGTTG | 120 | 540 |
|  | R6 | CGAAATCCTACTTC |  | 541 |
|  | P6 | CGTTTTTTTTTGGGGATTGTAGA |  | 521 |
| 257 | F257 | AGGGGCGAGGTTGT | 119 | 542 |
|  | R6 | CGAAATCCTACTTC |  | 543 |
|  | P6 | CGTTTTTTTTTGGGGATTGTAGA |  | 521 |
| 258 | F258 | GGGGCGAGGTTGTT | 118 | 544 |
|  | R6 | CGAAATCCTACTTC |  | 545 |
|  | P6 | CGTTTTTTTTTGGGGATTGTAGA |  | 521 |
| 259 | F259 | GGGCGAGGTTGTTA | 117 | 546 |
|  | R6 | CGAAATCCTACTTC |  | 547 |
|  | P6 | CGTTTTTTTTTGGGGATTGTAGA |  | 521 |
| 260 | F260 | GGCGAGGTTGTTAT | 116 | 548 |
|  | R6 | CGAAATCCTACTTC |  | 549 |
|  | P6 | CGTTTTTTTTTGGGGATTGTAGA |  | 521 |
| 261 | F261 | GCGAGGTTGTTATT | 115 | 550 |
|  | R6 | CGAAATCCTACTTC |  | 551 |
|  | P6 | CGTTTTTTTTTGGGGATTGTAGA |  | 521 |
| 262 | F262 | CGAGGTTGTTATTT | 114 | 552 |
|  | R6 | CGAAATCCTACTTC |  | 553 |
|  | P6 | CGTTTTTTTTTGGGGATTGTAGA |  | 521 |
| 263 | F263 | GAGGTTGTTATTTG | 113 | 554 |
|  | R6 | CGAAATCCTACTTC |  | 555 |
|  | P6 | CGTTTTTTTTTGGGGATTGTAGA |  | 521 |
| 264 | F264 | AGGTTGTTATTTGT | 112 | 556 |
|  | R6 | CGAAATCCTACTTC |  | 557 |
|  | P6 | CGTTTTTTTTTGGGGATTGTAGA |  | 521 |
| 265 | F265 | GGTTGTTATTTGTT | 111 | 558 |
|  | R6 | CGAAATCCTACTTC |  | 559 |
|  | P6 | CGTTTTTTTTTGGGGATTGTAGA |  | 521 |
| 266 | F266 | GTTGTTATTTGTTA | 110 | 560 |
|  | R6 | CGAAATCCTACTTC |  | 561 |
|  | P6 | CGTTTTTTTTTGGGGATTGTAGA |  | 521 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 267 | F267 | TTGTTATTTGTTAG | 109 | 562 |
|  | R6 | CGAAATCCTACTTC |  | 563 |
|  | P6 | CGTTTTTTTTTGGGGATTGTAGA |  | 521 |
| 268 | F268 | TGTTATTTGTTAGG | 108 | 564 |
|  | R6 | CGAAATCCTACTTC |  | 565 |
|  | P6 | CGTTTTTTTTTGGGGATTGTAGA |  | 521 |
| 269 | F269 | GTTATTTGTTAGGG | 107 | 566 |
|  | R6 | CGAAATCCTACTTC |  | 567 |
|  | P6 | CGTTTTTTTTTGGGGATTGTAGA |  | 521 |
| 270 | F270 | TTATTTGTTAGGGC | 106 | 568 |
|  | R6 | CGAAATCCTACTTC |  | 569 |
|  | P6 | CGTTTTTTTTTGGGGATTGTAGA |  | 521 |
| 271 | F271 | TATTTGTTAGGGCG | 105 | 570 |
|  | R6 | CGAAATCCTACTTC |  | 571 |
|  | P6 | CGTTTTTTTTTGGGGATTGTAGA |  | 521 |
| 272 | F272 | ATTTGTTAGGGCGC | 104 | 572 |
|  | R6 | CGAAATCCTACTTC |  | 573 |
|  | P6 | CGTTTTTTTTTGGGGATTGTAGA |  | 521 |
| 273 | F273 | TTTGTTAGGGCGCG | 103 | 574 |
|  | R6 | CGAAATCCTACTTC |  | 575 |
|  | P6 | CGTTTTTTTTTGGGGATTGTAGA |  | 521 |
| 274 | F274 | TTGTTAGGGCGCGA | 102 | 576 |
|  | R6 | CGAAATCCTACTTC |  | 577 |
|  | P6 | CGTTTTTTTTTGGGGATTGTAGA |  | 521 |
| 275 | F275 | TGTTAGGGCGCGAG | 101 | 578 |
|  | R6 | CGAAATCCTACTTC |  | 579 |
|  | P6 | CGTTTTTTTTTGGGGATTGTAGA |  | 521 |
| 276 | F276 | GTTAGGGCGCGAGG | 100 | 580 |
|  | R6 | CGAAATCCTACTTC |  | 581 |
|  | P6 | CGTTTTTTTTTGGGGATTGTAGA |  | 521 |
| 277 | F277 | TTAGGGCGCGAGGA | 99 | 582 |
|  | R6 | CGAAATCCTACTTC |  | 583 |
|  | P6 | CGTTTTTTTTTGGGGATTGTAGA |  | 521 |
| 278 | F278 | TAGGGCGCGAGGAG | 98 | 584 |
|  | R6 | CGAAATCCTACTTC |  | 585 |
|  | P6 | CGTTTTTTTTTGGGGATTGTAGA |  | 521 |
| 279 | F279 | AGGGCGCGAGGAGT | 97 | 586 |
|  | R6 | CGAAATCCTACTTC |  | 587 |
|  | P6 | CGTTTTTTTTTGGGGATTGTAGA |  | 521 |
| 280 | F280 | GGGCGCGAGGAGTT | 96 | 588 |
|  | R6 | CGAAATCCTACTTC |  | 589 |
|  | P6 | CGTTTTTTTTTGGGGATTGTAGA |  | 521 |
| 281 | F281 | GGCGCGAGGAGTTT | 95 | 590 |
|  | R6 | CGAAATCCTACTTC |  | 591 |
|  | P6 | CGTTTTTTTTTGGGGATTGTAGA |  | 521 |
| 282 | F282 | GCGCGAGGAGTTTT | 94 | 592 |
|  | R6 | CGAAATCCTACTTC |  | 593 |
|  | P6 | CGTTTTTTTTTGGGGATTGTAGA |  | 521 |
| 283 | F283 | CGCGAGGAGTTTTA | 93 | 594 |
|  | R6 | CGAAATCCTACTTC |  | 595 |
|  | P6 | CGTTTTTTTTTGGGGATTGTAGA |  | 521 |
| 284 | F284 | GCGAGGAGTTTTAG | 92 | 596 |
|  | R6 | CGAAATCCTACTTC |  | 597 |
|  | P6 | CGTTTTTTTTTGGGGATTGTAGA |  | 521 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 285 | F285 | CGAGGAGTTTTAGC | 91 | 598 |
|  | R6 | CGAAATCCTACTTC |  | 599 |
|  | P6 | CGTTTTTTTTTGGGGATTGTAGA |  | 521 |
| 286 | F286 | GAGGAGTTTTAGCG | 90 | 600 |
|  | R6 | CGAAATCCTACTTC |  | 601 |
|  | P6 | CGTTTTTTTTTGGGGATTGTAGA |  | 521 |
| 287 | F287 | AGGAGTTTTAGCGC | 89 | 602 |
|  | R6 | CGAAATCCTACTTC |  | 603 |
|  | P6 | CGTTTTTTTTTGGGGATTGTAGA |  | 521 |
| 288 | F288 | GGAGTTTTAGCGCG | 88 | 604 |
|  | R6 | CGAAATCCTACTTC |  | 605 |
|  | P6 | CGTTTTTTTTTGGGGATTGTAGA |  | 521 |
| 289 | F289 | GAGTTTTAGCGCGG | 87 | 606 |
|  | R6 | CGAAATCCTACTTC |  | 607 |
|  | P6 | CGTTTTTTTTTGGGGATTGTAGA |  | 521 |
| 290 | F290 | AGTTTTAGCGCGGT | 86 | 608 |
|  | R6 | CGAAATCCTACTTC |  | 609 |
|  | P6 | CGTTTTTTTTTGGGGATTGTAGA |  | 521 |
| 291 | F291 | GTTTTAGCGCGGTT | 85 | 610 |
|  | R6 | CGAAATCCTACTTC |  | 611 |
|  | P6 | CGTTTTTTTTTGGGGATTGTAGA |  | 521 |
| 292 | F292 | TTTTAGCGCGGTTT | 84 | 612 |
|  | R6 | CGAAATCCTACTTC |  | 613 |
|  | P6 | CGTTTTTTTTTGGGGATTGTAGA |  | 521 |
| 293 | F293 | TTTAGCGCGGTTTG | 83 | 614 |
|  | R6 | CGAAATCCTACTTC |  | 615 |
|  | P6 | CGTTTTTTTTTGGGGATTGTAGA |  | 521 |
| 294 | F294 | TTAGCGCGGTTTGG | 82 | 616 |
|  | R6 | CGAAATCCTACTTC |  | 617 |
|  | P6 | CGTTTTTTTTTGGGGATTGTAGA |  | 521 |
| 295 | F295 | TAGCGCGGTTTGGA | 81 | 618 |
|  | R6 | CGAAATCCTACTTC |  | 619 |
|  | P6 | CGTTTTTTTTTGGGGATTGTAGA |  | 521 |
| 296 | F296 | AGCGCGGTTTGGAG | 80 | 620 |
|  | R6 | CGAAATCCTACTTC |  | 621 |
|  | P6 | CGTTTTTTTTTGGGGATTGTAGA |  | 521 |
| 297 | F297 | GCGCGGTTTGGAGA | 130 | 622 |
|  | R7 | CCGAACCTTTAAAC |  | 623 |
|  | P7 | GTGCGCGGGCGGGCGCGTATATTTC |  | 624 |
| 298 | F298 | CGCGGTTTGGAGAA | 129 | 625 |
|  | R7 | CCGAACCTTTAAAC |  | 626 |
|  | P7 | GTGCGCGGGCGGGCGCGTATATTTC |  | 624 |
| 299 | F299 | GCGGTTTGGAGAAT | 128 | 627 |
|  | R7 | CCGAACCTTTAAAC |  | 628 |
|  | P7 | GTGCGCGGGCGGGCGCGTATATTTC |  | 624 |
| 300 | F300 | CGGTTTGGAGAATT | 127 | 629 |
|  | R7 | CCGAACCTTTAAAC |  | 630 |
|  | P7 | GTGCGCGGGCGGGCGCGTATATTTC |  | 624 |
| 301 | F301 | GGTTTGGAGAATTT | 126 | 631 |
|  | R7 | CCGAACCTTTAAAC |  | 632 |
|  | P7 | GTGCGCGGGCGGGCGCGTATATTTC |  | 624 |
| 302 | F302 | GTTTGGAGAATTTG | 125 | 633 |
|  | R7 | CCGAACCTTTAAAC |  | 634 |
|  | 7 | GTGCGCGGGCGGGCGCGTATATTTC |  | 624 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 303 | F303 | TTTGGAGAATTTGG | 124 | 635 |
|  | R7 | CCGAACCTTTAAAC |  | 636 |
|  | P7 | GTGCGCGGGCGGGCGCGTATATTTC |  | 624 |
| 304 | F304 | TTGGAGAATTTGGT | 123 | 637 |
|  | R7 | CCGAACCTTTAAAC |  | 638 |
|  | P7 | GTGCGCGGGCGGGCGCGTATATTTC |  | 624 |
| 305 | F305 | TGGAGAATTTGGTT | 122 | 639 |
|  | R7 | CCGAACCTTTAAAC |  | 640 |
|  | P7 | GTGCGCGGGCGGGCGCGTATATTTC |  | 624 |
| 306 | F306 | GGAGAATTTGGTTT | 121 | 641 |
|  | R7 | CCGAACCTTTAAAC |  | 642 |
|  | P7 | GTGCGCGGGCGGGCGCGTATATTTC |  | 624 |
| 307 | F307 | GAGAATTTGGTTTC | 120 | 643 |
|  | R7 | CCGAACCTTTAAAC |  | 644 |
|  | P7 | GTGCGCGGGCGGGCGCGTATATTTC |  | 624 |
| 308 | F308 | AGAATTTGGTTTCG | 119 | 645 |
|  | R7 | CCGAACCTTTAAAC |  | 646 |
|  | P7 | GTGCGCGGGCGGGCGCGTATATTTC |  | 624 |
| 309 | F309 | GAATTTGGTTTCGC | 118 | 647 |
|  | R7 | CCGAACCTTTAAAC |  | 648 |
|  | P7 | GTGCGCGGGCGGGCGCGTATATTTC |  | 624 |
| 310 | F310 | AATTTGGTTTCGCG | 117 | 649 |
|  | R7 | CCGAACCTTTAAAC |  | 650 |
|  | P7 | GTGCGCGGGCGGGCGCGTATATTTC |  | 624 |
| 311 | F311 | ATTTGGTTTCGCGT | 116 | 651 |
|  | R7 | CCGAACCTTTAAAC |  | 652 |
|  | P7 | GTGCGCGGGCGGGCGCGTATATTTC |  | 624 |
| 312 | F312 | TTTGGTTTCGCGTA | 115 | 653 |
|  | R7 | CCGAACCTTTAAAC |  | 654 |
|  | P7 | GTGCGCGGGCGGGCGCGTATATTTC |  | 624 |
| 313 | F313 | TTGGTTTCGCGTAG | 114 | 655 |
|  | R7 | CCGAACCTTTAAAC |  | 656 |
|  | P7 | GTGCGCGGGCGGGCGCGTATATTTC |  | 624 |
| 314 | F314 | TGGTTTCGCGTAGC | 113 | 657 |
|  | R7 | CCGAACCTTTAAAC |  | 658 |
|  | P7 | GTGCGCGGGCGGGCGCGTATATTTC |  | 624 |
| 315 | F315 | GGTTTCGCGTAGCG | 112 | 659 |
|  | R7 | CCGAACCTTTAAAC |  | 660 |
|  | P7 | GTGCGCGGGCGGGCGCGTATATTTC |  | 624 |
| 316 | F316 | GTTTCGCGTAGCGT | 111 | 661 |
|  | R7 | CCGAACCTTTAAAC |  | 662 |
|  | P7 | GTGCGCGGGCGGGCGCGTATATTTC |  | 624 |
| 317 | F317 | TTTCGCGTAGCGTT | 110 | 663 |
|  | R7 | CCGAACCTTTAAAC |  | 664 |
|  | P7 | GTGCGCGGGCGGGCGCGTATATTTC |  | 624 |
| 318 | F318 | TTCGCGTAGCGTTT | 109 | 665 |
|  | R7 | CCGAACCTTTAAAC |  | 666 |
|  | P7 | GTGCGCGGGCGGGCGCGTATATTTC |  | 624 |
| 319 | F319 | TCGCGTAGCGTTTG | 108 | 667 |
|  | R7 | CCGAACCTTTAAAC |  | 668 |
|  | P7 | GTGCGCGGGCGGGCGCGTATATTTC |  | 624 |
| 320 | F320 | CGCGTAGCGTTTGG | 107 | 669 |
|  | R7 | CCGAACCTTTAAAC |  | 670 |
|  | P7 | GTGCGCGGGCGGGCGCGTATATTTC |  | 624 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 321 | F321 | GCGTAGCGTTTGGT | 106 | 671 |
| | R7 | CCGAACCTTTAAAC | | 672 |
| | P7 | GTGCGCGGGCGGGCGCGTATATTTC | | 624 |
| 322 | F322 | CGTAGCGTTTGGTT | 105 | 673 |
| | R7 | CCGAACCTTTAAAC | | 674 |
| | P7 | GTGCGCGGGCGGGCGCGTATATTTC | | 624 |
| 323 | F323 | GTAGCGTTTGGTTA | 104 | 675 |
| | R7 | CCGAACCTTTAAAC | | 676 |
| | P7 | GTGCGCGGGCGGGCGCGTATATTTC | | 624 |
| 324 | F324 | TAGCGTTTGGTTAT | 103 | 677 |
| | R7 | CCGAACCTTTAAAC | | 678 |
| | P7 | GTGCGCGGGCGGGCGCGTATATTTC | | 624 |
| 325 | F325 | AGCGTTTGGTTATT | 102 | 679 |
| | R7 | CCGAACCTTTAAAC | | 680 |
| | P7 | GTGCGCGGGCGGGCGCGTATATTTC | | 624 |
| 326 | F326 | GCGTTTGGTTATTC | 101 | 681 |
| | R7 | CCGAACCTTTAAAC | | 682 |
| | P7 | GTGCGCGGGCGGGCGCGTATATTTC | | 624 |
| 327 | F327 | CGTTTGGTTATTCG | 100 | 683 |
| | R7 | CCGAACCTTTAAAC | | 684 |
| | P7 | GTGCGCGGGCGGGCGCGTATATTTC | | 624 |
| 328 | F328 | GTTTGGTTATTCGT | 99 | 685 |
| | R7 | CCGAACCTTTAAAC | | 686 |
| | P7 | GTGCGCGGGCGGGCGCGTATATTTC | | 624 |
| 329 | F329 | TTTGGTTATTCGTT | 98 | 687 |
| | R7 | CCGAACCTTTAAAC | | 688 |
| | P7 | GTGCGCGGGCGGGCGCGTATATTTC | | 624 |
| 330 | F330 | TTGGTTATTCGTTT | 97 | 689 |
| | R7 | CCGAACCTTTAAAC | | 690 |
| | P7 | GTGCGCGGGCGGGCGCGTATATTTC | | 624 |
| 331 | F331 | TGGTTATTCGTTTT | 96 | 691 |
| | R7 | CCGAACCTTTAAAC | | 692 |
| | P7 | GTGCGCGGGCGGGCGCGTATATTTC | | 624 |
| 332 | F332 | GGTTATTCGTTTTT | 95 | 693 |
| | R7 | CCGAACCTTTAAAC | | 694 |
| | P7 | GTGCGCGGGCGGGCGCGTATATTTC | | 624 |
| 333 | F333 | GTTATTCGTTTTTT | 94 | 695 |
| | R7 | CCGAACCTTTAAAC | | 696 |
| | P7 | GTGCGCGGGCGGGCGCGTATATTTC | | 624 |
| 334 | F334 | TTATTCGTTTTTTT | 93 | 697 |
| | R7 | CCGAACCTTTAAAC | | 698 |
| | P7 | GTGCGCGGGCGGGCGCGTATATTTC | | 624 |
| 335 | F335 | TATTCGTTTTTTTT | 92 | 699 |
| | R7 | CCGAACCTTTAAAC | | 700 |
| | P7 | GTGCGCGGGCGGGCGCGTATATTTC | | 624 |
| 336 | F336 | ATTCGTTTTTTTTT | 91 | 701 |
| | R7 | CCGAACCTTTAAAC | | 702 |
| | P7 | GTGCGCGGGCGGGCGCGTATATTTC | | 624 |
| 337 | F337 | TTCGTTTTTTTTTG | 90 | 703 |
| | R7 | CCGAACCTTTAAAC | | 704 |
| | P7 | GTGCGCGGGCGGGCGCGTATATTTC | | 624 |
| 338 | F338 | TCGTTTTTTTTTGG | 89 | 705 |
| | R7 | CCGAACCTTTAAAC | | 706 |
| | P7 | GTGCGCGGGCGGGCGCGTATATTTC | | 624 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 339 | F339 | CGTTTTTTTTGGG | 88 | 707 |
|  | R7 | CCGAACCTTTAAAC |  | 708 |
|  | P7 | GTGCGCGGGCGGGCGCGTATATTTC |  | 624 |
| 340 | F340 | GTTTTTTTTGGGG | 87 | 709 |
|  | R7 | CCGAACCTTTAAAC |  | 710 |
|  | P7 | GTGCGCGGGCGGGCGCGTATATTTC |  | 624 |
| 341 | F341 | TTTTTTTTGGGGA | 86 | 711 |
|  | R7 | CCGAACCTTTAAAC |  | 712 |
|  | P7 | GTGCGCGGGCGGGCGCGTATATTTC |  | 624 |
| 342 | F342 | TTTTTTTGGGGAT | 85 | 713 |
|  | R7 | CCGAACCTTTAAAC |  | 714 |
|  | P7 | GTGCGCGGGCGGGCGCGTATATTTC |  | 624 |
| 343 | F343 | TTTTTTGGGGATT | 84 | 715 |
|  | R7 | CCGAACCTTTAAAC |  | 716 |
|  | P7 | GTGCGCGGGCGGGCGCGTATATTTC |  | 624 |
| 344 | F344 | TTTTTGGGGATTG | 83 | 717 |
|  | R7 | CCGAACCTTTAAAC |  | 718 |
|  | P7 | GTGCGCGGGCGGGCGCGTATATTTC |  | 624 |
| 345 | F345 | TTTTGGGGATTGT | 82 | 719 |
|  | R7 | CCGAACCTTTAAAC |  | 720 |
|  | P7 | GTGCGCGGGCGGGCGCGTATATTTC |  | 624 |
| 346 | F346 | TTTTGGGGATTGTA | 81 | 721 |
|  | R7 | CCGAACCTTTAAAC |  | 722 |
|  | P7 | GTGCGCGGGCGGGCGCGTATATTTC |  | 624 |
| 347 | F347 | TTTGGGGATTGTAG | 80 | 723 |
|  | R7 | CCGAACCTTTAAAC |  | 724 |
|  | P7 | GTGCGCGGGCGGGCGCGTATATTTC |  | 624 |
| 348 | F348 | TTGGGGATTGTAGA | 130 | 725 |
|  | R8 | ATCTAAAACCGAAA |  | 726 |
|  | P8 | ATTATAGAAAGAAAATGAATGTT |  | 727 |
| 349 | F349 | TGGGGATTGTAGAG | 129 | 728 |
|  | R8 | ATCTAAAACCGAAA |  | 729 |
|  | P8 | ATTATAGAAAGAAAATGAATGTT |  | 727 |
| 350 | F350 | GGGGATTGTAGAGA | 128 | 730 |
|  | R8 | ATCTAAAACCGAAA |  | 731 |
|  | P8 | ATTATAGAAAGAAAATGAATGTT |  | 727 |
| 351 | F351 | GGGATTGTAGAGAA | 127 | 732 |
|  | R8 | ATCTAAAACCGAAA |  | 733 |
|  | P8 | ATTATAGAAAGAAAATGAATGTT |  | 727 |
| 352 | F352 | GGATTGTAGAGAAG | 126 | 734 |
|  | R8 | ATCTAAAACCGAAA |  | 735 |
|  | P8 | ATTATAGAAAGAAAATGAATGTT |  | 727 |
| 353 | F353 | GATTGTAGAGAAGT | 125 | 736 |
|  | R8 | ATCTAAAACCGAAA |  | 737 |
|  | P8 | ATTATAGAAAGAAAATGAATGTT |  | 727 |
| 354 | F354 | ATTGTAGAGAAGTA | 124 | 738 |
|  | R8 | ATCTAAAACCGAAA |  | 739 |
|  | P8 | ATTATAGAAAGAAAATGAATGTT |  | 727 |
| 355 | F355 | TTGTAGAGAAGTAG | 123 | 740 |
|  | R8 | ATCTAAAACCGAAA |  | 741 |
|  | P8 | ATTATAGAAAGAAAATGAATGTT |  | 727 |
| 356 | F356 | TGTAGAGAAGTAGG | 122 | 742 |
|  | R8 | ATCTAAAACCGAAA |  | 743 |
|  | P8 | ATTATAGAAAGAAAATGAATGTT |  | 727 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 357 | F357 | GTAGAGAAGTAGGA | 121 | 744 |
|  | R8 | ATCTAAAACCGAAA |  | 745 |
|  | P8 | ATTATAGAAAGAAAATGAATGTT |  | 727 |
| 358 | F358 | TAGAGAAGTAGGAT | 120 | 746 |
|  | R8 | ATCTAAAACCGAAA |  | 747 |
|  | P8 | ATTATAGAAAGAAAATGAATGTT |  | 727 |
| 359 | F359 | AGAGAAGTAGGATT | 119 | 748 |
|  | R8 | ATCTAAAACCGAAA |  | 749 |
|  | P8 | ATTATAGAAAGAAAATGAATGTT |  | 727 |
| 360 | F360 | GAGAAGTAGGATTT | 118 | 750 |
|  | R8 | ATCTAAAACCGAAA |  | 751 |
|  | P8 | ATTATAGAAAGAAAATGAATGTT |  | 727 |
| 361 | F361 | AGAAGTAGGATTTC | 117 | 752 |
|  | R8 | ATCTAAAACCGAAA |  | 753 |
|  | P8 | ATTATAGAAAGAAAATGAATGTT |  | 727 |
| 362 | F362 | GAAGTAGGATTTCG | 116 | 754 |
|  | R8 | ATCTAAAACCGAAA |  | 755 |
|  | P8 | ATTATAGAAAGAAAATGAATGTT |  | 727 |
| 363 | F363 | AAGTAGGATTTCGG | 115 | 756 |
|  | R8 | ATCTAAAACCGAAA |  | 757 |
|  | P8 | ATTATAGAAAGAAAATGAATGTT |  | 727 |
| 364 | F364 | AGTAGGATTTCGGG | 114 | 758 |
|  | R8 | ATCTAAAACCGAAA |  | 759 |
|  | P8 | ATTATAGAAAGAAAATGAATGTT |  | 727 |
| 365 | F365 | GTAGGATTTCGGGT | 113 | 760 |
|  | R8 | ATCTAAAACCGAAA |  | 761 |
|  | P8 | ATTATAGAAAGAAAATGAATGTT |  | 727 |
| 366 | F366 | TAGGATTTCGGGTT | 112 | 762 |
|  | R8 | ATCTAAAACCGAAA |  | 763 |
|  | P8 | ATTATAGAAAGAAAATGAATGTT |  | 727 |
| 367 | F367 | AGGATTTCGGGTTA | 111 | 764 |
|  | R8 | ATCTAAAACCGAAA |  | 765 |
|  | P8 | ATTATAGAAAGAAAATGAATGTT |  | 727 |
| 368 | F368 | GGATTTCGGGTTAT | 110 | 766 |
|  | R8 | ATCTAAAACCGAAA |  | 767 |
|  | P8 | ATTATAGAAAGAAAATGAATGTT |  | 727 |
| 369 | F369 | GATTTCGGGTTATG | 109 | 768 |
|  | R8 | ATCTAAAACCGAAA |  | 769 |
|  | P8 | ATTATAGAAAGAAAATGAATGTT |  | 727 |
| 370 | F370 | ATTTCGGGTTATGG | 108 | 770 |
|  | R8 | ATCTAAAACCGAAA |  | 771 |
|  | P8 | ATTATAGAAAGAAAATGAATGTT |  | 727 |
| 371 | F371 | TTTCGGGTTATGGG | 107 | 772 |
|  | R8 | ATCTAAAACCGAAA |  | 773 |
|  | P8 | ATTATAGAAAGAAAATGAATGTT |  | 727 |
| 372 | F372 | TTCGGGTTATGGGT | 106 | 774 |
|  | R8 | ATCTAAAACCGAAA |  | 775 |
|  | P8 | ATTATAGAAAGAAAATGAATGTT |  | 727 |
| 373 | F373 | TCGGGTTATGGGTG | 105 | 776 |
|  | R8 | ATCTAAAACCGAAA |  | 777 |
|  | P8 | ATTATAGAAAGAAAATGAATGTT |  | 727 |
| 374 | F374 | CGGGTTATGGGTGA | 104 | 778 |
|  | R8 | ATCTAAAACCGAAA |  | 779 |
|  | P8 | ATTATAGAAAGAAAATGAATGTT |  | 727 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 375 | F375 | GGGTTATGGGTGAG | 103 | 780 |
|  | R8 | ATCTAAAACCGAAA |  | 781 |
|  | P8 | ATTATAGAAAGAAAATGAATGTT |  | 727 |
| 376 | F376 | GGTTATGGGTGAGT | 102 | 782 |
|  | R8 | ATCTAAAACCGAAA |  | 783 |
|  | P8 | ATTATAGAAAGAAAATGAATGTT |  | 727 |
| 377 | F377 | GTTATGGGTGAGTG | 101 | 784 |
|  | R8 | ATCTAAAACCGAAA |  | 785 |
|  | P8 | ATTATAGAAAGAAAATGAATGTT |  | 727 |
| 378 | F378 | TTATGGGTGAGTGC | 100 | 786 |
|  | R8 | ATCTAAAACCGAAA |  | 787 |
|  | P8 | ATTATAGAAAGAAAATGAATGTT |  | 727 |
| 379 | F379 | TATGGGTGAGTGCG | 99 | 788 |
|  | R8 | ATCTAAAACCGAAA |  | 789 |
|  | P8 | ATTATAGAAAGAAAATGAATGTT |  | 727 |
| 380 | F380 | ATGGGTGAGTGCGC | 98 | 790 |
|  | R8 | ATCTAAAACCGAAA |  | 791 |
|  | P8 | ATTATAGAAAGAAAATGAATGTT |  | 727 |
| 381 | F381 | TGGGTGAGTGCGCG | 97 | 792 |
|  | R8 | ATCTAAAACCGAAA |  | 793 |
|  | P8 | ATTATAGAAAGAAAATGAATGTT |  | 727 |
| 382 | F382 | GGGTGAGTGCGCGG | 96 | 794 |
|  | R8 | ATCTAAAACCGAAA |  | 795 |
|  | P8 | ATTATAGAAAGAAAATGAATGTT |  | 727 |
| 383 | F383 | GGTGAGTGCGCGGG | 95 | 796 |
|  | R8 | ATCTAAAACCGAAA |  | 797 |
|  | P8 | ATTATAGAAAGAAAATGAATGTT |  | 727 |
| 384 | F384 | GTGAGTGCGCGGGC | 94 | 798 |
|  | R8 | ATCTAAAACCGAAA |  | 799 |
|  | P8 | ATTATAGAAAGAAAATGAATGTT |  | 727 |
| 385 | F385 | TGAGTGCGCGGGCG | 93 | 800 |
|  | R8 | ATCTAAAACCGAAA |  | 801 |
|  | P8 | ATTATAGAAAGAAAATGAATGTT |  | 727 |
| 386 | F386 | GAGTGCGCGGGCGG | 92 | 802 |
|  | R8 | ATCTAAAACCGAAA |  | 803 |
|  | P8 | ATTATAGAAAGAAAATGAATGTT |  | 727 |
| 387 | F387 | AGTGCGCGGGCGGG | 91 | 804 |
|  | R8 | ATCTAAAACCGAAA |  | 805 |
|  | P8 | ATTATAGAAAGAAAATGAATGTT |  | 727 |
| 388 | F388 | GTGCGCGGGCGGGC | 90 | 806 |
|  | R8 | ATCTAAAACCGAAA |  | 807 |
|  | P8 | ATTATAGAAAGAAAATGAATGTT |  | 727 |
| 389 | F389 | TGCGCGGGCGGGCG | 89 | 808 |
|  | R8 | ATCTAAAACCGAAA |  | 809 |
|  | P8 | ATTATAGAAAGAAAATGAATGTT |  | 727 |
| 390 | F390 | GCGCGGGCGGGCGC | 88 | 810 |
|  | R8 | ATCTAAAACCGAAA |  | 811 |
|  | P8 | ATTATAGAAAGAAAATGAATGTT |  | 727 |
| 391 | F391 | CGCGGGCGGGCGCG | 87 | 812 |
|  | R8 | ATCTAAAACCGAAA |  | 813 |
|  | P8 | ATTATAGAAAGAAAATGAATGTT |  | 727 |
| 392 | F392 | GCGGGCGGGCGCGT | 86 | 814 |
|  | R8 | ATCTAAAACCGAAA |  | 815 |
|  | P8 | ATTATAGAAAGAAAATGAATGTT |  | 727 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 393 | F393 | CGGGCGGGCGCGTA | 85 | 816 |
|  | R8 | ATCTAAAACCGAAA |  | 817 |
|  | P8 | ATTATAGAAAGAAAATGAATGTT |  | 727 |
| 394 | F394 | GGGCGGGCGCGTAT | 84 | 818 |
|  | R8 | ATCTAAAACCGAAA |  | 819 |
|  | P8 | ATTATAGAAAGAAAATGAATGTT |  | 727 |
| 395 | F395 | GGCGGGCGCGTATA | 83 | 820 |
|  | R8 | ATCTAAAACCGAAA |  | 821 |
|  | P8 | ATTATAGAAAGAAAATGAATGTT |  | 727 |
| 396 | F396 | GCGGGCGCGTATAT | 82 | 822 |
|  | R8 | ATCTAAAACCGAAA |  | 823 |
|  | P8 | ATTATAGAAAGAAAATGAATGTT |  | 727 |
| 397 | F397 | CGGGCGCGTATATT | 81 | 824 |
|  | R8 | ATCTAAAACCGAAA |  | 825 |
|  | P8 | ATTATAGAAAGAAAATGAATGTT |  | 727 |
| 398 | F398 | GGGCGCGTATATTT | 80 | 826 |
|  | R8 | ATCTAAAACCGAAA |  | 827 |
|  | P8 | ATTATAGAAAGAAAATGAATGTT |  | 727 |
| 399 | F399 | GGCGCGTATATTTC | 130 | 828 |
|  | R9 | CGAAAAACGAAAAA |  | 829 |
|  | P9 | GTTTTGTTTTTTTCGCGTTTGGCG |  | 830 |
| 400 | F400 | GCGCGTATATTTCG | 129 | 831 |
|  | R9 | CGAAAAACGAAAAA |  | 832 |
|  | P9 | GTTTTGTTTTTTTCGCGTTTGGCG |  | 830 |
| 401 | F401 | CGCGTATATTTCGT | 128 | 833 |
|  | R9 | CGAAAAACGAAAAA |  | 834 |
|  | P9 | GTTTTGTTTTTTTCGCGTTTGGCG |  | 830 |
| 402 | F402 | GCGTATATTTCGTT | 127 | 835 |
|  | R9 | CGAAAAACGAAAAA |  | 836 |
|  | P9 | GTTTTGTTTTTTTCGCGTTTGGCG |  | 830 |
| 403 | F403 | CGTATATTTCGTTT | 126 | 837 |
|  | R9 | CGAAAAACGAAAAA |  | 838 |
|  | P9 | GTTTTGTTTTTTTCGCGTTTGGCG |  | 830 |
| 404 | F404 | GTATATTTCGTTTA | 125 | 839 |
|  | R9 | CGAAAAACGAAAAA |  | 840 |
|  | P9 | GTTTTGTTTTTTTCGCGTTTGGCG |  | 830 |
| 405 | F405 | TATATTTCGTTTAA | 124 | 841 |
|  | R9 | CGAAAAACGAAAAA |  | 842 |
|  | P9 | GTTTTGTTTTTTTCGCGTTTGGCG |  | 830 |
| 406 | F406 | ATATTTCGTTTAAA | 123 | 843 |
|  | R9 | CGAAAAACGAAAAA |  | 844 |
|  | P9 | GTTTTGTTTTTTTCGCGTTTGGCG |  | 830 |
| 407 | F407 | TATTTCGTTTAAAG | 122 | 845 |
|  | R9 | CGAAAAACGAAAAA |  | 846 |
|  | P9 | GTTTTGTTTTTTTCGCGTTTGGCG |  | 830 |
| 408 | F408 | ATTTCGTTTAAAGG | 121 | 847 |
|  | R9 | CGAAAAACGAAAAA |  | 848 |
|  | P9 | GTTTTGTTTTTTTCGCGTTTGGCG |  | 830 |
| 409 | F409 | TTTCGTTTAAAGGT | 120 | 849 |
|  | R9 | CGAAAAACGAAAAA |  | 850 |
|  | P9 | GTTTTGTTTTTTTCGCGTTTGGCG |  | 830 |
| 410 | F410 | TTCGTTTAAAGGTT | 119 | 851 |
|  | R9 | CGAAAAACGAAAAA |  | 852 |
|  | P9 | GTTTTGTTTTTTTCGCGTTTGGCG |  | 830 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 411 | F411 | TCGTTTAAAGGTTC | 118 | 853 |
|  | R9 | CGAAAAACGAAAAA |  | 854 |
|  | P9 | GTTTTGTTTTTTTCGCGTTTGGCG |  | 830 |
| 412 | F412 | CGTTTAAAGGTTCG | 117 | 855 |
|  | R9 | CGAAAAACGAAAAA |  | 856 |
|  | P9 | GTTTTGTTTTTTTCGCGTTTGGCG |  | 830 |
| 413 | F413 | GTTTAAAGGTTCGG | 116 | 857 |
|  | R9 | CGAAAAACGAAAAA |  | 858 |
|  | P9 | GTTTTGTTTTTTTCGCGTTTGGCG |  | 830 |
| 414 | F414 | TTTAAAGGTTCGGT | 115 | 859 |
|  | R9 | CGAAAAACGAAAAA |  | 860 |
|  | P9 | GTTTTGTTTTTTTCGCGTTTGGCG |  | 830 |
| 415 | F415 | TTAAAGGTTCGGTT | 114 | 861 |
|  | R9 | CGAAAAACGAAAAA |  | 862 |
|  | P9 | GTTTTGTTTTTTTCGCGTTTGGCG |  | 830 |
| 416 | F416 | TAAAGGTTCGGTTT | 113 | 863 |
|  | R9 | CGAAAAACGAAAAA |  | 864 |
|  | P9 | GTTTTGTTTTTTTCGCGTTTGGCG |  | 830 |
| 417 | F417 | AAAGGTTCGGTTTC | 112 | 865 |
|  | R9 | CGAAAAACGAAAAA |  | 866 |
|  | P9 | GTTTTGTTTTTTTCGCGTTTGGCG |  | 830 |
| 418 | F418 | AAGGTTCGGTTTCG | 111 | 867 |
|  | R9 | CGAAAAACGAAAAA |  | 868 |
|  | P9 | GTTTTGTTTTTTTCGCGTTTGGCG |  | 830 |
| 419 | F419 | AGGTTCGGTTTCGG | 110 | 869 |
|  | R9 | CGAAAAACGAAAAA |  | 870 |
|  | P9 | GTTTTGTTTTTTTCGCGTTTGGCG |  | 830 |
| 420 | F420 | GGTTCGGTTTCGGG | 109 | 871 |
|  | R9 | CGAAAAACGAAAAA |  | 872 |
|  | P9 | GTTTTGTTTTTTTCGCGTTTGGCG |  | 830 |
| 421 | F421 | GTTCGGTTTCGGGA | 108 | 873 |
|  | R9 | CGAAAAACGAAAAA |  | 874 |
|  | P9 | GTTTTGTTTTTTTCGCGTTTGGCG |  | 830 |
| 422 | F422 | TTCGGTTTCGGGAA | 107 | 875 |
|  | R9 | CGAAAAACGAAAAA |  | 876 |
|  | P9 | GTTTTGTTTTTTTCGCGTTTGGCG |  | 830 |
| 423 | F423 | TCGGTTTCGGGAAT | 106 | 877 |
|  | R9 | CGAAAAACGAAAAA |  | 878 |
|  | P9 | GTTTTGTTTTTTTCGCGTTTGGCG |  | 830 |
| 424 | F424 | CGGTTTCGGGAATG | 105 | 879 |
|  | R9 | CGAAAAACGAAAAA |  | 880 |
|  | P9 | GTTTTGTTTTTTTCGCGTTTGGCG |  | 830 |
| 425 | F425 | GGTTTCGGGAATGG | 104 | 881 |
|  | R9 | CGAAAAACGAAAAA |  | 882 |
|  | P9 | GTTTTGTTTTTTTCGCGTTTGGCG |  | 830 |
| 426 | F426 | GTTTCGGGAATGGG | 103 | 883 |
|  | R9 | CGAAAAACGAAAAA |  | 884 |
|  | P9 | GTTTTGTTTTTTTCGCGTTTGGCG |  | 830 |
| 427 | F427 | TTTCGGGAATGGGT | 102 | 885 |
|  | R9 | CGAAAAACGAAAAA |  | 886 |
|  | P9 | GTTTTGTTTTTTTCGCGTTTGGCG |  | 830 |
| 428 | F428 | TTCGGGAATGGGTA | 101 | 887 |
|  | R9 | CGAAAAACGAAAAA |  | 888 |
|  | P9 | GTTTTGTTTTTTTCGCGTTTGGCG |  | 830 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 429 | F429 | TCGGGAATGGGTAT | 100 | 889 |
|  | R9 | CGAAAAACGAAAAA |  | 890 |
|  | P9 | GTTTTGTTTTTTTCGCGTTTGGCG |  | 830 |
| 430 | F430 | CGGGAATGGGTATT | 99 | 891 |
|  | R9 | CGAAAAACGAAAAA |  | 892 |
|  | P9 | GTTTTGTTTTTTTCGCGTTTGGCG |  | 830 |
| 431 | F431 | GGGAATGGGTATTA | 98 | 893 |
|  | R9 | CGAAAAACGAAAAA |  | 894 |
|  | P9 | GTTTTGTTTTTTTCGCGTTTGGCG |  | 830 |
| 432 | F432 | GGAATGGGTATTAT | 97 | 895 |
|  | R9 | CGAAAAACGAAAAA |  | 896 |
|  | P9 | GTTTTGTTTTTTTCGCGTTTGGCG |  | 830 |
| 433 | F433 | GAATGGGTATTATA | 96 | 897 |
|  | R9 | CGAAAAACGAAAAA |  | 898 |
|  | P9 | GTTTTGTTTTTTTCGCGTTTGGCG |  | 830 |
| 434 | F434 | AATGGGTATTATAG | 95 | 899 |
|  | R9 | CGAAAAACGAAAAA |  | 900 |
|  | P9 | GTTTTGTTTTTTTCGCGTTTGGCG |  | 830 |
| 435 | F435 | ATGGGTATTATAGA | 94 | 901 |
|  | R9 | CGAAAAACGAAAAA |  | 902 |
|  | P9 | GTTTTGTTTTTTTCGCGTTTGGCG |  | 830 |
| 436 | F436 | TGGGTATTATAGAA | 93 | 903 |
|  | R9 | CGAAAAACGAAAAA |  | 904 |
|  | P9 | GTTTTGTTTTTTTCGCGTTTGGCG |  | 830 |
| 437 | F437 | GGGTATTATAGAAA | 92 | 905 |
|  | R9 | CGAAAAACGAAAAA |  | 906 |
|  | P9 | GTTTTGTTTTTTTCGCGTTTGGCG |  | 830 |
| 438 | F438 | GGTATTATAGAAAG | 91 | 907 |
|  | R9 | CGAAAAACGAAAAA |  | 908 |
|  | P9 | GTTTTGTTTTTTTCGCGTTTGGCG |  | 830 |
| 439 | F439 | GTATTATAGAAAGA | 90 | 909 |
|  | R9 | CGAAAAACGAAAAA |  | 910 |
|  | P9 | GTTTTGTTTTTTTCGCGTTTGGCG |  | 830 |
| 440 | F440 | TATTATAGAAAGAA | 89 | 911 |
|  | R9 | CGAAAAACGAAAAA |  | 912 |
|  | P9 | GTTTTGTTTTTTTCGCGTTTGGCG |  | 830 |
| 441 | F441 | ATTATAGAAAGAAA | 88 | 913 |
|  | R9 | CGAAAAACGAAAAA |  | 914 |
|  | P9 | GTTTTGTTTTTTTCGCGTTTGGCG |  | 830 |
| 442 | F442 | TTATAGAAAGAAAA | 87 | 915 |
|  | R9 | CGAAAAACGAAAAA |  | 916 |
|  | P9 | GTTTTGTTTTTTTCGCGTTTGGCG |  | 830 |
| 443 | F443 | TATAGAAAGAAAAT | 86 | 917 |
|  | R9 | CGAAAAACGAAAAA |  | 918 |
|  | P9 | GTTTTGTTTTTTTCGCGTTTGGCG |  | 830 |
| 444 | F444 | ATAGAAAGAAAATG | 85 | 919 |
|  | R9 | CGAAAAACGAAAAA |  | 920 |
|  | 9 | GTTTTGTTTTTTTCGCGTTTGGCG |  | 830 |
| 445 | F445 | TAGAAAGAAAATGA | 84 | 921 |
|  | R9 | CGAAAAACGAAAAA |  | 922 |
|  | P9 | GTTTTGTTTTTTTCGCGTTTGGCG |  | 830 |
| 446 | F446 | AGAAAGAAAATGAA | 83 | 923 |
|  | R9 | CGAAAAACGAAAAA |  | 924 |
|  | P9 | GTTTTGTTTTTTTCGCGTTTGGCG |  | 830 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 447 | F447 | GAAAGAAAATGAAT | 82 | 925 |
|  | R9 | CGAAAAACGAAAAA |  | 926 |
|  | P9 | GTTTTGTTTTTTCGCGTTTGGCG |  | 830 |
| 448 | F448 | AAAGAAAATGAATG | 81 | 927 |
|  | R9 | CGAAAAACGAAAAA |  | 928 |
|  | P9 | GTTTTGTTTTTTCGCGTTTGGCG |  | 830 |
| 449 | F449 | AAGAAAATGAATGT | 80 | 929 |
|  | R9 | CGAAAAACGAAAAA |  | 930 |
|  | P9 | GTTTTGTTTTTTCGCGTTTGGCG |  | 830 |
| 450 | F450 | AGAAAATGAATGTT | 130 | 931 |
|  | R10 | CCCCATCGCCATCG |  | 932 |
|  | P10 | CGGATTTTTTTTTTGGGAGAGAGG |  | 933 |
| 451 | F451 | GAAAATGAATGTTT | 129 | 934 |
|  | R10 | CCCCATCGCCATCG |  | 935 |
|  | P10 | CGGATTTTTTTTTTGGGAGAGAGG |  | 933 |
| 452 | F452 | AAAATGAATGTTTT | 128 | 936 |
|  | R10 | CCCCATCGCCATCG |  | 937 |
|  | P10 | CGGATTTTTTTTTTGGGAGAGAGG |  | 933 |
| 453 | F453 | AAATGAATGTTTTT | 127 | 938 |
|  | R10 | CCCCATCGCCATCG |  | 939 |
|  | P10 | CGGATTTTTTTTTTGGGAGAGAGG |  | 933 |
| 454 | F454 | AATGAATGTTTTTC | 126 | 940 |
|  | R10 | CCCCATCGCCATCG |  | 941 |
|  | P10 | CGGATTTTTTTTTTGGGAGAGAGG |  | 933 |
| 455 | F455 | ATGAATGTTTTTCG | 125 | 942 |
|  | R10 | CCCCATCGCCATCG |  | 943 |
|  | P10 | CGGATTTTTTTTTTGGGAGAGAGG |  | 933 |
| 456 | F456 | TGAATGTTTTTCGG | 124 | 944 |
|  | R10 | CCCCATCGCCATCG |  | 945 |
|  | P10 | CGGATTTTTTTTTTGGGAGAGAGG |  | 933 |
| 457 | F457 | GAATGTTTTTCGGT | 123 | 946 |
|  | R10 | CCCCATCGCCATCG |  | 947 |
|  | P10 | CGGATTTTTTTTTTGGGAGAGAGG |  | 933 |
| 458 | F458 | AATGTTTTTCGGTT | 122 | 948 |
|  | R10 | CCCCATCGCCATCG |  | 949 |
|  | P10 | CGGATTTTTTTTTTGGGAGAGAGG |  | 933 |
| 459 | F459 | ATGTTTTTCGGTTT | 121 | 950 |
|  | R10 | CCCCATCGCCATCG |  | 951 |
|  | P10 | CGGATTTTTTTTTTGGGAGAGAGG |  | 933 |
| 460 | F460 | TGTTTTTCGGTTTT | 120 | 952 |
|  | R10 | CCCCATCGCCATCG |  | 953 |
|  | P10 | CGGATTTTTTTTTTGGGAGAGAGG |  | 933 |
| 461 | F461 | GTTTTTCGGTTTTA | 119 | 954 |
|  | R10 | CCCCATCGCCATCG |  | 955 |
|  | P10 | CGGATTTTTTTTTTGGGAGAGAGG |  | 933 |
| 462 | F462 | TTTTTCGGTTTTAG | 118 | 956 |
|  | R10 | CCCCATCGCCATCG |  | 957 |
|  | P10 | CGGATTTTTTTTTTGGGAGAGAGG |  | 933 |
| 463 | F463 | TTTTCGGTTTTAGA | 117 | 958 |
|  | R10 | CCCCATCGCCATCG |  | 959 |
|  | P10 | CGGATTTTTTTTTTGGGAGAGAGG |  | 933 |
| 464 | F464 | TTTCGGTTTTAGAT | 116 | 960 |
|  | R10 | CCCCATCGCCATCG |  | 961 |
|  | P10 | CGGATTTTTTTTTTGGGAGAGAGG |  | 933 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 465 | F465 | TTCGGTTTTAGATT | 115 | 962 |
|  | R10 | CCCCATCGCCATCG |  | 963 |
|  | P10 | CGGATTTTTTTTTTGGGAGAGAGG |  | 933 |
| 466 | F466 | TCGGTTTTAGATTG | 114 | 964 |
|  | R10 | CCCCATCGCCATCG |  | 965 |
|  | P10 | CGGATTTTTTTTTTGGGAGAGAGG |  | 933 |
| 467 | F467 | CGGTTTTAGATTGC | 113 | 966 |
|  | R10 | CCCCATCGCCATCG |  | 967 |
|  | P10 | CGGATTTTTTTTTTGGGAGAGAGG |  | 933 |
| 468 | F468 | GGTTTTAGATTGCG | 112 | 968 |
|  | R10 | CCCCATCGCCATCG |  | 969 |
|  | P10 | CGGATTTTTTTTTTGGGAGAGAGG |  | 933 |
| 469 | F469 | GTTTTAGATTGCGT | 111 | 970 |
|  | R10 | CCCCATCGCCATCG |  | 971 |
|  | P10 | CGGATTTTTTTTTTGGGAGAGAGG |  | 933 |
| 470 | F470 | TTTTAGATTGCGTT | 110 | 972 |
|  | R10 | CCCCATCGCCATCG |  | 973 |
|  | P10 | CGGATTTTTTTTTTGGGAGAGAGG |  | 933 |
| 471 | F471 | TTTAGATTGCGTTT | 109 | 974 |
|  | R10 | CCCCATCGCCATCG |  | 975 |
|  | P10 | CGGATTTTTTTTTTGGGAGAGAGG |  | 933 |
| 472 | F472 | TTAGATTGCGTTTT | 108 | 976 |
|  | R10 | CCCCATCGCCATCG |  | 977 |
|  | P10 | CGGATTTTTTTTTTGGGAGAGAGG |  | 933 |
| 473 | F473 | TAGATTGCGTTTTT | 107 | 978 |
|  | R10 | CCCCATCGCCATCG |  | 979 |
|  | P10 | CGGATTTTTTTTTTGGGAGAGAGG |  | 933 |
| 474 | F474 | AGATTGCGTTTTTT | 106 | 980 |
|  | R10 | CCCCATCGCCATCG |  | 981 |
|  | P10 | CGGATTTTTTTTTTGGGAGAGAGG |  | 933 |
| 475 | F475 | GATTGCGTTTTTTT | 105 | 982 |
|  | R10 | CCCCATCGCCATCG |  | 983 |
|  | P10 | CGGATTTTTTTTTTGGGAGAGAGG |  | 933 |
| 476 | F476 | ATTGCGTTTTTTTT | 104 | 984 |
|  | R10 | CCCCATCGCCATCG |  | 985 |
|  | P10 | CGGATTTTTTTTTTGGGAGAGAGG |  | 933 |
| 477 | F477 | TTGCGTTTTTTTA | 103 | 986 |
|  | R10 | CCCCATCGCCATCG |  | 987 |
|  | P10 | CGGATTTTTTTTTTGGGAGAGAGG |  | 933 |
| 478 | F478 | TGCGTTTTTTTAG | 102 | 988 |
|  | R10 | CCCCATCGCCATCG |  | 989 |
|  | P10 | CGGATTTTTTTTTTGGGAGAGAGG |  | 933 |
| 479 | F479 | GCGTTTTTTTAGT | 101 | 990 |
|  | R10 | CCCCATCGCCATCG |  | 991 |
|  | P10 | CGGATTTTTTTTTTGGGAGAGAGG |  | 933 |
| 480 | F480 | CGTTTTTTTAGTT | 100 | 992 |
|  | R10 | CCCCATCGCCATCG |  | 993 |
|  | P10 | CGGATTTTTTTTTTGGGAGAGAGG |  | 933 |
| 481 | F481 | GTTTTTTTAGTTT | 99 | 994 |
|  | R10 | CCCCATCGCCATCG |  | 995 |
|  | P10 | CGGATTTTTTTTTTGGGAGAGAGG |  | 933 |
| 482 | F482 | TTTTTTTAGTTTT | 98 | 996 |
|  | R10 | CCCCATCGCCATCG |  | 997 |
|  | P10 | CGGATTTTTTTTTTGGGAGAGAGG |  | 933 |

TABLE 7-continued

Sequences of primer and probes for qMSP of GPM6A gene

| Set | Primer | Sequences (5'→3') | Size of amplification product (bp) | SEQ ID NOs: |
|-----|--------|-------------------|-----------------------------------|-------------|
| 483 | F483 | TTTTTTTAGTTTTG | 97 | 998 |
|     | R10  | CCCCATCGCCATCG | | 999 |
|     | P10  | CGGATTTTTTTTTTGGGAGAGAGG | | 933 |
| 484 | F484 | TTTTTTAGTTTTGT | 96 | 1000 |
|     | R10  | CCCCATCGCCATCG | | 1001 |
|     | P10  | CGGATTTTTTTTTTGGGAGAGAGG | | 933 |
| 485 | F485 | TTTTTAGTTTTGTT | 95 | 1002 |
|     | R10  | CCCCATCGCCATCG | | 1003 |
|     | P10  | CGGATTTTTTTTTTGGGAGAGAGG | | 933 |
| 486 | F486 | TTTTAGTTTTGTTT | 94 | 1004 |
|     | R10  | CCCCATCGCCATCG | | 1005 |
|     | P10  | CGGATTTTTTTTTTGGGAGAGAGG | | 933 |
| 487 | F487 | TTTAGTTTTGTTTT | 93 | 1006 |
|     | R10  | CCCCATCGCCATCG | | 1007 |
|     | P10  | CGGATTTTTTTTTTGGGAGAGAGG | | 933 |
| 488 | F488 | TTAGTTTTGTTTTT | 92 | 1008 |
|     | R10  | CCCCATCGCCATCG | | 1009 |
|     | P10  | CGGATTTTTTTTTTGGGAGAGAGG | | 933 |
| 489 | F489 | TAGTTTTGTTTTTT | 91 | 1010 |
|     | R10  | CCCCATCGCCATCG | | 1011 |
|     | P10  | CGGATTTTTTTTTTGGGAGAGAGG | | 933 |
| 490 | F490 | AGTTTTGTTTTTTT | 90 | 1012 |
|     | R10  | CCCCATCGCCATCG | | 1013 |
|     | P10  | CGGATTTTTTTTTTGGGAGAGAGG | | 933 |
| 491 | F491 | GTTTTGTTTTTTTC | 89 | 1014 |
|     | R10  | CCCCATCGCCATCG | | 1015 |
|     | P10  | CGGATTTTTTTTTTGGGAGAGAGG | | 933 |
| 492 | F492 | TTTTGTTTTTTTCG | 88 | 1016 |
|     | R10  | CCCCATCGCCATCG | | 1017 |
|     | P10  | CGGATTTTTTTTTTGGGAGAGAGG | | 933 |
| 493 | F493 | TTTGTTTTTTTCGC | 87 | 1018 |
|     | R10  | CCCCATCGCCATCG | | 1019 |
|     | P10  | CGGATTTTTTTTTTGGGAGAGAGG | | 933 |
| 494 | F494 | TTGTTTTTTTCGCG | 86 | 1020 |
|     | R10  | CCCCATCGCCATCG | | 1021 |
|     | P10  | CGGATTTTTTTTTTGGGAGAGAGG | | 933 |
| 495 | F495 | TGTTTTTTTCGCGT | 85 | 1022 |
|     | R10  | CCCCATCGCCATCG | | 1023 |
|     | P10  | CGGATTTTTTTTTTGGGAGAGAGG | | 933 |
| 496 | F496 | GTTTTTTTCGCGTT | 84 | 1024 |
|     | R10  | CCCCATCGCCATCG | | 1025 |
|     | P10  | CGGATTTTTTTTTTGGGAGAGAGG | | 933 |
| 497 | F497 | TTTTTTTCGCGTTT | 83 | 1026 |
|     | R10  | CCCCATCGCCATCG | | 1027 |
|     | P10  | CGGATTTTTTTTTTGGGAGAGAGG | | 933 |
| 498 | F498 | TTTTTTCGCGTTTG | 82 | 1028 |
|     | R10  | CCCCATCGCCATCG | | 1029 |
|     | P10  | CGGATTTTTTTTTTGGGAGAGAGG | | 933 |
| 499 | F499 | TTTTTCGCGTTTGG | 81 | 1030 |
|     | R10  | CCCCATCGCCATCG | | 1031 |
|     | P10  | CGGATTTTTTTTTTGGGAGAGAGG | | 933 |
| 500 | F500 | TTTTCGCGTTTGGC | 80 | 1032 |
|     | R10  | CCCCATCGCCATCG | | 1033 |
|     | P10  | CGGATTTTTTTTTTGGGAGAGAGG | | 933 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 501 | F501 | TTTCGCGTTTGGCG | 130 | 1034 |
|  | R11 | CTCCCGACCCACTA |  | 1035 |
|  | P11 | CGAGGGAGGGTGTTCGATTGTTTA |  | 1036 |
| 502 | F502 | TTCGCGTTTGGCGT | 129 | 1037 |
|  | R11 | CTCCCGACCCACTA |  | 1038 |
|  | P11 | CGAGGGAGGGTGTTCGATTGTTTA |  | 1036 |
| 503 | F503 | TCGCGTTTGGCGTT | 128 | 1039 |
|  | R11 | CTCCCGACCCACTA |  | 1040 |
|  | P11 | CGAGGGAGGGTGTTCGATTGTTTA |  | 1036 |
| 504 | F504 | CGCGTTTGGCGTTT | 127 | 1041 |
|  | R11 | CTCCCGACCCACTA |  | 1042 |
|  | P11 | CGAGGGAGGGTGTTCGATTGTTTA |  | 1036 |
| 505 | F505 | GCGTTTGGCGTTTT | 126 | 1043 |
|  | R11 | CTCCCGACCCACTA |  | 1044 |
|  | P11 | CGAGGGAGGGTGTTCGATTGTTTA |  | 1036 |
| 506 | F506 | CGTTTGGCGTTTTT | 125 | 1045 |
|  | R11 | CTCCCGACCCACTA |  | 1046 |
|  | P11 | CGAGGGAGGGTGTTCGATTGTTTA |  | 1036 |
| 507 | F507 | GTTTGGCGTTTTTC | 124 | 1047 |
|  | R11 | CTCCCGACCCACTA |  | 1048 |
|  | P11 | CGAGGGAGGGTGTTCGATTGTTTA |  | 1036 |
| 508 | F508 | TTTGGCGTTTTTCG | 123 | 1049 |
|  | R11 | CTCCCGACCCACTA |  | 1050 |
|  | P11 | CGAGGGAGGGTGTTCGATTGTTTA |  | 1036 |
| 509 | F509 | TTGGCGTTTTTCGT | 122 | 1051 |
|  | R11 | CTCCCGACCCACTA |  | 1052 |
|  | P11 | CGAGGGAGGGTGTTCGATTGTTTA |  | 1036 |
| 510 | F510 | TGGCGTTTTTCGTT | 121 | 1053 |
|  | R11 | CTCCCGACCCACTA |  | 1054 |
|  | P11 | CGAGGGAGGGTGTTCGATTGTTTA |  | 1036 |
| 511 | F511 | GGCGTTTTTCGTTT | 120 | 1055 |
|  | R11 | CTCCCGACCCACTA |  | 1056 |
|  | P11 | CGAGGGAGGGTGTTCGATTGTTTA |  | 1036 |
| 512 | F512 | GCGTTTTTCGTTTT | 119 | 1057 |
|  | R11 | CTCCCGACCCACTA |  | 1058 |
|  | P11 | CGAGGGAGGGTGTTCGATTGTTTA |  | 1036 |
| 513 | F513 | CGTTTTTCGTTTTT | 118 | 1059 |
|  | R11 | CTCCCGACCCACTA |  | 1060 |
|  | P11 | CGAGGGAGGGTGTTCGATTGTTTA |  | 1036 |
| 514 | F514 | GTTTTTCGTTTTTC | 117 | 1061 |
|  | R11 | CTCCCGACCCACTA |  | 1062 |
|  | P11 | CGAGGGAGGGTGTTCGATTGTTTA |  | 1036 |
| 515 | F515 | TTTTTCGTTTTTCG | 116 | 1063 |
|  | R11 | CTCCCGACCCACTA |  | 1064 |
|  | P11 | CGAGGGAGGGTGTTCGATTGTTTA |  | 1036 |
| 516 | F516 | TTTTCGTTTTTCGT | 115 | 1065 |
|  | R11 | CTCCCGACCCACTA |  | 1066 |
|  | P11 | CGAGGGAGGGTGTTCGATTGTTTA |  | 1036 |
| 517 | F517 | TTTCGTTTTTCGTT | 114 | 1067 |
|  | R11 | CTCCCGACCCACTA |  | 1068 |
|  | P11 | CGAGGGAGGGTGTTCGATTGTTTA |  | 1036 |
| 518 | F518 | TTCGTTTTTCGTTT | 113 | 1069 |
|  | R11 | CTCCCGACCCACTA |  | 1070 |
|  | P11 | CGAGGGAGGGTGTTCGATTGTTTA |  | 1036 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 519 | F519 | TCGTTTTTCGTTTT | 112 | 1071 |
|  | R11 | CTCCCGACCCACTA |  | 1072 |
|  | P11 | CGAGGGAGGGTGTTCGATTGTTTA |  | 1036 |
| 520 | F520 | CGTTTTTCGTTTTT | 111 | 1073 |
|  | R11 | CTCCCGACCCACTA |  | 1074 |
|  | P11 | CGAGGGAGGGTGTTCGATTGTTTA |  | 1036 |
| 521 | F521 | GTTTTTCGTTTTTT | 110 | 1075 |
|  | R11 | CTCCCGACCCACTA |  | 1076 |
|  | P11 | CGAGGGAGGGTGTTCGATTGTTTA |  | 1036 |
| 522 | F522 | TTTTTCGTTTTTTT | 109 | 1077 |
|  | R11 | CTCCCGACCCACTA |  | 1078 |
|  | P11 | CGAGGGAGGGTGTTCGATTGTTTA |  | 1036 |
| 523 | F523 | TTTTCGTTTTTTTG | 108 | 1079 |
|  | R11 | CTCCCGACCCACTA |  | 1080 |
|  | P11 | CGAGGGAGGGTGTTCGATTGTTTA |  | 1036 |
| 524 | F524 | TTTCGTTTTTTTGT | 107 | 1081 |
|  | R11 | CTCCCGACCCACTA |  | 1082 |
|  | P11 | CGAGGGAGGGTGTTCGATTGTTTA |  | 1036 |
| 525 | F525 | TTCGTTTTTTTGTT | 106 | 1083 |
|  | R11 | CTCCCGACCCACTA |  | 1084 |
|  | P11 | CGAGGGAGGGTGTTCGATTGTTTA |  | 1036 |
| 526 | F526 | TCGTTTTTTTGTTT | 105 | 1085 |
|  | R11 | CTCCCGACCCACTA |  | 1086 |
|  | P11 | CGAGGGAGGGTGTTCGATTGTTTA |  | 1036 |
| 527 | F527 | CGTTTTTTTGTTTT | 104 | 1087 |
|  | R11 | CTCCCGACCCACTA |  | 1088 |
|  | P11 | CGAGGGAGGGTGTTCGATTGTTTA |  | 1036 |
| 528 | F528 | GTTTTTTTGTTTTC | 103 | 1089 |
|  | R11 | CTCCCGACCCACTA |  | 1090 |
|  | P11 | CGAGGGAGGGTGTTCGATTGTTTA |  | 1036 |
| 529 | F529 | TTTTTTTGTTTTCG | 102 | 1091 |
|  | R11 | CTCCCGACCCACTA |  | 1092 |
|  | P11 | CGAGGGAGGGTGTTCGATTGTTTA |  | 1036 |
| 530 | F530 | TTTTTTGTTTTCGG | 101 | 1093 |
|  | R11 | CTCCCGACCCACTA |  | 1094 |
|  | P11 | CGAGGGAGGGTGTTCGATTGTTTA |  | 1036 |
| 531 | F531 | TTTTTGTTTTCGGA | 100 | 1095 |
|  | R11 | CTCCCGACCCACTA |  | 1096 |
|  | P11 | CGAGGGAGGGTGTTCGATTGTTTA |  | 1036 |
| 532 | F532 | TTTTGTTTTCGGAT | 99 | 1097 |
|  | R11 | CTCCCGACCCACTA |  | 1098 |
|  | P11 | CGAGGGAGGGTGTTCGATTGTTTA |  | 1036 |
| 533 | F533 | TTTGTTTTCGGATT | 98 |  |
|  | R11 | CTCCCGACCCACTA |  | 1100 |
|  | P11 | CGAGGGAGGGTGTTCGATTGTTTA |  | 1036 |
| 534 | F534 | TTGTTTTCGGATTT | 97 | 1101 |
|  | R11 | CTCCCGACCCACTA |  | 1102 |
|  | P11 | CGAGGGAGGGTGTTCGATTGTTTA |  | 1036 |
| 535 | F535 | TGTTTTCGGATTTT | 96 | 1103 |
|  | R11 | CTCCCGACCCACTA |  | 1104 |
|  | P11 | CGAGGGAGGGTGTTCGATTGTTTA |  | 1036 |
| 536 | F536 | GTTTTCGGATTTTT | 95 | 1105 |
|  | R11 | CTCCCGACCCACTA |  | 1106 |
|  | P11 | CGAGGGAGGGTGTTCGATTGTTTA |  | 1036 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 537 | F537 | TTTTCGGATTTTTTT | 94 | 1107 |
|  | R11 | CTCCCGACCCACTA |  | 1108 |
|  | P11 | CGAGGGAGGGTGTTCGATTGTTTA |  | 1036 |
| 538 | F538 | TTTCGGATTTTTTTT | 93 | 1109 |
|  | R11 | CTCCCGACCCACTA |  | 1110 |
|  | P11 | CGAGGGAGGGTGTTCGATTGTTTA |  | 1036 |
| 539 | F539 | TTCGGATTTTTTTTT | 92 | 1111 |
|  | R11 | CTCCCGACCCACTA |  | 1112 |
|  | P11 | CGAGGGAGGGTGTTCGATTGTTTA |  | 1036 |
| 540 | F540 | TCGGATTTTTTTTT | 91 | 1113 |
|  | R11 | CTCCCGACCCACTA |  | 1114 |
|  | P11 | CGAGGGAGGGTGTTCGATTGTTTA |  | 1036 |
| 541 | F541 | CGGATTTTTTTTTT | 90 | 1115 |
|  | R11 | CTCCCGACCCACTA |  | 1116 |
|  | P11 | CGAGGGAGGGTGTTCGATTGTTTA |  | 1036 |
| 542 | F542 | GGATTTTTTTTTT | 89 | 1117 |
|  | R11 | CTCCCGACCCACTA |  | 1118 |
|  | P11 | CGAGGGAGGGTGTTCGATTGTTTA |  | 1036 |
| 543 | F543 | GATTTTTTTTTTG | 88 | 1119 |
|  | R11 | CTCCCGACCCACTA |  | 1120 |
|  | P11 | CGAGGGAGGGTGTTCGATTGTTTA |  | 1036 |
| 544 | F544 | ATTTTTTTTTTGG | 87 | 1121 |
|  | R11 | CTCCCGACCCACTA |  | 1122 |
|  | P11 | CGAGGGAGGGTGTTCGATTGTTTA |  | 1036 |
| 545 | F545 | TTTTTTTTTTGGG | 86 | 1123 |
|  | R11 | CTCCCGACCCACTA |  | 1124 |
|  | P11 | CGAGGGAGGGTGTTCGATTGTTTA |  | 1036 |
| 546 | F546 | TTTTTTTTTGGGA | 85 | 1125 |
|  | R11 | CTCCCGACCCACTA |  | 1126 |
|  | P11 | CGAGGGAGGGTGTTCGATTGTTTA |  | 1036 |
| 547 | F547 | TTTTTTTTGGGAG | 84 | 1127 |
|  | R11 | CTCCCGACCCACTA |  | 1128 |
|  | P11 | CGAGGGAGGGTGTTCGATTGTTTA |  | 1036 |
| 548 | F548 | TTTTTTTGGGAGA | 83 | 1129 |
|  | R11 | CTCCCGACCCACTA |  | 1130 |
|  | P11 | CGAGGGAGGGTGTTCGATTGTTTA |  | 1036 |
| 549 | F549 | TTTTTTGGGAGAG | 82 | 1131 |
|  | R11 | CTCCCGACCCACTA |  | 1132 |
|  | P11 | CGAGGGAGGGTGTTCGATTGTTTA |  | 1036 |
| 550 | F550 | TTTTTGGGAGAGA | 81 | 1133 |
|  | R11 | CTCCCGACCCACTA |  | 1134 |
|  | P11 | CGAGGGAGGGTGTTCGATTGTTTA |  | 1036 |
| 551 | F551 | TTTTGGGAGAGAG | 80 | 1135 |
|  | R11 | CTCCCGACCCACTA |  | 1136 |
|  | P11 | CGAGGGAGGGTGTTCGATTGTTTA |  | 1036 |
| 552 | F552 | TTTTGGGAGAGAGG | 120 | 1137 |
|  | R12 | AACCGACGCAAAAA |  | 1138 |
|  | P12 | TGGGGGGTTGCGTTTGGGCGTTGAT |  | 1139 |
| 553 | F553 | TTTGGGAGAGAGGC | 119 | 1140 |
|  | R12 | AACCGACGCAAAAA |  | 1141 |
|  | P12 | TGGGGGGTTGCGTTTGGGCGTTGAT |  | 1139 |
| 554 | F554 | TTGGGAGAGAGGCG | 118 | 1142 |
|  | R12 | AACCGACGCAAAAA |  | 1143 |
|  | P12 | TGGGGGGTTGCGTTTGGGCGTTGAT |  | 1139 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 555 | F555 | TGGGAGAGAGGCGA | 117 | 1144 |
|  | R12 | AACCGACGCAAAAA |  | 1145 |
|  | P12 | TGGGGGGTTGCGTTTGGGCGTTGAT |  | 1139 |
| 556 | F556 | GGGAGAGAGGCGAT | 116 | 1146 |
|  | R12 | AACCGACGCAAAAA |  | 1147 |
|  | P12 | TGGGGGGTTGCGTTTGGGCGTTGAT |  | 1139 |
| 557 | F557 | GGAGAGAGGCGATG | 115 | 1148 |
|  | R12 | AACCGACGCAAAAA |  | 1149 |
|  | P12 | TGGGGGGTTGCGTTTGGGCGTTGAT |  | 1139 |
| 558 | F558 | GAGAGAGGCGATGG | 114 | 1150 |
|  | R12 | AACCGACGCAAAAA |  | 1151 |
|  | P12 | TGGGGGGTTGCGTTTGGGCGTTGAT |  | 1139 |
| 559 | F559 | AGAGAGGCGATGGC | 113 | 1152 |
|  | R12 | AACCGACGCAAAAA |  | 1153 |
|  | P12 | TGGGGGGTTGCGTTTGGGCGTTGAT |  | 1139 |
| 560 | F560 | GAGAGGCGATGGCG | 112 | 1154 |
|  | R12 | AACCGACGCAAAAA |  | 1155 |
|  | P12 | TGGGGGGTTGCGTTTGGGCGTTGAT |  | 1139 |
| 561 | F561 | AGAGGCGATGGCGA | 111 | 1156 |
|  | R12 | AACCGACGCAAAAA |  | 1157 |
|  | P12 | TGGGGGGTTGCGTTTGGGCGTTGAT |  | 1139 |
| 562 | F562 | GAGGCGATGGCGAT | 110 | 1158 |
|  | R12 | AACCGACGCAAAAA |  | 1159 |
|  | P12 | TGGGGGGTTGCGTTTGGGCGTTGAT |  | 1139 |
| 563 | F563 | AGGCGATGGCGATG | 109 | 1160 |
|  | R12 | AACCGACGCAAAAA |  | 1161 |
|  | P12 | TGGGGGGTTGCGTTTGGGCGTTGAT |  | 1139 |
| 564 | F564 | GGCGATGGCGATGG | 108 | 1162 |
|  | R12 | AACCGACGCAAAAA |  | 1163 |
|  | P12 | TGGGGGGTTGCGTTTGGGCGTTGAT |  | 1139 |
| 565 | F565 | GCGATGGCGATGGG | 107 | 1164 |
|  | R12 | AACCGACGCAAAAA |  | 1165 |
|  | P12 | TGGGGGGTTGCGTTTGGGCGTTGAT |  | 1139 |
| 566 | F566 | CGATGGCGATGGGG | 106 | 1166 |
|  | R12 | AACCGACGCAAAAA |  | 1167 |
|  | P12 | TGGGGGGTTGCGTTTGGGCGTTGAT |  | 1139 |
| 567 | F567 | GATGGCGATGGGGT | 105 | 1168 |
|  | R12 | AACCGACGCAAAAA |  | 1169 |
|  | P12 | TGGGGGGTTGCGTTTGGGCGTTGAT |  | 1139 |
| 568 | F568 | ATGGCGATGGGGTG | 104 | 1170 |
|  | R12 | AACCGACGCAAAAA |  | 1171 |
|  | P12 | TGGGGGGTTGCGTTTGGGCGTTGAT |  | 1139 |
| 569 | F569 | TGGCGATGGGGTGG | 103 | 1172 |
|  | R12 | AACCGACGCAAAAA |  | 1173 |
|  | P12 | TGGGGGGTTGCGTTTGGGCGTTGAT |  | 1139 |
| 570 | F570 | GGCGATGGGGTGGT | 102 | 1174 |
|  | R12 | AACCGACGCAAAAA |  | 1175 |
|  | P12 | TGGGGGGTTGCGTTTGGGCGTTGAT |  | 1139 |
| 571 | F571 | GCGATGGGGTGGTA | 101 | 1176 |
|  | R12 | AACCGACGCAAAAA |  | 1177 |
|  | P12 | TGGGGGGTTGCGTTTGGGCGTTGAT |  | 1139 |
| 572 | F572 | CGATGGGGTGGTAT | 100 | 1178 |
|  | R12 | AACCGACGCAAAAA |  | 1179 |
|  | P12 | TGGGGGGTTGCGTTTGGGCGTTGAT |  | 1139 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 573 | F573 | GATGGGGTGGTATT | 99 | 1180 |
|  | R12 | AACCGACGCAAAAA |  | 1181 |
|  | P12 | TGGGGGGTTGCGTTTGGGCGTTGAT |  | 1139 |
| 574 | F574 | ATGGGGTGGTATTT | 98 | 1182 |
|  | R12 | AACCGACGCAAAAA |  | 1183 |
|  | P12 | TGGGGGGTTGCGTTTGGGCGTTGAT |  | 1139 |
| 575 | F575 | TGGGGTGGTATTTG | 97 | 1184 |
|  | R12 | AACCGACGCAAAAA |  | 1185 |
|  | P12 | TGGGGGGTTGCGTTTGGGCGTTGAT |  | 1139 |
| 576 | F576 | GGGGTGGTATTTGG | 96 | 1186 |
|  | R12 | AACCGACGCAAAAA |  | 1187 |
|  | P12 | TGGGGGGTTGCGTTTGGGCGTTGAT |  | 1139 |
| 577 | F577 | GGGTGGTATTTGGA | 95 | 1188 |
|  | R12 | AACCGACGCAAAAA |  | 1189 |
|  | P12 | TGGGGGGTTGCGTTTGGGCGTTGAT |  | 1139 |
| 578 | F578 | GGTGGTATTTGGAG | 94 | 1190 |
|  | R12 | AACCGACGCAAAAA |  | 1191 |
|  | P12 | TGGGGGGTTGCGTTTGGGCGTTGAT |  | 1139 |
| 579 | F579 | GTGGTATTTGGAGG | 93 | 1192 |
|  | R12 | AACCGACGCAAAAA |  | 1193 |
|  | P12 | TGGGGGGTTGCGTTTGGGCGTTGAT |  | 1139 |
| 580 | F580 | TGGTATTTGGAGGC | 92 | 1194 |
|  | R12 | AACCGACGCAAAAA |  | 1195 |
|  | P12 | TGGGGGGTTGCGTTTGGGCGTTGAT |  | 1139 |
| 581 | F581 | GGTATTTGGAGGCG | 91 | 1196 |
|  | R12 | AACCGACGCAAAAA |  | 1197 |
|  | P12 | TGGGGGGTTGCGTTTGGGCGTTGAT |  | 1139 |
| 582 | F582 | GTATTTGGAGGCGA | 90 | 1198 |
|  | R12 | AACCGACGCAAAAA |  | 1199 |
|  | P12 | TGGGGGGTTGCGTTTGGGCGTTGAT |  | 1139 |
| 583 | F583 | TATTTGGAGGCGAG | 89 | 1200 |
|  | R12 | AACCGACGCAAAAA |  | 1201 |
|  | P12 | TGGGGGGTTGCGTTTGGGCGTTGAT |  | 1139 |
| 584 | F584 | ATTTGGAGGCGAGG | 88 | 1202 |
|  | R12 | AACCGACGCAAAAA |  | 1203 |
|  | P12 | TGGGGGGTTGCGTTTGGGCGTTGAT |  | 1139 |
| 585 | F585 | TTTGGAGGCGAGGG | 87 | 1204 |
|  | R12 | AACCGACGCAAAAA |  | 1205 |
|  | P12 | TGGGGGGTTGCGTTTGGGCGTTGAT |  | 1139 |
| 586 | F586 | TTGGAGGCGAGGGA | 86 | 1206 |
|  | R12 | AACCGACGCAAAAA |  | 1207 |
|  | P12 | TGGGGGGTTGCGTTTGGGCGTTGAT |  | 1139 |
| 587 | F587 | TGGAGGCGAGGGAG | 85 | 1208 |
|  | R12 | AACCGACGCAAAAA |  | 1209 |
|  | P12 | TGGGGGGTTGCGTTTGGGCGTTGAT |  | 1139 |
| 588 | F588 | GGAGGCGAGGGAGG | 84 | 1210 |
|  | R12 | AACCGACGCAAAAA |  | 1211 |
|  | P12 | TGGGGGGTTGCGTTTGGGCGTTGAT |  | 1139 |
| 589 | F589 | GAGGCGAGGGAGGG | 83 | 1212 |
|  | R12 | AACCGACGCAAAAA |  | 1213 |
|  | P12 | TGGGGGGTTGCGTTTGGGCGTTGAT |  | 1139 |
| 590 | F590 | AGGCGAGGGAGGGT | 82 | 1214 |
|  | R12 | AACCGACGCAAAAA |  | 1215 |
|  | P12 | TGGGGGGTTGCGTTTGGGCGTTGAT |  | 1139 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 591 | F591 | GGCGAGGGAGGGTG | 81 | 1216 |
|  | R12 | AACCGACGCAAAAA |  | 1217 |
|  | P12 | TGGGGGGTTGCGTTTGGGCGTTGAT |  | 1139 |
| 592 | F592 | GCGAGGGAGGGTGT | 80 | 1218 |
|  | R12 | AACCGACGCAAAAA |  | 1219 |
|  | P12 | TGGGGGGTTGCGTTTGGGCGTTGAT |  | 1139 |
| 593 | F593 | CGAGGGAGGGTGTT | 130 | 1220 |
|  | R13 | CCAAATACCGCCCC |  | 1221 |
|  | P13 | TTGGGGGTTCGGTTTATCGTGTTG |  | 1222 |
| 594 | F594 | GAGGGAGGGTGTTC | 129 | 1223 |
|  | R13 | CCAAATACCGCCCC |  | 1224 |
|  | P13 | TTGGGGGTTCGGTTTATCGTGTTG |  | 1222 |
| 595 | F595 | AGGGAGGGTGTTCG | 128 | 1225 |
|  | R13 | CCAAATACCGCCCC |  | 1226 |
|  | P13 | TTGGGGGTTCGGTTTATCGTGTTG |  | 1222 |
| 596 | F596 | GGGAGGGTGTTCGA | 127 | 1227 |
|  | R13 | CCAAATACCGCCCC |  | 1228 |
|  | P13 | TTGGGGGTTCGGTTTATCGTGTTG |  | 1222 |
| 597 | F597 | GGAGGGTGTTCGAT | 126 | 1229 |
|  | R13 | CCAAATACCGCCCC |  | 1230 |
|  | P13 | TTGGGGGTTCGGTTTATCGTGTTG |  | 1222 |
| 598 | F598 | GAGGGTGTTCGATT | 125 | 1231 |
|  | R13 | CCAAATACCGCCCC |  | 1232 |
|  | P13 | TTGGGGGTTCGGTTTATCGTGTTG |  | 1222 |
| 599 | F599 | AGGGTGTTCGATTG | 124 | 1233 |
|  | R13 | CCAAATACCGCCCC |  | 1234 |
|  | P13 | TTGGGGGTTCGGTTTATCGTGTTG |  | 1222 |
| 600 | F600 | GGGTGTTCGATTGT | 123 | 1235 |
|  | R13 | CCAAATACCGCCCC |  | 1236 |
|  | P13 | TTGGGGGTTCGGTTTATCGTGTTG |  | 1222 |
| 601 | F601 | GGTGTTCGATTGTT | 122 | 1237 |
|  | R13 | CCAAATACCGCCCC |  | 1238 |
|  | P13 | TTGGGGGTTCGGTTTATCGTGTTG |  | 1222 |
| 602 | F602 | GTGTTCGATTGTTT | 121 | 1239 |
|  | R13 | CCAAATACCGCCCC |  | 1240 |
|  | P13 | TTGGGGGTTCGGTTTATCGTGTTG |  | 1222 |
| 603 | F603 | TGTTCGATTGTTTA | 120 | 1241 |
|  | R13 | CCAAATACCGCCCC |  | 1242 |
|  | P13 | TTGGGGGTTCGGTTTATCGTGTTG |  | 1222 |
| 604 | F604 | GTTCGATTGTTTAT | 119 | 1243 |
|  | R13 | CCAAATACCGCCCC |  | 1244 |
|  | P13 | TTGGGGGTTCGGTTTATCGTGTTG |  | 1222 |
| 605 | F605 | TTCGATTGTTTATA | 118 | 1245 |
|  | R13 | CCAAATACCGCCCC |  | 1246 |
|  | P13 | TTGGGGGTTCGGTTTATCGTGTTG |  | 1222 |
| 606 | F606 | TCGATTGTTTATAG | 117 | 1247 |
|  | R13 | CCAAATACCGCCCC |  | 1248 |
|  | P13 | TTGGGGGTTCGGTTTATCGTGTTG |  | 1222 |
| 607 | F607 | CGATTGTTTATAGT | 116 | 1249 |
|  | R13 | CCAAATACCGCCCC |  | 1250 |
|  | P13 | TTGGGGGTTCGGTTTATCGTGTTG |  | 1222 |
| 608 | F608 | GATTGTTTATAGTG | 115 | 1251 |
|  | R13 | CCAAATACCGCCCC |  | 1252 |
|  | P13 | TTGGGGGTTCGGTTTATCGTGTTG |  | 1222 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 609 | F609 | ATTGTTTATAGTGG | 114 | 1253 |
|  | R13 | CCAAATACCGCCCC |  | 1254 |
|  | P13 | TTGGGGGTTCGGTTTATCGTGTTG |  | 1222 |
| 610 | F610 | TTGTTTATAGTGGG | 113 | 1255 |
|  | R13 | CCAAATACCGCCCC |  | 1256 |
|  | P13 | TTGGGGGTTCGGTTTATCGTGTTG |  | 1222 |
| 611 | F611 | TGTTTATAGTGGGT | 112 | 1257 |
|  | R13 | CCAAATACCGCCCC |  | 1258 |
|  | P13 | TTGGGGGTTCGGTTTATCGTGTTG |  | 1222 |
| 612 | F612 | GTTTATAGTGGGTC | 111 | 1259 |
|  | R13 | CCAAATACCGCCCC |  | 1260 |
|  | P13 | TTGGGGGTTCGGTTTATCGTGTTG |  | 1222 |
| 613 | F613 | TTTATAGTGGGTCG | 110 | 1261 |
|  | R13 | CCAAATACCGCCCC |  | 1262 |
|  | P13 | TTGGGGGTTCGGTTTATCGTGTTG |  | 1222 |
| 614 | F614 | TTATAGTGGGTCGG | 109 | 1263 |
|  | R13 | CCAAATACCGCCCC |  | 1264 |
|  | P13 | TTGGGGGTTCGGTTTATCGTGTTG |  | 1222 |
| 615 | F615 | TATAGTGGGTCGGG | 108 | 1265 |
|  | R13 | CCAAATACCGCCCC |  | 1266 |
|  | P13 | TTGGGGGTTCGGTTTATCGTGTTG |  | 1222 |
| 616 | F616 | ATAGTGGGTCGGGA | 107 | 1267 |
|  | R13 | CCAAATACCGCCCC |  | 1268 |
|  | P13 | TTGGGGGTTCGGTTTATCGTGTTG |  | 1222 |
| 617 | F617 | TAGTGGGTCGGGAG | 106 | 1269 |
|  | R13 | CCAAATACCGCCCC |  | 1270 |
|  | P13 | TTGGGGGTTCGGTTTATCGTGTTG |  | 1222 |
| 618 | F618 | AGTGGGTCGGGAGG | 105 | 1271 |
|  | R13 | CCAAATACCGCCCC |  | 1272 |
|  | P13 | TTGGGGGTTCGGTTTATCGTGTTG |  | 1222 |
| 619 | F619 | GTGGGTCGGGAGGG | 104 | 1273 |
|  | R13 | CCAAATACCGCCCC |  | 1274 |
|  | P13 | TTGGGGGTTCGGTTTATCGTGTTG |  | 1222 |
| 620 | F620 | TGGGTCGGGAGGGT | 103 | 1275 |
|  | R13 | CCAAATACCGCCCC |  | 1276 |
|  | P13 | TTGGGGGTTCGGTTTATCGTGTTG |  | 1222 |
| 621 | F621 | GGGTCGGGAGGGTG | 102 | 1277 |
|  | R13 | CCAAATACCGCCCC |  | 1278 |
|  | P13 | TTGGGGGTTCGGTTTATCGTGTTG |  | 1222 |
| 622 | F622 | GGTCGGGAGGGTGG | 101 | 1279 |
|  | R13 | CCAAATACCGCCCC |  | 1280 |
|  | P13 | TTGGGGGTTCGGTTTATCGTGTTG |  | 1222 |
| 623 | F623 | GTCGGGAGGGTGGG | 100 | 1281 |
|  | R13 | CCAAATACCGCCCC |  | 1282 |
|  | P13 | TTGGGGGTTCGGTTTATCGTGTTG |  | 1222 |
| 624 | F624 | TCGGGAGGGTGGGG | 99 | 1283 |
|  | R13 | CCAAATACCGCCCC |  | 1284 |
|  | P13 | TTGGGGGTTCGGTTTATCGTGTTG |  | 1222 |
| 625 | F625 | CGGGAGGGTGGGGG | 98 | 1285 |
|  | R13 | CCAAATACCGCCCC |  | 1286 |
|  | P13 | TTGGGGGTTCGGTTTATCGTGTTG |  | 1222 |
| 626 | F626 | GGGAGGGTGGGGGG | 97 | 1287 |
|  | R13 | CCAAATACCGCCCC |  | 1288 |
|  | P13 | TTGGGGGTTCGGTTTATCGTGTTG |  | 1222 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 627 | F627 | GGAGGGTGGGGGGT | 96 | 1289 |
|  | R13 | CCAAATACCGCCCC |  | 1290 |
|  | P13 | TTGGGGGTTCGGTTTATCGTGTTG |  | 1222 |
| 628 | F628 | GAGGGTGGGGGGTT | 95 | 1291 |
|  | R13 | CCAAATACCGCCCC |  | 1292 |
|  | P13 | TTGGGGGTTCGGTTTATCGTGTTG |  | 1222 |
| 629 | F629 | AGGGTGGGGGGTTG | 94 | 1293 |
|  | R13 | CCAAATACCGCCCC |  | 1294 |
|  | P13 | TTGGGGGTTCGGTTTATCGTGTTG |  | 1222 |
| 630 | F630 | GGGTGGGGGGTTGC | 93 | 1295 |
|  | R13 | CCAAATACCGCCCC |  | 1296 |
|  | P13 | TTGGGGGTTCGGTTTATCGTGTTG |  | 1222 |
| 631 | F631 | GGTGGGGGGTTGCG | 92 | 1297 |
|  | R13 | CCAAATACCGCCCC |  | 1298 |
|  | P13 | TTGGGGGTTCGGTTTATCGTGTTG |  | 1222 |
| 632 | F632 | GTGGGGGGTTGCGT | 91 | 1299 |
|  | R13 | CCAAATACCGCCCC |  | 1300 |
|  | P13 | TTGGGGGTTCGGTTTATCGTGTTG |  | 1222 |
| 633 | F633 | TGGGGGGTTGCGTT | 90 | 1301 |
|  | R13 | CCAAATACCGCCCC |  | 1302 |
|  | P13 | TTGGGGGTTCGGTTTATCGTGTTG |  | 1222 |
| 634 | F634 | GGGGGGTTGCGTTT | 89 | 1303 |
|  | R13 | CCAAATACCGCCCC |  | 1304 |
|  | P13 | TTGGGGGTTCGGTTTATCGTGTTG |  | 1222 |
| 635 | F635 | GGGGGTTGCGTTTG | 88 | 1305 |
|  | R13 | CCAAATACCGCCCC |  | 1306 |
|  | P13 | TTGGGGGTTCGGTTTATCGTGTTG |  | 1222 |
| 636 | F636 | GGGGTTGCGTTTGG | 87 | 1307 |
|  | R13 | CCAAATACCGCCCC |  | 1308 |
|  | P13 | TTGGGGGTTCGGTTTATCGTGTTG |  | 1222 |
| 637 | F637 | GGGTTGCGTTTGGG | 86 | 1309 |
|  | R13 | CCAAATACCGCCCC |  | 1310 |
|  | P13 | TTGGGGGTTCGGTTTATCGTGTTG |  | 1222 |
| 638 | F638 | GGTTGCGTTTGGGC | 85 | 1311 |
|  | R13 | CCAAATACCGCCCC |  | 1312 |
|  | P13 | TTGGGGGTTCGGTTTATCGTGTTG |  | 1222 |
| 639 | F639 | GTTGCGTTTGGGCG | 84 | 1313 |
|  | R13 | CCAAATACCGCCCC |  | 1314 |
|  | P13 | TTGGGGGTTCGGTTTATCGTGTTG |  | 1222 |
| 640 | F640 | TTGCGTTTGGGCGT | 83 | 1315 |
|  | R13 | CCAAATACCGCCCC |  | 1316 |
|  | P13 | TTGGGGGTTCGGTTTATCGTGTTG |  | 1222 |
| 641 | F641 | TGCGTTTGGGCGTT | 82 | 1317 |
|  | R13 | CCAAATACCGCCCC |  | 1318 |
|  | P13 | TTGGGGGTTCGGTTTATCGTGTTG |  | 1222 |
| 642 | F642 | GCGTTTGGGCGTTG | 81 | 1319 |
|  | R13 | CCAAATACCGCCCC |  | 1320 |
|  | P13 | TTGGGGGTTCGGTTTATCGTGTTG |  | 1222 |
| 643 | F643 | CGTTTGGGCGTTGA | 80 | 1321 |
|  | R13 | CCAAATACCGCCCC |  | 1322 |
|  | P13 | TTGGGGGTTCGGTTTATCGTGTTG |  | 1222 |
| 644 | F644 | GTTTGGGCGTTGAT | 130 | 1323 |
|  | R14 | TATAATCGCCTCGC |  | 1324 |
|  | P14 | ATTAAGAGATTTAGGATTCGAATA |  | 1325 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 645 | F645 | TTTGGGCGTTGATT | 129 | 1326 |
|  | R14 | TATAATCGCCTCGC |  | 1327 |
|  | P14 | ATTAAGAGATTTAGGATTCGAATA |  | 1325 |
| 646 | F646 | TTGGGCGTTGATTT | 128 | 1328 |
|  | R14 | TATAATCGCCTCGC |  | 1329 |
|  | P14 | ATTAAGAGATTTAGGATTCGAATA |  | 1325 |
| 647 | F647 | TGGGCGTTGATTTT | 127 | 1330 |
|  | R14 | TATAATCGCCTCGC |  | 1331 |
|  | P14 | ATTAAGAGATTTAGGATTCGAATA |  | 1325 |
| 648 | F648 | GGGCGTTGATTTTT | 126 | 1332 |
|  | R14 | TATAATCGCCTCGC |  | 1333 |
|  | P14 | ATTAAGAGATTTAGGATTCGAATA |  | 1325 |
| 649 | F649 | GGCGTTGATTTTTT | 125 | 1334 |
|  | R14 | TATAATCGCCTCGC |  | 1335 |
|  | P14 | ATTAAGAGATTTAGGATTCGAATA |  | 1325 |
| 650 | F650 | GCGTTGATTTTTTG | 124 | 1336 |
|  | R14 | TATAATCGCCTCGC |  | 1337 |
|  | P14 | ATTAAGAGATTTAGGATTCGAATA |  | 1325 |
| 651 | F651 | CGTTGATTTTTTGC | 123 | 1338 |
|  | R14 | TATAATCGCCTCGC |  | 1339 |
|  | P14 | ATTAAGAGATTTAGGATTCGAATA |  | 1325 |
| 652 | F652 | GTTGATTTTTTGCG | 122 | 1340 |
|  | R14 | TATAATCGCCTCGC |  | 1341 |
|  | P14 | ATTAAGAGATTTAGGATTCGAATA |  | 1325 |
| 653 | F653 | TTGATTTTTTGCGT | 121 | 1342 |
|  | R14 | TATAATCGCCTCGC |  | 1343 |
|  | P14 | ATTAAGAGATTTAGGATTCGAATA |  | 1325 |
| 654 | F654 | TGATTTTTTGCGTC | 120 | 1344 |
|  | R14 | TATAATCGCCTCGC |  | 1345 |
|  | P14 | ATTAAGAGATTTAGGATTCGAATA |  | 1325 |
| 655 | F655 | GATTTTTTGCGTCG | 119 | 1346 |
|  | R14 | TATAATCGCCTCGC |  | 1347 |
|  | P14 | ATTAAGAGATTTAGGATTCGAATA |  | 1325 |
| 656 | F656 | ATTTTTTGCGTCGG | 118 | 1348 |
|  | R14 | TATAATCGCCTCGC |  | 1349 |
|  | P14 | ATTAAGAGATTTAGGATTCGAATA |  | 1325 |
| 657 | F657 | TTTTTTGCGTCGGT | 117 | 1350 |
|  | R14 | TATAATCGCCTCGC |  | 1351 |
|  | P14 | ATTAAGAGATTTAGGATTCGAATA |  | 1325 |
| 658 | F658 | TTTTTGCGTCGGTT | 116 | 1352 |
|  | R14 | TATAATCGCCTCGC |  | 1353 |
|  | P14 | ATTAAGAGATTTAGGATTCGAATA |  | 1325 |
| 659 | F659 | TTTTGCGTCGGTTT | 115 | 1354 |
|  | R14 | TATAATCGCCTCGC |  | 1355 |
|  | P14 | ATTAAGAGATTTAGGATTCGAATA |  | 1325 |
| 660 | F660 | TTTGCGTCGGTTTT | 114 | 1356 |
|  | R14 | TATAATCGCCTCGC |  | 1357 |
|  | P14 | ATTAAGAGATTTAGGATTCGAATA |  | 1325 |
| 661 | F661 | TTGCGTCGGTTTTA | 113 | 1358 |
|  | R14 | TATAATCGCCTCGC |  | 1359 |
|  | P14 | ATTAAGAGATTTAGGATTCGAATA |  | 1325 |
| 662 | F662 | TGCGTCGGTTTTAG | 112 | 1360 |
|  | R14 | TATAATCGCCTCGC |  | 1361 |
|  | P14 | ATTAAGAGATTTAGGATTCGAATA |  | 1325 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 663 | F663 | GCGTCGGTTTTAGG | 111 | 1362 |
|  | R14 | TATAATCGCCTCGC |  | 1363 |
|  | P14 | ATTAAGAGATTTAGGATTCGAATA |  | 1325 |
| 664 | F664 | CGTCGGTTTTAGGA | 110 | 1364 |
|  | R14 | TATAATCGCCTCGC |  | 1365 |
|  | P14 | ATTAAGAGATTTAGGATTCGAATA |  | 1325 |
| 665 | F665 | GTCGGTTTTAGGAT | 109 | 1366 |
|  | R14 | TATAATCGCCTCGC |  | 1367 |
|  | P14 | ATTAAGAGATTTAGGATTCGAATA |  | 1325 |
| 666 | F666 | TCGGTTTTAGGATT | 108 | 1368 |
|  | R14 | TATAATCGCCTCGC |  | 1369 |
|  | P14 | ATTAAGAGATTTAGGATTCGAATA |  | 1325 |
| 667 | F667 | CGGTTTTAGGATTT | 107 | 1370 |
|  | R14 | TATAATCGCCTCGC |  | 1371 |
|  | P14 | ATTAAGAGATTTAGGATTCGAATA |  | 1325 |
| 668 | F668 | GGTTTTAGGATTTA | 106 | 1372 |
|  | R14 | TATAATCGCCTCGC |  | 1373 |
|  | P14 | ATTAAGAGATTTAGGATTCGAATA |  | 1325 |
| 669 | F669 | GTTTTAGGATTTAA | 105 | 1374 |
|  | R14 | TATAATCGCCTCGC |  | 1375 |
|  | P14 | ATTAAGAGATTTAGGATTCGAATA |  | 1325 |
| 670 | F670 | TTTTAGGATTTAAG | 104 | 1376 |
|  | R14 | TATAATCGCCTCGC |  | 1377 |
|  | P14 | ATTAAGAGATTTAGGATTCGAATA |  | 1325 |
| 671 | F671 | TTTAGGATTTAAGT | 103 | 1378 |
|  | R14 | TATAATCGCCTCGC |  | 1379 |
|  | P14 | ATTAAGAGATTTAGGATTCGAATA |  | 1325 |
| 672 | F672 | TTAGGATTTAAGTT | 102 | 1380 |
|  | R14 | TATAATCGCCTCGC |  | 1381 |
|  | P14 | ATTAAGAGATTTAGGATTCGAATA |  | 1325 |
| 673 | F673 | TAGGATTTAAGTTT | 101 | 1382 |
|  | R14 | TATAATCGCCTCGC |  | 1383 |
|  | P14 | ATTAAGAGATTTAGGATTCGAATA |  | 1325 |
| 674 | F674 | AGGATTTAAGTTTG | 100 | 1384 |
|  | R14 | TATAATCGCCTCGC |  | 1385 |
|  | P14 | ATTAAGAGATTTAGGATTCGAATA |  | 1325 |
| 675 | F675 | GGATTTAAGTTTGG | 99 | 1386 |
|  | R14 | TATAATCGCCTCGC |  | 1387 |
|  | P14 | ATTAAGAGATTTAGGATTCGAATA |  | 1325 |
| 676 | F676 | GATTTAAGTTTGGG | 98 | 1388 |
|  | R14 | TATAATCGCCTCGC |  | 1389 |
|  | P14 | ATTAAGAGATTTAGGATTCGAATA |  | 1325 |
| 677 | F677 | ATTTAAGTTTGGGG | 97 | 1390 |
|  | R14 | TATAATCGCCTCGC |  | 1391 |
|  | P14 | ATTAAGAGATTTAGGATTCGAATA |  | 1325 |
| 678 | F678 | TTTAAGTTTGGGGG | 96 | 1392 |
|  | R14 | TATAATCGCCTCGC |  | 1393 |
|  | P14 | ATTAAGAGATTTAGGATTCGAATA |  | 1325 |
| 679 | F679 | TTAAGTTTGGGGGT | 95 | 1394 |
|  | R14 | TATAATCGCCTCGC |  | 1395 |
|  | P14 | ATTAAGAGATTTAGGATTCGAATA |  | 1325 |
| 680 | F680 | TAAGTTTGGGGGTT | 94 | 1396 |
|  | R14 | TATAATCGCCTCGC |  | 1397 |
|  | P14 | ATTAAGAGATTTAGGATTCGAATA |  | 1325 |

TABLE 7-continued

Sequences of primer and probes for qMSP of GPM6A gene

| Set | Primer | Sequences (5'→3') | Size of amplification product (bp) | SEQ ID NOs: |
|---|---|---|---|---|
| 681 | F681 | AAGTTTGGGGGTTC | 93 | 1398 |
|  | R14 | TATAATCGCCTCGC |  | 1399 |
|  | P14 | ATTAAGAGATTTAGGATTCGAATA |  | 1325 |
| 682 | F682 | AGTTTGGGGGTTCG | 92 | 1400 |
|  | R14 | TATAATCGCCTCGC |  | 1401 |
|  | P14 | ATTAAGAGATTTAGGATTCGAATA |  | 1325 |
| 683 | F683 | GTTTGGGGGTTCGG | 91 | 1402 |
|  | R14 | TATAATCGCCTCGC |  | 1403 |
|  | P14 | ATTAAGAGATTTAGGATTCGAATA |  | 1325 |
| 684 | F684 | TTTGGGGGTTCGGT | 90 | 1404 |
|  | R14 | TATAATCGCCTCGC |  | 1405 |
|  | P14 | ATTAAGAGATTTAGGATTCGAATA |  | 1325 |
| 685 | F685 | TTGGGGGTTCGGTT | 89 | 1406 |
|  | R14 | TATAATCGCCTCGC |  | 1407 |
|  | P14 | ATTAAGAGATTTAGGATTCGAATA |  | 1325 |
| 686 | F686 | TGGGGGTTCGGTTT | 88 | 1408 |
|  | R14 | TATAATCGCCTCGC |  | 1409 |
|  | P14 | ATTAAGAGATTTAGGATTCGAATA |  | 1325 |
| 687 | F687 | GGGGGTTCGGTTTA | 87 | 1410 |
|  | R14 | TATAATCGCCTCGC |  | 1411 |
|  | P14 | ATTAAGAGATTTAGGATTCGAATA |  | 1325 |
| 688 | F688 | GGGGTTCGGTTTAT | 86 | 1412 |
|  | R14 | TATAATCGCCTCGC |  | 1413 |
|  | P14 | ATTAAGAGATTTAGGATTCGAATA |  | 1325 |
| 689 | F689 | GGGTTCGGTTTATC | 85 | 1414 |
|  | R14 | TATAATCGCCTCGC |  | 1415 |
|  | P14 | ATTAAGAGATTTAGGATTCGAATA |  | 1325 |
| 690 | F690 | GGTTCGGTTTATCG | 84 | 1416 |
|  | R14 | TATAATCGCCTCGC |  | 1417 |
|  | P14 | ATTAAGAGATTTAGGATTCGAATA |  | 1325 |
| 691 | F691 | GTTCGGTTTATCGT | 83 | 1418 |
|  | R14 | TATAATCGCCTCGC |  | 1419 |
|  | P14 | ATTAAGAGATTTAGGATTCGAATA |  | 1325 |
| 692 | F692 | TTCGGTTTATCGTG | 82 | 1420 |
|  | R14 | TATAATCGCCTCGC |  | 1421 |
|  | P14 | ATTAAGAGATTTAGGATTCGAATA |  | 1325 |
| 693 | F693 | TCGGTTTATCGTGT | 81 | 1422 |
|  | R14 | TATAATCGCCTCGC |  | 1423 |
|  | P14 | ATTAAGAGATTTAGGATTCGAATA |  | 1325 |
| 694 | F694 | CGGTTTATCGTGTT | 80 | 1424 |
|  | R14 | TATAATCGCCTCGC |  | 1425 |
|  | P14 | ATTAAGAGATTTAGGATTCGAATA |  | 1325 |
| 695 | F695 | GGTTTATCGTGTTG | 120 | 1426 |
|  | R15 | AAACATAAAAACGT |  | 1427 |
|  | P15 | GGGAGATTTTGTTTTTTCGAGTTTTT |  | 1428 |

As a result of evaluating methylation of GPM6A gene using DNA from colorectal cancer tissues and normal tissues adjacent to cancer tissues, it was found that the high sensitivity of GPM6A gene for colorectal cancer diagnosis was 75% (15/20)~90% (20/20) and the specificity of the GPM6A gene was 80.0% (4/20)~95% (1/20). Such results suggest that the GPM6A methylation biomarker gene is highly useful for diagnosis of colorectal cancer.

TABLE 8

Evaluation of ability to diagnose colorectal cancer using GPM6A gene

| Set of primers and probes | Cut-off (PMR) | Sensitivity (%), n = 20 | Specificity (%), n = 20 |
|---|---|---|---|
| 1 | >3.0 | 75 | 95 |
| 2 | >3.2 | 85 | 90 |
| 3 | >5.7 | 90 | 85 |
| 4 | >5.7 | 85 | 90 |
| 5 | >2.0 | 80 | 95 |
| 6 | >4.3 | 90 | 85 |
| 7 | >2.7 | 75 | 90 |
| 8 | >0.4 | 80 | 90 |
| 9 | >4.3 | 75 | 95 |
| 10 | >2.3 | 75 | 90 |
| 11 | >3.5 | 85 | 90 |
| 12 | >4.5 | 85 | 85 |
| 13 | >4.5 | 75 | 90 |
| 14 | >2.2 | 75 | 90 |
| 15 | >4.2 | 85 | 90 |
| 16 | >2.2 | 80 | 90 |
| 17 | >4.5 | 85 | 85 |
| 18 | >2.7 | 80 | 85 |
| 19 | >4.2 | 80 | 90 |
| 20 | >4.3 | 75 | 85 |
| 21 | >0.4 | 75 | 95 |
| 22 | >2.1 | 80 | 90 |
| 23 | >4.2 | 90 | 85 |
| 24 | >5.7 | 85 | 90 |
| 25 | >3.6 | 75 | 95 |
| 26 | >2.7 | 80 | 90 |
| 27 | >4.2 | 80 | 85 |
| 28 | >3.2 | 85 | 90 |
| 29 | >2.3 | 85 | 90 |
| 30 | >2.7 | 75 | 90 |
| 31 | >2.7 | 75 | 90 |
| 32 | >1.2 | 90 | 85 |
| 33 | >2.1 | 85 | 90 |
| 34 | >0.5 | 85 | 90 |
| 35 | >2.9 | 90 | 85 |
| 36 | >2.1 | 75 | 90 |
| 37 | >1.2 | 80 | 90 |
| 38 | >2.7 | 80 | 90 |
| 39 | >0.4 | 75 | 85 |
| 40 | >2.2 | 80 | 90 |
| 41 | >2.0 | 90 | 90 |
| 42 | >0.4 | 80 | 90 |
| 43 | >2.1 | 75 | 95 |
| 44 | >3.0 | 85 | 90 |
| 45 | >2.4 | 80 | 90 |
| 46 | >1.2 | 90 | 85 |
| 47 | >2.0 | 80 | 90 |
| 48 | >0.4 | 80 | 90 |
| 49 | >3.0 | 85 | 85 |
| 50 | >2.1 | 75 | 90 |
| 51 | >2.3 | 85 | 90 |
| 52 | >2.7 | 75 | 85 |
| 53 | >2.7 | 75 | 80 |
| 54 | >1.2 | 90 | 85 |
| 55 | >2.1 | 80 | 90 |
| 56 | >0.7 | 80 | 90 |
| 57 | >4.3 | 90 | 85 |
| 58 | >2.1 | 85 | 85 |
| 59 | >2.3 | 75 | 90 |
| 60 | >2.3 | 85 | 90 |
| 61 | >2.1 | 80 | 85 |
| 62 | >2.1 | 85 | 90 |
| 63 | >2.1 | 80 | 90 |
| 64 | >2.1 | 85 | 90 |
| 65 | >1.2 | 75 | 95 |
| 66 | >2.1 | 80 | 95 |
| 67 | >2.1 | 80 | 85 |
| 68 | >2.0 | 80 | 90 |
| 69 | >0.5 | 80 | 90 |
| 70 | >0.4 | 85 | 90 |
| 71 | >0.4 | 90 | 85 |
| 72 | >0.4 | 80 | 90 |
| 73 | >0.4 | 85 | 85 |
| 74 | >0.5 | 80 | 90 |
| 75 | >0.5 | 85 | 90 |
| 76 | >0.5 | 75 | 80 |
| 77 | >0.5 | 75 | 95 |
| 78 | >0.7 | 85 | 85 |
| 79 | >0.7 | 75 | 90 |
| 80 | >1.2 | 75 | 90 |
| 81 | >1.2 | 85 | 85 |
| 82 | >1.2 | 85 | 90 |
| 83 | >1.2 | 75 | 95 |
| 84 | >1.2 | 85 | 90 |
| 85 | >1.2 | 85 | 90 |
| 86 | >2.0 | 80 | 90 |
| 87 | >2.0 | 90 | 80 |
| 88 | >2.1 | 80 | 90 |
| 89 | >2.1 | 90 | 85 |
| 90 | >2.1 | 85 | 90 |
| 91 | >2.1 | 85 | 90 |
| 92 | >2.1 | 80 | 90 |
| 93 | >2.1 | 75 | 90 |
| 94 | >2.1 | 85 | 90 |
| 95 | >2.1 | 80 | 95 |
| 96 | >2.2 | 85 | 85 |
| 97 | >2.2 | 85 | 85 |
| 98 | >2.3 | 85 | 90 |
| 99 | >2.4 | 90 | 85 |
| 100 | >2.3 | 75 | 95 |
| 101 | >2.3 | 80 | 90 |
| 102 | >2.6 | 80 | 90 |
| 103 | >2.3 | 90 | 85 |
| 104 | >2.3 | 85 | 90 |
| 105 | >2.3 | 75 | 95 |
| 106 | >2.4 | 80 | 90 |
| 107 | >2.4 | 80 | 85 |
| 108 | >2.7 | 85 | 90 |
| 109 | >2.7 | 85 | 90 |
| 110 | >2.7 | 75 | 90 |
| 111 | >0.9 | 75 | 90 |
| 112 | >2.7 | 90 | 85 |
| 113 | >2.7 | 85 | 90 |
| 114 | >2.9 | 85 | 90 |
| 115 | >1.9 | 90 | 85 |
| 116 | >3.0 | 75 | 90 |
| 117 | >3.0 | 80 | 90 |
| 118 | >3.2 | 80 | 90 |
| 119 | >3.2 | 75 | 85 |
| 120 | >3.3 | 80 | 90 |
| 121 | >3.3 | 90 | 90 |
| 122 | >3.5 | 80 | 90 |
| 123 | >3.5 | 75 | 95 |
| 124 | >3.5 | 85 | 90 |
| 125 | >3.6 | 80 | 90 |
| 126 | >3.6 | 90 | 85 |
| 127 | >3.6 | 80 | 90 |
| 128 | >4.2 | 80 | 90 |
| 129 | >4.2 | 85 | 85 |
| 130 | >4.3 | 75 | 90 |
| 131 | >4.9 | 85 | 90 |
| 132 | >4.3 | 75 | 85 |
| 133 | >4.5 | 75 | 80 |
| 134 | >4.5 | 90 | 85 |
| 135 | >5.6 | 80 | 90 |
| 136 | >5.7 | 80 | 90 |
| 137 | >5.7 | 90 | 85 |
| 138 | >1.2 | 85 | 85 |
| 139 | >2.7 | 75 | 90 |

TABLE 8-continued

Evaluation of ability to diagnose colorectal cancer using GPM6A gene

| Set of primers and probes | Cut-off (PMR) | Sensitivity (%), n = 20 | Specificity (%), n = 20 |
|---|---|---|---|
| 140 | >2.4 | 85 | 90 |
| 141 | >1.2 | 80 | 85 |
| 142 | >3.3 | 85 | 90 |
| 143 | >0.5 | 80 | 90 |
| 144 | >3.5 | 85 | 90 |
| 145 | >2.1 | 75 | 95 |
| 146 | >0.4 | 80 | 95 |
| 147 | >2.7 | 80 | 85 |
| 148 | >2.1 | 80 | 90 |
| 149 | >2.2 | 80 | 90 |
| 150 | >2.1 | 85 | 90 |
| 151 | >0.4 | 90 | 85 |
| 152 | >2.7 | 80 | 90 |
| 153 | >3.0 | 85 | 85 |
| 154 | >2.3 | 80 | 90 |
| 155 | >1.2 | 85 | 90 |
| 156 | >4.5 | 75 | 80 |
| 157 | >0.4 | 75 | 95 |
| 158 | >2.2 | 85 | 85 |
| 159 | >2.1 | 75 | 90 |
| 160 | >0.5 | 85 | 90 |
| 161 | >2.7 | 90 | 85 |
| 162 | >2.3 | 80 | 90 |
| 163 | >1.2 | 75 | 95 |
| 164 | >3.6 | 85 | 90 |
| 165 | >0.7 | 80 | 90 |
| 166 | >2.2 | 85 | 85 |
| 167 | >2.1 | 90 | 85 |
| 168 | >2.3 | 85 | 90 |
| 169 | >2.6 | 85 | 85 |
| 170 | >2.3 | 85 | 90 |
| 171 | >2.1 | 75 | 90 |
| 172 | >2.0 | 80 | 90 |
| 173 | >2.1 | 80 | 95 |
| 174 | >3.2 | 85 | 85 |
| 175 | >2.1 | 80 | 90 |
| 176 | >2.1 | 85 | 90 |
| 177 | >2.0 | 85 | 90 |
| 178 | >0.4 | 85 | 90 |
| 179 | >1.4 | 90 | 85 |
| 180 | >0.4 | 85 | 85 |
| 181 | >2.5 | 85 | 90 |
| 182 | >0.4 | 80 | 85 |
| 183 | >0.5 | 80 | 90 |
| 184 | >0.8 | 75 | 90 |
| 185 | >0.5 | 80 | 90 |
| 186 | >0.7 | 90 | 85 |
| 187 | >0.7 | 85 | 90 |
| 188 | >1.2 | 85 | 85 |
| 189 | >1.7 | 90 | 85 |
| 190 | >1.2 | 85 | 95 |
| 191 | >2.2 | 80 | 95 |
| 192 | >1.2 | 75 | 90 |
| 193 | >3.2 | 80 | 90 |
| 194 | >2.0 | 85 | 85 |
| 195 | >2.0 | 80 | 95 |
| 196 | >2.1 | 80 | 90 |
| 197 | >2.1 | 85 | 90 |
| 198 | >2.9 | 85 | 90 |
| 199 | >2.1 | 75 | 90 |
| 200 | >1.2 | 90 | 80 |
| 201 | >3.3 | 85 | 90 |
| 202 | >2.1 | 80 | 90 |
| 203 | >2.1 | 80 | 90 |
| 204 | >2.2 | 90 | 80 |
| 205 | >5.2 | 85 | 90 |
| 206 | >2.3 | 75 | 90 |
| 207 | >2.3 | 85 | 85 |
| 208 | >3.2 | 80 | 95 |
| 209 | >2.3 | 80 | 85 |
| 210 | >4.3 | 75 | 85 |
| 211 | >4.6 | 85 | 90 |
| 212 | >2.3 | 90 | 85 |
| 213 | >2.3 | 75 | 90 |
| 214 | >2.4 | 75 | 95 |
| 215 | >2.4 | 80 | 95 |
| 216 | >2.4 | 85 | 85 |
| 217 | >2.7 | 75 | 90 |
| 218 | >3.5 | 75 | 95 |
| 219 | >2.7 | 80 | 95 |
| 220 | >2.7 | 85 | 90 |
| 221 | >2.7 | 75 | 95 |
| 222 | >2.9 | 75 | 95 |
| 223 | >2.9 | 85 | 90 |
| 224 | >3.0 | 90 | 85 |
| 225 | >3.0 | 80 | 90 |
| 226 | >3.2 | 90 | 85 |
| 227 | >3.2 | 75 | 85 |
| 228 | >3.3 | 80 | 90 |
| 229 | >3.3 | 80 | 90 |
| 230 | >3.5 | 80 | 90 |
| 231 | >4.3 | 85 | 90 |
| 232 | >3.5 | 85 | 90 |
| 233 | >3.5 | 80 | 85 |
| 234 | >3.6 | 85 | 90 |
| 235 | >3.6 | 75 | 90 |
| 236 | >4.2 | 80 | 90 |
| 237 | >4.7 | 80 | 90 |
| 238 | >4.2 | 80 | 90 |
| 239 | >4.3 | 80 | 90 |
| 240 | >4.3 | 75 | 90 |
| 241 | >4.3 | 75 | 95 |
| 242 | >4.5 | 85 | 85 |
| 243 | >4.5 | 80 | 90 |
| 244 | >5.7 | 85 | 85 |
| 245 | >5.7 | 85 | 90 |
| 246 | >1.2 | 90 | 80 |
| 247 | >4.5 | 85 | 90 |
| 248 | >3.2 | 80 | 90 |
| 249 | >5.7 | 75 | 90 |
| 250 | >2.2 | 75 | 85 |
| 251 | >3.6 | 75 | 95 |
| 252 | >2.1 | 80 | 90 |
| 253 | >0.4 | 80 | 90 |
| 254 | >0.4 | 90 | 85 |
| 255 | >3.3 | 85 | 90 |
| 256 | >2.0 | 80 | 90 |
| 257 | >0.5 | 85 | 90 |
| 258 | >1.2 | 85 | 85 |
| 259 | >2.9 | 85 | 90 |
| 260 | >4.5 | 90 | 85 |
| 261 | >0.4 | 85 | 90 |
| 262 | >3.5 | 80 | 85 |
| 263 | >2.7 | 80 | 90 |
| 264 | >1.2 | 75 | 90 |
| 265 | >2.9 | 80 | 90 |
| 266 | >2.0 | 90 | 85 |
| 267 | >0.4 | 85 | 90 |
| 268 | >4.5 | 85 | 85 |
| 269 | >1.2 | 90 | 85 |
| 270 | >0.4 | 85 | 95 |
| 271 | >3.6 | 80 | 95 |
| 272 | >4.3 | 75 | 90 |
| 273 | >0.4 | 80 | 90 |
| 274 | >2.1 | 85 | 85 |
| 275 | >4.2 | 80 | 95 |
| 276 | >5.7 | 80 | 90 |
| 277 | >3.6 | 85 | 90 |
| 278 | >2.7 | 85 | 90 |
| 279 | >4.2 | 75 | 90 |
| 280 | >3.2 | 90 | 80 |
| 281 | >2.3 | 85 | 90 |
| 282 | >2.7 | 80 | 90 |
| 283 | >2.7 | 80 | 90 |
| 284 | >1.2 | 90 | 80 |
| 285 | >2.1 | 85 | 90 |
| 286 | >0.5 | 75 | 90 |
| 287 | >2.9 | 85 | 85 |
| 288 | >2.1 | 80 | 95 |
| 289 | >1.2 | 80 | 85 |

TABLE 8-continued

Evaluation of ability to diagnose colorectal cancer using GPM6A gene

| Set of primers and probes | Cut-off (PMR) | Sensitivity (%), n = 20 | Specificity (%), n = 20 |
|---|---|---|---|
| 290 | >2.7 | 75 | 85 |
| 291 | >0.4 | 85 | 90 |
| 292 | >2.2 | 90 | 85 |
| 293 | >2.0 | 75 | 90 |
| 294 | >0.4 | 75 | 95 |
| 295 | >2.1 | 80 | 95 |
| 296 | >3.0 | 85 | 85 |
| 297 | >2.4 | 75 | 90 |
| 298 | >1.2 | 75 | 95 |
| 299 | >2.0 | 80 | 95 |
| 300 | >0.4 | 85 | 90 |
| 301 | >3.0 | 75 | 95 |
| 302 | >2.1 | 75 | 95 |
| 303 | >2.3 | 85 | 90 |
| 304 | >2.7 | 90 | 85 |
| 305 | >2.7 | 80 | 90 |
| 306 | >1.2 | 90 | 85 |
| 307 | >2.1 | 75 | 85 |
| 308 | >0.7 | 80 | 90 |
| 309 | >4.3 | 80 | 90 |
| 310 | >2.1 | 80 | 90 |
| 311 | >2.3 | 85 | 90 |
| 312 | >2.3 | 85 | 90 |
| 313 | >2.1 | 80 | 85 |
| 314 | >2.1 | 85 | 90 |
| 315 | >5.2 | 75 | 90 |
| 316 | >2.1 | 80 | 90 |
| 317 | >1.2 | 80 | 90 |
| 318 | >2.1 | 80 | 90 |
| 319 | >2.1 | 90 | 90 |
| 320 | >2.6 | 80 | 95 |
| 321 | >2.0 | 85 | 90 |
| 322 | >2.1 | 75 | 95 |
| 323 | >3.3 | 85 | 90 |
| 324 | >0.7 | 85 | 90 |
| 325 | >0.4 | 90 | 85 |
| 326 | >3.0 | 80 | 90 |
| 327 | >0.4 | 80 | 90 |
| 328 | >5.7 | 80 | 90 |
| 329 | >3.5 | 75 | 90 |
| 330 | >2.0 | 85 | 90 |
| 331 | >3.3 | 85 | 85 |
| 332 | >2.7 | 90 | 85 |
| 333 | >1.2 | 75 | 90 |
| 334 | >4.3 | 75 | 95 |
| 335 | >2.4 | 80 | 90 |
| 336 | >3.5 | 80 | 90 |
| 337 | >2.1 | 80 | 85 |
| 338 | >4.5 | 85 | 90 |
| 339 | >3.5 | 75 | 85 |
| 340 | >4.2 | 90 | 80 |
| 341 | >2.3 | 80 | 90 |
| 342 | >4.5 | 85 | 90 |
| 343 | >0.5 | 85 | 90 |
| 344 | >4.2 | 80 | 90 |
| 345 | >2.8 | 80 | 90 |
| 346 | >0.4 | 75 | 90 |
| 347 | >4.2 | 80 | 95 |
| 348 | >1.2 | 85 | 85 |
| 349 | >2.3 | 80 | 90 |
| 350 | >2.2 | 85 | 90 |
| 351 | >3.5 | 90 | 85 |
| 352 | >2.4 | 80 | 90 |
| 353 | >3.5 | 85 | 90 |
| 354 | >0.7 | 80 | 90 |
| 355 | >2.3 | 85 | 85 |
| 356 | >3.2 | 75 | 95 |
| 357 | >2.0 | 85 | 90 |
| 358 | >2.8 | 90 | 85 |
| 359 | >2.9 | 85 | 85 |
| 360 | >1.2 | 90 | 80 |
| 361 | >0.5 | 75 | 85 |
| 362 | >4.3 | 80 | 90 |
| 363 | >0.5 | 85 | 90 |
| 364 | >2.1 | 80 | 95 |
| 365 | >1.2 | 85 | 95 |
| 366 | >2.7 | 75 | 90 |
| 367 | >2.1 | 85 | 85 |
| 368 | >3.5 | 90 | 90 |
| 369 | >2.4 | 85 | 90 |
| 370 | >3.0 | 85 | 90 |
| 371 | >2.3 | 90 | 80 |
| 372 | >4.2 | 80 | 90 |
| 373 | >5.7 | 85 | 95 |
| 374 | >2.3 | 85 | 90 |
| 375 | >4.2 | 85 | 85 |
| 376 | >2.3 | 75 | 90 |
| 377 | >4.3 | 75 | 85 |
| 378 | >2.0 | 80 | 90 |
| 379 | >0.4 | 75 | 90 |
| 380 | >3.6 | 75 | 85 |
| 381 | >2.9 | 75 | 90 |
| 382 | >2.3 | 75 | 90 |
| 383 | >0.7 | 85 | 90 |
| 384 | >0.7 | 80 | 90 |
| 385 | >2.3 | 85 | 90 |
| 386 | >3.2 | 85 | 85 |
| 387 | >2.7 | 75 | 85 |
| 388 | >0.4 | 80 | 90 |
| 389 | >0.4 | 80 | 90 |
| 390 | >0.4 | 80 | 90 |
| 391 | >0.4 | 75 | 90 |
| 392 | >0.5 | 75 | 95 |
| 393 | >0.7 | 80 | 90 |
| 394 | >0.7 | 75 | 90 |
| 395 | >1.2 | 75 | 90 |
| 396 | >1.2 | 80 | 90 |
| 397 | >1.2 | 75 | 90 |
| 398 | >2.0 | 75 | 95 |
| 399 | >2.1 | 85 | 90 |
| 400 | >2.1 | 75 | 95 |
| 401 | >2.1 | 75 | 85 |
| 402 | >2.1 | 85 | 85 |
| 403 | >2.1 | 90 | 85 |
| 404 | >2.2 | 75 | 90 |
| 405 | >2.2 | 85 | 90 |
| 406 | >2.3 | 75 | 90 |
| 407 | >2.3 | 90 | 85 |
| 408 | >2.3 | 90 | 80 |
| 409 | >2.3 | 75 | 85 |
| 410 | >2.4 | 80 | 90 |
| 411 | >2.4 | 85 | 90 |
| 412 | >2.7 | 80 | 95 |
| 413 | >2.7 | 85 | 95 |
| 414 | >2.7 | 75 | 90 |
| 415 | >2.9 | 85 | 85 |
| 416 | >3.0 | 90 | 90 |
| 417 | >3.2 | 85 | 90 |
| 418 | >3.2 | 85 | 90 |
| 419 | >3.3 | 90 | 80 |
| 420 | >3.5 | 80 | 90 |
| 421 | >3.5 | 85 | 95 |
| 422 | >3.6 | 85 | 90 |
| 423 | >4.2 | 85 | 85 |
| 424 | >4.2 | 75 | 90 |
| 425 | >4.3 | 75 | 85 |
| 426 | >4.5 | 80 | 90 |
| 427 | >4.5 | 75 | 90 |
| 428 | >5.7 | 75 | 85 |
| 429 | >4.3 | 75 | 90 |
| 430 | >2.7 | 75 | 90 |
| 431 | >2.7 | 85 | 90 |
| 432 | >2.1 | 80 | 90 |
| 433 | >1.2 | 85 | 90 |
| 434 | >3.2 | 85 | 85 |
| 435 | >5.7 | 75 | 85 |
| 436 | >2.0 | 80 | 90 |
| 437 | >4.2 | 80 | 90 |
| 438 | >5.7 | 80 | 90 |
| 439 | >3.2 | 75 | 90 |

TABLE 8-continued

Evaluation of ability to diagnose colorectal cancer using GPM6A gene

| Set of primers and probes | Cut-off (PMR) | Sensitivity (%), n = 20 | Specificity (%), n = 20 |
|---|---|---|---|
| 440 | >0.4 | 75 | 95 |
| 441 | >3.2 | 80 | 90 |
| 442 | >2.3 | 80 | 85 |
| 443 | >2.0 | 80 | 95 |
| 444 | >0.4 | 85 | 90 |
| 445 | >3.5 | 80 | 95 |
| 446 | >2.4 | 80 | 85 |
| 447 | >0.7 | 80 | 90 |
| 448 | >2.1 | 85 | 90 |
| 449 | >0.7 | 85 | 90 |
| 450 | >2.3 | 75 | 95 |
| 451 | >1.2 | 85 | 90 |
| 452 | >2.1 | 85 | 85 |
| 453 | >0.6 | 80 | 85 |
| 454 | >0.4 | 80 | 90 |
| 455 | >0.4 | 90 | 80 |
| 456 | >0.4 | 75 | 90 |
| 457 | >0.5 | 75 | 95 |
| 458 | >0.7 | 85 | 85 |
| 459 | >0.7 | 85 | 90 |
| 460 | >1.2 | 85 | 85 |
| 461 | >1.2 | 80 | 95 |
| 462 | >1.2 | 90 | 90 |
| 463 | >2.0 | 90 | 85 |
| 464 | >2.0 | 85 | 85 |
| 465 | >2.1 | 80 | 90 |
| 466 | >1.2 | 85 | 90 |
| 467 | >2.1 | 90 | 85 |
| 468 | >3.5 | 80 | 95 |
| 469 | >2.2 | 80 | 90 |
| 470 | >2.2 | 75 | 90 |
| 471 | >2.3 | 80 | 90 |
| 472 | >4.2 | 80 | 90 |
| 473 | >2.3 | 85 | 90 |
| 474 | >2.3 | 80 | 85 |
| 475 | >2.4 | 80 | 90 |
| 476 | >2.4 | 75 | 90 |
| 477 | >2.7 | 85 | 85 |
| 478 | >5.7 | 80 | 90 |
| 479 | >2.7 | 75 | 95 |
| 480 | >2.9 | 85 | 85 |
| 481 | >3.0 | 75 | 95 |
| 482 | >3.2 | 85 | 95 |
| 483 | >3.2 | 80 | 90 |
| 484 | >3.3 | 75 | 90 |
| 485 | >3.5 | 75 | 95 |
| 486 | >3.5 | 90 | 85 |
| 487 | >3.6 | 85 | 90 |
| 488 | >4.2 | 85 | 90 |
| 489 | >4.2 | 85 | 85 |
| 490 | >4.3 | 80 | 90 |
| 491 | >4.5 | 85 | 90 |
| 492 | >4.5 | 80 | 90 |
| 493 | >5.7 | 85 | 90 |
| 494 | >2.7 | 80 | 90 |
| 495 | >0.4 | 80 | 90 |
| 496 | >3.0 | 90 | 85 |
| 497 | >2.3 | 85 | 90 |
| 498 | >2.7 | 80 | 90 |
| 499 | >0.7 | 80 | 95 |
| 500 | >2.3 | 75 | 95 |
| 501 | >3.6 | 85 | 90 |
| 502 | >2.7 | 75 | 90 |
| 503 | >2.3 | 90 | 80 |
| 504 | >2.9 | 75 | 90 |
| 505 | >0.4 | 75 | 95 |
| 506 | >2.2 | 85 | 85 |
| 507 | >3.6 | 85 | 90 |
| 508 | >2.1 | 85 | 85 |
| 509 | >0.7 | 80 | 95 |
| 510 | >2.3 | 90 | 90 |
| 511 | >3.2 | 90 | 85 |
| 512 | >3.3 | 85 | 85 |
| 513 | >1.2 | 80 | 90 |
| 514 | >2.0 | 85 | 90 |
| 515 | >4.3 | 90 | 85 |
| 516 | >2.1 | 80 | 95 |
| 517 | >0.7 | 80 | 90 |
| 518 | >3.3 | 75 | 90 |
| 519 | >1.2 | 80 | 90 |
| 520 | >3.2 | 80 | 90 |
| 521 | >5.7 | 85 | 90 |
| 522 | >3.0 | 80 | 85 |
| 523 | >2.3 | 80 | 90 |
| 524 | >2.7 | 75 | 90 |
| 525 | >3.2 | 85 | 85 |
| 526 | >0.4 | 80 | 90 |
| 527 | >3.2 | 75 | 95 |
| 528 | >2.3 | 85 | 85 |
| 529 | >2.2 | 75 | 95 |
| 530 | >2.3 | 85 | 95 |
| 531 | >3.5 | 80 | 90 |
| 532 | >2.4 | 75 | 90 |
| 533 | >0.7 | 75 | 95 |
| 534 | >0.4 | 90 | 85 |
| 535 | >0.4 | 85 | 90 |
| 536 | >2.0 | 85 | 90 |
| 537 | >1.2 | 85 | 85 |
| 538 | >2.1 | 75 | 95 |
| 539 | >3.0 | 85 | 85 |
| 540 | >2.9 | 80 | 90 |
| 541 | >0.7 | 80 | 90 |
| 542 | >0.4 | 90 | 85 |
| 543 | >3.3 | 85 | 90 |
| 544 | >2.3 | 85 | 90 |
| 545 | >3.6 | 80 | 90 |
| 546 | >0.5 | 85 | 85 |
| 547 | >1.2 | 80 | 90 |
| 548 | >2.3 | 75 | 85 |
| 549 | >2.4 | 85 | 90 |
| 550 | >1.2 | 75 | 95 |
| 551 | >1.2 | 90 | 80 |
| 552 | >2.1 | 75 | 85 |
| 553 | >3.8 | 80 | 90 |
| 554 | >3.5 | 85 | 85 |
| 555 | >3.5 | 85 | 90 |
| 556 | >0.4 | 85 | 90 |
| 557 | >1.2 | 90 | 85 |
| 558 | >2.2 | 85 | 90 |
| 559 | >2.4 | 75 | 90 |
| 560 | >3.5 | 75 | 95 |
| 561 | >1.2 | 80 | 90 |
| 562 | >0.5 | 75 | 85 |
| 563 | >2.4 | 85 | 90 |
| 564 | >0.7 | 85 | 90 |
| 565 | >3.3 | 85 | 90 |
| 566 | >1.2 | 80 | 90 |
| 567 | >2.7 | 85 | 90 |
| 568 | >1.2 | 85 | 90 |
| 569 | >0.7 | 80 | 90 |
| 570 | >3.3 | 85 | 90 |
| 571 | >0.5 | 85 | 85 |
| 572 | >4.2 | 85 | 95 |
| 573 | >3.0 | 85 | 85 |
| 574 | >2.3 | 90 | 85 |
| 575 | >1.2 | 90 | 80 |
| 576 | >3.0 | 75 | 90 |
| 577 | >3.2 | 80 | 95 |
| 578 | >2.3 | 85 | 85 |
| 579 | >4.2 | 80 | 85 |
| 580 | >2.7 | 75 | 95 |
| 581 | >2.4 | 90 | 85 |
| 582 | >0.7 | 75 | 95 |
| 583 | >0.4 | 75 | 95 |
| 584 | >2.1 | 85 | 85 |
| 585 | >1.2 | 80 | 90 |
| 586 | >2.1 | 75 | 90 |
| 587 | >0.4 | 85 | 85 |
| 588 | >0.4 | 85 | 90 |
| 589 | >0.4 | 90 | 85 |

TABLE 8-continued

Evaluation of ability to diagnose colorectal cancer using GPM6A gene

| Set of primers and probes | Cut-off (PMR) | Sensitivity (%), n = 20 | Specificity (%), n = 20 |
|---|---|---|---|
| 590 | >0.5 | 75 | 90 |
| 591 | >0.7 | 80 | 85 |
| 592 | >1.2 | 90 | 85 |
| 593 | >2.3 | 85 | 90 |
| 594 | >1.2 | 75 | 90 |
| 595 | >2.0 | 80 | 90 |
| 596 | >2.1 | 90 | 85 |
| 597 | >2.1 | 80 | 85 |
| 598 | >3.1 | 85 | 90 |
| 599 | >2.2 | 90 | 85 |
| 600 | >2.2 | 75 | 95 |
| 601 | >2.3 | 85 | 85 |
| 602 | >3.3 | 85 | 90 |
| 603 | >2.3 | 75 | 90 |
| 604 | >2.3 | 75 | 90 |
| 605 | >2.4 | 85 | 85 |
| 606 | >2.7 | 85 | 85 |
| 607 | >2.7 | 80 | 95 |
| 608 | >2.9 | 90 | 90 |
| 609 | >3.0 | 80 | 95 |
| 610 | >3.2 | 80 | 90 |
| 611 | >3.3 | 85 | 85 |
| 612 | >3.3 | 85 | 90 |
| 613 | >3.5 | 85 | 90 |
| 614 | >3.6 | 85 | 90 |
| 615 | >4.2 | 75 | 95 |
| 616 | >4.2 | 75 | 95 |
| 617 | >4.3 | 80 | 90 |
| 618 | >4.5 | 85 | 90 |
| 619 | >5.7 | 75 | 90 |
| 620 | >2.4 | 90 | 80 |
| 621 | >0.7 | 80 | 85 |
| 622 | >3.5 | 80 | 90 |
| 623 | >0.5 | 90 | 85 |
| 624 | >4.2 | 85 | 95 |
| 625 | >3.0 | 80 | 90 |
| 626 | >2.3 | 85 | 85 |
| 627 | >2.4 | 90 | 85 |
| 628 | >3.0 | 85 | 90 |
| 629 | >3.0 | 85 | 90 |
| 630 | >2.3 | 80 | 90 |
| 631 | >1.2 | 85 | 90 |
| 632 | >2.1 | 80 | 90 |
| 633 | >2.1 | 90 | 85 |
| 634 | >2.3 | 85 | 90 |
| 635 | >2.3 | 85 | 90 |
| 636 | >2.7 | 85 | 85 |
| 637 | >1.2 | 80 | 90 |
| 638 | >3.6 | 80 | 90 |
| 639 | >0.4 | 80 | 90 |
| 640 | >0.4 | 85 | 90 |
| 641 | >0.4 | 90 | 85 |
| 642 | >0.5 | 75 | 95 |
| 643 | >0.7 | 85 | 85 |
| 644 | >0.7 | 85 | 90 |
| 645 | >1.2 | 85 | 90 |
| 646 | >1.2 | 85 | 90 |
| 647 | >2.0 | 90 | 90 |
| 648 | >2.1 | 80 | 90 |
| 649 | >2.1 | 85 | 85 |
| 650 | >4.3 | 80 | 85 |
| 651 | >2.1 | 85 | 95 |
| 652 | >2.2 | 85 | 90 |
| 653 | >2.3 | 75 | 95 |
| 654 | >2.3 | 75 | 95 |
| 655 | >5.1 | 75 | 85 |
| 656 | >2.3 | 75 | 90 |
| 657 | >2.4 | 80 | 90 |
| 658 | >2.7 | 90 | 80 |
| 659 | >2.7 | 80 | 85 |
| 660 | >2.8 | 85 | 90 |
| 661 | >3.0 | 90 | 85 |
| 662 | >3.0 | 80 | 95 |
| 663 | >3.3 | 80 | 90 |
| 664 | >3.3 | 85 | 85 |
| 665 | >3.5 | 85 | 85 |
| 666 | >3.6 | 85 | 85 |
| 667 | >4.2 | 85 | 90 |
| 668 | >4.2 | 75 | 90 |
| 669 | >4.3 | 80 | 90 |
| 670 | >4.5 | 75 | 95 |
| 671 | >5.7 | 75 | 95 |
| 672 | >2.7 | 85 | 90 |
| 673 | >2.3 | 75 | 90 |
| 674 | >3.5 | 90 | 85 |
| 675 | >2.7 | 90 | 85 |
| 676 | >3.2 | 75 | 90 |
| 677 | >3.5 | 80 | 90 |
| 678 | >2.1 | 80 | 90 |
| 679 | >4.5 | 80 | 90 |
| 680 | >3.2 | 75 | 85 |
| 681 | >0.4 | 80 | 90 |
| 682 | >2.9 | 85 | 90 |
| 683 | >4.3 | 75 | 95 |
| 684 | >3.2 | 90 | 85 |
| 685 | >5.7 | 80 | 90 |
| 686 | >2.9 | 75 | 90 |
| 687 | >3.6 | 75 | 85 |
| 688 | >2.3 | 85 | 85 |
| 689 | >2.2 | 75 | 95 |
| 690 | >2.4 | 85 | 90 |
| 691 | >2.2 | 90 | 80 |
| 692 | >4.5 | 85 | 85 |
| 693 | >2.0 | 85 | 90 |
| 694 | >0.4 | 75 | 80 |
| 695 | >5.7 | 75 | 85 |

INDUSTRIAL APPLICABILITY

As described above, the present disclosure enables the methylation of the CpG island of a colorectal cancer-specific marker gene to be detected to thereby provide information for diagnosing colorectal cancer. The use of the inventive method for detecting methylation and the inventive composition, kit and nucleic acid chip for diagnosing colorectal cancer makes it possible to diagnose colorectal cancer at an early transformation stage, thus enabling the early diagnosis of colorectal cancer. In addition, the inventive method enables colorectal cancer to be effectively diagnosed in an accurate and rapid manner compared to conventional methods.

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

What is claimed is:

1. A method for detecting CpG methylation of GPM6A (glycoprotein M6A) gene, the method comprising the steps of:
   (a) isolating genomic DNA from a clinical sample;
   (b) treating the genomic DNA or a fragment thereof with bisulfite;
   (c) amplifying a methylated CpG of GPM6A gene in the bisulfite-treated genomic DNA or fragment thereof from step (b) by using primer pair comprising:
   a primer comprising the sequence of SEQ ID NO: 25, and a primer comprising the sequence of SEQ ID NO: 29, 31, 33, 35, 37, 39, 41, 43, 45, 47, 49, 51, 53, 55, 57, 59, 61, or 63 to amplify a methylated CpG of the bisulfite-treated GPM6A gene; and
   (d) determining whether the CpG of GPM6A was methylated based on whether the DNA was amplified in step (c).

2. The method of claim 1, wherein the detection of methylation is performed by real-time methylation-specific PCR.

3. The method of claim 1, wherein the clinical sample is selected from the group consisting of a tissue, cell, blood, blood plasma, serum, feces, and urine from a patient suspected of cancer or a subject to be diagnosed.

4. The method of claim 1, wherein step (d) is performed by using probe(s) capable of hybridizing with a methylated CpG of GPM6A comprising at least one or more CpG dinucleotide in a region which hybridizes to the methylated CpG of GPM6A.

5. The method of claim 4, wherein the probe(s) comprise sequence(s) of SEQ ID NO: 26.

* * * * *

UNITED STATES PATENT AND TRADEMARK OFFICE
CERTIFICATE OF CORRECTION

PATENT NO. : 10,428,389 B2
APPLICATION NO. : 15/661054
DATED : October 1, 2019
INVENTOR(S) : Sung Whan An Page 1 of 1

It is certified that error appears in the above-identified patent and that said Letters Patent is hereby corrected as shown below:

In the Specification

Column 18, Lines 2 – 3, "(http://itsa.ucstedu/~urolab/methprimer/index1.html)" should be
-- (http://itsa.ucsf.edu/~urolab/methprimer/index1.html) --.

Signed and Sealed this
Twelfth Day of November, 2019

Andrei Iancu
*Director of the United States Patent and Trademark Office*